US008466145B2

(12) United States Patent
Balasubramanian et al.

(10) Patent No.: US 8,466,145 B2
(45) Date of Patent: Jun. 18, 2013

(54) DIPEPTIDYL PEPTIDASE IV INHIBITORS

(75) Inventors: Gopalan Balasubramanian, Chennai (IN); Sukumar Sakamuri, San Diego, CA (US); Gajendra Singh, Chennai (IN); Sivanesan Dharmalingam, Seoul (KR); Franklin Pooppady Xavier, Chennai (IN); Shridhar Narayanan, Chennai (IN); Jeyamurugan Mookkan, Chennai (IN); Jeganatha Sivakumar Balasubramanian, Chennai (IN); Agneeswari Rajalingam, Chennai (IN); Jayanarayan Kulathingal, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 23 days.

(21) Appl. No.: 13/140,997

(22) PCT Filed: Jan. 7, 2010

(86) PCT No.: PCT/IB2010/000008
§ 371 (c)(1),
(2), (4) Date: Jun. 20, 2011

(87) PCT Pub. No.: WO2010/079413
PCT Pub. Date: Jul. 15, 2010

(65) Prior Publication Data
US 2011/0257164 A1  Oct. 20, 2011

(30) Foreign Application Priority Data
Jan. 9, 2009 (IN) .............................. 65/CHE/2009

(51) Int. Cl.
*A61K 31/541* (2006.01)
*A61K 31/4196* (2006.01)
*A61K 31/4025* (2006.01)
*A61K 31/46* (2006.01)
*A61K 31/4245* (2006.01)
*A61K 31/497* (2006.01)
*A61K 31/4439* (2006.01)
*A61K 31/40* (2006.01)
*A61K 31/454* (2006.01)
*C07D 413/12* (2006.01)
*C07D 405/12* (2006.01)

(52) U.S. Cl.
USPC ........ 514/222.2; 514/383; 514/422; 514/299; 514/364; 514/255.05; 514/343; 514/423; 514/326; 514/235.5; 514/381; 548/262.2; 548/215; 548/193; 548/200; 548/131; 548/146; 548/525; 548/540; 548/253; 546/112; 546/269.4; 546/208; 544/141

(58) Field of Classification Search
USPC ................... 548/518, 527, 131, 215
See application file for complete search history.

(56) References Cited

U.S. PATENT DOCUMENTS

| 7,132,104 B1 | 11/2006 | Von Horsten et al. |
| 7,205,323 B2 * | 4/2007 | Thomas et al. ............... 514/365 |
| 2007/0112059 A1 | 5/2007 | Fukushima et al. |
| 2009/0017015 A1 | 1/2009 | Hughes |

FOREIGN PATENT DOCUMENTS

| EP | 0 222 371 A2 | 5/1987 |
| WO | WO 98/19998 A2 | 5/1998 |
| WO | WO 98/58902 | 12/1998 |
| WO | WO 00/34241 A1 | 6/2000 |
| WO | WO 03/002553 A2 | 1/2003 |
| WO | WO 03/004498 A1 | 1/2003 |
| WO | WO 03/082817 A2 | 10/2003 |
| WO | WO 2004/064778 A2 | 8/2004 |
| WO | WO 2005/075426 A1 | 8/2005 |
| WO | WO 2005/095339 A1 | 10/2005 |
| WO | WO 2006/011035 A1 | 2/2006 |
| WO | WO 2006/012441 A1 | 2/2006 |
| WO | WO 2006/040625 A1 | 4/2006 |
| WO | WO 2007/113634 A1 | 10/2007 |

OTHER PUBLICATIONS

Wu and Farrelly, Toxicology 236:1-6, 2007.*
Vippagunta et al., Advanced Drug Delivery Reviews, (2001), vol. 48, p. 3-26.*
International Preliminary Report on Patentability issued in International Patent Application No. PCT/IB2010/000008 dated Jul. 12, 2011.
Jens-Uwe Peters, "11 Years of Cyanopyrrolidines as DPP-IV Inhibitors," *Current Topics in Medicinal Chemistry*, vol. 7, 2007, pp. 579-595.

(Continued)

*Primary Examiner* — Yong Chu
(74) *Attorney, Agent, or Firm* — Oliff & Berridge, PLC

(57) ABSTRACT

Described are novel compounds of the Formula (I), their derivatives, analogs, tautomeric forms, regioisomers, stereoisomers, polymorphs, solvates, intermediates, pharmaceutically acceptable salts, pharmaceutical compositions, metabolites and prodrugs thereof. These compounds are effective in lowering blood glucose, serum insulin, free fatty acids, cholesterol, triglyceride levels; treatment of obesity, inflammation, autoimmune diseases such as multiple sclerosis, rheumatoid arthritis; treatment and/or prophylaxis of type II diabetes. These compounds are more particularly dipeptidyl peptidase (DPP IV) inhibitors.

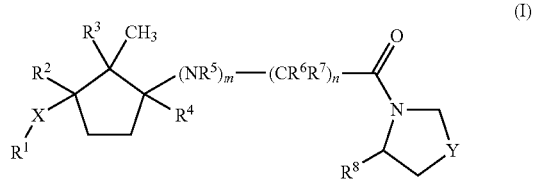

11 Claims, No Drawings

OTHER PUBLICATIONS

Lankas et al., "Dipeptidyl Peptidase IV Inhibition for the Treatment of Type 2 Diabetes," *Diabetes*, vol. 54, Oct. 2005, pp. 2988-2994.

Hildebrandt et al., "Alterations in Expression and in Serum Activity of Dipeptidyl Peptidase IV (DPP IV, CD26) in Patients with Hyporectic Eating Disorders," *Scandinavian Journal of Immunology*, vol. 50, 1999, pp. 536-540.

Moritoh et al., "Chronic administration of Alogliptin, a novel, potent, and highly selective dipeptidyl peptidase-4 inhibitor, improves glycemic control and beta-cell function in obese diabetic ob/ob mice," *European Journal of Pharmacology*, vol. 588, 2008, pp. 325-332.

Ahren et al., "Improved glucose tolerance and insulin secretion by inhibition of dipeptidyl peptidase IV in mice," *European Journal of Pharmacology*, vol. 404, 2000, pp. 239-245.

Takashina et al., "MP-513, a Novel DPP-IV Inhibitor, Prevents High-Fat Diet-Induced Viceral Obesity in Mice," *69th scientific session ADA*, Abstract No. 543-P, 2009.

Green et al., "Dipeptidyl peptidase IV (DPP IV) inhibitors: a newly emerging drug class for the treatment of type 2 diabetes," *Diabetes and Vascular Disease Research*, vol. 3, Issue 3, Dec. 2006, pp. 159-165.

Thomas Jax, "Treatment of patients with diabetes with GLP-1 analogues or DPP-4- inhibitors: a hot topic for Cardiologists?" *Clinical Research in Cardiology*, vol. 98, 2009, pp. 75-79.

Yilmaz et al., "Dipeptidyl peptidase IV inhibitors: Therapeutic potential in nonalcoholic fatty liver disease," *Medicinal Science Monitor*, vol. 15, No. 4, 2009, pp. HY1-HY5.

Marfella et al., "Effects of Vildagliptin twice daily vs. sitagliptin once daily on 24-hour acute glucose fluctuations," *Journal of Diabetes and Its Complications*, vol. 24, 2010, pp. 79-83.

Yazbeck et al., "Dipeptidyl peptidase inhibitors, an emerging drug class for inflammatory disease?" *Trends in Pharmacological Sciences*, vol. 30, No. 11, Nov. 2009, pp. 600-607.

Kim et al., "Improvement of Islet Graft Survival in Diabetic NOD Mice through Sitagliptin (MK0431) Inhibition of Dipeptidyl Peptidase IV (DPP-IV) Involves Modulation of the Immune System," *69th scientific Session ADA*, Abstract No. 1948-P, 2009.

Linke et al., "The DPP-4 Inhibitor Linagliptin (B1 1356) Improves Wound Healing in ob/ob Mice," *69th scientific session ADA*, Abstract No. 596-P, 2009.

Hunziker et al., "Inhibitors of Dipeptidyl Peptidase IV—Recent Advances and Structural Views," *Current Topics in Medicinal Chemistry*, vol. 5, 2005, pp. 1623-1637.

Villhauer et al., "1-[[(3-Hydroxy-1-adamantyl)amino]acetyl]-2-cyano-(S)-pyrrolidine: A Potent, Selective and Orally Bioavailable Dipeptidyl Peptidase IV Inhibitor with Antihyperglycemic Properties," *Journal of Medicinal Chemistry*, vol. 46, No. 13, 2003, pp. 2774-2789.

Fukushima et al., "Synthesis and structure—activity relationships of potent 4-fluoro-2-cyanopyrrolidine dipeptidyl peptidase IV inhibitors," *Bioorganic & Medicinal Chemistry*, vol. 16, 2008, pp. 4093-4106.

Baumgarten et al., "Reactions of Amines. XVIII. The Oxidative Rearrangement of Amides with Lead Tetraacetate," *Journal of Organic Chemistry*, vol. 40, No. 24, 1975, pp. 3554-3561.

Wanner et al., "Neue chirale Hilfsgruppen aus (+)-Camphersaure," *Liebigs Annalen*, 1996, pp. 1941-1948 (With English-language Abstract).

Koenig et al., "A Facile Deprotection of Secondary Acetamides," *Organic Letters*. vol. 11, No. 2, 2009, pp. 433-436.

Demange et al., "Practical Synthesis of Boc and Fmoc Protected 4-Fluoro and 4-Difluoroprolines from *Trans*-4-Hydroxyproline," *Tetrahedron Letters*, vol. 39, 1998, pp. 1169-1172.

Hanyu et al., "New chiral 1,4-aminoalcohols derived from (+)-camphor and (−)-fenchone for the enantioselective addition of diethylzinc to aldehyde," *Tetrahedron: Asymmetry*, vol. 11, 2000, pp. 4127-4136.

Nieto et al., "Synthetic Approaches to (1$S$,3$R$)-3-Aminomethyl-2,2,3-trimethylcyclopentylmethanol and (1$S$,3$R$)-3-Amino-2,2,3-trimethylcyclopentylmethanol from (+)-Camphoric Acid," *Tetrahedron*, vol. 54, 1998, pp. 7819-7830.

International Search Report issued in Application No. PCT/IB2010/000008; Dated Oct. 11, 2010.

\* cited by examiner

DIPEPTIDYL PEPTIDASE IV INHIBITORS

FIELD

Described are compounds of the formula (I), their derivatives, analogs, tautomeric forms, stereoisomers, polymorphs, hydrates, solvates, intermediates, pharmaceutically acceptable salts, pharmaceutical compositions, metabolites and prodrugs thereof.

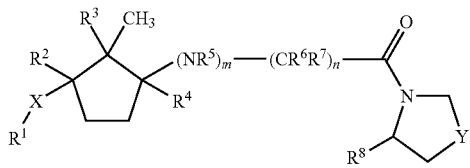

Described herein is also a process for the preparation of the above said compounds and compositions containing them.

The compounds are dipeptidyl peptidase (DPP-IV) inhibitors and are used for treating conditions that are regulated or normalized via inhibition of DPP-IV such as treatment and/or prophylaxis of type II diabetes.

Described herein is also a method for delaying the onset of type II diabetes and alleviating the physiological consequences of type II diabetes. Diabetes is a disease in which the body does not produce or properly use insulin. Around 150 million people have diabetes mellitus worldwide and this number will be double by the year 2025. Much of this increase will occur in developing countries and will be due to population growth, ageing, unhealthy diets, obesity and sedentary lifestyles. By 2025, while most people with diabetes in developed countries will be aged 65 years or more, in developing countries most will be in the 45-64 year age bracket and affected in their most productive years. Diabetes is the leading cause of blindness, lower limb amputations, and renal failure in the United States. The healthcare cost of diabetes is high, with the total estimated cost in the United States exceeding $100 billion. Estimated number of diabetes cases in India in 2002 was 31.7 million. A report by American Diabetes Association, April 2004 stated that by 2030, 79.4 million are going to be affected by diabetes. As of today, approximately 5% of world population is suffering from type II diabetes.

BACKGROUND

Diabetes refers to a disease process derived from multiple causative factors and is characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic diseases. Therefore patients with Type II diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

Diabetes mellitus has serious effects on people's health and accompanies various complications. There are two major types of diabetes mellitus: type I diabetes mellitus characterized by little or no insulin secretory capacity due to the destruction of the pancreatic cells, and type II diabetes mellitus characterized by insulin deficiency and insulin resistance due to other causes. The prevalence of type II diabetes mellitus is 90% or more of total patients with diabetes mellitus.

The worldwide epidemic of type II diabetes has been stimulating the search for new concepts and targets for the treatment of this incurable disease. Most current therapies were developed in the absence of defined molecular, targets. Increasing knowledge on the biochemical and cellular alterations occurring in NIDDM (Non-insulin dependent diabetes mellitus) has led to the development of novel and potentially more effective therapeutic approaches to treat the disease. The role of peroxisome proliferator activated receptor in the regulation of lipid metabolism, insulin and triglycerides led to the rational design of several PPAR agonists. However, these drugs have side effects such as hypoglycemia, weight gain and the like. Accordingly, there is a strong need to develop therapeutic agents with decreased side effects, which in particular would not induce hypoglycemia and weight gain.

The other targets are: Protein Tyrosine Phosphatase 1B (PTP1B); Glycogen Synthase Kinase-3 (GSK-3); Adiponectin; Insulin Receptor Mimetic and Glucagon-like Peptidel (GLP-1).

The serine protease DPP-IV is responsible for the rapid degradation of the insulinotropic hormone GLP-1 (glucagon like peptide 1). DPP-IV inhibition results in an increase of circulating GLP-1 levels and as a consequence, improves the insulin secretion in type II diabetic patients. Other physiological effects of enhanced GLP-1 levels, such as reduction of hepatic glucose output, delayed gastric emptying and possibly an increased insulin sensitivity as well as preservation of pancreatic beta cell function, are believed to contribute to the beneficial effects (*Current Topics in Medicinal Chemistry*, 2007, 7, 579-595). Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues.

Compounds, which are inhibitors of the dipeptidyl peptidase-IV ("DPP-4") enzyme, approved as drugs for the treatment of diabetes and particularly Type II diabetes are Sitagliptin of Merck and Vildagliptin of Novartis. To date, many candidate molecules, as DPP-IV inhibitors have been on clinical trials. A lot of research for developing DPP-IV inhibitors has been focused on molecules in which the cyano group is bonded to the pyrrolidine ring (*Current Topics in Medicinal Chemistry*, 2007, 7, 579-595). Representative examples of these DPP-IV inhibitors are cited in WO9819998, WO00/34241, WO04/064778, WO03/004498 and WO03/082817.

WO 2005/075426 discloses compounds of the general formula (A),

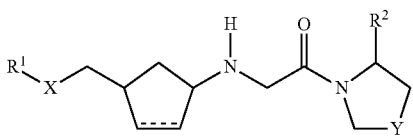

wherein Y is —S(O)$_m$—, —CH$_2$—, CHF, or —CF$_2$; X is NR$^3$, O or S(O)$_m$; m is 0, 1 or 2; the dotted line [---] in the carbocyclic ring represents an optional double bond (i.e., a single or double bond); R$^1$ is substituted or unsubstituted aryl, substituted or unsubstituted arylalkyl, substituted or unsubstituted heteroaryl, substituted or unsubstituted heterocyclic ring, substituted or unsubstituted heterocyclylalkyl, or substituted or unsubstituted heteroarylalkyl; R$^2$ is hydrogen, nitrile (—CN), COOH, or isosteres of carboxylic acids, including, but not limited to, SO$_3$H, CONHOH, B(OH)$_2$, PO$_3$R$^4$R$^5$, SO$_2$NR$^4$R$^5$, tetrazole, amides, esters and acid anhydrides;

WO 2006/040625 discloses compounds of formula (B),

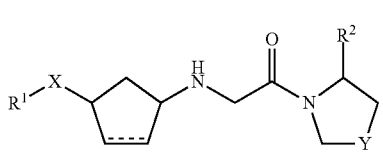

wherein Y is —S(O)$_n$—, —CH$_2$—, CHF, or —CF$_2$; n is 0, 1, or 2; X is a bond, C$_1$-C$_5$ alkyl (eg, —CH$_2$—), or —C(=O)—; the dotted line [---] in the carbocyclic ring represents an optional double bond; R$^1$ is substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, —CN, —COOR$^3$, CONR$^3$R$^4$, —OR$^3$, —NR$^3$R$^4$, or NR$^3$COR$^3$; R$^2$ is hydrogen, cyano, COOH, or an isostere of a carboxylic acid (such as SO$_3$H, CONOH, B(OH)$_2$, PO$_3$R$^3$R$^4$, SO$_2$NR$^3$R$^4$, tetrazole, —COOR$^3$, —CONR$^3$R$^4$, NR$^3$COR$^4$, or —COO-COR$^3$).

WO 2007/113634 discloses compounds of formula (C),

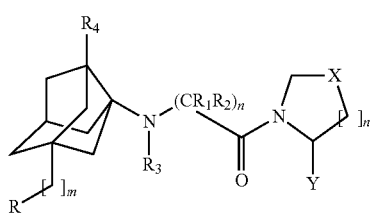

wherein X=CH$_2$, CHF, CF$_2$, CHCl, CHOH, CHOCH$_3$, NH, NCOCH$_3$, CHPh, O, or S, Y=CN; R$_1$ and R$_5$ are selected from hydrogen, C$_{1-4}$ alkyl and hydroxy, R$_2$ is selected from hydrogen, C$_1$-C$_4$ alkyl, substituted alkyl, C$_{1-4}$ alkoxy C$_{1-4}$ alkyl, C$_{1-4}$ hydroxyalkyl, R$_5$NHC$_{1-4}$ alkyl, and R$_5$NHC(NH) NHC$_{1-4}$ alkyl, R$_3$ is selected from hydrogen and C$_1$-C$_4$ alkyl, R$_4$ is selected from hydrogen, C$_{1-4}$ alkyl, substituted alkyl, C$_1$-C$_4$ alkoxy, C$_1$-C$_4$ alkanoyloxy, hydroxy, amino, nitro, C$_2$-C$_6$ alkenyl, acyl and halogen, n=1 or 2, m=0, 1, or 2, R is as defined in the patent.

WO 2005095339 discloses compounds of formula (D),

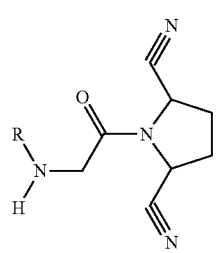

wherein R is R$_1$—X—Y—(CH$_2$)$_m$— or R$_1$—X—Y—(CH$_2$)$_n$(C(CH$_3$)$_2$)—, (C$_3$-C$_{12}$)cycloalkyl, optionally substituted independently with one to three hydroxy, trifluoromethyl, cyano, (C$_1$-C$_3$)hydroxyalkyl, (C$_1$-C$_8$)alkyl, or R$_1$—X—Y—(CH$_2$)$_p$—, wherein p is zero, one, two, or three; R$_1$ is heterocyclyl(C$_0$-C$_8$)alkyl. X is a bond, —O—, —S—, —CO—. Y is a bond or NR$_2$.

OBJECTIVE

Although DPP IV inhibitors such as Sitagliptin and Vildagliptin are approved as drugs and many more are in different stages of development, there is still a need for novel compounds that are selective over other members of the family of serine peptidases that includes quiescent cell proline dipeptidase (QPP), DPP8, and DPP9 (G. Lankas, et al., "Dipeptidyl Peptidase-IV Inhibition for the Treatment of Type II Diabetes," Diabetes, 2005, 54, 2988-2994).

With an objective of developing novel DPP IV inhibitors for lowering blood glucose, free fatty acids, cholesterol and triglyceride levels in type II diabetes, treating food intake disorder (Scand. J. Immunol., 1999, 50, 536-540) and treating autoimmune diseases such as multiple sclerosis and rheumatoid arthritis we focused our research to develop potent, stable and selective novel DPP IV inhibitors; efforts in this direction have led to compounds having the general formula (I).

The main objective is to provide novel DPP IV inhibitors and their pharmaceutically acceptable salts useful for treatment of disorders associated with insulin resistance such as hyperglycemia, low glucose tolerance, insulin resistance (European Journal of Pharmacology, 2008, 588 325-332; European Journal of Pharmacology, 2000, 404, 239-245), obesity (69$^{th}$ scientific session ADA Abstract No: 543-P, 2009), lipid disorders (Diabetes. Vasc. Dis. Res., 2006, 3, 159-65), dyslipidemia, hyperlipidemia, hypertriglyceridemia, hypercholesterolemia, low HDL levels, high LDL levels, atherosclerosis, coronary artery disease, peripheral vascular disease [Clin. Res. Cardiol., 2009, 98, 75-79], and its sequelae, vascular restenosis, pancreatitis, abdominal obesity (69th scientific session, ADA, Abs No. 543-P, 2009), nonalcoholic fatty liver disease (Med. Sci. Monit., 2009, 15(4): HY1-5), nonalcoholic steatohepatitis (Med Sci Monit, 2009, 15(4): HY1-5), syndrome X, polycystic ovarian syndrome and other disorders where insulin resistance is a component.

Yet another objective is to provide novel DPP IV inhibitors and their pharmaceutically acceptable salts that are also useful for the treatment of diabetic complications ("Effects of Vildagliptin twice daily vs. Sitagliptin once daily on 24-hour acute glucose fluctuations" Journal of Diabetes and Its Complications, 2009, Article in Press) such as diabetic retinopathy, diabetic nephropathy, diabetic neuropathy, diabetic cataract and the like.

Another objective herein is to provide novel DPP IV inhibitors and their pharmaceutically acceptable salts that are also useful for the treatment of irritable bowel syndrome, inflammatory bowel disease, including Crohn's disease and ulcerative colitis, other inflammatory conditions (Trends in Pharmacological Sciences, 2009, 30, 600-607), neurodegenerative diseases cognition disorders, anxiolytic, analgesic (US2009/0017015, U.S. Pat. No. 7,132,104), Immune modulators (69th scientific session ADA Abstract No: 1948-P, 2009), Wound Healing (69th scientific session ADA, Abstract No: 596-P, 2009).

Another objective herein is to provide novel DPP IV inhibitors and their pharmaceutically acceptable salts having enhanced activities, without toxic effects or with reduced toxic effects.

As most of the cyanopyrrolidine class of DPP IV inhibitors are associated with inherent chemical instability due to formation of inactive diketopiperazine (*Current Topics in Medicinal Chemistry*, 2005, 5, 1623-1637), one of our objective is to provide novel DPP IV inhibitors devoid of such inherent chemical instability due to formation of inactive diketopiperazine.

Yet another objective herein is to provide a process for the preparation of novel DPP IV inhibitors of the formula (I) and their pharmaceutically acceptable salts.

SUMMARY OF THE INVENTION

Described are compounds of the formula (I),

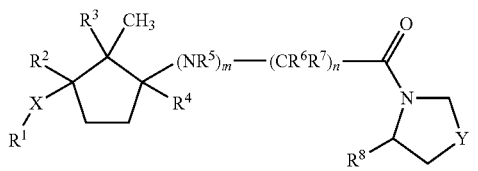

(I)

their derivatives, analogs, tautomeric forms, stereoisomers, polymorphs, hydrates, solvates, intermediates, pharmaceutically acceptable salts, pharmaceutical compositions, metabolites and prodrugs thereof; wherein Y represents —O—, —S(O)$_p$—, —CH$_2$—, —CHOH—, —CHF— or —CF$_2$—; m, n and p are integers and independently selected from 0, 1 or 2; X represents a bond, C$_1$-C$_5$ alkylene (e.g., —CH$_2$—) or —C(=O)—;

R$^1$ represents hydrogen, optionally substituted groups selected from alkyl, cycloalkyl, cycloalkylalkyl, cycloalkenyl, aryl, arylalkyl, arylalkenyl, arylalkynyl, heteroaryl, heterocyclyl, heterocycloalkyl, heterocyclylalkyl, heteroarylalkyl, heteroarylalkenyl, heteroarylalkynyl, —N$_3$, —S(O)$_p$R$^{10}$, —NR$^{10}$S(O)$_p$R$^{11}$, —CN, —COOR$^{10}$, —CONR$^{10}$R$^{11}$, —OR$^{10}$, —NR$^{10}$R$^{11}$ or —NR$^{10}$COR$^{11}$ or a group selected from:

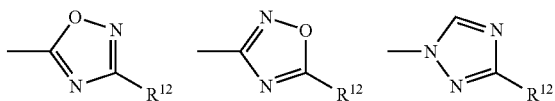

-continued

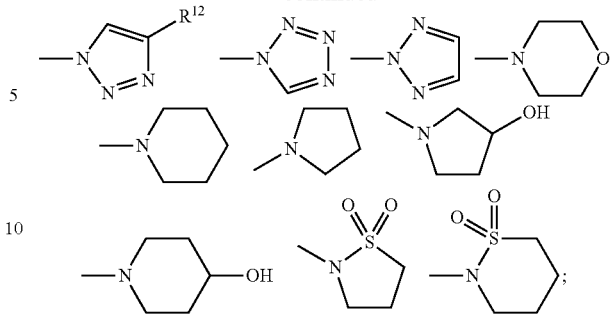

wherein R$^{12}$ represents hydrogen or substituted or unsubstituted groups selected from alkyl, alkoxy, acyl, hydroxyalkyl, haloalkyl, alkenyl, alkynyl, cycloalkyl, cycloalkylalkyl, cycloalkenyl, aryl, arylalkyl, heteroaryl, heterocyclyl, heterocyclylalkyl, heterocycloalkyl, heteroarylalkyl, carboxylic acid or carboxylic acid derivatives selected from esters, amides, acid halides, hydroxamic acid and hydroxamates.

R$^2$, R$^3$ and R$^4$ independently represents hydrogen, hydroxy, halogen, alkyl, haloalkyl, cyano, hydroxyalkyl, alkoxy, alkylsulfonyl, alkylthio, phenyl-S(O)$_p$-alkyl, amino, NR$^{10}$R$^{11}$ or phenylalkyl, wherein said phenyl is optionally substituted independently with one or more alkyl, cycloalkyl, alkoxy, cyano, halogen, alkylsulfonyl, alkylthio, —CO$_2$-alkyl, —COOH, —CONH$_2$, —CHO, —CH$_2$OH, hydroxyl, haloalkyl, amino, nitro or R$^2$ and R$^4$ can be combined together to form an optionally substituted 4-10 membered ring having 0-4 hetero atoms selected from N, O and S;

R$^5$ is selected from hydrogen and optionally substituted alkyl group;

R$^6$ is selected from hydrogen, optionally substituted groups selected from alkyl, alkoxyalkyl, hydroxyalkyl, amino, R$^9$NHalkyl and R$^9$NHC(NH)NHalkyl;

R$^7$ and R$^9$ are selected from hydrogen, alkyl and hydroxyl;

R$^8$ is hydrogen, —CN, —COOH, or an isosterate of a carboxylic acid (such as —SO$_3$H, —B(OH)$_2$, —PO$_3$R$^{10}$R$^{11}$, —SO$_2$NR$^{10}$R$^{11}$, -tetrazole, —COOR$^{10}$, —CONR$^{10}$R$^{11}$, —NR$^{10}$COR$^{11}$ or —COOCOR$^{10}$); and R$^{10}$ and R$^{11}$ may be the same or different and are independently hydrogen, nitro, hydroxy, cyano, formyl, acetyl, halogen, optionally substituted groups selected from amino, alkyl, alkoxy, alkenyl, alkynyl, cycloalkyl, cycloalkylalkyl, cycloalkenyl, aryl, arylalkyl, heteroaryl, heterocyclic ring, heterocyclylalkyl, heteroarylalkyl, carboxylic acid or carboxylic acid derivatives selected from esters, amides, acid halides, hydroxamic acid and hydroxamates.

DETAILED DESCRIPTION

Described are compounds of the formula (I),

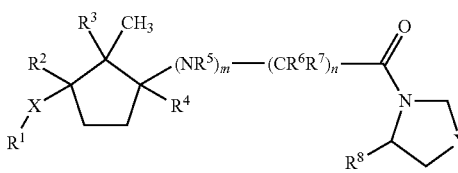

(I)

their derivatives, analogs, tautomeric forms, stereoisomers, polymorphs, hydrates, solvates, intermediates, pharmaceutically acceptable salts, pharmaceutical compositions, metabolites and prodrugs thereof;

wherein Y represents —O—, —S(O)$_p$—, —CH$_2$—, —CHOH—, —CHF— or —CF$_2$—;

m, n and p are integers and independently selected from 0, 1, or 2;

X represents a bond, C$_1$-C$_5$ alkylene chain (e.g., —CH$_2$—) or —C(=O)—;

R$^1$ represents hydrogen, optionally substituted groups selected from alkyl, cycloalkyl, cycloalkylalkyl, cycloalkenyl, aryl, arylalkyl, arylalkenyl, arylalkynyl, heteroaryl, heterocyclic ring, heterocyclylalkyl, heteroarylalkyl, heteroarylalkenyl, heteroarylalkynyl, —N$_3$, —S(O)$_p$R$^{10}$, —NR$^{10}$S(O)$_p$R$^{11}$, —CN, —COOR$^{10}$, —CONR$^{10}$R$^{11}$, —OR$^{10}$, —NR$^{10}$R$^{11}$, or —NR$^{10}$COR$^{11}$ or a group selected from:

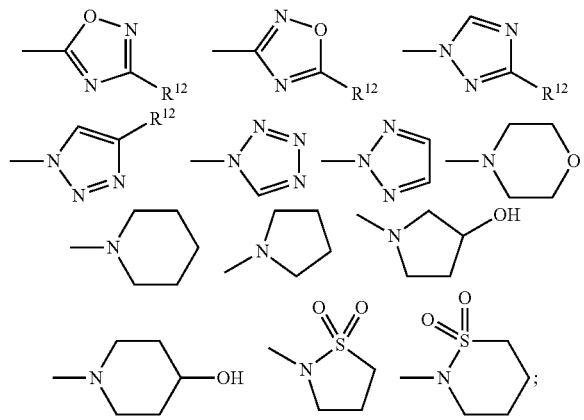

wherein R$^{12}$ represents hydrogen or substituted or unsubstituted groups selected from alkyl, alkoxy, acyl, hydroxyalkyl, haloalkyl, alkenyl, alkynyl, cycloalkyl, cycloalkylalkyl, cycloalkenyl, aryl, arylalkyl, heteroaryl, heterocyclyl, heterocyclylalkyl, heterocycloalkyl, heteroarylalkyl or a carboxylic acid or carboxylic acid derivatives selected from esters, amides, acid halides, hydroxamic acid and hydroxamates.

R$^2$, R$^3$ and R$^4$ independently represents hydrogen, hydroxy, halogen, alkyl, haloalkyl, cyano, hydroxyalkyl, alkoxy, alkylsulfonyl, alkylthio, phenyl-S(O)$_p$-alkyl, amino, —NR$^{10}$R$^{11}$ or phenylalkyl, wherein said phenyl is optionally substituted independently with one or more alkyl, cycloalkyl, alkoxy, cyano, halogen, alkylsulfonyl, alkylthio, —CO$_2$alkyl, —COOH, —CONH$_2$, —CHO, —CH$_2$OH, hydroxyl, haloalkyl, amino, nitro or R$^2$ and R$^4$ can be combined together to form a optionally substituted 4-10 membered ring having 0-4 hetero atoms selected from N, O and S; Non-limiting examples include:

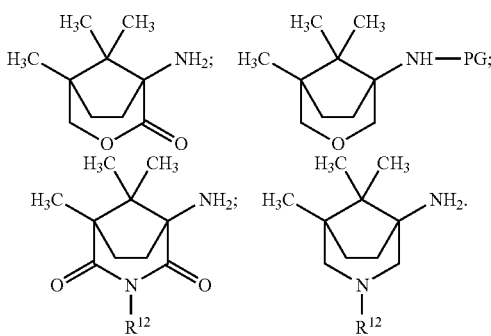

R$^5$ is selected from hydrogen and optionally substituted alkyl group;

R$^6$ is selected from hydrogen, optionally substituted groups selected from alkyl, alkoxyalkyl, hydroxyalkyl, amino, R$^9$NHalkyl and R$^9$NHC(NH)NHalkyl;

R$^7$ and R$^9$ are selected from hydrogen, alkyl and hydroxyl;

R$^8$ is hydrogen, —CN, —COOH, or an isosterate of a carboxylic acid (such as —SO$_3$H, —B(OH)$_2$, —PO$_3$R$^{10}$R$^{11}$, —SO$_2$NR$^{10}$R$^{11}$, -tetrazole, —COOR$^{10}$, —CONR$^{10}$R$^{11}$, —NR$^{10}$COR$^{11}$ or —COOCOR$^{10}$);

R$^{10}$ and R$^{11}$ may be the same or different and are independently hydrogen, nitro, hydroxy, cyano, formyl, acetyl, halogen, optionally substituted groups selected from amino, alkyl, alkoxy, alkenyl, alkynyl, cycloalkyl, cycloalkylalkyl, cycloalkenyl, aryl, arylalkyl, heteroaryl, heterocyclyl, heterocycloalkyl, heterocyclylalkyl, heteroarylalkyl or a carboxylic acid and its derivatives.

The term "substituted" as used herein refers to substitution with any one or any combination of the following substituents: halogens such as fluorine, chlorine, bromine and iodine; hydroxy; nitro; cyano; oxo (=O); thioxo (=S); azido; nitroso; amino; hydrazino; formyl; alkyl; alkoxy; aryl; haloalkyl groups such as trifluoromethyl, tribromomethyl, trichloromethyl and the like; haloalkoxy groups such as —OCH$_2$Cl, —OCHF$_2$, —OCF$_3$ and the like; arylalkoxy groups such as benzyloxy, phenylethoxy and the like; cycloalkyl; —O-cycloalkyl; heterocyclyl; heteroaryl; alkylamino; —O—CH$_2$-cycloalkyl; —COOR$^a$; —C(O)R$^b$; —C(S)R$^a$; —C(O)NR$^a$R$^b$; —NR$^a$C(O)NR$^b$R$^c$; —N(R$^a$)SOR$^b$; —N(R$^a$)SO$_2$R$^b$; —NR$^a$C(O)OR$^b$; —NR$^a$R$^b$; —NR$^a$C(O)R$^b$; —NR$^a$C(S)R$^b$; —SONR$^a$R$^b$; —SO$_2$NR$^a$R$^b$; —OR$^a$; —OR$^a$C(O)OR$^b$; —OC(O)NR$^a$R$^b$; —OC(O)R$^a$; —R$^a$NR$^b$R$^c$; —R$^a$OR$^b$; —SR$^a$; —SOR$^a$ and —SO$_2$R$^a$; R$^a$, R$^b$ and R$^c$ each independently represent hydrogen atom; substituted or unsubstituted groups selected from alkyl; alkylene; aryl; arylalkyl; cycloalkyl; heterocyclyl; heteroaryl and heteroarylalkyl and R$^a$, R$^b$ and R$^c$ are also combined to form a 3-7 membered ring having 0-2 hetero atoms. The substitutents may be optionally further substituted.

The term "alkyl" refers to straight or branched aliphatic hydrocarbon groups having the specified number of carbon atoms that are attached to the rest of the molecule by a single atom. Preferred alkyl groups include, without limitation, methyl, ethyl, n-propyl, isopropyl, butyl, isobutyl, t-butyl, pentyl, hexyl, heptyl and the like.

The term "alkylene" refers to —(CH$_2$)$_n$— wherein n represents an integer. Non limiting examples of alkylene group include —CH$_2$—, —CH$_2$CH$_2$—, —CH$_2$CH$_2$CH$_2$— and like The term "hydroxyalkyl" refers to an alkyl group as defined above, wherein one or more of the alkyl group's hydrogen has been replaced with an —OH group. Non-limiting examples of hydroxyalkyl groups include —CH$_2$OH, —CH$_2$CH$_2$OH, —CH$_2$CH$_2$CH$_2$OH and the like.

The term "aryl" refers to aromatic radicals having, 6 to 14 carbon atoms, which may be optionally substituted by one or more substituents. Preferred aryl groups include, without limitation, phenyl, naphthyl, indanyl, biphenyl and the like. Substituted or unsubstituted arylene groups such as phenylene, biphenylene, naphthylene, anthracenylene, phenanthrylene, indanylene and the like.

The term "arylalkyl" refers to an aryl group directly bonded to an alkyl group, which may be optionally substituted by one or more substituents. Preferred arylalkyl groups include, without limitation, —CH$_2$C$_6$H$_5$, —C$_2$H$_4$C$_6$H$_5$ and the like.

The term "heterocyclyl" refers to a stable 3 to 15 membered ring radical, which consists of carbon atoms and from one to five heteroatoms selected from nitrogen, phosphorus, oxygen and sulfur. For purposes of this invention the heterocyclic ring radical may be a monocyclic, bicyclic or tricyclic ring system and the nitrogen, phosphorus, carbon, oxygen or sulfur atoms in the heterocyclic ring radical may be optionally oxidized to various oxidation states. In addition, the nitrogen atom may be optionally quaternized and the ring radical may be partially or fully saturated. Preferred heterocyclyl groups include, without limitation, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxadiazolyl, triazolyl, indanyl, isoxazolyl, isoxazolidinyl, thiazolyl, thiazolinyl, thiazolidinyl, isothiazolyl, isothiazolidine 1,1-dioxide, quinuclidinyl, isothiazolidinyl, indolyl, isoindolyl, indolinyl, isoindolinyl, octahydroindolyl, octahydroisoindolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl, isochromanyl, oxabicyclo[3.2.1]octane, 3-oxabicyclo[3.2.1]octanone, 3-azabicyclo[3.2.1]octane-2,4-dione and 3-azabicyclo[3.2.1]octane. The heterocyclyl ring radical may be attached to the main structure at any heteroatom or carbon atom that results in the creation of a stable structure.

The term "heteroaryl" refers to an aromatic heterocyclic ring radical as defined above. The heteroaryl ring radical may be attached to the main structure at any heteroatom or carbon atom that results in the creation of a stable structure. The term "heterocycloalkyl" refers to a heterocyclic ring radical as defined above. The heterocycloalkyl ring radical may be attached to the main structure at any heteroatom or carbon atom that results in the creation of a stable structure.

The term "heteroarylalkyl" refers to a heteroaryl ring radical as defined above, directly bonded to an alkyl group. The heteroarylalkyl radical may be attached to the main structure at any carbon atom from an alkyl group.

The term "heterocyclylalkyl" refers to a heterocyclyl ring radical as defined above, directly bonded to an alkyl group. The heteroarylalkyl radical may be attached to the main structure at any carbon atom from an alkyl group.

The term "cycloalkyl" refers to non-aromatic mono or polycyclic ring systems of about 3 to 12 carbon atoms. Preferred cycloalkyl groups include, without limitation, cyclopropyl, cyclobutyl, cyclopentyl, cyclohexyl, cyclooctyl and the like; preferred polycyclic rings include, without limitation, perhydronaphthyl, adamantyl and norbornyl groups, bridged cyclic groups or spirobicyclic groups e.g. Spiro[4.4]-non-2-yl and the like.

The term "alkenyl" refers to an aliphatic hydrocarbon group containing a carbon-carbon double bond, which may be straight or branched chain having about 2 to 10 carbon atoms, which may be optionally substituted by one or more substituents. Preferred alkenyl groups include, without limitation, ethenyl, 1-propenyl, 2-propenyl, iso-propenyl, 2-methyl-1-propenyl, 1-butenyl, 2-butenyl and the like.

The term "arylalkenyl" refers to an aromatic ring radical directly bonded to an alkenyl group. The aryl radical may be attached to the main structure at any carbon from the alkenyl group. Preferred arylalkenyl groups include, without limitation, phenylethenyl, phenylpropenyl and the like.

The term "heteroarylalkenyl" refers to a heteroaryl ring radical directly bonded to an alkenyl group. The heteroaryl radical may be attached to the main structure at any carbon from the alkenyl group. Preferred heteroarylalkenyl groups include, without limitation, thienylpropenyl, pyridinylethenyl and indolylpropenyl.

The term "alkylthio" refers to an alkyl group attached via a sulfur linkage to the rest of the molecule, which may be optionally substituted by one or more substituents. Preferred alkylthio groups include, without limitation, —SCH$_3$, —SC$_2$H$_5$ and the like.

The term "alkoxy" refers to an alkyl group attached via an oxygen linkage to the rest of the molecule. Preferred alkoxy groups include, without limitation, —OCH$_3$, —OC$_2$H$_5$ and the like.

The term "aryloxy" refers to an aryl group attached via an oxygen linkage to the rest of the molecule. Preferred aryloxy groups include, without limitation, —O-phenyl, —O-biphenyl and the like.

The term "alkylamino" refers to an alkyl group as defined above attached via an amino linkage to the rest of the molecule. Preferred alkylamino groups include, without limitation, —NHCH$_3$, —N(CH$_3$)$_2$ and the like.

The term "alkynyl" refers to straight or branched hydrocarbyl radicals having at least one carbon-carbon triple bond and having in the range of 2-12 carbon atoms. Preferred alkynyl groups include, without limitation, ethynyl, propynyl, butynyl and the like.

The term "arylalkynyl" refers to an aromatic ring radical directly bonded to an alkynyl group. The aryl radical may be attached to the main structure at any carbon atom from the alkynyl group.

The term "heteroarylalkynyl" refers to a heteroaryl radical directly bonded to an alkynyl group. The heteroaryl radical may be attached to the main structure at any carbon atom from the alkynyl group.

The term "ring" refers to substituted or unsubstituted monocyclic or polycyclic, saturated or partially saturated or aromatic containing 0 to 4 heteroatoms selected from O, S or N.

The term "analogs" refers to a set of compounds, which differ from parent structure by one or more C, O, S, or N atoms. For example, a compound in which one of the N atom in the parent structure is replaced with oxygen is an analog of former.

The term "derivative" refers to a chemical compound or molecule made from a parent compound by one or more chemical reactions such as, by oxidation, hydrogenation, alkylation, esterification, halogenation and the like.

Typical analogs or derivatives include molecules which demonstrate equivalent or improved biologically useful and relevant function, but which differ structurally from the parent compounds.

The term "metabolite" refers to the degradation products of the compound of formula (I) by one or more metabolic processes, exerting desired biological activity.

"Tautomers" are defined as compounds that undergo rapid proton shifts from one atom of the compound to another atom of the compound. Some of the compounds described herein may exist as tautomers with different points of attachment of hydrogen. The individual tautomers as well as mixture thereof are encompassed with compounds of formula (I).

Furthermore, the compound of formula (I) can be its derivatives, analogs, tautomeric forms, stereoisomers, geometrical isomers, rotomers, polymorphs, solvates, intermediates, pharmaceutically acceptable salts, pharmaceutical compositions, metabolites and prodrugs.

It is understood that included in the family of compounds of formula (I) are isomeric forms including tautomers and stereoisomers (diastereoisomers, enantiomers and geometrical isomers in "E" or "Z" configurational isomer or a mixture of E and Z isomers). It is also understood that some isomeric forms such as diastereomers, enantiomers and geometrical isomers can be separated by physical and/or chemical methods and by those skilled in the art.

Compounds disclosed herein may exist as single stereoisomers, racemates and or mixtures of enantiomers and or/diastereomers. All such single stereoisomers, racemates and mixtures thereof are intended to be within the scope of the subject matter described.

The active compounds disclosed can also be prepared in any solid or liquid physical form, for example the compound can be in a crystalline form, in amorphous form (different polymorph) and have any particle size. Furthermore, the compound particles may be micronized or nanoized, or agglomerated, particulate granules, powders, oils, oily suspensions or any other form of solid or liquid physical forms.

The term "protecting group" or "PG" refers to a substituent that block or protects a particular functionality while permitting other functional groups on the compound to react. For example, an "amino-protecting group" is a substituent attached to an amino group that block or protects the amino functionality in the compound. Suitable amino-protecting groups include, but are not limited to, acetyl, trifluoroacetyl, t-butoxycarbonyl (Boc), benzyloxycarbonyl (CBz) and 9-fluorenylmethylen oxycarbonyl (Fmoc). Similarly, a "hydroxy-protecting group" refers to a substituent of a hydroxy group that blocks or protects the hydroxy functionality. Suitable hydroxy-protecting groups, but are not limited to, include acetyl and silyl. A "carboxy-protecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl)ethyl, 2-(trimethylsilyl) ethoxymethyl, 2-(p-toluenesulfonyl)ethyl, 2-(p-nitrophenylsulfenyl)ethyl, 2-(diphenyl phosphino)ethyl, nitroethyl and the like.

The term "treating" or "treatment" of a state, disorder or condition includes: (1) inhibiting the state, disorder or condition, i.e., arresting or reducing the development of the disease or at least one clinical or subclinical symptom thereof; or (2) relieving the disease, i.e., causing regression of the state, disorder or condition or at least one of their clinical or subclinical symptoms.

The term "prevention" means preventing or delaying the appearance of one or more clinical symptoms of the state, disorder or condition developing in a subject that may be afflicted with or predisposed to the state, disorder or condition but does not yet experience or display clinical or subclinical symptoms of the state, disorder or condition.

The benefit to a subject to be treated is either statistically significant or at least perceptible to the subject or to the physician. The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

Pharmaceutically acceptable salts forming part of this invention include salts derived from inorganic bases such as Li, Na, K, Ca, Mg, Fe, Cu, Zn, and Mn, salts of organic bases such as N,N'-diacetylethylenediamine, glucamine, triethylamine, choline, hydroxide, dicyclohexylamine, metformin, benzylamine, trialkylamine, and thiamine, salts of chiral bases such as alkylphenylamine, glycinol, and phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine and serine, salts of non-natural amino acids such as D-isomers or substituted amino acids, salts of guanidine, salts of substituted guanidine wherein the substituents are selected from nitro, amino, alkyl, alkenyl or alkynyl, ammonium salts, substituted ammonium salts, and aluminum salts. Other pharmaceutically acceptable salts include acid addition salts where appropriate such as sulphates, nitrates, phosphates, perchlorates, borates, hydrohalides, and acetates such as trifluoroacetate, tartrates, maleates, citrates, fumarates, succinates, palmoates, methanesulphonates, benzoates, salicylates, benzenesulfonates, ascorbates, glycerophosphates, and ketoglutarates. Yet other pharmaceutically acceptable salts include, but are not limited to, quaternary ammonium salts of the compounds of the invention with alkyl halides or alkyl sulphates such as MeI or $(Me)_2SO_4$. Preferred pharmaceutically acceptable salts of the compounds of the present invention include, but are not limited to, hydrochloride, maleate, methanesulfonate, oxalate, succinate, 2-oxoglutarate, benzoate, salicylate, benzenesulfonate, and naphthalene-1,5-disulfonic acid.

Pharmaceutically acceptable solvates include hydrates and other solvents of crystallization such as alcohols. The compounds of the present invention may form solvates with standard low molecular weight solvents using methods known in the art.

The pharmaceutical compositions of the present invention comprise at least one compound of the present invention and a pharmaceutically acceptable excipient such as a pharmaceutically acceptable carrier or diluent. For example, the compounds of the present invention may be associated with a pharmaceutically acceptable excipient such as a carrier or a diluent or be diluted by a carrier, or enclosed within a carrier, which may be in the form of an ampoule, capsule, sachet, paper, or other container. When the carrier serves as a diluent, it may be a solid, semi solid, or liquid material that acts as a vehicle, excipient, or medium for the active compound. The active compound can be adsorbed on a granular solid container, for example, in a sachet.

The carrier or diluent may include a sustained release material, such as glyceryl monostearate or glyceryl distearate, alone or mixed with a wax. The pharmaceutical composition may also include one or more pharmaceutically acceptable auxiliary agents, wetting agents, emulsifying agents, suspending agents, preserving agents, salts for influencing oxmetic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical compositions may be in conventional forms, for example capsules, tablets, soft or hard gelatin, dragees containing the active ingredient in powder or pellet form, troches and lozenges, aerosols, solutions, suspensions or products for topical applications. Tablets, dragees, or capsules having talc and/or a carbohydrate carrier or binder or the like are particularly suitable for oral application.

The route of administration may be any route, which effectively transports the active compound of the invention, which inhibits the enzymatic activity of DPP-IV to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic such as with an ophthalmic solution or topical such as with a topical ointment. The oral route is preferred.

Preferable carriers for tablets, dragees, or capsules include lactose, cornstarch, and/or potato starch. A syrup or elixir can be used in cases where a sweetened vehicle can be employed.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Described herein is also a method of treating a condition that is regulated or normalized via inhibition of DPP-IV in a subject by administering a therapeutically effective amount of a compound or pharmaceutical composition of present invention.

Described herein is also a method of treating a metabolic disorder, lowering blood glucose, treating Type II diabetes, treating impaired glucose tolerance (IGT), treating impaired fasting glucose (IFG), preventing or treating hyperglycemia, delaying the progression of impaired glucose tolerance (IGT) to Type II diabetes, delaying the progression of non-insulin requiring Type II diabetes to insulin requiring Type II diabetes, increasing the number and/or the size of beta cells, preventing or treating beta cell degeneration, such as apoptosis of beta cells, treating food intake disorders, treating obesity, regulating appetite or inducing satiety, treating dyslipidemia, hypercholesterolemia, or diabetic complications comprising stroke, coronary artery disease, hypertension, peripheral vascular disease, neuropathy, retinopathy, non-alcoholic fatty liver disease, non-alcoholic steatohepatitis, treating functional dyspepsia, such as irritable bowel syndrome, treatment and/or prophylaxis of a disease selected from diabetes, non-insulin dependent diabetes mellitus, impaired glucose tolerance, inflammatory bowel disease, pain, wound healing, ulcerative colitis, Crohn's disease, obesity, metabolic syndrome, neurodegenerative diseases, cognition disorders and anxiolytic diseases in a subject by administering a therapeutically effective amount or pharmaceutical composition of compounds of formula. (I).

The compounds of formula (I) may be administered to a mammal, especially a human in need of such treatment, prevention, elimination, alleviation or amelioration of the various diseases as mentioned above, e.g., Type II diabetes, IGT, IFG, obesity, appetite regulation or as a blood glucose lowering agent.

Use of a Compound of formula (I), for the manufacture of a medicament for the treatment of the above said diseases.

The compounds of formula (I) are effective over a wide dosage range. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated.

Described herein are also prodrugs of a compound of the invention, which on administration undergo chemical conversion by metabolic processes before becoming active pharmacological substances. In general, such prodrugs will be functional derivatives of a compound of the invention that are readily convertible in vivo into compound of formula (I).

Described herein also encompasses active metabolites of a compound of formula (I).

A term once described, the same meaning applies for it, throughout the patent.

Representative compounds include:

1. (2S,4S)-1-(2-((1R,3S)-3-((1H-1,2,4-Triazol-1-yl)methyl)-1,2,2-trimethylcyclopentylamino)acetyl)-4-fluoropyrrolidine-2-carbonitrile;
2. (2S,4R)-1-(2-((1R,3S)-3-((1H-1,2,4-Triazol-1-yl)methyl)-1,2,2-trimethyl cyclopentylamino)acetyl)-4-fluoropyrrolidine-2-carbonitrile methanesulfonate;
3. (2S,4S)-1-(2-((1S,3R)-3-((1H-1,2,4-Triazol-1-yl)methyl)-1,2,2-trimethylcyclopentylamino)acetyl)-4-fluoropyrrolidine-2-carbonitrile;
4. (2S,4S)-1-(2-((1S,3R)-3-((1H-1,2,4-Triazol-1-yl)methyl)-1,2,2-trimethyl cyclopentylamino)acetyl)-4-fluoropyrrolidine-2-carbonitrile methanesulfonate;
5. (2S,4R)-1-(2-((1S,3R)-3-((1H-1,2,4-Triazol-1-yl)methyl)-1,2,2-trimethyl cyclopentylamino)acetyl)-4-fluoropyrrolidine-2-carbonitrile methanesulfonate;
6. (S)-1-(2-((1S,3R)-3-((1H-1,2,4-Triazol-1-yl)methyl)-1,2,2-trimethylcyclopentylamino)acetyl)pyrrolidine-2-carbonitrile;
7. (S)-1-(2-((1S,3R)-3-((1H-1,2,4-Triazol-1-yl)methyl)-1,2,2-trimethyl cyclopentylamino)acetyl)pyrrolidine-2-carbonitrile methanesulfonate;
8. (S)-1-(2-((1R,3S)-3-((1H-1,2,4-Triazol-1-yl)methyl)-1,2,2-trimethyl cyclopentylamino)acetyl)pyrrolidine-2-carbonitrile;
9. (S)-1-(2-((1R,3S)-3-((1H-1,2,4-Triazol-1-yl)methyl)-1,2,2-trimethyl cyclopentylamino)acetyl)pyrrolidine-2-carbonitrile methanesulfonate;
10. (2S,4S)-1-(2-((1R,3S)-3-((2H-1,2,3-Triazol-2-yl)methyl)-1,2,2-trimethyl cyclopentylamino)acetyl)-4-fluoropyrrolidine-2-carbonitrile;
11. (2S,4S)-1-(2-((1R,3S)-3-((1H-1,2,3-Triazol-1-yl)methyl)-1,2,2-trimethyl cyclopentylamino)acetyl)-4-fluoropyrrolidine-2-carbonitrile;
12. (2S,4S)-1-(2-((1S,3R)-3-((2H-1,2,3-Triazol-2-yl)methyl)-1,2,2-trimethyl cyclopentylamino)acetyl)-4-fluoropyrrolidine-2-carbonitrile;
13. (2S,4S)-1-(2-((1S,3R)-3-((1H-1,2,3-Triazol-1-yl)methyl)-1,2,2-trimethyl cyclopentylamino)acetyl)-4-fluoropyrrolidine-2-carbonitrile methanesulfonate;
14. (2S,4S)-4-Fluoro-1-(2-((1R,3S)-1,2,2-trimethyl-3-(piperidine-1-carbonyl)cyclopentylamino)acetyl)pyrrolidine-2-carbonitrile;
15. (2S,4S)-4-Fluoro-1-(2-((1R,3S)-3-((4-(hydroxymethyl)-1H-1,2,3-triazol-1-yl)methyl)-1,2,2-trimethylcyclopentylamino)acetyl)pyrrolidine-2-carbonitrile;
16. (2S,4S)-4-Fluoro-1-(2-((1S,3R)-3-((4-(hydroxymethyl)-1H-1,2,3-triazol-1-yl)methyl)-1,2,2-trimethylcyclopentylamino)acetyl)pyrrolidine-2-carbonitrile;

17. N-(((1S,3R)-3-(2-((2S,4S)-2-Cyano-4-fluoropyrrolidin-1-yl)-2-oxoethylamino)-2,2,3-trimethylcyclopentyl)methyl)methanesulfonamide;
18. N-(((1R,3S)-3-(2-((2S,4S)-2-Cyano-4-fluoropyrrolidin-1-yl)-2-oxoethylamino)-2,2,3-trimethylcyclopentyl)methyl)methanesulfonamide;
19. N-(((1S,3R)-3-(2-((2S,4S)-2-Cyano-4-fluoropyrrolidin-1-yl)-2-oxoethylamino)-2,2,3-trimethylcyclopentyl)methyl)-4-fluorobenzenesulfonamide;
20. N-(((1R,3S)-3-(2-((2S,4S)-2-Cyano-4-fluoropyrrolidin-1-yl)-2-oxoethylamino)-2,2,3-trimethylcyclopentyl)methyl)-4-fluorobenzenesulfonamide;
21. N-(((1S,3R)-3-(2-((2S,4S)-2-Cyano-4-fluoropyrrolidin-1-yl)-2-oxoethylamino)-2,2,3-trimethylcyclopentyl)methyl)-2-fluorobenzamide;
22. N-(((1S,3R)-3-(2-((2S,4S)-2-Cyano-4-fluoropyrrolidin-1-yl)-2-oxoethylamino)-2,2,3-trimethylcyclopentyl)methyl)-4,4-difluorocyclohexanecarboxamide;
23. N-(((1R,3S)-3-(2-((2S,4S)-2-Cyano-4-fluoropyrrolidin-1-yl)-2-oxoethylamino)-2,2,3-trimethylcyclopentyl)methyl)-4,4-difluorocyclohexanecarboxamide;
24. 6-(((1S,3R)-3-(2-((2S,4S)-2-Cyano-4-fluoropyrrolidin-1-yl)-2-oxoethylamino)-2,2,3-trimethylcyclopentyl)methylamino)nicotinonitrile;
25. 6-(((1R,3S)-3-(2-((2S,4S)-2-Cyano-4-fluoropyrrolidin-1-yl)-2-oxoethylamino)-2,2,3-trimethylcyclopentyl)methylamino)nicotinonitrile;
26. 2-(((1S,3R)-3-(2-((2S,4S)-2-Cyano-4-fluoropyrrolidin-1-yl)-2-oxoethylamino)-2,2,3-trimethylcyclopentyl)methylamino)nicotinonitrile;
27. (2S,4S)-4-Fluoro-1-(2-((1R,3S)-1,2,2-trimethyl-3-((5-(trifluoromethyl)pyridin-2-ylamino)methyl)cyclopentylamino)acetyl)pyrrolidine-2-carbonitrile;
28. (2S,4S)-1-(2-((1R,3S)-3-[(1,1-Dioxidoisothiazolidin-2-yl)methyl]-1,2,2-trimethylcyclopentylamino)acetyl)-4-fluoropyrrolidine-2-carbonitrile;
29. (2S,4S)-1-(2-((1S,3R)-3-[(1,1-Dioxidoisothiazolidin-2-yl)methyl]-1,2,2-trimethylcyclopentylamino)acetyl)-4-fluoropyrrolidine-2-carbonitrile;
30. (2S,4S)-1-(2-((1S,3R)-3-[(1,1-Dioxido-1,2-thiazinan-2-yl)methyl]-1,2,2-trimethylcyclopentylamino)acetyl)-4-fluoropyrrolidine-2-carbonitrile;
31. (2S,4S)-1-(2-((1R,3S)-3-((1H-Tetrazol-1-yl)methyl)-1,2,2-trimethylcyclopentyl amino)acetyl)-4-fluoropyrrolidine-2-carbonitrile methanesulfonate;
32. (2S,4S)-1-(2-((1S,3R)-3-((1H-Tetrazol-1-yl)methyl)-1,2,2-trimethylcyclopentylamino)acetyl)-4-fluoropyrrolidine-2-carbonitrile;
33. (2S,4S)-4-Fluoro-1-(2-((1R,3S)-1,2,2-trimethyl-3-(morpholinomethyl)cyclopentylamino)acetyl)pyrrolidine-2-carbonitrile;
34. (2S,4S)-4-Fluoro-1-(2-((1S,3R)-1,2,2-trimethyl-3-(morpholinomethyl)cyclopentylamino)acetyl)pyrrolidine-2-carbonitrile;
35. (2S,4S)-4-Fluoro-1-(2-((1S,3R)-1,2,2-trimethyl-3-(morpholinomethyl)cyclo pentylamino)acetyl)pyrrolidine-2-carbonitrile dimethanesulfonate;
36. (2S,4S)-4-Fluoro-1-(2-((1R,3S)-1,2,2-trimethyl-3-(pyrrolidin-1-ylmethyl)cyclo pentylamino)acetyl)pyrrolidine-2-carbonitrile;
37. (2S,4S)-4-Fluoro-1-(2-((1S,3R)-1,2,2-trimethyl-3-(pyrrolidin-1-ylmethyl)cyclopentylamino)acetyl)pyrrolidine-2-carbonitrile;
38. (2S,4S)-4-Fluoro-1-(2-((1R,3S)-3-(((R)-3-hydroxypyrrolidin-1-yl)methyl)-1,2,2-trimethylcyclopentylamino)acetyl)pyrrolidine-2-carbonitrile;
39. (2S,4S)-4-Fluoro-1-(2-((1R,3S)-1,2,2-trimethyl-3-(piperidin-1-ylmethyl)cyclopentylamino)acetyl)pyrrolidine-2-carbonitrile;
40. (2S,4S)-4-Fluoro-1-(2-((1S,3R)-1,2,2-trimethyl-3-(piperidin-1-ylmethyl)cyclopentylamino)acetyl)pyrrolidine-2-carbonitrile;
41. (2S,4S)-4-Fluoro-1-(2-((1R,3S)-3-((4-hydroxypiperidin-1-yl)methyl)-1,2,2-trimethylcyclopentylamino)acetyl)pyrrolidine-2-carbonitrile;
42. (2S,4S)-4-Fluoro-1-(2-((1R,3S)-1,2,2-trimethyl-3-((4-(methylsulfonyl)phenylsulfonyl)methyl)cyclopentylamino)acetyl)pyrrolidine-2-carbonitrile;
43. (2S,4R)-4-Fluoro-1-(2-((1R,3S)-1,2,2-trimethyl-3-((4-(methylsulfonyl)phenylsulfonyl)methyl)cyclopentylamino)acetyl)pyrrolidine-2-carbonitrile;
44. (S)-1-(2-((1R,3S)-1,2,2-Trimethyl-3-((4-(methylsulfonyl)phenylsulfonyl)methyl)cyclopentylamino)acetyl)pyrrolidine-2-carbonitrile;
45. (2S,4S)-4-Fluoro-1-(2-((1S,3R)-1,2,2-trimethyl-3-((4-(methylsulfonyl)phenylsulfonyl)methyl)cyclopentylamino)acetyl)pyrrolidine-2-carbonitrile;
46. (S)-1-(2-((1S,3R)-1,2,2-Trimethyl-3-((4-(methylsulfonyl)phenylsulfonyl)methyl)cyclopentylamino)acetyl)pyrrolidine-2-carbonitrile;
47. (2S,4R)-4-Fluoro-1-(2-((1S,3R)-1,2,2-trimethyl-3-((4-(methylsulfonyl)phenylsulfonyl)methyl)cyclopentylamino)acetyl)pyrrolidine-2-carbonitrile;
48. (2S,4S)-4-Fluoro-1-(2-((1R,3S)-3-(3-(4-fluorophenyl)-1,2,4-oxadiazol-5-yl)-1,2,2-trimethylcyclopentylamino)acetyl)pyrrolidine-2-carbonitrile;
49. (2S,4S)-4-Fluoro-1-(2-((1S,3R)-3-(3-(4-fluorophenyl)-1,2,4-oxadiazol-5-yl)-1,2,2-trimethylcyclopentylamino)acetyl)pyrrolidine-2-carbonitrile;
50. (2S,4S)-4-Fluoro-1-(2-((1R,3S)-1,2,2-trimethyl-3-(3-methyl-1,2,4-oxadiazol-5-yl)cyclopentylamino)acetyl)pyrrolidine-2-carbonitrile;
51. (2S,4S)-4-Fluoro-1-(2-((1S,3R)-1,2,2-trimethyl-3-(3-methyl-1,2,4-oxadiazol-5-yl)cyclopentylamino)acetyl)pyrrolidine-2-carbonitrile;
52. (2S,4S)-4-Fluoro-1-(2-((1R,3S)-3-(3-isopropyl-1,2,4-oxadiazol-5-yl)-1,2,2-trimethylcyclopentylamino)acetyl)pyrrolidine-2-carbonitrile;
53. (2S,4S)-1-(2-((1R,3R)-3-(Cyanomethyl)-1,2,2-trimethylcyclopentylamino)acetyl)-4-fluoropyrrolidine-2-carbonitrile;
54. (2S,4S)-4-Fluoro-1-(2-((1R,3R)-1,2,2-trimethyl-3-((5-methyl-1,2,4-oxadiazol-3-yl)methyl)cyclopentylamino)acetyl)pyrrolidine-2-carbonitrile;
55. (2S,4S)-4-Fluoro-1-(2-((1S,3S)-1,2,2-trimethyl-3-((5-methyl-1,2,4-oxadiazol-3-yl)methyl)cyclopentylamino)acetyl)pyrrolidine-2-carbonitrile;
56. (2S,4S)-4-Fluoro-1-(2-((1S,3S)-1,2,2-trimethyl-3-((5-(trifluoromethyl)-1,2,4-oxadiazol-3-yl)methyl)cyclopentylamino)acetyl)pyrrolidine-2-carbonitrile;
57. (2S,4S)-4-Fluoro-1-(2-((1S,3S)-1,2,2-trimethyl-3-((5-(trifluoromethyl)-1,2,4-oxadiazol-3-yl)methyl)cyclopentylamino)acetyl)pyrrolidine-2-carbonitrile methanesulfonate;
58. (2S,4S)-1-(2-((1S,3S)-3-((5-tert-Butyl-1,2,4-oxadiazol-3-yl)methyl)-1,2,2-trimethylcyclopentylamino)acetyl)-4-fluoropyrrolidine-2-carbonitrile;
59. (2S,4S)-1-(2-((1S,3S)-3-((5-Cyclohexyl-1,2,4-oxadiazol-3-yl)methyl)-1,2,2-trimethylcyclopentylamino)acetyl)-4-fluoropyrrolidine-2-carbonitrile;
60. (2S,4S)-4-Fluoro-1-(2-((1S,3S)-3-((5-(hydroxymethyl)-1,2,4-oxadiazol-3-yl)methyl)-1,2,2-trimethylcyclopentylamino)acetyl)pyrrolidine-2-carbonitrile;

61. (2S,4S)-4-Fluoro-1-(2-((1S,3S)-3-((5-isopropyl-1,2,4-oxadiazol-3-yl)methyl)-1,2,2-trimethylcyclopentylamino)acetyl)pyrrolidine-2-carbonitrile methanesulfonate;
62. (2S,4S)-4-Fluoro-1-(2-((1S,3S)-3-((5-(4-fluorophenyl)-1,2,4-oxadiazol-3-yl)methyl)-1,2,2-trimethylcyclopentylamino)acetyl)pyrrolidine-2-carbonitrile;
63. (2S,4S)-4-Fluoro-1-(2-((1S,3S)-1,2,2-trimethyl-3-((5-(pyridin-4-yl)-1,2,4-oxadiazol-3-yl)methyl)cyclopentylamino)acetyl)pyrrolidine-2-carbonitrile;
64. (2S,4S)-4-Fluoro-1-(2-((1R,3S)-3-(3-(4-fluorophenyl)-1,2,4-oxadiazol-5-yl)-2,2,3-trimethylcyclopentylamino)acetyl)pyrrolidine-2-carbonitrile
65. (2S,4S)-4-Fluoro-1-(2-((1S,3R)-3-(3-(4-fluorophenyl)-1,2,4-oxadiazol-5-yl)-2,2,3-trimethylcyclopentylamino)acetyl)pyrrolidine-2-carbonitrile;
66. (S)-1-(2-((1S,3R)-3-(3-(4-Fluorophenyl)-1,2,4-oxadiazol-5-yl)-2,2,3-trimethylcyclopentylamino)acetyl)pyrrolidine-2-carbonitrile methanesulfonate;
67. (2S,4S)-4-Fluoro-1-(2-((1S,3R)-3-(3-isopropyl-1,2,4-oxadiazol-5-yl)-2,2,3-trimethylcyclopentylamino)acetyl)pyrrolidine-2-carbonitrile;
68. (2S,4S)-4-Fluoro-1-(2-((1S,3R)-2,2,3-trimethyl-3-(3-(pyridin-3-yl)-1,2,4-oxadiazol-5-yl)cyclopentylamino)acetyl)pyrrolidine-2-carbonitrile;
69. (2S,4S)-4-Fluoro-1-(2-((1R,3S)-2,2,3-trimethyl-3-(3-(pyridin-3-yl)-1,2,4-oxadiazol-5-yl)cyclopentylamino)acetyl)pyrrolidine-2-carbonitrile;
70. (2S,4S)-4-Fluoro-1-(2-((1S,3R)-2,2,3-trimethyl-3-(3-(pyridin-4-yl)-1,2,4-oxadiazol-5-yl)cyclopentylamino)acetyl)pyrrolidine-2-carbonitrile;
71. (2S,4S)-4-Fluoro-1-(2-((1R,3S)-2,2,3-trimethyl-3-(3-(pyridin-4-yl)-1,2,4-oxadiazol-5-yl)cyclopentylamino)acetyl)pyrrolidine-2-carbonitrile
72. (2S,4S)-4-Fluoro-1-(2-((1S,3R)-2,2,3-trimethyl-3-(3-(pyrazin-2-yl)-1,2,4-oxadiazol-5-yl)cyclopentylamino)acetyl)pyrrolidine-2-carbonitrile;
73. (2S,4S)-4-Fluoro-1-(2-((1R,3S)-2,2,3-trimethyl-3-(3-methyl-1,2,4-oxadiazol-5-yl)cyclopentylamino)acetyl)pyrrolidine-2-carbonitrile;
74. (2S,4S)-4-Fluoro-1-(2-((1S,3R)-2,2,3-trimethyl-3-(3-methyl-1,2,4-oxadiazol-5-yl)cyclopentylamino)acetyl)pyrrolidine-2-carbonitrile;
75. (S)-1-(2-((1R,5R)-3,5,8,8-Tetramethyl-2,4-dioxo-3-azabicyclo[3.2.1]octan-1-ylamino)acetyl)pyrrolidine-2-carbonitrile;
76. (2S,4S)-4-Fluoro-1-(2-((1R,5R)-3,5,8,8-tetramethyl-3-azabicyclo[3.2.1]octan-1-ylamino)acetyl)pyrrolidine-2-carbonitrile;
77. (2S,4R)-4-Fluoro-1-(2-((1R,5R)-3,5,8,8-tetramethyl-3-azabicyclo[3.2.1]octan-1-ylamino)acetyl)pyrrolidine-2-carbonitrile;
78. (S)-1-(2-((1R,5R)-3,5,8,8-Tetramethyl-3-azabicyclo[3.2.1]octan-1-ylamino)acetyl)pyrrolidine-2-carbonitrile;
79. (S)-1-(2-((1R,5R)-5,8,8-Trimethyl-2-oxo-3-oxabicyclo[3.2.1]octan-1-ylamino)acetyl)pyrrolidine-2-carbonitrile;
80. (S)-1-(2-((1R,5R)-5,8,8-Trimethyl-3-oxabicyclo[3.2.1]octan-1-ylamino)acetyl)pyrrolidine-2-carbonitrile;
81. (2S,4S)-4-Fluoro-1-(2-((1R,5R)-5,8,8-trimethyl-3-oxabicyclo[3.2.1]octan-1-ylamino)acetyl)pyrrolidine-2-carbonitrile;
82. (2S,4S)-4-Fluoro-1-(2-((1S,5S)-5,8,8-trimethyl-3-oxabicyclo[3.2.1]octan-1-ylamino)acetyl)pyrrolidine-2-carbonitrile; and
83. (2S,4S)-1-(2-((1S,3R)-3-(3-(1H-1,2,4-triazol-1-yl)propyl)-2,2,3-trimethylcyclopentyl amino)acetyl)-4-fluoropyrrolidine-2-carbonitrile According to another feature of the present invention, there is provided a process for the preparation of compounds of the formula (I), wherein all other symbols are as defined earlier, as shown in the scheme-I.

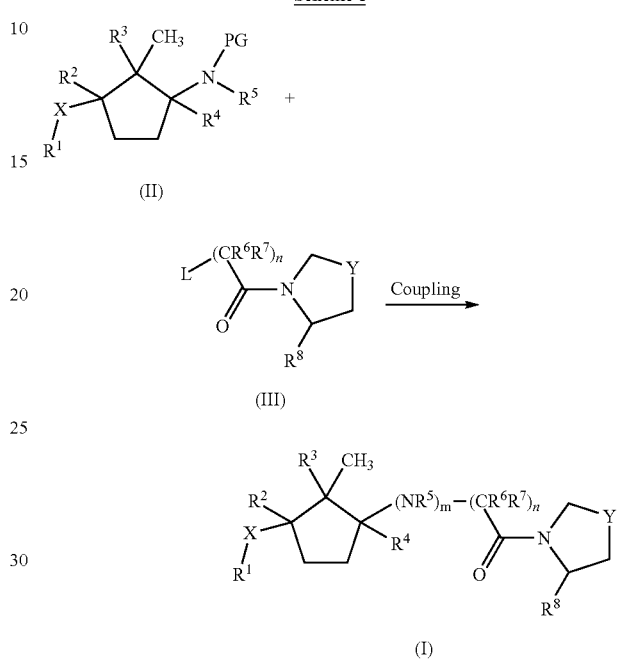

Wherein; L represent suitable leaving groups selected from chloro, bromo, iodo, tosylates, mesylates, triflates and similar leaving groups; PG represents hydrogen or protecting groups such as acetyl, trifluoroacetyl, Fmoc, arylsulphonyl, nosyl, tosyl, Boc or CBz; m=1 and all the other symbols are same as described above.

The reactions described in the processes outlined above are performed using the methods described herein:

Compound of formula (II) is coupled with compound of formula (III) in solvents selected from toluene, N,N-dimethylformamide (DMF), tetrahydrofuran (THF), acetonitrile, ethyl acetate, N-methyl-2-pyrrolidone, dimethylsulphoxide (DMSO), dichloroethane, chloroform or a mixture thereof, in the presence of a base such as triethylamine, pyridine, diisopropylethylamine, 4-dimethylaminopyridine, alkali hydroxides such as sodium hydroxide, potassium hydroxide, potassium carbonate, alkaline earth metal hydroxides, alkali carbonates such as, cesium carbonate and the like, and potassium iodide or sodium iodide to give the compound of formula (I). The reaction is carried out at a temperature ranging from room temperature to reflux temperature, mostly 0° C.-100° C.

The compound of formula (III) can be prepared by the methods known in *Journal of Medicinal Chemistry*, 2003, 46, 2774-2789; Bioorganic Medicinal Chemistry, 2008, 16, 4093-4106; WO2007/113634; WO2003/002553 and WO98/19998.

The compound of formula (II) can be prepared by following reaction sequence as summarized in scheme (II-IX)

Scheme II:

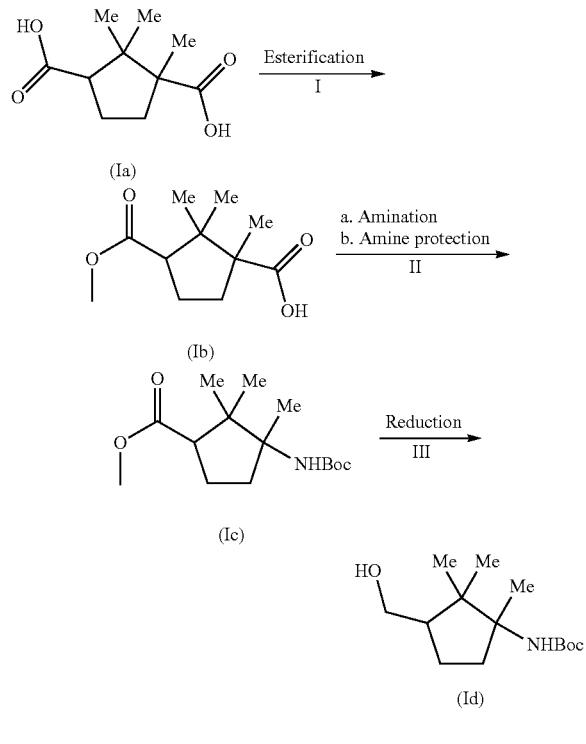

The reactions in the processes outlined in Scheme II are described in following steps Step I: Mono esterification of camphoric acid (Ia) by purging anhydrous hydrogen chloride to alcoholic solution of camphoric acid at ambient temperature gave (Ib).

Step IIa: Carboxylic acid function of formula (Ib) is converted to amine function of formula (Ic) by the usual methods known in the art. For example, first converting acid to acid chloride using oxalyl chloride or thionyl chloride in a solvent like dichloromethane, toluene, tetrahydrofuran, chloroform or a mixture thereof. The reaction is carried out at a temperature ranging from 0° C. to reflux temperature, mostly 0-100° C. The acid chloride was treated with ammonia in organic solvents such as ethyl acetate, tetrahydrofuran, dichloromethane or aqueous ammonia to afford amide. Amide is converted to amine under conventional Hofmann conditions. Amine can also be prepared by phenyliodonium bis(trifluoroacetate) (PIFA) or phenyliodonium diacetate (PIDA)-promoted Hofmann rearrangement of amide.

Alternatively, acid is converted to amine by treatment with an azide like $NaN_3$ or, diphenylphosphoryl azide (DPPA) under acidic conditions in presence of solvents like dichloromethane, chloroform, acetonitrile at a temperature range 30-50° C.

Step IIb: The amine thus formed is protected by conventional amine protecting groups like Boc, CBz, Fmoc etc.

Alternatively, Boc protected amine of formula (Ic) is prepared by oxidative rearrangement of amide with lead tetraacetate in t-BuOH as described in *J. Org. Chem.*, 1975, 40, 3554-3561.

Step III: Reduction of compound of formula (Ic) using suitable reducing agents such as $LiAlH_4$, $NaBH_4$ and DIBAL-H in inert solvent like THF, ether or mixture thereof at a temperature ranging from 0° C.-70° C. to afford alcohol of formula (Id).

Scheme III:

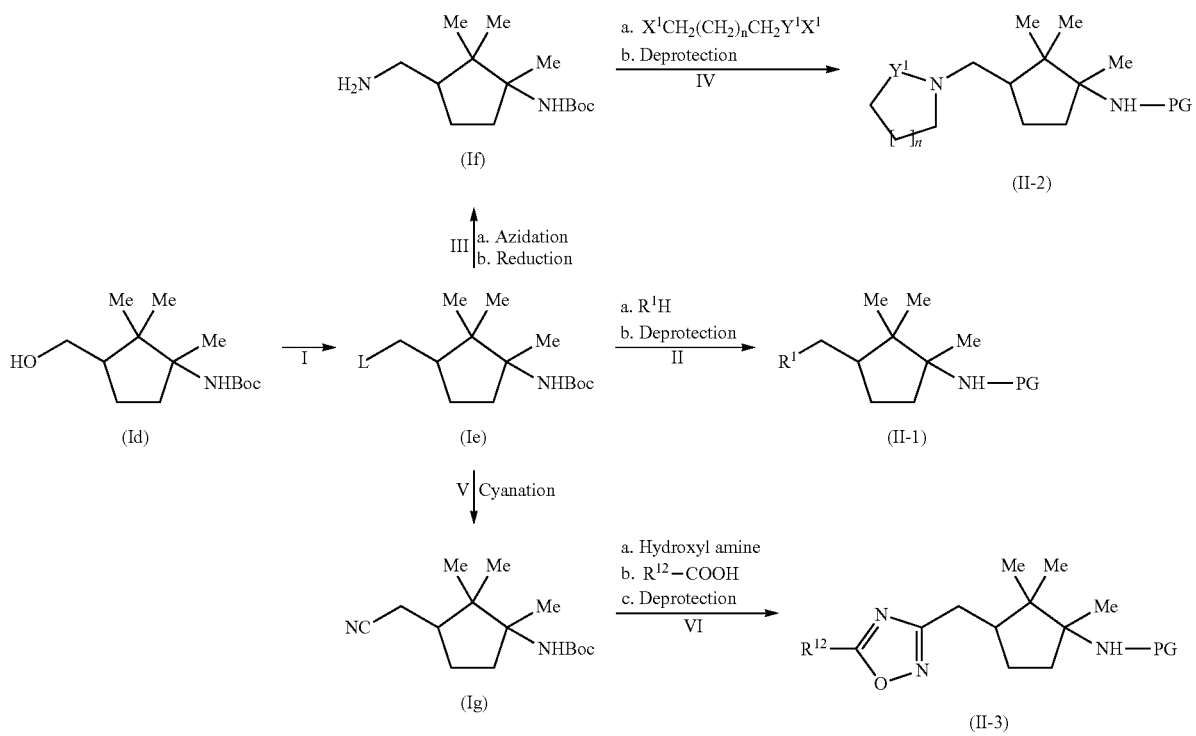

The reactions in the processes outlined in Scheme III are described in following steps.

Step I: Compound of formula (Ie) is prepared by transforming hydroxyl group of compound of formula (Id) to a leaving group L by mesylation, tosylation or halogenation in presence of organic base such as triethylamine, N,N-diisopropylethylamine, pyridine, N-methylmorpholine, N-methylpyrrolidine in an inert solvent such as DCM, tetrahydrofuran (THF), CHCl$_3$ or similar at about 0° C.-10° C.

Step IIa: Coupling of compound of formula (Ie) with a compound of formula R$^1$H gave the Compound of formula (II-1) in the solvents selected from toluene, DMF, tetrahydrofuran, acetonitrile, ethyl acetate, N-methyl-2-pyrrolidone, DMSO, dichloroethane, chloroform or a mixture thereof, in the presence of a base such as triethylamine, pyridine, diisopropylethylamine, 4-dimethylaminopyridine, alkali hydroxides such as sodium hydroxide, potassium hydroxide, alkaline earth metal hydroxides, alkali carbonates such as, potassium carbonate, cesium carbonate and the like, to give the compound of formula (II-1) (R$^1$ is as defined earlier). The reaction is carried out at a temperature ranging from 0° C. to reflux temperature, mostly 0-150° C.

Step IIb: Amine deprotection of compound of formula (II-1) wherein PG is protecting group affords the compound of formula (II-1) wherein PG is hydrogen, in its salt or free base form. Deprotection may be carried out by conventional methods known in the art, using acids such as hydrochloric acid, acetic acid, trifluoroacetic acid or by hydrogenation using catalysts such as Pd/C, Rh/C, Pt/C, Raney Nickel in the presence of solvents such as dichloromethane, ethyl acetate, water and the like or a mixture thereof, at a temperature in the range of −10° C. to 50° C.

Step IIIa: Azidation reaction is carried out by reacting compound of formula (Ie) with sodium azide in the solvents selected from toluene, DMF, dimethylacetamide (DMA), tetrahydrofuran, N-methyl-2-pyrrolidone, DMSO or a mixture thereof at 50-90° C.

Step IIIb: Azide compounds thus formed is reduced to amine of formula (If) by hydrogenation using catalysts such as Pd/C, Rh/C, Pt/C, Raney Nickel in the presence of solvents such as dichloromethane, ethylacetate, water and the like or a mixture thereof, at a temperature in the range of 0° C. to 50° C.

Step IVa: The amine prepared in step IIIb is reacted with X$^1$CH$_2$(CH$_2$)$_n$CH$_2$Y$^1$X$^1$, wherein X$^1$ is a halogen selected from F, Cl, Br and I; Y$^1$ is SO$_2$ or CO, in presence of organic bases like triethylamine, N,N-diisopropylethylamine, pyridine, N-methylmorpholine, N-methylpyrrolidine in an inert solvent such as DCM, THF, CHCl$_3$ and the like at about 0-10° C. followed by cyclization in presence of bases like NaOH, KOH, LiOH, sodium methoxide, sodium ethoxide in solvents such as methanol, ethanol gave compound of formula (II-2), wherein PG represents a protecting group.

Step V: Compound of formula (Ie) is treated with a cyanating agent like NaCN, KCN, CuCN in presence of aprotic solvents such as DMF at 80-100° C. to afford compound of formula (Ig).

Step VI: Compound of formula (Ig) on treatment with hydroxylamine (50% aqueous solution) gave amidoxime, which on coupling with appropriate acid followed by cyclization under acidic condition affords compound of formula (II-3) wherein PG represents protecting group. Amine deprotection is carried out similar to step IIb to afford compound of formula (II-3) in its salt or freebase form.

Compounds of formula (II-1), (II-2) and (II-3) were treated with compound of formula (III) as shown in scheme I to form final compound of formula (I).

Scheme IV:

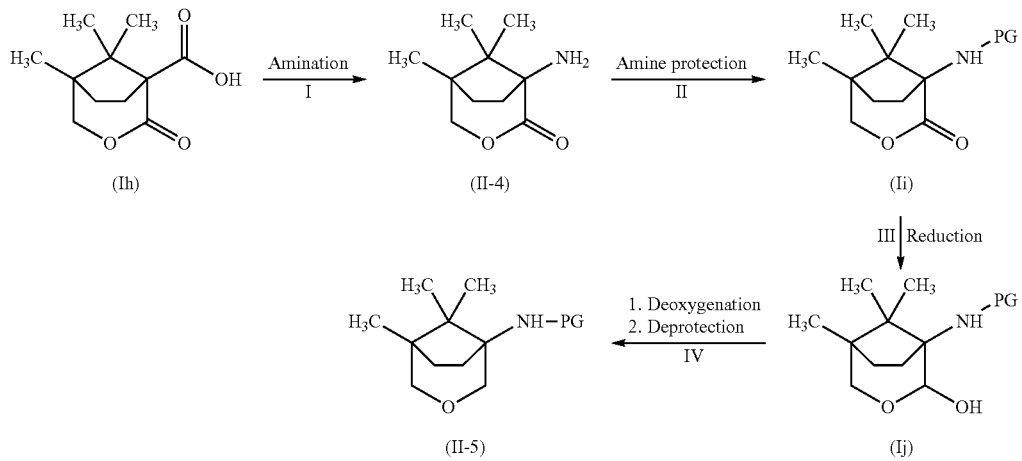

The reactions in the processes outlined in Scheme IV are described in following steps Step I: Amination of compound of formula (Ih) as described in amination step of scheme II affords the compound of formula (II-4). Compound of formula (Ih) was prepared according to method described in *Liebigs Ann.* 1996, 1941-1948.

Step II: The amine formed in step I is protected by conventional amine protecting groups like Boc, Cbz, Fmoc, acetyl, benzoyl, and benzyl and the like to give compound of formula (Ii). The reaction can be carried out in presence of organic base like triethylamine, N,N-diisopropyl-ethylamine, pyridine, N-methylmorpholine, N-methylpyrrolidine in an inert solvent such as DCM, THF, CHCl$_3$ and like at temperature ranging from 0° C.-50° C.

Step III: Reduction of lactone to lactol is carried out by using suitable reducing agents selected from LiAlH$_4$, NaBH$_4$, LiBH$_4$, LiEt$_3$BH in an inert solvent like THF at temperature ranging from −78° C. to 70° C. to afford compound of formula (Ij).

Step IV: Lactol is deoxygenated to cyclic ether of formula (II-5) using Et₃SiH and BF₃.Et₂O in an inert solvent like THF, DCM at temperature ranging from −10 to 10° C. Amine protected lactol is deprotected similar to deprotection step of scheme III to afford compound of formula (II-5) in its salt or freebase form. If protecting group is acetyl, it is deprotected by method described in *Org. Lett.*, 2009, 11 (2), 433-436. Compounds of formula (II-4) and (II-5) were treated with compound of formula (III) as shown in scheme I to form final compound of formula (I).

Scheme V:

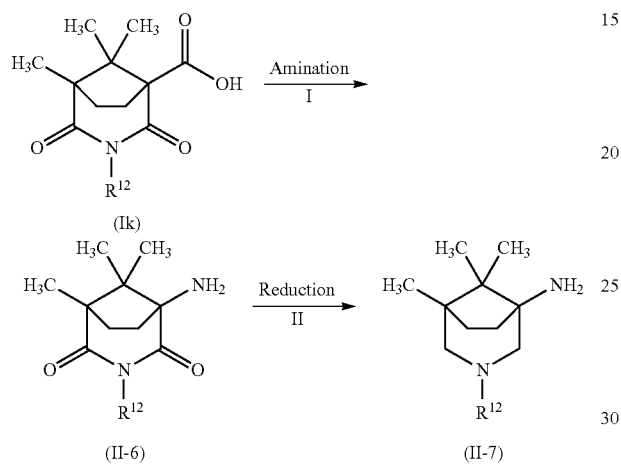

The reactions in the processes outlined in Scheme V are described in following steps Step I: Amination of compound of formula (Ik) as described in amination step of scheme II affords the compound of formula (II-6). Compound of formula (Ik) prepared according to method described in *Liebigs Ann.* 1996, 1941-1948.

Step II: Reduction of imide to amine is carried out by using suitable reducing agents selected from LiAlH₄, NaBH₄, LiBH₄, LiEt₃BH in an inert solvent like THF at temperature ranging from 0° C. to 70° C. to afford compound of formula (II-7). Compounds of formula (II-6) and (II-7) were treated with compound of formula (III) as shown in scheme I to form final compound of formula (I).

Scheme VI:

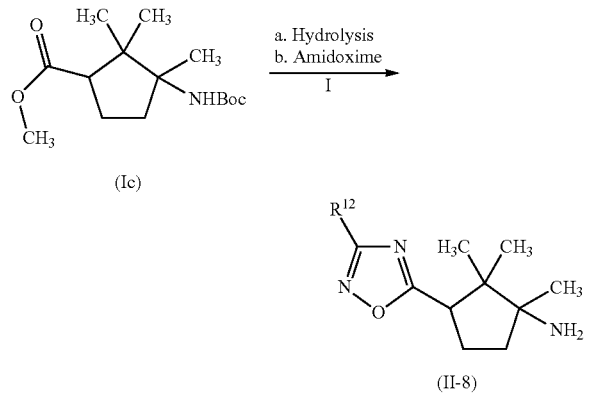

The reactions in the processes outlined in Scheme VI are described in following steps Step Ia: Hydrolysis of ester is carried out in presence of suitable base like NaOH, KOH in solvents like tetrahydrofuran, methanol, ethanol, 1,4-dioxane or mixture thereof to afford acid.

Step Ib: The above acid is coupled with appropriate amidoxime using coupling agents like N,N'-Dicyclohexylcarbodiimide (DCC), 1-ethyl-3-(3-dimethylaminopropyl) carbodiimide (EDCI), carbonyldiimidazole (CDI) and the like in suitable solvents like tetrahydrofuran, dichloromethane, toluene and the like followed by cyclization in presence of catalytic amount acid in refluxing toluene afforded the compound of formula (II-8).

Compound of formula (II-8) was treated with compound of formula (III) as shown in scheme I to form final compound of formula (I).

Scheme VII:

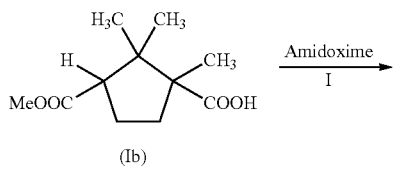

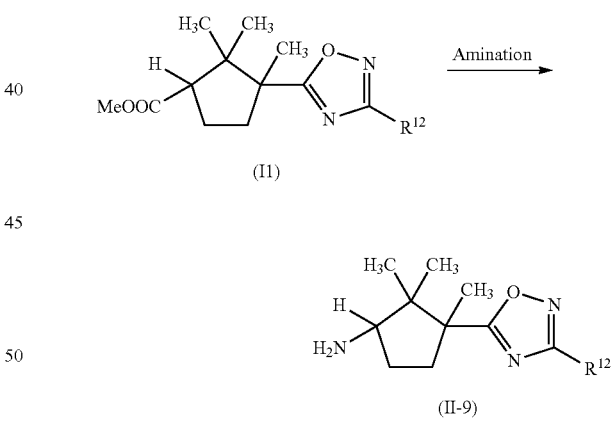

The reactions in the processes outlined in Scheme VII are described in following steps Step I: The acid (Ib) is transformed to compound of formula (II) as described in scheme VI.

Step II: Hydrolysis of ester function of compound of formula (II) followed by amination as described in amination step of scheme II affords the compound of formula (II-9).

Compounds of formula (II-9) was treated with compound of formula (III) as shown in scheme I to give final compound of formula (I).

Scheme VIII:

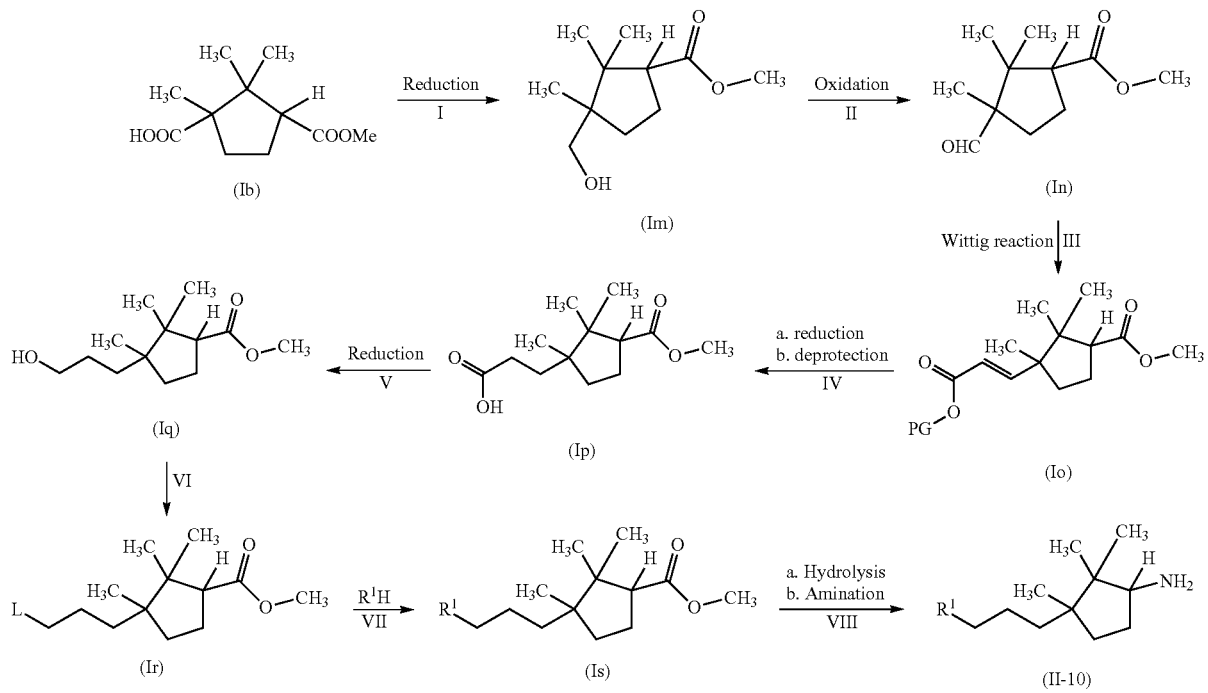

The reactions in the processes outlined in Scheme VIII are described in following steps Step I: Carboxylic acid function of compound of formula (Ib) is selectively reduced by borane-dimethylsulfide complex in presence of ester to afford alcohol of formula (Im).

Step II: Oxidation of alcohol (Im) to aldehyde is carried out using oxidizing agents like pyridinium chlorochromate, Jones reagent, Collins reagent, Dess-Martin periodinane or with DMSO activated with oxalyl chloride (Swern oxidation) to give aldehyde of formula (In). Reaction can be carried out in inert solvents like DCM, THF and like at temperature ranging from −78° C. to room temperature.

Step III: Alkene of formula (Io) from aldehyde of formula (In) was prepared by means of Wittig reaction conditions. Reaction are carried out in solvents inert like DCM, THF and the like at temperature ranging from 0° C. to room temperature in presence of sodium hydride.

Step IVa: Alkene of formula (Io) was reduced by reducing agents such as Pd/C, Raney Nickel in presence of hydrogen in suitable solvents like THF, MeOH, ethylacetate and the like at temperature ranging from room temperature to reflux temperature of the solvent used.

Step IVb: Deprotection of the above reduced compound is carried out by the conventional methods known in the art, for instance, by acids such as hydrochloric acid, trifluoroacetic acid or by catalytic amount hydrogenation conditions in suitable solvents like THF, MeOH, ethyl acetate and like at temperature ranging from room temperature to reflux temperature of the solvent used.

Step V: Compound of formula (Ip) is reduced to alcohol of formula (Iq) as described in step I.

Step VI: Compound of formula (Ir) is prepared by transforming hydroxyl group of compound of formula (Iq) to a leaving group L by mesylation, tosylation or halogenation in presence of organic base such as triethylamine, N,N-diisopropylethylamine, pyridine, N-methylmorpholine, N-methylpyrrolidine in an inert solvent such as DCM, THF, CHCl$_3$ and the like at about 0° C.-10° C.

Step VII: Coupling of compound of formula (Ir) with compound of formula R$^1$H gave the compound of formula (Is) in solvents selected from toluene, DMF, tetrahydrofuran, acetonitrile, ethyl acetate, N-methyl-2-pyrrolidone, DMSO, dichloroethane, chloroform or a mixture thereof, in the presence of a base such as triethylamine, pyridine, diisopropylethylamine, 4-dimethylaminopyridine, alkali hydroxides such as sodium hydroxide, potassium hydroxide, alkaline earth metal hydroxides, alkali carbonates such as, potassium carbonate, cesium carbonate and the like, to give the intermediate of formula (Is). The reaction is carried out at a temperature ranging from 0° C. to reflux temperature, mostly 0° C.-150° C.

Step VIII: Hydrolysis of ester function of compound of formula (Is) followed by amination as described in amination step of scheme II affords the compound of formula (II-10).

Compound of formula (II-10) was treated with compound of formula (III) as shown in scheme I to form final compound of formula (I).

Scheme IX:

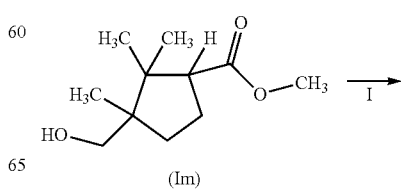

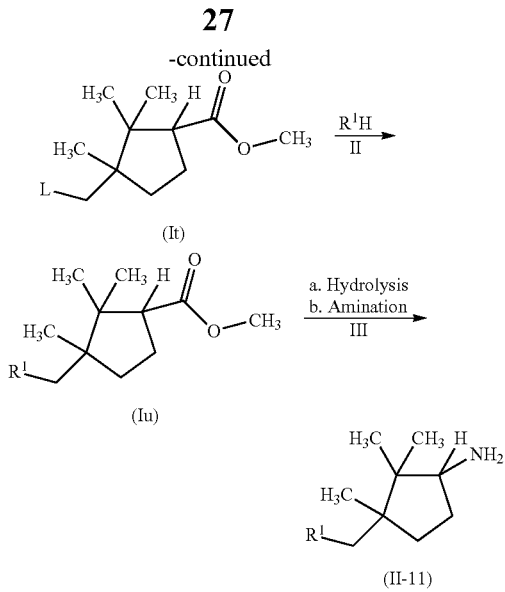

The reactions in the processes outlined in Scheme IX are described in following steps Step I: Compound of formula (Im) can be prepared similar to step 1 of scheme III.

Step II: Coupling of compound of formula (It) with compound of formula R¹H according to Step II of scheme III gave the Compound of formula (Iu).

Step III: Hydrolysis of ester function of compound of formula (Iu) followed by amination as described in amination step of scheme II affords the compound of formula (II-11).

Compound of formula (II-11) was treated with compound of formula (III) as shown in scheme I to form final compound of formula (I).

The examples given below are provided by the way of illustration only and therefore should not be construed to limit the scope of the invention.

Intermediate-1: (1S,3R)-Methyl 3-(tert-butoxycarbonylamino)-2,2,3-trimethyl cyclopentanecarboxylate

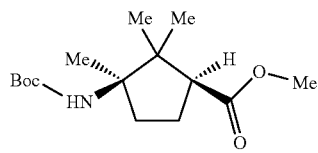 [SMILES: COC(=O)[C@H]1CC[C@@](C)(NC(=O)OC(C)(C)C)C1(C)C]

The above intermediate was prepared as per the procedure as described below.

Step I: To a stirred solution of (1R,3S)-(+)-camphoric acid (5 g, 25 mmol) in 30 mL of methanol, anhydrous HCl was bubbled for 2 h at room temperature. Methanol was evaporated and the residue was mixed with 5% sodium bicarbonate solution until the effervescence ceased and then 5% sodium hydroxide was added. The diester by-product was removed by extraction with diisopropyl ether. The aqueous layer was acidified with 10% HCl and extracted with diisopropyl ether. The combined ether extracts were dried over anhydrous sodium sulfate and evaporated to obtain (1R,3S)-3-(methoxycarbonyl)-1,2,2-trimethylcyclopentanecarboxylic acid (4.38 g) in 83% yield. $^1$H NMR (400 MHz, CDCl$_3$) δ ppm 0.84 (s, 3H), 1.25 (s, 6H), 1.53-1.55 (m, 1H), 1.80-1.84 (m, 1H), 2.19-2.22 (m, 1H), 2.25-2.57 (m, 1H), 239-2.84 (m, 1H); 3.70 (s, 3H); m/z (M+1): 214.

Step II: To a solution of (1R,3S)-3-(methoxycarbonyl)-1,2,2-trimethyl cyclopentanecarboxylic acid (4.1 g, 19.2 mmol) in 18 mL of DCM and oxalyl chloride (2.1 mL, 24.9 mmol), 2 drops of DMF were added. The solution was stirred for 5 hours at –15° C. All the volatiles were removed by passing nitrogen gas. The residue was dissolved in THF and the solution added dropwise to 80 mL of anhydrous acetonitrile saturated with NH$_3$ gas maintained at –30° C. The reaction mixture was stirred for another 15 minutes and the volatiles were removed under reduced pressure. The residue was taken in hot ethyl acetate and the solution was filtered; the crude product obtained after evaporation of the solvent was purified by column chromatography to furnish methyl (1S,3R)-3-carbamoyl-2,2,3-trimethyl cyclopentanecarboxylate (3.45 g) in 84% yield. $^1$H NMR (400 MHz, CDCl$_3$) δ ppm 0.85 (s, 3H), 1.22 (s, 3H), 1.30 (s, 3H), 1.45-1.48 (m, 1H), 1.80-1.91 (m, 1H), 2.20-2.27 (m, 1H), 2.35-2.43 (m, 1H), 2.79-2.84 (m, 1H), 3.69 (s, 3H), 5.60 (d, J=37.96, 2H); m/z (M+1): 213.

Step III: To a stirred solution of methyl (1S,3R)-3-carbamoyl-2,2,3-trimethyl cyclopentanecarboxylate (2.6 g; 12.2 mmol) in 12 mL of t-butanol, 0.2 mL of stannic chloride was added followed by lead tetraacetate (7.02 g, 15.86 mmol). The reaction mixture was heated under reflux for 24 hours. The solvent was evaporated under reduced pressure; the residue was taken up in diethyl ether, washed with 10% K$_2$CO$_3$ solution. The ether extract was concentrated and the crude product was purified by column chromatography to obtain methyl (1S,3R)-3-[(t-butoxycarbonyl)amino]-2,2,3-trimethylcyclopentanecarboxylate (2.58 g) in 74% yield. $^1$H NMR (400 MHz, CDCl$_3$) δ ppm 0.86 (s, 3H), 1.18 (s, 3H), 1.35 (s, 3H), 1.43 (s, 9H), 1.8-1.9 (m, 1H), 1.98-2.05 (m, 3H), 2.72-2.76 (m, 1H), 3.71 (s, 3H), 4.73 (bs, 1H); m/z (M+1): 285.

Intermediate-2: t-Butyl(1R,3S)-3-(hydroxymethyl)-1,2,2-trimethylcyclopentyl carbamate

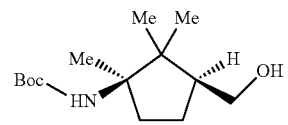 [SMILES: CC(C)(C)OC(=O)N[C@]1(C)CC[C@H](CO)C1(C)C]

To a suspension of methyl (1S,3R)-3-[(t-butoxycarbonyl)amino]-2,2,3-trimethyl cyclopentanecarboxylate (2.38 g, 8.3 mmol) in THF (50 mL) and water (5 mL), NaBH$_4$ (2.52 g, 66.8 mmol) was added over a period of three hours. The reaction mixture was heated under reflux for 24 hours. After completion of the reaction, the reaction mixture was diluted with ethyl acetate and water. The organic layer was separated, dried over anhydrous Na$_2$SO$_4$. The solvent was evaporated to obtain t-butyl [(1R,3S)-3-(hydroxymethyl)-1,2,2-trimethylcyclopentyl]carbamate (2 g) in 93% yield as a white solid. $^1$H NMR (400 MHz, CDCl$_3$) δ ppm 0.85 (s, 3H), 1.05 (s, 3H), 1.36 (s, 3H), 1.43 (s, 9H), 1.52 (m, 1H), 1.82-1.96 (m, 4H), 3.53-3.57 (dd, J=7.8 & 17.7 Hz, 1H), 3.70-3.74 (dd, J=5.4 & 10.2 Hz, 1H), 4.63 (bs, 1H); m/z (M+1): 258.

Intermediate-3: ((1S,3R)-3-(t-Butoxycarbonylamino)-2,2,3-trimethylcyclopentyl) methylmethanesulfonate

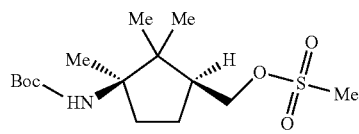 [SMILES: CC(C)(C)OC(=O)N[C@]1(C)CC[C@H](COS(C)(=O)=O)C1(C)C]

To a stirred solution of t-butyl [(1R,3S)-3-(hydroxymethyl)-1,2,2-trimethyl cyclopentyl]carbamate (2.0 g, 7.78 mmol) in 30 mL of dichloromethane maintained at 0° C., triethylamine (5.4 mL, 38.9 mmol) was added. To this reaction mixture, methanesulphonyl chloride (1.91 mL, 23.3 mmol) was added dropwise over a period of 30 minutes and the stirring continued for two hours. Subsequently, the reaction mixture was diluted with dichloromethane and water. The layers were separated and the organic layer was dried over anhydrous $Na_2SO_4$, concentrated and dried to give a light yellow colored crude sticky mass, which was purified by column chromatography to furnish methanesulfonic acid (1S, 3R)-3-t-butoxycarbonylamino-2,2,3-trimethyl-cyclopentylmethyl ester (2.01 g) in 76% yield as an off-white solid. $^1$H NMR (400 MHz, $CDCl_3$) δ ppm 0.85 (s, 3H), 1.05 (s, 3H), 1.32 (s, 3H), 1.43 (s, 9H), 1.49 (m, 1H), 1.85-2.04 (m, 3H), 2.20-2.24 (m, 1H), 3.01 (s, 3H), 4.10-4.15 (dd, J=8 & 9.24 Hz, 1H), 4.24-4.29 (dd, J=6.44 & 9.52 Hz, 1H), 4.47 (s, 1H); m/z (M−55): 280.1; $[\alpha]_D$ +36.3° (C., 1.0, methanol).

Intermediate-4: t-Butyl(1R,3S)-3-(azidomethyl)-1,2,2-trimethylcyclopentyl carbamate

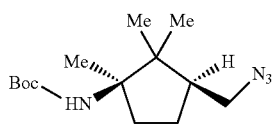 [SMILES: CC(C)(C)OC(=O)N[C@]1(C)CC[C@H](CN=[N+]=[N-])C1(C)C]

To a solution of intermediate-3 (1.48 g, 4.41 mmol) in DMF (20 mL), $NaN_3$ (0.57 g, 8.82 mmol) was added and stirred under $N_2$ atmosphere for 12 hours, maintaining the temperature 60° C. The reaction mixture was cooled to room temperature, diluted with water (100 mL) and extracted with ethyl acetate (2×100 mL). The ethyl acetate layers were combined, washed with water, brine, dried over $Na_2SO_4$ and concentrated to 0.65 g of azide. $^1$H NMR (400 MHz, $CDCl_3$) δ ppm 0.8 (s, 3H), 0.9 (d, 3H), 1.15 (s, 3H), 1.43 (s, 9H), 1.68-1.80 (m, 1H), 1.90-2.04 (m, 4H), 3.15-3.20 (dd, J=8.64 & 8.88, 1H), 3.31-3.42 (dd, J=5.4 & 5.56, 1H), 3.08-3.41 (m, 2H), 4.51 (s, 1H).

Intermediate-5: t-Butyl[(1R,3S)-3-(aminomethyl)-1,2,2-trimethylcyclopentyl]carbamate

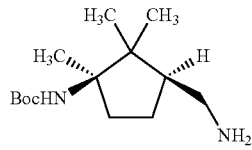

The intermediate (4) azide (0.65 g) was dissolved in ethyl acetate and added 5% Pd/C (85 mg) and hydrogenated at 50 psi for 1 hour to give 0.6 g of amine as semi-solid. $^1$H NMR (400 MHz, DMSO-$d_6$) δ ppm: 400 MHz δ 0.69 (s, 3H), 0.98 (d, 3H), 1.22 (s, 3H), 1.37 (s, 9H), 1.71-1.78 (m, 4H), 1.93-1.98 (m, 1H), 2.45-2.76 (m, 2H), 6.37 (bs, 2H); m/z (M+H): 257.2.

Intermediate-6: (1S,3R)-3-[(t-Butoxycarbonyl)amino]-2,2,3-trimethyl cyclopentanecarboxylic acid

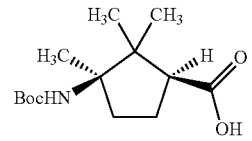 [SMILES: CC(C)(C)OC(=O)N[C@]1(C)CC[C@H](C(=O)O)C1(C)C]

To a solution of intermediate-1 in methanol, NaOH solution was added and refluxed for 3 hours. The reaction mixture was concentrated and acidified with 0.1N HCl and extracted with ethyl acetate (2×50 mL). Combined ethyl acetate layers were washed with brine, dried with anhydrous $Na_2SO_4$ and concentrated. $^1$H NMR (400 MHz, $CDCl_3$) δ ppm 0.93 (s, 3H), 1.18 (s, 3H), 1.35 (s, 3H), 1.43 (s, 9H), 1.8-1.9 (m, 1H), 1.98-2.05 (m, 3H), 2.72-2.76 (m, 1H), 4.73 (bs, 1H); m/z (M−H): 270.1.

Intermediate-7: t-Butyl [(1S,3S)-3-(cyanomethyl)-1,2,2-trimethylcyclopentyl]carbamate

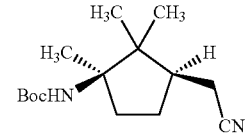

To a mixture of NaCN (1.18 g, 0.0287 mol) in DMF 70 mL, intermediate-3 (4.18 g, 0.0124 mol) was added and heated to 80-85° C. for six hours. After completion of reaction, it was diluted with ethyl acetate and water and the organic layers were separated. The organic layer was dried over anhydrous $Na_2SO_4$ and concentrated on a rotavapor to give brown coloured sticky mass, which is purified by column chromatography. 1.75 g, Off white solid; $^1$H NMR (400 MHz, $CDCl_3$) δ ppm: 0.81 (s, 3H), 1.09 (s, 3H), 1.32 (s, 3H), 1.43 (s, 9H), 2.01-2.22 (m, 5H), 2.33-2.39 (dd, J=4.88 Hz & J=4.68 Hz, 1H), 2.38-2.41 (m, 1H), 4.47 (m, 1H). m/z (M−1): 265.2.

Intermediate-8: Methyl (1R,3S)-3-[(tert-butoxycarbonyl)amino]-2,2,3-trimethyl cyclopentanecarboxylate Prepared similar to intermediate 1 starting from (1S,3R)(−) camphoric acid) in step 1

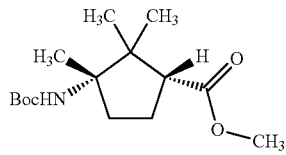 [SMILES: COC(=O)[C@@H]1CC[C@](C)(NC(=O)OC(C)(C)C)C1(C)C]

$^1$H NMR (400 MHz, CDCl$_3$) δ ppm 0.86 (s, 3H), 1.18 (s, 3H), 1.35 (s, 3H), 1.43 (s, 9H), 1.8-1.9 (m, 1H), 1.98-2.05 (m, 3H), 2.72-2.76 (m, 1H), 3.71 (s, 3H), 4.73 (bs, 1H); m/z (M+1): 285.

Intermediate-9: t-Butyl[(1S,3R)-3-(hydroxymethyl)-1,2,2-trimethylcyclopentyl]carbamate Prepared similar to intermediate 2 starting from intermediate 8

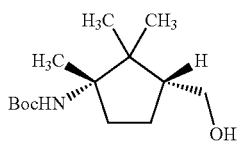

$^1$H NMR (400 MHz, CDCl$_3$) δ ppm 0.85 (s, 3H), 1.02 (s, 3H), 1.27 (s, 3H), 1.43 (s, 9H), 1.52 (m, 1H), 1.81-1.89 (m, 1H), 1.96-2.01 (m, 3H), 3.53-3.57 (dd, J=7.8 Hz & 17.7 Hz, 1H), 3.71-3.74 (dd, J=5.4 & 10.2 1H), 4.62 (bs, 1H); m/z (M+1): 258.

Intermediate-10: Methanesulfonic acid (1R,3S)-3-t-butoxycarbonylamino-2,2,3-trimethyl-1-cyclopentyl-methyl ester Prepared similar to intermediate 3 starting from intermediate 9

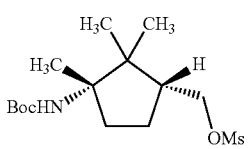 [SMILES: CC(C)(C)OC(=O)N[C@@]1(C)CC[C@@H](COS(C)(=O)=O)C1(C)C]

$^1$H NMR (400 MHz, CDCl$_3$) δ ppm 0.85 (s, 3H), 1.06 (s, 3H), 1.32 (s, 3H), 1.43 (s, 9H), 1.49 (m, 1H), 1.85-2.04 (m, 3H), 2.16-2.24 (m, 1H), 3.01 (s, 3H), 4.10-4.15 (dd, J=8 & 9.24, 1H), 4.25-4.29 (dd, J=6.44 & 9.52, 1H), 4.48 (s, 1H).

Intermediate-11: t-Butyl [(1S,3R)-3-(azidomethyl)-1,2,2-trimethylcyclopentyl]carbamate Prepared similar to intermediate 4 starting from intermediate 10.

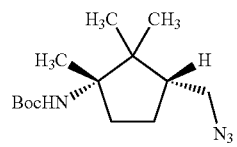

$^1$H NMR (400 MHz, CDCl$_3$) δ ppm 0.8 (s, 3H), 0.9 (d, 3H), 1.15 (s, 3H), 1.43 (s, 9H), 1.68-1.80 (m, 1H), 1.90-2.04 (m, 4H), 3.08-3.41 (m, 2H), 4.51 (s, 1H).

Intermediate-12: t-Butyl[(1S,3R)-3-(aminomethyl)-1,2,2-trimethylcyclopentyl]carbamate Prepared similar to intermediate 5 starting from intermediate 11 and used as such without purification. m/z (M+H): 257.2.

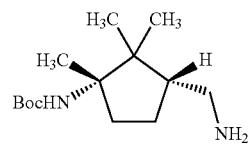

Intermediate-13: (1R,3S)-3-[(t-Butoxycarbonyl)amino]-2,2,3-trimethyl cyclopentanecarboxylic acid

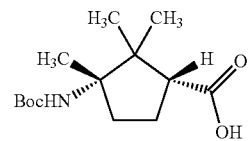

Prepared similar to intermediate 6 starting from intermediate 8. $^1$H NMR (400 MHz, CDCl$_3$) δ ppm 0.94 (s, 3H), 1.17 (s, 3H), 1.35 (s, 3H), 1.43 (s, 9H), 1.82-1.89 (m, 1H), 1.98-2.05 (m, 3H), 2.72-2.76 (m, 1H), 4.73-4.75 (bs, 1H); m/z (M−H): 270.1.

Intermediate-14: t-Butyl [(1S,3S)-3-(cyanomethyl)-1,2,2-trimethylcyclopentyl]carbamate Prepared similar to intermediate 7 starting from intermediate 10

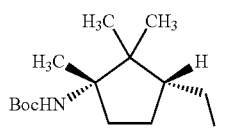

$^1$H NMR (400 MHz, CDCl$_3$) δ ppm: 0.81 (s, 3H), 1.09 (s, 3H), 1.32 (s, 3H), 1.43 (s, 9H), 2.01-2.22 (m, 5H), 2.33-2.39 (dd, J=4.88 Hz & J=4.68 Hz, 1H), 2.38-2.41 (m, 1H), 4.47 (m, 1H). m/z (M−1): 265.2.

Intermediate-15: (1R,5R)-1-Amino-3,5,8,8-tetramethyl-3-azabicyclo[3.2.1]octane-2,4-dione

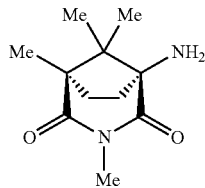 [SMILES: CN1C(=O)[C@]2(C)CC[C@](N)(C1=O)C2(C)C]

Step 1: (1R,3S)-1,2,2-Trimethyl-3-(methylcarbamoyl)cyclopentanecarboxylic acid

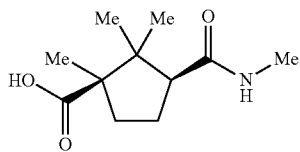 [SMILES: CNC(=O)[C@H]1CC[C@@](C)(C(=O)O)C1(C)C]

A mixture of 40% aqueous methylamine (70 mL) and camphoric anhydride (5 g) was stirred at room temperature for 30 minutes. To this N,N-dimethyl-4-aminopyridine (DMAP) (0.67 g, 5.4 mmol) was added and stirred further for 24 hours. The reaction mixture was allowed to cool to room temperature and acidified with con. HCl at 0-5° C. White precipitate formed was filtered and dried (5.2 g). m/z (M+H): 214.1.

Step 2: (1R)-1,3,8,8-Tetramethyl-3-azabicyclo[3.2.1]octane-2,4-dione

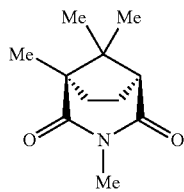

To a solution of step 1 intermediate (4.5 g, 21 mmol) in ethyl acetate, acetyl chloride (5.25 mL, 73 mmol) was added and refluxed for 24 hours. After the reaction, ethyl acetate was removed under reduced pressure, crude material purified by column, using ethyl acetate and hexane. (3.7 g) $^1$H NMR (400 MHz, CDCl$_3$) δ ppm: 0.8 (s, 3H), 0.9 (s, 3H), 1.1 (s, 3H), 1.60-1.61 (m, 1H), 1.71-1.83 (m, 1H), 1.88-1.95 (m, 1H), 2.11-2.2 (m, 1H), 2.65 (d, 1H), 2.91 (s, 3H). m/z (M+H): 196.1.

Step 3: (1R,5R)-3,5,8,8-Tetramethyl-2,4-dioxo-3-azabicyclo[3.2.1]octane-1-carboxylic acid

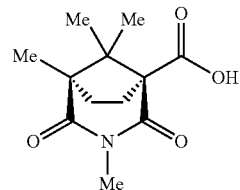 [SMILES: CN1C(=O)[C@@]2(C(=O)O)CC[C@@](C)(C1=O)C2(C)C]

To a solution of step 2 intermediate (2 g, 10.2 mmol) in THF maintained at −95° C. under N$_2$ atmosphere, 1.2N Sec.BuLi in cyclohexane (9.5 mL, 13.3 mmol) was added. After stirring for 15 min at −95° C., small pieces of dry ice (2 g) were added and the reaction mixture was kept at this temperature for 1 h before quenching with water (3 mL). The reaction mixture was allowed to warm to room temperature. To this 5% NaHCO$_3$ solution (100 mL) and diethyl ether (50 mL) was added, the aqueous layer was separated and acidified with KHSO$_4$ to pH 2. This was extracted again with diethyl ether, washed with brine, dried with anhydrous Na$_2$SO$_4$ and concentrated. (1.85 g). $^1$H NMR (400 MHz, CDCl$_3$) δ ppm: 1.0 (s, 3H), 1.1 (s, 3H), 1.26 (s, 3H), 1.88-1.98 (m, 2H), 2.64-2.72 (m, 1H), 2.8 (m, 1H), 3.13 (s, 3H). m/z (M−H): 238.

Step 4: (1S,5R)-3,5,8,8-Tetramethyl-2,4-dioxo-3-azabicyclo[3.2.1]octane-1-carboxamide

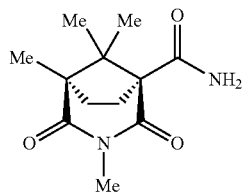 [SMILES: CN1C(=O)[C@@]2(C(N)=O)CC[C@@](C)(C1=O)C2(C)C]

A solution of step 3 intermediate in thionyl chloride was refluxed for 2 hours. After that, thionyl chloride was removed completely by distillation. The residue was dissolved in dichloromethane and 23% aqueous NH$_3$ (40 mL) was added maintaining the temperature at 0° C. The reaction was stirred for another 2 hours, diluted with dichloromethane. The organic layer was separated, washed with water and brine, dried with anhydrous Na$_2$SO$_4$ and concentrated to get light brown solid (2.69 g). $^1$H NMR (400 MHz, CDCl$_3$) δ ppm:

0.95 (s, 3H), 0.96 (s, 3H), 1.21 (s, 3H), 1.88-1.94 (m, 2H), 1.97-2.02 (m, 1H), 2.88-2.94 (m, 1H), 3.13 (s, 3H), 5.8-6.1 (d, 1H). m/z (M+H): 239.1.

Step 5: (1R,5R)-1-Amino-3,5,8,8-tetramethyl-3-azabicyclo[3.2.1]octane-2,4-dione

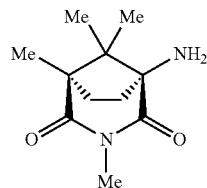 [SMILES: CN1C(=O)[C@]2(C)CC[C@](N)(C1=O)C2(C)C]

Step 4 intermediate (2.5 g) was dissolved in a 20 mL solvent mixture of ethyl acetate, acetonitrile and water in the ratio 1:1:0.5, respectively. To this PIFA (6.3 g, 14.6 mmol) was added and stirred at temperature at 45° C. for 5 hours. The reaction was further was stirred at room temperature for 8 hours. Excess PIFA was decomposed by heating at 70° C. for 10 minutes. Reaction mixture was concentrated under reduced pressure, acidified with dilute HCl, and washed with diethyl ether. Aqueous layer was separated, basified with NaHCO$_3$ and extracted with dichloromethane, washed with water, brine, dried and concentrated. Crude material was purified by column chromatography to get 1.5 g solid. $^1$H NMR (400 MHz, CDCl$_3$) δ ppm: 0.76 (s, 3H), 0.98 (s, 3H), 1.23 (s, 3H), 1.77-1.97 (m, 4H), 3.11 (s, 3H). m/z (M+H): 211.

Intermediate-16: (1R,5R)-3,5,8,8-tetramethyl-3-azabicyclo[3.2.1]octan-1-amine

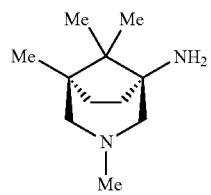

To a stirred suspension of lithium aluminumhydride in dry THF at 0° C., a solution of intermediate 15 in THF was added slowly. After completion of the reaction (monitored by TLC), water was added and the precipitate that separated out was filtered off. The filtrate was extracted with ethyl acetate (2×100 mL). Ethyl acetate layers were combined together, dried with anhydrous Na$_2$SO$_4$, filtered and concentrated. 65 mg of pure product was obtained by purification of the crude material by silica column chromatography. $^1$H NMR (400 MHz, CDCl$_3$) δ ppm: 0.8 (s, 3H), 0.9 (s, 6H), 1.21-1.29 (m, 4H), 1.67-1.72 (m, 1H), 1.83-1.9 (m, 1H), 2.19-2.2 (d, J=10.8 Hz, 1H), 2.29 (s, 3H), 2.32 (d, J=10.84 Hz, 1H), 2.39 (s, 2H). m/z (M+H): 183.1.

Intermediate-17: (1R,5R)-1-Amino-5,8,8-trimethyl-3-oxabicyclo[3.2.1]octan-2-one

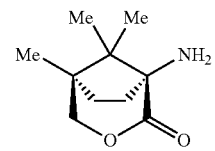 [SMILES: CC1(C)[C@@]2(C)CC[C@]1(N)C(=O)OC2]

Step 1: (1S,5R)-5,8,8-Trimethyl-2-oxo-3-oxabicyclo[3.2.1]octane-1-carboxylic acid This intermediate was prepared starting from (+)Camphoric anhydride using literature procedures (*Liebigs Ann.* 1996, 1941-1948)

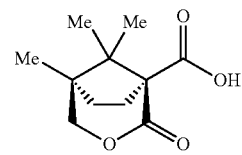 [SMILES: CC1(C)[C@@]2(C)CC[C@]1(C(=O)O)C(=O)OC2]

Melting point 243° C. $^1$H NMR (400 MHz, CDCl$_3$) δ ppm: 0.93 (s, 3H), 0.98 (s, 3H), 1.23 (s, 3H), 1.78-1.98 (m, 3H), 2.31-2.39 (m, 1H), 3.93 (d, J=10.84 Hz, 1H), 4.17 (d, J=10.88 Hz, 1H) 12.77 (bs, 1H); m/z (M−H): 211.

Step 2: (1S,5R)-5,8,8-Trimethyl-2-oxo-3-oxabicyclo[3.2.1]octane-1-carboxamide

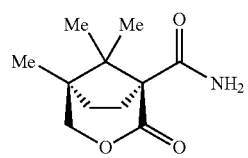 [SMILES: CC1(C)[C@@]2(C)CC[C@]1(C(N)=O)C(=O)OC2]

To a solution of step 1 intermediate in dichloromethane (0.7 g, 3.29 mmol), oxalyl chloride (0.32 mL, 3.62 mmol) was added and stirred for 2 hours at −10° C. The volatiles were removed by purging N$_2$ gas. The residue was dissolved in 25 mL diethyl ether and to this 25 mL of 23% aqueous ammonia was added. The reaction mixture was stirred for 2 hours and extracted with dichloromethane (2×100 mL). The organic layers were combined, washed with brine, dried with Na$_2$SO$_4$ and concentrated. $^1$H-NMR (400 MHz, CDCl$_3$) δ ppm: 0.93 (s, 6H), 1.15 (s, 3H), 1.88-2.05 (m, 3H), 2.73-2.82 (m, 1H), 3.97 (d, J=10.9 Hz, 1H), 4.17 (d, J=10.9 Hz, 1H), 5.85 (bs, 1H), 6.25 (bs, 1H); m/z (M+H): 212.3.

Step 3: (1R,5R)-1-Amino-5,8,8-trimethyl-3-oxabicyclo[3.2.1]octan-2-one

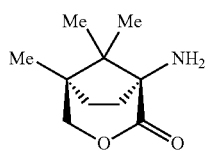

Step 2 intermediate (0.4 g, 1.89 mmol) was dissolved in a 5 mL solvent mixture of ethyl acetate, acetonitrile and water in the ratio 1:1:0.5 respectively. To this PIFA (1.14 g, 2.65 mmol) was added and stirred maintaining the temperature 45° C. for 5 hours. The reaction was further stirred at room temperature for 8 hours. Excess PIFA was decomposed by heating at 70° C. for 10 minutes. Reaction mixture was concentrated under reduced pressure, acidified with dilute HCl, washed with dichloromethane. Aqueous layer was separated, basified with $NaHCO_3$, extracted with dichloromethane, washed with water, brine, dried and concentrated. Crude material was purified by column chromatography to give 0.26 g of solid. $^1$H NMR (400 MHz, $CDCl_3$) δ ppm: 0.9 (s, 3H), 0.93 (s, 3H), 0.94 (s, 3H), 1.77-1.93 (m, 3H), 2.06-2.12 (m, 1H), 3.89 (d, J=10.76 Hz, 1H), 4.09 (d, J=10.72 Hz, 1H); m/z (M+H): 184.1.

Intermediate-18: 1R,5R)-5,8,8-Trimethyl-3-oxabicyclo[3.2.1]octan-1-amine

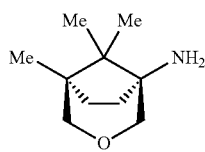 [SMILES: CC1(C)[C@@]2(C)CC[C@]1(N)COC2]

Step 1: N-[(1R,5R)-5,8,8-Trimethyl-2-oxo-3-oxabicyclo[3.2.1]oct-1-yl]acetamide

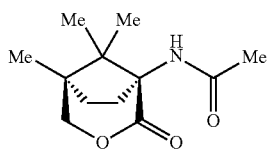 [SMILES: CC(=O)N[C@@]12CC[C@@](C)(COC1=O)C2(C)C]

To a stirred solution of intermediate 17 in 5 mL of dichloromethane maintained at 0° C., triethylamine (0.34 mL, 2.4 mmol) was added. To this reaction mixture, acetyl chloride (0.17 mL, 2.4 mmol) was added over a period of 15 minutes and stirred for further 1 hour. After completion of the reaction, the reaction mixture was diluted with dichloromethane and water. The organic layer was separated and dried over anhydrous $Na_2SO_4$. The solvent was evaporated to give 0.17 g of off-white solid product. $^1$H NMR (400 MHz, $CDCl_3$) δ ppm: 0.91 (s, 3H), 0.96 (s, 3H), 1.0 (s, 3H), 1.81-1.90 (m, 1H), 1.96-2.29 (m, 2H), 2.1 (s, 3H), 3.1-3.2 (m, 1H), 3.95 (d, J=10.84 Hz, 1H), 4.08 (m, J=9.72 Hz, 1H), 5.96 (bs, 1H). m/z (M+H): 226.2.

Step 2: N-[(1R,5R)-2-Hydroxy-5,8,8-trimethyl-3-oxabicyclo[3.2.1]oct-1-yl]acetamide

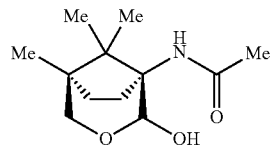

To a suspension of lithium aluminumhydride (0.253 g, 6.6 mmol) in dry THF, step 1 intermediate in 2 mL THF was added dropwise at room temperature and stirred for 30 minutes. After completion, the reaction mixture was quenched with a few drops of water maintaining the temperature below 0° C. and stirred until a white precipitate formed. Reaction was filtered and residue obtained was washed with ethyl acetate. The filtrate was dried with anhydrous $Na_2SO_4$ and concentrated under reduced pressure. The crude material was purified by silica column chromatography to give a pair of diastereomeric mixture. $^1$H NMR (400 MHz, $CDCl_3$) δ ppm: 0.81 (s, 3H), 0.95 (s, 3H), 1.05 (s, 3H), 1.68-1.92 (m, 3H), 2.03 (s, 3H), 2.34-3.36 (m, 0.25H), 2.75-2.81 (m, 0.75H), 3.06 (d, J=10.8 Hz, 0.25H), 3.21 (d, J=11.32 Hz, 0.75H), 3.74 (d, J=11.32 Hz, 0.75H), 3.95 (d, J=10.70 Hz, 0.25H), 5.2 (d, J=6.4 Hz, 0.75H), 5.34 (s, 0.25H), 5.50 (bs, 1H), 5.73 (d, J=6.6 Hz, 1H). m/z (M+59; -ve mode): 286.2.

Step 3: N-[(1R,5R)-5,8,8-Trimethyl-3-oxabicyclo[3.2.1]oct-1-yl]acetamide

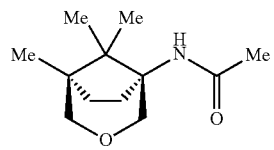 [SMILES: CC(=O)N[C@@]12CC[C@@](C)(COC1)C2(C)C]

To a stirred solution of step 2 intermediate (0.2 g, 0.88 mmol) in dry dichloromethane (5 mL) under nitrogen atmosphere, was added $Et_3SiH$ (0.84 mL; 5.28 mmol) at 0° C. To this boron trifluoride etherate (0.33 mL, 2.6 mmol) was added dropwise over a period of 10 minutes. Stirring was continued for 5 hours at room temperature. After completion, the reaction mixture was quenched with saturated $NaHCO_3$ solution and extracted with dichloromethane. Organic layer was separated and dried over anhydrous $Na_2SO_4$. Dichloromethane layer was concentrated under reduced pressure to obtain 165 mg of title compound. $^1$H NMR (400 MHz, $CDCl_3$) δ ppm: 0.78 (s, 3H), 0.89 (s, 3H), 1.1 (s, 3H), 1.60-1.64 (m, 1H), 1.72-1.78 (m, 2H), 1.85 (s, 3H), 2.60-2.67 (m, 1H), 3.06 (d, J=10.96 Hz, 1H), 3.67 (d, J=10.92 Hz, 1H), 3.78 (d, J=10.48 Hz, 1H), 3.92 (d, J=10.48 Hz, 1H) 5.16 (bs, 1H). m/z (M+1): 212.2.

Step 4: (1R,5R)-5,8,8-Trimethyl-3-oxabicyclo[3.2.1]octan-1-amine

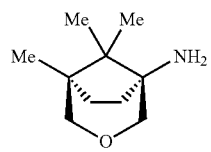

To a solution of step 3 intermediate (0.165 g, 0.78 mmol) in 3 mL of dry THF and pyridine (0.37 mL, 47 mmol) maintained at 0° C., oxalyl chloride was added with stirring. After 30 minutes propylene glycol (0.46 mL, 63 mmol) was added to the above reaction mixture and reaction warmed to room temperature. Reaction mixture was concentrated after adding ethyl alcohol. The residue was partitioned between 1N HCl and tert-butyl ether. Aqueous layer was separated and basified with 4N NaOH and extracted with ethyl acetate. Ethyl acetate layer was separated, dried and concentrated. Crude material was carried to next step without further purification. m/z (M+1): 170.2.

Intermediate-19: (1S,5S)-5,8,8-Trimethyl-3-oxabicyclo[3.2.1]octan-1-amine

Prepared similar to intermediate 17 starting from (1S,3R) (−)Camphoric acid m/z (M+1): 170.2

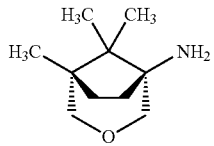

Intermediate-20: (2S,4S)-1-(Chloroacetyl)-4-fluoropyrrolidine-2-carbonitrile

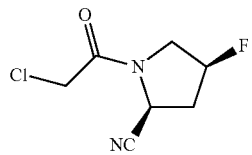 [SMILES: N#C[C@@H]1C[C@H](F)CN1C(=O)CCl]

This intermediate was prepared starting from trans-4-hydroxyproline using literature procedures (*Bioorganic Medicinal Chemistry* 2008, 16, 4093-4106; WO2007/113634 and US2007/0112059) as a white solid, mp 139-141° C.; IR cm$^{-1}$: 3031, 3007, 2962, 2241, 1679, 1407, 1280, 1225, 1076, 860; $^1$H NMR (400 MHz, CDCl$_3$) δ ppm (3:1 mixture of two rotomers) 2.25-2.5 (m, 1H), 2.55-2.65 (m, 1H), 4.06 (s, 2H), 3.55-4.3 (m, 2H), 4.96 (d, 0.8H, J=9.2 Hz), 5.07 (d, 0.2H, J=9.2 Hz), 5.45 (d, 0.8H, J=51.5 Hz), 5.41 (d, 0.2H, J=51.5 Hz); m/z (M+18): 208; [α]$_D$ −120.6° (C., 1.0, methanol).

Intermediate-21: (2S)-1-(Chloroacetyl)pyrrolidine-2-carbonitrile

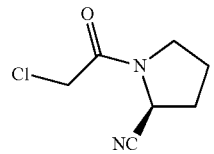 [SMILES: N#C[C@@H]1CCCN1C(=O)CCl]

This intermediate was prepared starting from L-proline using literature procedures (*Journal of Medicinal Chemistry*, 2003, 46, 2774-2789) as off-white solid; mp 53-57° C.; $^1$H NMR (400 MHz, CDCl$_3$) δ ppm (4 to 1 mixture of trans/cis amide rotomers) 2.10-2.40 (m, 4H), 3.55-3.66 (m, 1H), 3.66-3.79 (m, 1H), 4.03-4.21 (m, 0.4H, CH$_2$Cl), 4.09 (s, 1.6H, CH$_2$Cl), 4.76 (m, 0.8H, CHCN), 4.87 (dd, 0.2H, J=7.4 and 2.2 Hz, CHCN); m/z (M+18): 190; [α]$_D$ −150.31° (C., 1.0, methanol).

Intermediate-22: (2S,4R)-1-(Chloroacetyl)-4-fluoropyrrolidine-2-carbonitrile

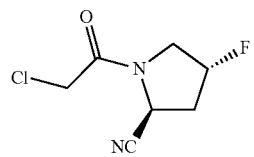 [SMILES: N#C[C@@H]1C[C@@H](F)CN1C(=O)CCl]

This intermediate was prepared according to procedure described in *Tetrahedron letters* 1998, 39, 1169-1172 and WO2007/113634. Melting point: 97-100° C. $^1$H NMR (400 MHz, CDCl$_3$) δ ppm 2.44-2.57 (m, 1H), 2.77-2.83 (m, 1H), 3.55-4.4 (m, 4H), 4.81 (t, J=8.3 Hz, 0.8H), 5.01 (t, J=8.36 Hz, 0.2H) 5.35 (d, J=51.3 Hz, 0.2H), 5.38 (d, J=51 Hz, 0.8H); m/z (M+18): 190; [α]$_D$ −153.39° (C., 1.0, methanol), m/z (M+18): 208.1

Example 1

(2S,4S)-1-(2-((1R,3S)-3-((1H-1,2,4-Triazol-1-yl)methyl)-1,2,2-trimethylcyclopentylamino)acetyl)-4-fluoropyrrolidine-2-carbonitrile

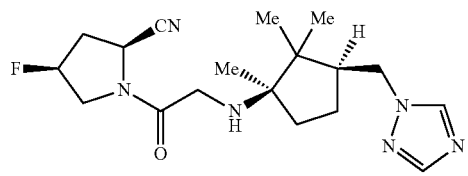 [SMILES: CC1(C)[C@@H](Cn2cncn2)CC[C@@]1(C)NCC(=O)N1C[C@@H](F)C[C@H]1C#N]

Step 1: tert-Butyl (1R,3S)-3-((1H-1,2,4-triazol-1-yl)methyl)-1,2,2-trimethyl cyclopentylcarbamate

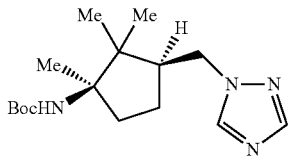 [SMILES: CC(C)(C)OC(=O)N[C@]1(C)CC[C@H](Cn2cncn2)C1(C)C]

To a suspension of 1H-1,2,4-triazole (0.232 g, 3.36 mmol) and K$_2$CO$_3$ (0.556 g, 4.03 mmol) in 5 mL of DMF, intermediate 3 (1.01 g, 3.02 mmol) was added and reaction mixture was stirred at 80-85° C. for 5 hours. The reaction mixture was brought to room temperature and diluted with water, extracted with ethyl acetate. The combined organic extract was washed with water and dried over anhydrous Na$_2$SO$_4$ and concentrated under reduced pressure. The crude product was purified by column chromatography to afford 135 mg of the title compound as a white solid. $^1$H NMR (CDCl$_3$): 400 MHz δ 0.91 (s, 3H), 0.99 (s, 3H), 1.31 (s, 3H), 1.43 (s, 9H), 1.45 (m, 1H), 1.67 (m, 1H), 1.98 (m, 2H), 2.40 (m, 1H), 3.95-4.01 (dd, J=10.3 & 13.2 Hz, 1H), 4.23-4.28 (dd, J=4.76 & 13.4 Hz, 1H), 4.48 (s, 1H), 7.93 (s, 1H), 8.05 (s, 1H); m/z (M+1): 309.2.

Step 2: (1R,3S)-3-((1H-1,2,4-Triazol-1-yl)methyl)-1,2,2-trimethylcyclopentanamine hydrochloride

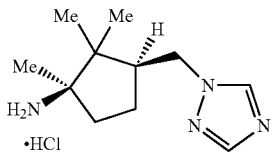 [SMILES: Cl ; CC1(C)[C@@H](Cn2cncn2)CC[C@@]1(C)N]

A solution of saturated HCl in ethyl acetate (2 mL) was added to a solution of the step 1 intermediate (0.130 g, 0.422 mmol) in ethyl acetate at 0° C. and the reaction mixture was stirred at room temperature for two hours. The volatiles were removed under reduced pressure to afford 90 mg of desired product. $^1$H NMR (d$_6$-DMSO): 400 MHz δ 0.91 (s, 6H), 1.19 (s, 3H), 1.53 (m, 2H), 1.65 (m, 1H), 1.94 (m, 1H), 2.32 (m, 1H), 4.10-4.15 (dd, J=9.88 and 13.1 Hz, 1H), 4.24-4.28 (dd, J=4.96 and 13.4 Hz, 1H), 8.00 (bs, 3H), 8.01 (s, 1H), 8.62 (s, 1H); m/z (M+1): 209.2.

Step 3: (2S,4S)-1-(2-((1R,3S)-3-((1H-1,2,4-Triazol-1-yl)methyl)-1,2,2-trimethyl cyclopentylamino)acetyl)-4-fluoropyrrolidine-2-carbonitrile

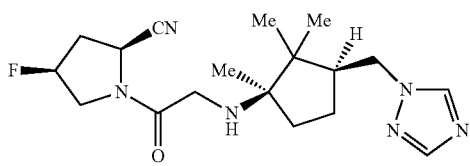 [SMILES: CC1(C)[C@@H](Cn2cncn2)CC[C@@]1(C)NCC(=O)N1C[C@@H](F)C[C@H]1C#N]

To a stirred suspension of the step-2 intermediate (0.097 g, 0.40 mmol), K$_2$CO$_3$ (0.218 g, 1.59 mmol) and KI (0.033 g, 0.2 mmol) in 1 mL of DMSO was added a DMSO solution of intermediate 20 (0.076 g, 0.40 mmol) and the reaction mixture was stirred for 24 hours under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by chromatography to yield the product as an off-white solid (0.042 g). mp: 186-188; IR (KBr): 2246 &1662 cm$^{-1}$; $^1$H NMR (CDCl$_3$): 400 MHz δ 0.93 (s, 3H), 0.98 (s, 3H), 1.03 (s, 3H), 1.40-1.44 (m, 1H), 1.63-1.70 (m, 4H), 2.39-2.44 (m, 2H), 2.66-2.74 (m, 1H), 3.35-3.52 (m, 2H), 3.65-4.1 (m, 2H), 4.10-4.14 (m, 1H), 4.25-4.30 (dd, dd, J=4.4 &13.6 Hz, 1H), 4.96 (d, J=9.2 Hz, 0.8H, rotomer) 5.12 (d, J=9.2 Hz, 0.2H, rotomer), 5.42 (d, J=48 Hz, 0.2H rotomer), 5.50 (d, J=48 Hz, 0.8H, rotomer), 8.07 (s, 1H), 8.09 (s, 1H); m/z (M+1): 363.2.

Example 2

(2S,4R)-1-(2-((1R,3S)-3-((1H-1,2,4-Triazol-1-yl)methyl)-1,2,2-trimethylcyclopentylamino)acetyl)-4-fluoropyrrolidine-2-carbonitrilemethane sulfonate

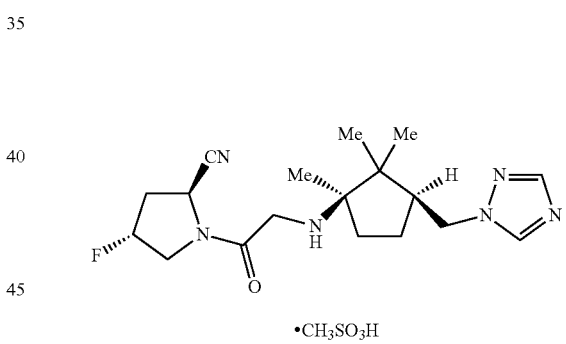

To a suspension of step 2 intermediate of example 1 (0.097 g, 0.40 mmol), K$_2$CO$_3$ (0.218 g, 1.59 mmol), KI (0.033 g, 0.2 mmol) in DMSO and intermediate-22 (0.076 g, 0.40 mmol) were added and stirred for 12 h at room temperature. The free base was isolated as described in step 3 of example 1. The free base isolated (20 mg, 0.005 mmol) was dissolved in ethyl acetate and treated with methanesulfonic acid (5.3 mg, 0.005 mmol) in ethyl acetate and stirred for 2 h. The volatiles were removed under reduced pressure and the residue was triturated several times with diethyl ether to yield 0.02 g of titled compound as white hygroscopic solid. $^1$H NMR (400 MHz, D$_2$O) δ ppm: 1.07 (s, 3H), 1.15 (s, 3H), 1.4 (s, 3H), 1.66-1.78 (m, 2H), 1.86-1.87 (m, 1H), 2.1-2.12 (m, 1H), 2.50-2.55 (m, 2H), 2.79 (s, 3H), 2.85-2.92 (m, 1H), 3.8-4.14 (m, 3H), 4.1-4.3 (m, 2H), 4.5-4.53 (m, 1H), 4.97 (t, J=8 Hz, 0.8H), 5.25 (t, J=8 Hz, 0.2H), 5.41 (d, J=48 Hz, 0.2H), 5.42 (d, J=48 Hz, 0.8H), 8.08 (s, 1H), 8.51 (s, 1H). m/z (M+H): 363.2.

Example 3

(2S,4S)-1-(2-((1S,3R)-3-((1H-1,2,4-Triazol-1-yl)methyl)-1,2,2-trimethylcyclopentylamino)acetyl)-4-fluoropyrrolidine-2-carbonitrile

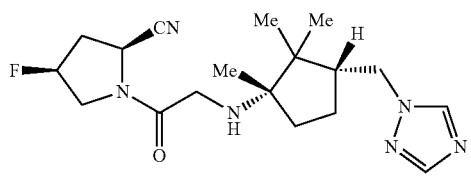 [SMILES: CC1(C)[C@H](Cn2cncn2)CC[C@]1(C)NCC(=O)N1C[C@@H](F)C[C@H]1C#N]

Step 1: (1S,3R)-1,2,2-Trimethyl-3-[1,2,4]triazol-1-ylmethyl-cyclopentylamine hydrochloride

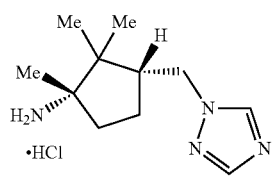 [SMILES: Cl ; CC1(C)[C@H](Cn2cncn2)CC[C@]1(C)N]

Prepared according to procedure described in example-1, using intermediate 10. $^1$H NMR (d$_6$-DMSO): 400 MHz δ 0.92 (s, 6H), 1.20 (s, 3H), 1.52 (m, 2H), 1.62 (m, 1H), 2.01 (m, 1H), 2.30 (m, 1H), 4.09-4.15 (dd, J=9.7 & 13.4 Hz, 1H), 4.24-4.30 (dd, J=5.1 & 13.5 Hz, 1H), 8.05 (bs, 3H), 8.07 (s, 1H), 8.68 (s, 1H); m/z (M+1): 209.2.

Step 2: (2S,4S)-4-Fluoro-1-[2-((1S,3R)-1,2,2-trimethyl-3-[1,2,4]triazol-1-yl methyl-cyclopentylamino)-acetyl]-pyrrolidine-2-carbonitrile

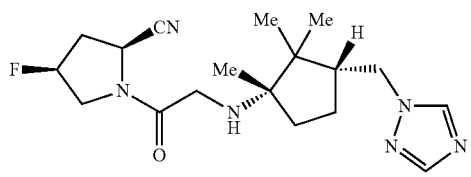 [SMILES: CC1(C)[C@H](Cn2cncn2)CC[C@]1(C)NCC(=O)N1C[C@@H](F)C[C@H]1C#N]

Coupling reaction of step 1 intermediate (0.048 g, 0.196 mmol) and intermediate-20 (0.037 g, 0.196 mmol), in the presence of K$_2$CO$_3$ (0.108 g, 0.78 mmol) and KI (0.016 g, 0.098 mmol) in 2 mL of DMSO as described in step-3 of Example-1 afforded 38 mg of product as an off-white solid. mp: 132-135° C.; IR (KBr): 2241 & 1655 cm$^{-1}$; $^1$H NMR (CDCl$_3$): 400 MHz δ 0.97 (s, 3H), 0.98 (s, 3H), 1.07 (s, 3H), 1.36-1.41 (m, 1H), 1.59-1.70 (m, 4H), 2.36-2.40 (m, 2H), 2.65-2.73 (m, 1H), 3.30 (d, J=15.5 Hz, 1H), 3.48 (d, J=15.5 Hz, 1H), 3.66-4.09 (m, 2H), 4.14 (dd, J=8.8 & 11.1 Hz, 1H), 4.28 (dd, J=4.4 & 11.1 Hz, 1H), 4.94 (d, J=9.8 HZ, 0.8H, rotomer), 5.01 (d, J=9.2 Hz, 0.2H, rotomer), 5.11 (d, J=51 Hz, 0.2H, rotomer), 5.50 (d, J=51 Hz, 0.8H, rotomer), 7.93 (s, 1H), 8.05 (s, 1H); m/z (M+1): 363.2.

Example 4

(2S,4S)-4-Fluoro-1-[2-((1S,3R)-1,2,2-trimethyl-3-[1,2,4]triazol-1-yl methylcyclopentylamino)-acetyl]-pyrrolidine-2-carbonitrile methanesulphonate

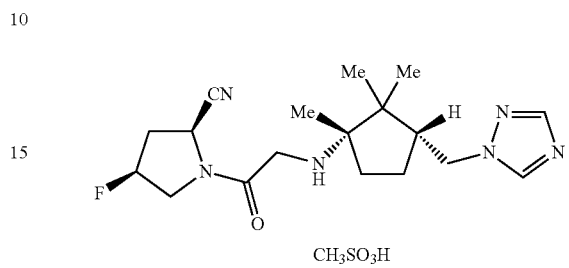

Example 3 (20 mg, 0.005 mmol) was dissolved in ethyl acetate. To this was added (5.3 mg, 0.005 mmol) methanesulfonic acid diluted in ethyl acetate and stirred for 2 h. The solid that separated out was decanted, washed with ethyl acetate and dried to obtain 22 mg of product as an off-white solid. mp: 167-170° C.; $^1$H NMR (D$_2$O): 400 MHz δ 1.08 (s, 3H), 1.14 (s, 3H), 1.38 (s, 3H), 1.62-1.75 (m, 2H), 1.87-1.89 (m, 1H), 2.09-2.11 (m, 1H), 2.49-2.52 (m, 2H), 2.69-2.72 (m, 1H), 2.80 (s, 3H), 3.77-3.79 (dd, 1H), 3.92-4.12 (m, 2H), 4.26-4.28 (m, 2H), 4.50-4.59 (m, 1H), 5.08 (d, J=9.3 Hz, 0.8H rotomer)-5.25 (d, J=9.1 Hz, 0.2H rotomer), 5.50 (d, J=50.8 Hz, 0.211 rotomer) 5.51 (d, J=50.8 Hz, 0.8H rotomer), 8.06 (s, 1H), 8.48 (s, 1H) m/z (M+1): 363.2.

Example 5

(2S,4R)-1-(2-((1S,3R)-3-((1H-1,2,4-Triazol-1-yl)methyl)-1,2,2-trimethyl cyclopentylamino)acetyl)-4-fluoropyrrolidine-2-carbonitrilemethanesulfonate

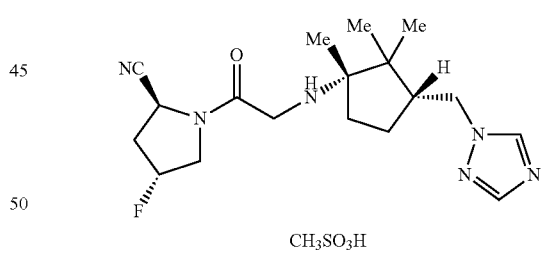

Coupling reaction of example 3, step 1 intermediate (0.048 g, 0.196 mmol) and intermediate 22 (0.037 g, 0.196 mmol), in presence of K$_2$CO$_3$ (0.108 g, 0.78 mmol) and KI (0.016 g, 0.098 mmol) in 2 mL of DMSO as described in step 3 of example 1 afforded 20 mg of product as an off-white solid. The product (20 mg, 0.005 mmol) was dissolved in ethyl acetate. To this methanesulfonic acid (5.3 mg, 0.005 mmol) diluted in ethyl acetate was added and stirred for 2 h. The solid that separated out was decanted washed with ethyl acetate and dried. (0.025 g), White hygroscopic solid. $^1$H NMR (400 MHz, D$_2$O) δ ppm: 0.92 (s, 3H), 1.05 (s, 3H), 1.25 (s, 3H), 1.53-1.62 (m, 2H), 1.71-1.76 (m, 1H), 1.94-1.99 (m, 1H), 2.39-2.42 (m, 2H), 2.67 (s, 3H), 2.7-2.74 (m, 1H), 3.69-3.91 (m, 2H), 4.0-4.13 (m, 2H), 4.26-4.31 (m, 1H), 4.32-4.35 (dd, 1H), 4.85 (d, J=8.5 Hz, 0.8H rotomer), 5.1 (d, J=8.4 Hz, 0.2H rotomer), 5.25 (d, J=51.3, 0.2H rotomer), 5.30 (d, J=51, 0.8H rotomer), 7.96 (s, 1H), 8.4 (s, 1H). m/z (M+H): 363.2.

Example 6

(S)-1-(2-((1S,3R)-3-((1H-1,2,4-Triazol-1-yl)methyl)-1,2,2-trimethyl cyclopentylamino)acetyl)pyrrolidine-2-carbonitrile

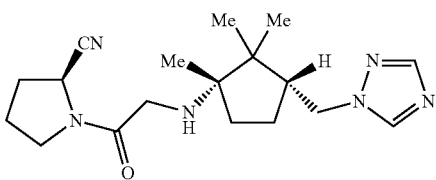

Coupling reaction of Example 3 step 1 intermediate (0.048 g, 0.229 mmol) and intermediate-21 (0.039 g, 0.229 mmol), in presence of $K_2CO_3$ (0.108 g, 0.78 mmol) and KI (0.016 g, 0.098 mmol) in 2 mL of DMSO as described in step-3 of Example-1 afforded 10 mg of product as off-white sticky mass. $^1$H NMR (400 MHz, CDCl$_3$) δ ppm: 0.94 (s, 3H), 0.96 (s, 3H), 1.06 (s, 3H), 1.37-1.42 (m, 1H), 1.6-1.71 (m, 3H), 2.16-2.42 (m, 5H), 3.33-3.62 (m, 4H), 4.06-4.12 (m, 1H), 4.24-4.29 (m, 1H), 4.79-4.77 (m, 1H), 8.05 (s, 1H), 8.06 (s, 1H). m/z (M+H): 345.2.

Example 7

(S)-1-(2-((1S,3R)-3-((1H-1,2,4-Triazol-1-yl)methyl)-1,2,2-trimethyl cyclopentylamino)acetyl)pyrrolidine-2-carbonitrile methanesulfonate

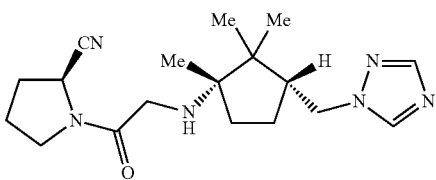 [SMILES: CC1(C)[C@H](Cn2cncn2)CC[C@]1(C)NCC(=O)N1CCC[C@H]1C#N]

Mesylate salt

Example 6 (25 mg, 0.072 mmol) was dissolved in ethyl acetate. To this was added a solution of methanesulfonic acid (6.8 mg, 0.072 mmol) in ethyl acetate (1 mL) and stirred for 2 h. The separated solid was decanted, washed with ethyl acetate and dried to obtain title compound 25 mg as white solid. Melting point: 150-154° C., $^1$H NMR (400 MHz, D$_2$O) δ ppm: 1.08 (s, 3H), 1.14 (s, 3H), 1.37 (s, 3H), 1.66-1.78 (m, 2H), 1.86-1.87 (m, 1H), 2.08-2.09 (m, 1H), 2.16-2.22 (m, 2H), 2.31-2.37 (m, 2H), 2.51-2.55 (m, 1H), 2.81 (s, 3H) 3.52-3.56 (m, 1H), 3.68-3.71 (m, 1H), 3.96-4.0 (m, 1H), 4.13-4.19 (m, 1H), 4.22-4.25 (, 1H), 4.39-4.44 (m, 1H), 8.07 (s, 1H), 8.48 (s, 1H), m/z (M+H): 345.2.

Example 8

(S)-1-(2-((1R,3S)-3-((1H-1,2,4-Triazol-1-yl)methyl)-1,2,2-trimethyleyclopentylamino)acetyl)pyrrolidine-2-carbonitrile

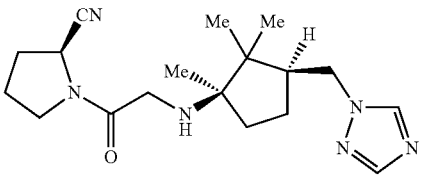

Intermediate 21 (0.01 g, 0.06 mmol) was added to a stirred suspension of step 2 intermediate of Example 1 (0.020 g, 0.08 mmol), $K_2CO_3$, (0.033 g, 0.239 mmol), KI (0.01 g, 0.06 mmol) in 2 mL THF and reaction mixture was stirred at room temperature for 24 h. After completion of the reaction, the reaction mixture was diluted with water and extracted with ethyl acetate. The organic layer was dried over anhydrous $Na_2SO_4$ and concentrated under reduced pressure. The crude product was purified by column chromatography using 0.5% methanol in dichloromethane to afford 8 mg product as a semisolid. IR (KBr): 2242 and 1654 cm$^{-1}$; $^1$H NMR (CDCl$_3$): 400 MHz δ 0.93 (s, 3H), 0.97 (s, 3H), 1.04 (s, 3H), 1.35-1.45 (m, 2H), 1.62-1.68 (m, 3H), 2.17-2.30 (m, 4H), 2.33-2.42 (m, 1H), 3.35-3.45 (m, 3H), 3.55-3.60 (m, 1H), 4.05-4.1 (m, 1H), 4.26 (dd, J=4.4 & 13.6 Hz, 1H), 4.76 (m, 1H), 7.93 (s, 1H), 8.06 (s, 1H); m/z (M+1): 345.1.

Example 9

(S)-1-(2-((1R,3S)-3-((1H-1,2,4-Triazol-1-yl)methyl)-1,2,2-trimethylcyclopentylamino)acetyl)pyrrolidine-2-carbonitrilemethanesulfonate

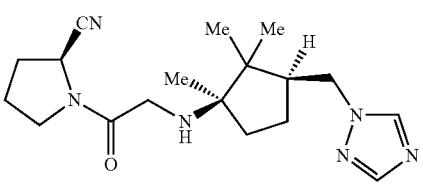 [SMILES: CC1(C)[C@@H](Cn2cncn2)CC[C@@]1(C)NCC(=O)N1CCC[C@H]1C#N]

CH$_3$SO$_3$H

To a solution of example 8 (0.022 g, 0.063 mmol) in acetone, methanesulphonic acid (0.0058 g. 0.0607 mmol) was added and stirred for 3 h to give a white precipitate. The precipitate was allowed to settle, the solvent was decanted and residue dried under vacuum to afford the title compound as off white solid. 0.025 g. mp: 150-155° C.; IR (KBr): 2246 & 1663 cm$^{-1}$; $^1$H NMR (D$_2$O): 400 MHz δ 1.10 (s, 3H), 1.15 (s, 3H), 1.37 (s, 3H), 1.66-1.75 (m, 2H), 1.86-1.90 (m, 1H), 2.10-2.23 (m, 3H), 2.33-2.36 (m, 2H), 2.52-2.56 (m, 1H), 2.81 (s, 3H), 3.54-3.58 (m, 1H), 3.68-3.72 (m, 1H), 4.02 (d, J=28.6, 1H), 4.12 (d, J=16.2, 1H), 4.21-4.24 (m, 1H), 4.39-4.45 (dd, J=4.4 & 13.6 1H), 4.76 (m, 1H), 8.07 (s, 1H), 8.49 (s, 1H); m/z (M+1): 345.2.

Example 10

(2S,4S)-1-(2-((1R,3S)-3-((2H-1,2,3-Triazol-2-yl)methyl)-1,2,2-trimethylcyclopentylamino)acetyl)-4-fluoropyrrolidine-2-carbonitrile

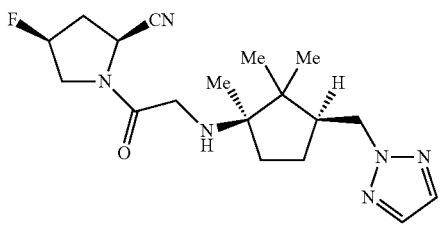 [SMILES: CC1(C)[C@@H](Cn2nccn2)CC[C@@]1(C)NCC(=O)N1C[C@@H](F)C[C@H]1C#N]

Step 1: tert-Butyl (1R,3S)-3-((2H-1,2,3-triazol-2-yl)methyl)-1,2,2-trimethyl cyclopentylcarbamate

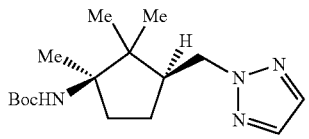 [SMILES: CC(C)(C)OC(=O)N[C@]1(C)CC[C@H](Cn2nccn2)C1(C)C]

To a suspension of 1H-1,2,3-triazole (0.5 g, 7.2 mmol) and K₂CO₃ (1.5 g, 10.86 mmol) in 5 mL of DMF, intermediate 3 (2.0 g, 6.0 mmol) was added and the reaction mixture was stirred at 80-85° C. for five hours. The reaction mixture was brought to room temperature and diluted with water, extracted with ethyl acetate; the combined organic extracts were washed with water and dried over anhydrous Na₂SO₄ and concentrated under reduced pressure to obtain isomeric mixture of products. The mixture was separated by silica column chromatography using methanol in dichloromethane.

The less polar compound was characterized as

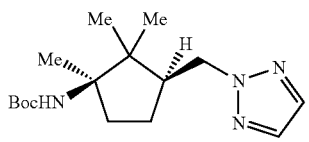 [SMILES: CC(C)(C)OC(=O)N[C@]1(C)CC[C@H](Cn2nccn2)C1(C)C]

Off white sticky mass, ¹H NMR (400 MHz, CDCl₃) δ ppm: 0.85 (s, 3H), 0.95 (s, 3H), 1.27 (s, 3H), 1.47 (s, 9H), 1.50-1.53 (m, 1H), 1.60-1.64 (m, 1H), 1.95-1.99 (m, 2H), 2.51-2.55 (m, 1H), 4.28-4.34 (m, 1H), 4.48-4.50 (m, 1H), 4.51 (s, 1H), 7.58 (s, 2H), m/z (M−100)+H, 209.2.

The polar compound was characterized as

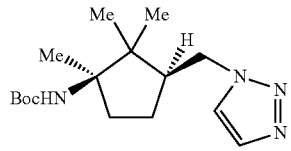 [SMILES: CC(C)(C)OC(=O)N[C@]1(C)CC[C@H](Cn2ccnn2)C1(C)C]

Off white sticky mass, m/z (M−100)+H: 209.2.

Step 2: (1R,3S)-3-((2H-1,2,3-Triazol-2-yl)methyl)-1,2,2-trimethyl cyclopentan aminehydrochloride

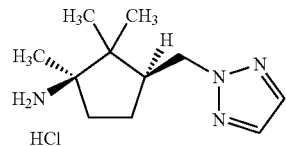

A solution of saturated HCl in ethyl acetate (2 mL) was added to a solution of the step 1 intermediate (0.130 g, 0.625 mmol) in ethyl acetate at 0° C. and reaction mixture was stirred at room temperature for 2 h. The volatiles were removed under reduced pressure to afford desired product. White solid, ¹H NMR (400 MHz, DMSO) δ ppm: 0.85 (s, 3H), 0.95 (s, 3H), 1.20 (s, 3H), 1.51-1.68 (m, 3H), 1.90-1.96 (m, 1H), 2.39-2.43 (m, 1H), 4.29-4.34 (m, 1H), 4.48-4.53 (m, 1H), 7.77 (s, 2H), 8.00 (bs, 3H), m/z (M+1): 209.2.

Step 3: (2S,4S)-1-(2-((1R,3S)-3-((2H-1,2,3-triazol-2-yl)methyl)-1,2,2-trimethyl cyclopentylamino)acetyl)-4-fluoropyrrolidine-2-carbonitrile

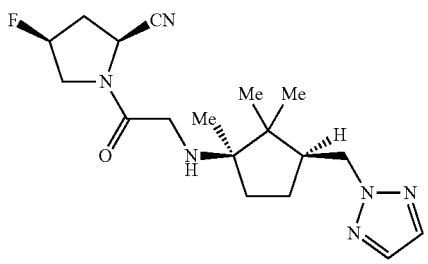 [SMILES: CC1(C)[C@@H](Cn2nccn2)CC[C@@]1(C)NCC(=O)N1C[C@@H](F)C[C@H]1C#N]

Coupling reaction of less polar step 2 intermediate (0.048 g, 0.196 mmol) and intermediate-20 (0.037 g, 0.196 mmol), in presence of K₂CO₃ (0.108 g, 0.78 mmol) and KI (0.016 g, 0.098 mmol) in 2 mL of DMSO as described in step-3 of Example-1 afforded the desired product solid as white solid. Yield: 0.025 g, Mp: 84-87° C. ¹H NMR (400 MHz, CDCl₃) δ ppm: 0.87 (s, 3H), 0.98 (s, 3H), 1.07 (s, 3H), 1.49-1.52 (m, 1H), 1.63-1.71 (m, 3H), 2.25-2.41 (m, 1H), 2.50-2.55 (m, 1H), 2.64-2.75 (m, 1H), 3.34-3.52 (m, 2H), 3.52-3.78 (m, 1H), 3.88-3.97 (m, 1H), 4.38-4.49 (m, 1H), 4.51-4.53 (m, 1H), 4.93-4.96 (d, J=9.2 Hz, 0.8H), 5.18 (d, J=9.2 Hz, 0.2H), 5.32 (d, J=50 Hz, 0.2H), 5.49 (d, 0.8H, J=50 Hz), 7.57 (s, 2H). m/z (M+H): 363.2.

Example 11

(2S,4S)-1-(2-((1R,3S)-3-((1H-1,2,3-Triazol-1-yl)methyl)-1,2,2-trimethylcyclopentylamino)acetyl)-4-fluoropyrrolidine-2-carbonitrile

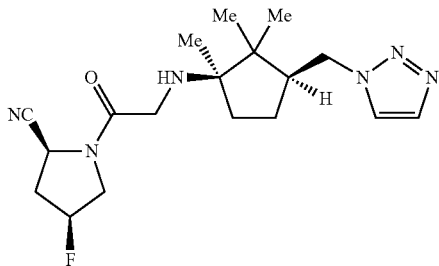 [SMILES: CC1(C)[C@@H](Cn2ccnn2)CC[C@@]1(C)NCC(=O)N1C[C@@H](F)C[C@H]1C#N]

Step-1: (1R,3S)-1,2,2-Trimethyl-3-(1H-1,2,3-triazol-1-ylmethyl)cyclopentanamine

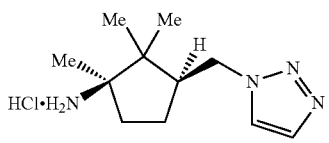

A solution of saturated HCl in ethyl acetate (2 mL) was added to a solution of the more polar step 1 intermediate from example 9 in ethyl acetate and the reaction mixture was stirred at room temperature for two hours. The volatiles were removed under reduced pressure to afford the desired product as white solid, $^1$H NMR (400 MHz, DMSO) δ ppm: 0.86 (s, 3H), 0.88 (s, 3H), 1.19 (s, 3H), 1.52-1.54 (m, 2H), 1.66-1.68 (m, 1H), 1.90-1.94 (m, 1H), 2.33-2.36 (m, 1H), 4.25-4.31 (m, 1H), 4.46-4.50 (m, 1H), 7.77 (s, 1H), 8.00 (bs, 3H), 8.16 (s, 1H), m/z (M+1): 209.2.

Step-2: (2S,4S)-1-(2-((1R,3S)-3-((1H-1,2,3-triazol-1-yl)methyl)-1,2,2-trimethyl cyclopentylamino)acetyl)-4-fluoropyrrolidine-2-carbonitrile

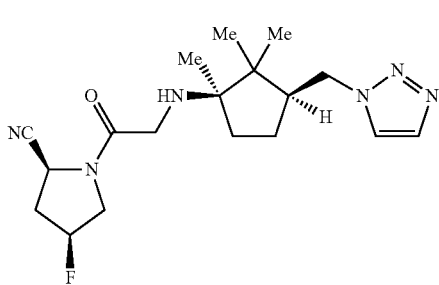 [SMILES: CC1(C)[C@@H](Cn2ccnn2)CC[C@@]1(C)NCC(=O)N1C[C@@H](F)C[C@H]1C#N]

Coupling reaction of step-1 intermediate (0.024 g, 0.098 mmol) and intermediate 20 (0.037 g, 0.098 mmol), in presence of K$_2$CO$_3$ (0.108 g, 0.78 mmol) and KI (0.016 g, 0.098 mmol) in 2 mL of DMSO as described in step-3 of Example-1 afforded the desired product 0.007 g as white solid. $^1$H NMR (400 MHz, CDCl$_3$) δ ppm: 0.93 (s, 3H), 0.96 (s, 3H), 0.99 (s, 3H), 1.49-1.59 (m. 1H), 1.59-1.66 (m, 2H), 1.60-1.78 (m, 3H), 2.38-2.46 (m, 2H), 2.65-2.73 (m, 1H), 3.3-3.52 (m, 2H), 3.68-3.88 (m, 1H), 3.99-3.94 (m, 1H), 4.23-4.29 (m, 1H), 4.49-4.54 (m, 1H), 4.94 (d, J=9.2 Hz, 0.8H), 5.18 (d, 0.2H, J=9.2 Hz), 5.35 (d, J=51.2 Hz, 0.2H), 5.5 (m, J=51.2 Hz, 0.8H). m/z (M+H): 363.2.

Example 12

(2S,4S)-1-(2-((1S,3R)-3-((2H-1,2,3-Triazol-2-yl)methyl)-1,2,2-trimethylcyclopentylamino)acetyl)-4-fluoropyrrolidine-2-carbonitrile

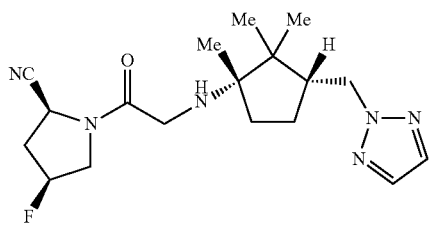 [SMILES: CC1(C)[C@H](Cn2nccn2)CC[C@]1(C)NCC(=O)N1C[C@@H](F)C[C@H]1C#N]

Prepared similar to example 10 using intermediate 10. White solid 0.045 g. Melting point: 142-144° C. $^1$H NMR (400 MHz, CDCl$_3$) δ ppm: 0.87 (s, 3H), 0.98 (s, 3H), 1.07 (s, 3H), 1.46-1.52 (m, 1H), 1.56-1.66 (m, 2H), 1.68-1.72 (m, 1H), 2.25-2.41 (m, 1H), 2.52-2.55 (m, 1H), 2.64-2.68 (m, 1H), 3.30-3.34 (d, 1H), 3.45-3.49 (m, 1H), 3.56-3.6 (m, 0.5H), 3.68-3.71 (m, 0.5H), 3.79-3.92 (m, 1H), 4.36-4.42 (m, 1H), 4.5-4.53 (m, 1H), 4.95 (d, J=9.3 Hz, 0.8H), 5.20 (d. J=9.3 Hz, 0.2H), 5.34 (d, J=51.2 Hz, 0.2H), 5.45 (m, J=51.2 Hz, 0.8H), 7.57 (s, 2H). m/z (M+H): 363.2.

Example 13

(2S,4S)-1-(2-((1S,3R)-3-((1H-1,2,3-Triazol-1-yl)methyl)-1,2,2-trimethylcyclopentylamino)acetyl)-4-fluoropyrrolidine-2-carbonitrilemethane sulfonate

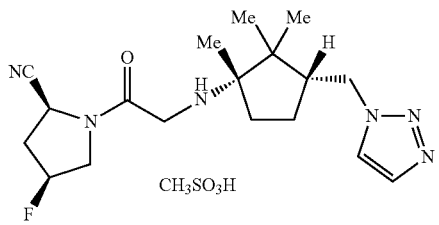

Prepared similar to example 11 using intermediate 10. The product (0.026 g, 0.071 mmol) obtained was dissolved in ethyl acetate. To this was added methanesulfonic acid (0.0062 g, 0.06 mmol) in ethyl acetate and stirred for 2 h. The solid that separated was decanted washed with ethyl acetate and dried to obtain the title 0.02 g compound as off-white hygroscopic solid. $^1$H NMR (400 MHz, CDCl$_3$) δ ppm: 1.05 (s, 3H), 1.16 (s, 3H), 1.35 (s, 3H), 1.62-1.76 (m. 2H), 1.8-1.87 (m, 1H), 2.08-2.15 (m, 1H), 2.45-2.55 (m, 2H), 2.6-2.7 (m, 1H), 2.81 (s, 3H), 3.91-3.94 (m, 1H), 4.02-4.07 (m, 1H), 4.13-4.15 (m, 1H), 4.2-4.24 (m. 1H), 4.38-4.44 (m, 1H), 4.61-4.66 (m, 1H), 5.08 (d, J=9.4 Hz, 0.8H), 5.22 (d, J=9.4 Hz, 0.2H), 5.5 (d, J=50.5 Hz, 0.2H), 5.51 (d, J=50.5 Hz, 0.8H), 7.81 (s, 1H), 8.02 (s, 1H). m/z (M+H): 363.2.

Example 14

(2S,4S)-4-Fluoro-1-(2-((1R,3S)-1,2,2-trimethyl-3-(piperidine-1-carbonyl)cyclo pentylamino)acetyl)pyrrolidine-2-carbonitrile

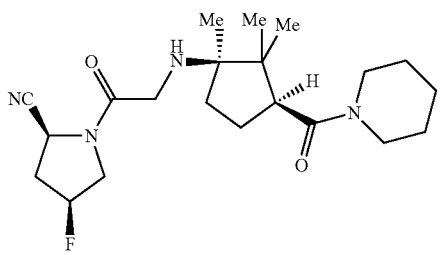 [SMILES: CC1(C)[C@@H](C(=O)N2CCCCC2)CC[C@@]1(C)NCC(=O)N1C[C@@H](F)C[C@H]1C#N]

Step-1: ((1S,3R)-3-Amino-2,2,3-trimethylcyclopentyl)(piperidin-1-yl)methanone hydrochloride)

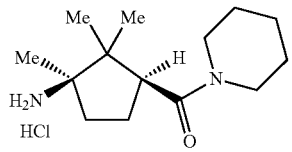 [SMILES: Cl ; CC1(C)[C@@H](C(=O)N2CCCCC2)CC[C@@]1(C)N]

A mixture of intermediate 6 (0.27 g. 1.0 mmol), 1,1'-Carbonyldiimidazole (0.19 g, 1.2 mmol) and piperidine (0.10 g, 1 mmol) in dichloromethane was stirred at room temperature for 8 h. The reaction mixture was diluted with dichloromethane, washed with water, dried over anhydrous Na$_2$SO$_4$ and concentrated. Crude material was purified by column chromatography to obtain tert-butyl (1R,3S)-1,2,2-trimethyl-3-(piperidine-1-carbonyl)cyclopentylcarbamate. To the solution of tert-butyl (1R,3S)-1,2,2-trimethyl-3-(piperidine-1-carbonyl)cyclopentylcarbamate in ethyl acetate was added hydrochloride solution in ethylacetate and stirred for 2 h to afford ((1S,3R)-3-amino-2,2,3-trimethylcyclopentyl)(piperidin-1-yl)methanone hydrochloride. $^1$H NMR (400 MHz, D$_2$O) δ ppm: 0.98 (s, 3H), 1.11 (s, 3H), 1.31 (s, 3H), 1.54-1.60 (m, 6H), 1.94-2.20 (m, 4H), 3.47-3.48 (m, 1H), 3.54-3.57 (m, 2H), 3.65-3.66 (m, 2H). m/z (M+H): 239.2.

Step 2: (2S,4S)-4-Fluoro-1-(2-((1R,3S)-1,2,2-trimethyl-3-(piperidine-1-carbonyl)cyclopentylamino)acetyl)pyrrolidine-2-carbonitrile

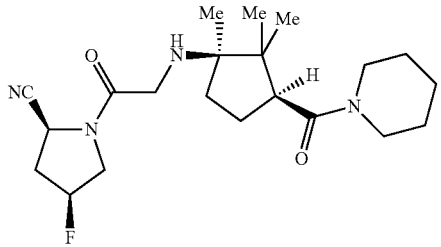 [SMILES: CC1(C)[C@@H](C(=O)N2CCCCC2)CC[C@@]1(C)NCC(=O)N1C[C@@H](F)C[C@H]1C#N]

Intermediate 20 (0.040 g, 0.21 mmol) was added to a stirred suspension of step-1 intermediate (0.050 g, 0.21 mmol), K$_2$CO$_3$, (0.15 g, 1.05 mmol), KI (0.034 g, 0.21 mmol) in 2 mL DMSO. The reaction mixture was stirred at room temperature for 24 h. After completion of the reaction, the reaction mixture was diluted with water and extracted with ethyl acetate. The organic layer was dried over anhydrous Na$_2$SO$_4$ and concentrated under reduced pressure. The crude product was purified by column chromatography using methanol in dichloromethane to obtain 0.01 g of desired compound as semi-solid. $^1$H NMR (400 MHz, CDCl$_3$) δ ppm: 0.85 (s, 3H), 1.04 (s, 6H), 1.53-1.72 (m, 8H), 1.92-1.94 (m, 1H), 2.15-2.4 (m; 2H), 2.63-2.75 (m, 1H), 3.01-3.05 (m, 1H), 3.46-3.61 (m, 8H), 4.2-4.3 (m, 1H), 4.97 (d, J=9.2 Hz, 0.8H), 5.30 (d, J=51.2 Hz, 0.2H), 5.32 (d, J=51.2 Hz, 0.8), 5.7 (d, J=9.2 Hz, 0.2H). m/z (M+H): 393.3.

Example 15

(2S,4S)-4-Fluoro-1-(2-((1R,3S)-3-((4-(hydroxymethyl)-1H-1,2,3-triazol-1-yl)methyl)-1,2,2-trimethyleyclopentylamino)acetyl)pyrrolidine-2-carbonitrile

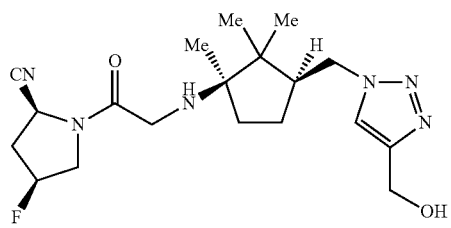 [SMILES: CC1(C)[C@@H](Cn2cc(CO)nn2)CC[C@@]1(C)NCC(=O)N1C[C@@H](F)C[C@H]1C#N]

Step 1: tert-Butyl (1R,3S)-3-((4-(hydroxymethyl)-1H-1,2,3-triazol-1-yl)methyl)-1,2,2-trimethylcyclopentylcarbamate

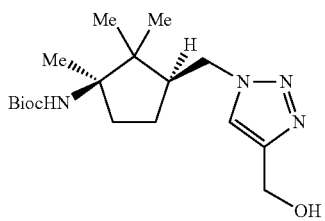

A suspension of intermediate 4 (0.25 g, 0.88 mmol), CuI (0.19 g, 0.88 mmol) in diisopropylethylamine (3.65 mL), was added propargyl alcohol (0.051 mL, 0.88 mmol) and stirred for 48 h at room temperature. The excess diisopropylethylamine was decanted and dried. The residue was purified by silica column using methanol in dichloromethane. $^1$H NMR (400 MHz, CDCl$_3$) δ ppm: 0.81 (s, 3H), 0.92 (s, 3H), 1.22 (s, 3H), 1.37 (s, 9H), 1.45 (d, 2H), 1.71 (m, 1H), 1.95 (m, 1H), 2.24 (m, 2H), 4.15 (t, 1H), 4.39 (m, 1H), 4.5 (s, 2H), 5.13 (bs, 1H), 6.36 (s, 1H), 7.98 (s, 1H). m/z (M+H): 339.1.

Step 2: (1-(((1S,3R)-3-Amino-2,2,3-trimethylcyclopentyl)methyl)-1H-1,2,3-triazol-4-yl)methanol hydrochloride

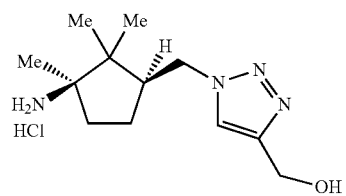 [SMILES: Cl ; CC1(C)[C@@H](Cn2cc(CO)nn2)CC[C@@]1(C)N]

A solution of saturated HCl in ethyl acetate (2 mL) was added to a solution of the step-1 intermediate (0.25 g, 0.7 mmol) in ethyl acetate and the reaction mixture was stirred at room temperature for two hours. The solid separated was washed with ethyl acetate to afford desired product. $^1$H NMR (400 MHz, d$_6$-DMSO) δ ppm: 0.93 (s, 3H), 1.03 (s, 3H), 1.32 (s, 3H), 1.64 (m, 1H), 1.74 (m, 1H), 1.83 (m, 1H), 2.05 (m, 1H), 2.48 (m, 1H), 4.36 (t, 1H), 4.59 (m, 1H), 4.70 (s, 2H). m/z (M+H): 239.2.

Step 3: (2S,4S)-4-Fluoro-1-(2-(((1R,3S)-3-((4-(hydroxymethyl)-1H-1,2,3-triazol-1-yl)methyl)-1,2,2-trimethylcyclopentylamino)acetyl)pyrrolidine-2-carbonitrile

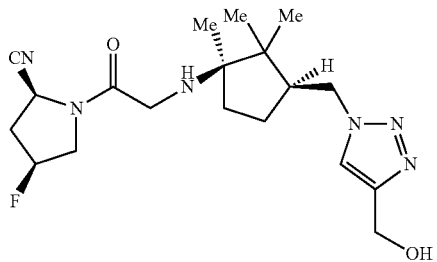 [SMILES: CC1(C)[C@@H](Cn2cc(CO)nn2)CC[C@@]1(C)NCC(=O)N1C[C@@H](F)C[C@H]1C#N]

Intermediate 20 (0.062 g, 0.33 mmol) was added to a stirred suspension of step-2 intermediate (0.10 g, 0.36 mmol), K$_2$CO$_3$ (0.20 g, 1.46 mmol), KI (0.03 g, 0.18 mmol) in 2 mL DMSO. The reaction mixture was stirred at room temperature for 24 hours. After completion of the reaction, the reaction mixture was diluted with water and extracted with ethyl acetate. The organic layer was dried over anhydrous Na$_2$SO$_4$ and concentrated under reduced pressure. The crude product was purified by column chromatography using methanol in dichloromethane to yield 0.02 g title compound as off white solid. Melting point: 240-279° C. $^1$H NMR (400 MHz, CDCl$_3$) δ ppm: 0.93 (s, 3H), 0.98 (s, 3H), 1.04 (s, 3H), 1.41-1.73 (m, 4H), 2.35-2.38 (m, 2H), 2.65-2.73 (m, 1H), 3.34-3.51 (m, 2H), 3.63-3.77 (m, 2H), 3.88-3.94 (m, 1H), 4.21-4.49 (m, 2H), 4.79 (s, 2H), 4.94 (d, J=9.2 Hz, 0.8H), 5.02 (d, J=9.2 Hz, 0.2H), 5.35 (d, J=51 Hz, 0.2H), 5.4 (d, J=51 Hz, 0.8H), 7.52 (s, 1H). m/z (M+H): 393.2.

Example 16

(2S,4S)-4-Fluoro-1-(2-(((1S,3R)-3-((4-(hydroxymethyl)-1H-1,2,3-triazol-1-yl)methyl)-1,2,2-trimethylcyclopentylamino)acetyl)pyrrolidine-2-carbonitrile

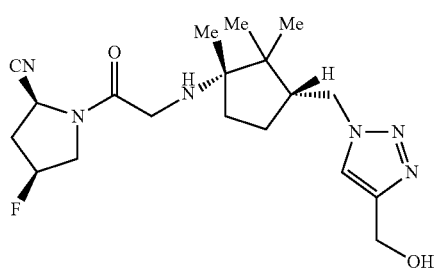 [SMILES: CC1(C)[C@H](Cn2cc(CO)nn2)CC[C@]1(C)NCC(=O)N1C[C@@H](F)C[C@H]1C#N]

Prepared according to procedure described in Example 15 using intermediate 11. 0.14 g; Melting point: 76-78° C. $^1$H NMR (400 MHz, CDCl$_3$) δ ppm: 0.93 (s, 3H), 0.96 (s, 3H), 1.06 (s, 3H), 1.41-1.70 (m, 4H), 2.35-2.38 (m, 2H), 2.69-2.73 (m, 1H), 3.29-3.96 (m, 5H), 4.29-4.45 (m, 2H), 4.79 (s, 2H) 4.94 (d, J=9.2 Hz, 0.8H), 5.02 (d, J=9.2 Hz, 0.2H), 5.32 (d, J=51 Hz, 0.2H), 5.4 (d, J=51 Hz, 0.8H), 7.52 (s, 1H). m/z (M+H): 393.2.

Example 17

N-(((1S,3R)-3-(2-((2S,4S)-2-Cyano-4-fluoropyrrolidin-1-yl)-2-oxoethylamino)-2,2,3-trimethylcyclopentyl)methyl)methanesulfonamide

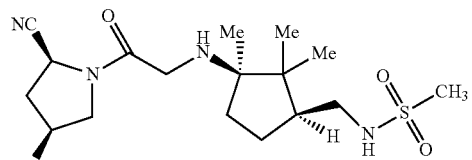

Step-1: N-{[(1S,3R)-3-tert-Butoxycarbonylamino-2,2,3-trimethylcyclopentyl]methyl}methanesulfonamide

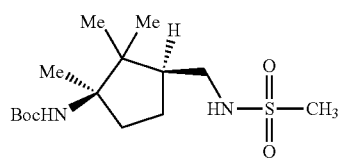 [SMILES: CC(C)(C)OC(=O)N[C@]1(C)CC[C@H](CNS(C)(=O)=O)C1(C)C]

To a solution of intermediate 5 (0.22 g, 0.85 mmol) in dichloromethane, triethylamine (0.11 g, 1.06 mmol) was added followed by methane sulfonyl chloride (0.2 g, 0.91 mmol) maintaining the temperature at 0° C. The reaction mixture was stirred for another 30 minutes. After adding 20 mL water, the reaction mixture was extracted with dichloromethane. Organic layer was separated, dried with anhydrous Na₂SO₄ and concentrated. The residue was purified by column chromatography using 20% ethyl acetate in hexane. ¹H NMR (400 MHz, CDCl₃) δ ppm: 0.81 (s, 3H), 1.03 (s, 3H), 1.31 (s, 3H), 1.4 (s, 9H), 1.96 (m, 4H), 2.96 (s, 3H), 3.23 (d, 1H), 4.13 (m, 1H), 4.48 (bs, 1H).

Step 2: N-(((1S,3R)-3-Amino-2,2,3-trimethylcyclopentyl)methyl)methane sulfonamidehydrochloride

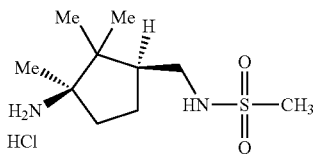

A solution of saturated HCl in ethyl acetate (2 mL) was added to a solution of the step 1 intermediate (0.09 g, 0.27 mmol) in ethyl acetate and the reaction mixture was stirred at room temperature for two hours. The solid that separated out was washed with ethyl acetate to afford 60 mg of desired product. ¹H NMR (400 MHz, d₆-DMSO) δ ppm: 0.81 (s, 3H), 0.99 (s, 3H), 1.81 (s, 3H), 1.71 (m, 1H), 1.88 (m, 3H), 2.71 (m, 1H), 2.88 (s, 3H), 3.1 (m, 1H), 6.9 (bs, 1H), 7.76 (bs, 3H).

Step 3: N-(((1S,3R)-3-(2-((2S,4S)-2-Cyano-4-fluoropyrrolidin-1-yl)-2-oxoethyl amino)-2,2,3-trimethylcyclopentyl)methyl)methanesulfonamide

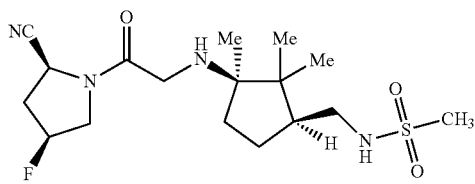 [SMILES: CC1(C)[C@@H](CNS(C)(=O)=O)CC[C@@]1(C)NCC(=O)N1C[C@@H](F)C[C@H]1C#N]

To a stirred suspension of the step-2 intermediate (0.06 g, 0.22 mmol), K₂CO₃ (0.11 g, 0.8 mmol) and KI (0.003 g, 0.02 mmol) in, 1 mL of DMSO, intermediate 20 (0.038 g, 0.22 mmol) was added. The reaction mixture was stirred for 24 hours under nitrogen atmosphere. After completion of the reaction; it was diluted with ethyl acetate and water. The layers were separated and the aqueous layer was washed twice with ethyl acetate. The combined organic layers was dried over anhydrous Na₂SO₄, concentrated and purified by chromatography to yield 0.018 g product as off White solid. Melting point: 157-160° C. ¹H NMR (400 MHz, CDCl₃) δ ppm: 0.8 (s, 3H), 0.9 (s, 3H), 1.07 (s, 3H), 1.63-1.77 (m, 2H), 1.89-1.93 (m, 1H), 2.03-2.05 (m, 1H), 2.2-2.28 (m, 1H), 2.3-2.45 (m, 1H), 2.62-2.63 (m, 1H), 2.79 (s, 3H), 2.88-3.01 (m, 2H), 3.3-3.5 (m, 2H), 3.65-3.75 (m, 2H), 3.92-4.01 (m, 1H), 4.93 (d, J=8.8, 0.2H), 5.02 (d, J=8.8, 0.8H), 5.3 (d, J=51.2, 0.8H), 5.35 (d, J=51.2, 0.2H) m/z (M+H): 469.2.

Example 18

N-(((1R,3S)-3-(2-((2S,4S)-2-Cyano-4-fluoropyrrolidin-1-yl)-2-oxoethylamino)-2,2,3-trimethylcyclopentyl)methyl)methanesulfonamide Prepared using intermediate 12 according to procedure described in Example 17

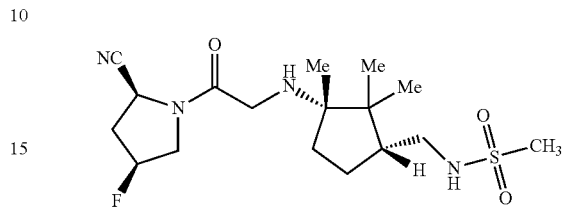

0.047 g, off-white solid. Melting point: 154-157° C. ¹H NMR (400 MHz, CDCl₃) δ ppm: 0.95 (s, 6H), 1.2 (s, 3H), 1.63-1.69 (m, 4H), 1.86-1.88 (m, 1H), 2.03-2.05 (m, 1H), 2.35-2.45 (m, 1H), 2.57-2.65 (m, 1H), 2.82 (s, 3H), 2.92-3.05 (m, 2H), 3.21-3.33 (m, 2H), 3.79-3.9 (m, 2H), 4.99 (d, J=9.4, 1H), 5.4 (dd, 54.4, 1H). m/z (M+H): 389.2.

Example 19

N-(((1S,3R)-3-(2-((2S,4S)-2-Cyano-4-fluoropyrrolidin-1-yl)-2-oxoethylamino)-2,2,3-trimethylcyclopentyl)methyl)-4-fluorobenzenesulfonamide

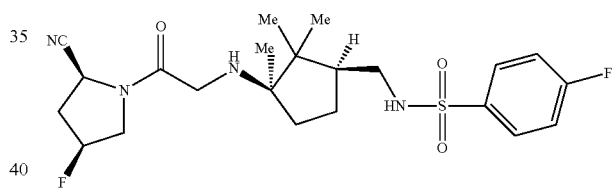

Step-1: tert-Butyl (1R,3S)-3-((4-fluorophenylsulfonamido)methyl)-1,2,2-trimethyl cyclopentylcarbamate

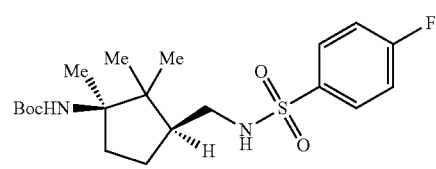 [SMILES: CC(C)(C)OC(=O)N[C@]1(C)CC[C@H](CNS(=O)(=O)c2ccc(F)cc2)C1(C)C]

To a solution of intermediate 5 (0.2 g, 0.78 mmol) in dichloromethane and triethylamine (0.26 g, 2.57 mmol), 4-fluorobenzenesulfonylchloride (0.13 g. 0.65 mmol) was added and stirred at room temperature for 2 hours. The reaction mixture was diluted with 50 mL dichloromethane; the organic layer was washed with water, dried and concentrated. The residue was purified by column chromatography using ethyl acetate and hexane. ¹H NMR (400 MHz, CDCl₃) δ ppm: 0.73 (s, 6H), 0.95 (s, 3H), 1.41 (s, 9H), 1.82 (m, 2H), 1.91 (m, 2H), 2.76 (m, 1H), 3.05 (d, 1H), 4.31 (d, 1H), 4.43 (bs, 1H), 7.21 (m, 2H), 7.87 (d, 2H). m/z (M+H): 415.1.

Step 2: N-(((1S,3R)-3-Amino-2,2,3-trimethylcyclopentyl)methyl)-4-fluorobenzene sulfonamide hydrochloride

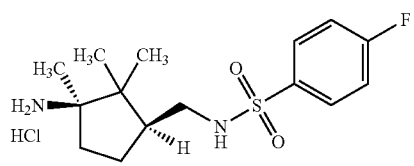 [SMILES: Cl ; CC1(C)[C@@H](CNS(=O)(=O)c2ccc(F)cc2)CC[C@@]1(C)N]

A solution of saturated HCl in ethyl acetate (2 mL) was added to a solution of the step-1 intermediate (0.13 g, 0.31 mmol) in ethyl acetate and the reaction mixture was stirred at room temperature for two hours. The solid that formed was decanted and washed twice with ethyl acetate. $^1$H NMR (400 MHz, d$_6$DMSO) δ ppm: 0.74 (s, 3H), 0.92 (s, 3H), 1.13 (s, 3H), 1.27 (s, 1H), 1.62 (m, 1H), 1.84 (m, 3H), 2.58 (m, 1H), 2.84 (m, 1H), 7.45 (d, 2H), 7.65 (bs, 1H), 7.85 (d, 2H), 7.95 (bs, 3H). m/z (M+H): 315.2.

Step 3: N-(((1S,3R)-3-(2-((2S,4S)-2-Cyano-4-fluoropyrrolidin-1-yl)-2-oxoethyl amino)-2,2,3-trimethylcyclopentyl)methyl)-4-fluorobenzenesulfonamide

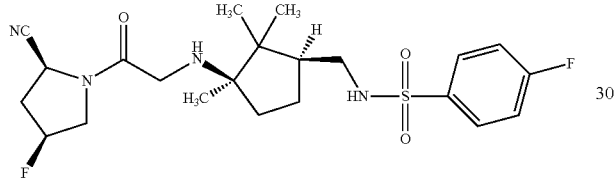

To a stirred suspension of the step-2 intermediate (0.06 g, 0.17 mmol), K$_2$CO$_3$, (0.070 g, 0.5 mmol) and KI (0.028 g, 0.17 mmol) in 1 mL of DMSO, intermediate 20 (0.032 g, 0.17 mmol) was added. The reaction mixture was stirred for 12 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by chromatography to yield 0.017 g of product. $^1$H NMR (400 MHz, CDCl$_3$) δ ppm: 0.58 (s, 3H), 0.85 (s, 3H), 1.07 (s, 3H), 1.14-1.23 (m, 1H), 1.51-1.52 (m, 2H), 1.64-1.79 (m, 2H), 2.55-2.71 (m, 2H), 2.89-2.96 (m, 1H), 3.38-3.99 (m, 5H), 4.5 (d, J=8.2 Hz, 0.2H), 4.95 (d, J=8.2 Hz, 0.8H), 5.41 (d, J=52 Hz, 0.2H), 5.55 (d, J=52 Hz, 0.8H), 7.12-7.16 (m, 2H), 7.76-7.87 (m, 2H). m/z (M+H): 469.2.

Example 20

N-(((1R,3S)-3-(2-((2S,4S)-2-Cyano-4-fluoropyrrolidin-1-yl)-2-oxoethylamino-2,2,3-trimethylcyclopentyl)methyl)-4-fluorobenzenesulfonamide

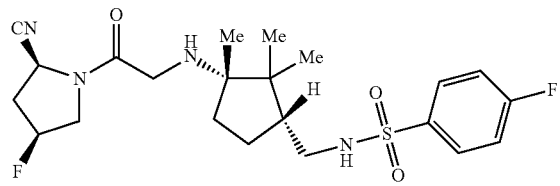

Prepared using intermediate 12 according to procedure described in Example 19. 0.027 g, Off-White solid. Melting point: 75-78° C. $^1$H NMR (400 MHz, CDCl$_3$) δ ppm: 0.68 (s, 3H), 0.88 (s, 3H), 0.99 (s, 3H), 1.62-1.73 (m, 2H), 1.88-2.18 (m, 2H), 2.42-2.65 (m, 3H), 2.92 (m, 1H), 3.25-3.39 (m, 2H), 3.86-3.97 (m, 2H), 5.03 (d, J=12 Hz, 0.2H), 5.04 (d, J=12 Hz, 0.8H), 5.32 (d, J=53.9 Hz, 0.2H), 5.36 (d, J=53.9 Hz, 0.8H), 7.13-7.18 (m, 2H), 7.79-7.83 (m, 2H). m/z (M+H): 469.2.

Example 21

N-(((1S,3R)-3-(2-((2S,4S)-2-Cyano-4-fluoropyrrolidin-1-yl)-2-oxoethylamino)-2,2,3-trimethylcyclopentyl)methyl)-2-fluorobenzamide

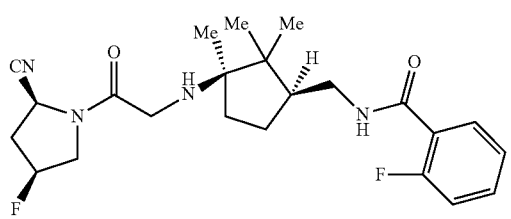 [SMILES: CC1(C)[C@@H](CNC(=O)c2ccccc2F)CC[C@@]1(C)NCC(=O)N1C[C@@H](F)C[C@H]1C#N]

Step 1: tert-Butyl (1R,3S)-3-((2-fluorobenzamido)methyl)-1,2,2-trimethylcyclo pentylcarbamate

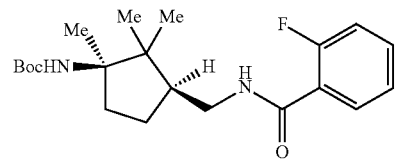 [SMILES: CC(C)(C)OC(=O)N[C@]1(C)CC[C@H](CNC(=O)c2ccccc2F)C1(C)C]

To a solution of intermediate 5 (0.1 g, 0.39 mmol) in dichloromethane and triethylamine (0.13 g, 12.8 mmol), 2-fluorobenzoylchloride (0.05 g. 0.32 mmol) was added and stirred overnight at room temperature. The reaction mixture was diluted with 50 mL dichloromethane; the organic layer was washed with water, dried and concentrated. $^1$H NMR (400 MHz, CDCl$_3$) δ ppm: 0.89 (s; 3H), 1.07 (s, 3H), 1.28 (s, 3H), 1.44 (s, 9H), 2.02 (m, 2H), 3.31 (m, 1H), 3.51 (m, 3H), 3.62 (m, 1H), 7.71 (m, 1H), 7.27 (m, 1H), 7.56 (d, 1H), 8.03 (d, 1H). m/z (M+H-100): 279.2.

Step 2: N-(((1S,3R)-3-Amino-2,2,3-trimethylcyclopentyl)methyl)-2-fluoro benzamidehydrochloride

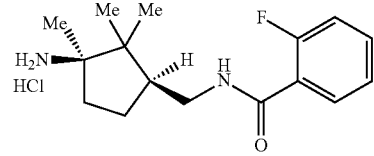 [SMILES: CC1(C)[C@@H](CNC(=O)c2ccccc2F)CC[C@@]1(C)N ; Cl]

A solution of saturated HCl in ethyl acetate (2 mL) was added to a solution of the step-1 intermediate (0.11 g, 2.9 mmol) in ethyl acetate and the reaction mixture was stirred at room temperature for two hours. The solid that separated out was washed with ethyl acetate to afford 50 mg of desired product. $^1$H NMR (400 MHz, $d_6$-DMSO) δ ppm: 0.98 (s, 3H), 0.99 (s, 3H), 1.01 (s, 3H), 1.2 (m, 1H), 1.46 (m, 1H), 1.68 (m, 1H), 1.9 (m, 1H), 3.33 (m, 2H), 7.27 (m, 2H), 7.54 (m, 2H), 8.33 (bs, 3H). m/z (M+H): 279.2.

Step 3: N-(((1S,3R)-3-(2-((2S,4S)-2-Cyano-4-fluoro-pyrrolidin-1-yl)-2-oxoethyl amino)-2,2,3-trimethyl-cyclopentyl)methyl)-2-fluorobenzamide

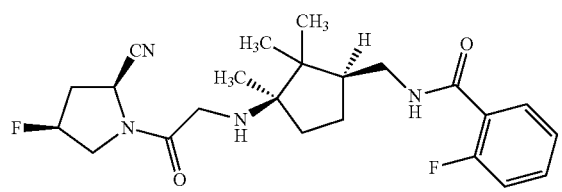 [SMILES: CC1(C)[C@@H](CNC(=O)c2ccccc2F)CC[C@@]1(C)NCC(=O)N1C[C@@H](F)C[C@H]1C#N]

To a stirred suspension of the step-2 intermediate (0.05 g, 0.15 mmol), $K_2CO_3$ (0.088 g, 0.64 mmol) and KI (0.013 g, 0.07 mmol) in 2 mL of DMSO, intermediate-20 (0.03 g, 0.15 mmol) was added. The reaction mixture was stirred for 24 h under nitrogen atmosphere. After completion of the reaction, it was diluted with ethyl acetate and water. The layers were separated and the aqueous layer was washed twice with ethyl acetate. The combined organic layers was dried over anhydrous $Na_2SO_4$, concentrated and purified by chromatography to yield the product as 0.010 g, Off White solid. Melting point 123-127° C. $^1$H NMR (400 MHz, $CDCl_3$) δ ppm: 0.96 (s. 3H), 0.99 (s, 3H), 1.02 (s, 3H), 1.08 (m, 1H), 1.25 (m, 1H), 1.86 (m, 1H), 2.41 (m, 2H), 2.69 (m, 1H), 3.32 (m, 2.5H), 3.73 (m, 2.5H), 3.89 (m, 1H), 4.93 (d, J=9.3 Hz, 0.8H), 5.08 (d, J=9.3 Hz, 0.2H), 5.3 (d, J=51.4 Hz, 0.2H) 5.45 (d, J=51.4 Hz, 0.8H), 7.15 (m, 1H), 7.24 (d, 1H), 7.43 (m, 1H), 7.81 (bs, 1H), 8.01 (m, 1H). m/z (M+H): 433.2.

Example 22

N-(((1S,3R)-3-(2-((2S,4S)-2-Cyano-4-fluoropyrroli-din-1-yl)-2-oxo ethylamino)-2,2,3-trimethylcyclo-pentyl)methyl)-4,4-difluorocyclohexane carboxam-ide

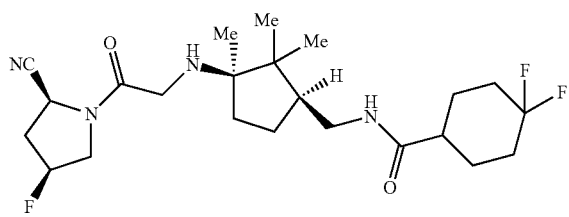 [SMILES: CC1(C)[C@@H](CNC(=O)C2CCC(F)(F)CC2)CC[C@@]1(C)NCC(=O)N1C[C@@H](F)C[C@H]1C#N]

Step-1: tert-Butyl (1R,3S)-3-((4,4-difluorocyclohex-anecarboxamido)methyl)-1,2,2-trimethylcyclopen-tylcarbamate

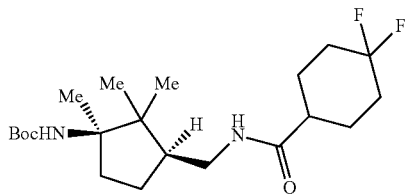 [SMILES: CC(C)(C)OC(=O)N[C@]1(C)CC[C@H](CNC(=O)C2CCC(F)(F)CC2)C1(C)C]

A solution of intermediate 5 (0.47 g, 1.8 mmol), 4,4-dif-luorocyclohexane carboxylic acid (0.2 g, 1.22 mmol), 1-ethyl-3-(3-dimethylaminopropyl) carbodiimide hydro-chloride (0.47 g, 2.4 mmol), N-hydroxybenzotriazole (0.066 g, 0.48 mmol) and diisopropylethylamine (0.47 g, 3.6 mmol) in DMF was stirred for 4 h. The reaction was diluted with water and extracted with ethyl acetate. The separated ethyl acetate layer washed with brine and dried over anhydrous $Na_2SO_4$ and concentrated. $^1$H NMR (400 MHz, $CDCl_3$) δ ppm: 0.82 (s. 3H), 0.93 (s, 3H), 1.12 (s, 3H), 1.43 (s, 9H), 1.69-1.73 (m, 2H), 1.8-1.87 (m, 5H), 1.88-1.98 (m, 4H), 2.15 (d, 2H), 2.67 (bs, 1H), 3.11 (m, 1H), 3.36-3.39 (m, 1H), 4.49 (s, 1H), 5.38 (bs, 1H). m/z (M−1H): 401.2.

Step-2: N-(((1S,3R)-3-Amino-2,2,3-trimethylcyclo-pentyl)methyl)-4,4-difluorocyclo hexanecarboxami-dehydrochloride

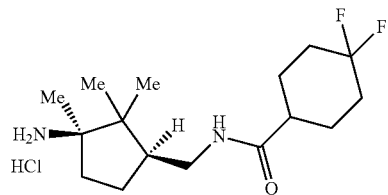 [SMILES: CC1(C)[C@@H](CNC(=O)C2CCC(F)(F)CC2)CC[C@@]1(C)N ; Cl]

A solution of saturated HCl in ethyl acetate (3 mL) was added to a solution of the step 1 intermediate (0.3 g, 0.7 mmol) in ethyl acetate and reaction mixture was stirred at room temperature for 2 h. The solid separated out was washed with ethyl acetate to afford 0.2 g of desired product. $^1$H NMR (400 MHz, $d_6$-DMSO) δ ppm: 0.82 (s, 3H), 0.96 (s, 3H), 1.17 (s, 3H), 1.31-1.4 (m, 1H), 1.6 (m, 3H), 1.74 (m, 3H), 1.89 (d, 2H), 2.03 (d, 2H), 2.23 (m, 1H), 2.75 (d, 1H), 3.1 (m, 2H), 3.19-3.21 (m, 1H). m/z (M+H): 303.2.

Step 3: N-(((1S,3R)-3-(2-((2S,4S)-2-Cyano-4-fluoro-pyrrolidin-1-yl)-2-oxoethyl amino)-2,2,3-trimethyl-cyclopentyl)methyl)-4,4-difluorocyclohexanecarboxamide

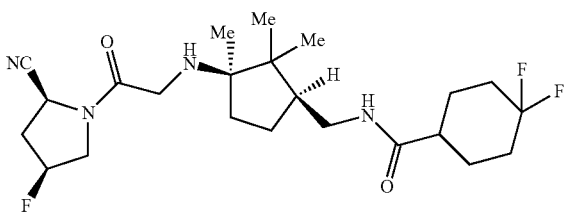 [SMILES: CC1(C)[C@@H](CNC(=O)C2CCC(F)(F)CC2)CC[C@@]1(C)NCC(=O)N1C[C@@H](F)C[C@H]1C#N]

To a stirred suspension of the step-2 intermediate (0.08 g, 0.238 mmol), K₂CO₃ (0.098 g, 0.71 mmol) and KI (0.039 g, 0.071 mmol) in 2 mL of DMSO, intermediate 20 (0.045 g, 0.238 mmol) was added. The reaction mixture was stirred for 12 hours. After completion of the reaction, it was diluted with ethyl acetate and water. The layers were separated and the aqueous layer was washed twice with ethyl acetate. The combined organic layers was dried over anhydrous Na₂SO₄, concentrated and purified by column chromatography to yield 0.03 g product as off-white solid. Melting point: 193-195° C. ¹H NMR (400 MHz, CDCl₃) δ ppm: 0.92 (s, 3H), 0.95 (s, 3H), 1.04 (s, 3H), 1.36-1.41 (m, 1H), 1.59-1.70 (m, 6H), 1.76-1.85 (m, 3H), 2.21-2.06 (m, 3H), 2.15-2.17 (m, 2H), 2.66-2.71 (m, 1H), 3.05-3.09 (m, 1H), 3.26-3.32 (m, 1H), 3.39-3.47 (m, 2H), 3.51-3.64 (m, 1H), 3.73-3.84 (m, 1H), 3.87-3.93 (m, 1H), 4.9 (d, J=9.2, 0.2H) 4.91 (d, J=9.2, 0.8H), 5.37 (d, J=52, 0.2H), 5.45 (d, J=52, 0.8H). m/z (M+H): 457.2.

Example 23

N-(((1R,3S)-3-(2-((2S,4S)-2-Cyano-4-fluoropyrrolidin-1-yl)-2-oxoethylamino)-2,2,3-trimethylcyclopentyl)methyl)-4,4-difluorocyclohexane carboxamide

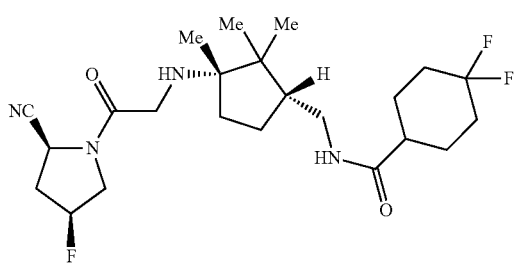 [SMILES: CC1(C)[C@H](CNC(=O)C2CCC(F)(F)CC2)CC[C@]1(C)NCC(=O)N1C[C@@H](F)C[C@H]1C#N]

Prepared similar to Example 22 using intermediate 12. 0.055 g, off-white solid. MP.: 189-194° C. ¹H NMR (400 MHz, CDCl₃) δ ppm: 0.93 (s, 3H), 0.95 (s, 3H), 1.04 (s, 3H), 1.39-1.42 (m, 1H), 1.59-1.7 (m, 6H), 1.78-1.85 (m, 3H), 2.0-2.17 (s, 5H), 2.21-3.12 (m, 1H), 2.66-2.74 (m, 1H), 3.05-3.1 (m, 1H), 3.26-3.51 (m, 3H), 3.61-3.93 (m, 2H), 4.87 (d, J=9.2 Hz, 0.2H) 4.90 (d, J=9.2 Hz, 0.8H), 5.37 (d, J=52, 0.2H), 5.40 (d, J=52, 0.8H); m/z (M+H): 457.2.

Example 24

6-(((1S,3R)-3-(2-((2S,4S)-2-Cyano-4-fluoropyrrolidin-1-yl)-2-oxoethylamino)-2,2,3-trimethylcyclopentyl)methylamino)nicotinonitrile

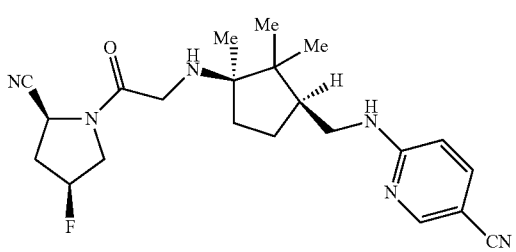 [SMILES: CC1(C)[C@@H](CNc2ccc(C#N)cn2)CC[C@@]1(C)NCC(=O)N1C[C@@H](F)C[C@H]1C#N]

Step 1: 6-(((1S,3R)-3-Amino-2,2,3-trimethylcyclopentyl)methylamino)nicotino nitrile hydrochloride To a suspension of intermediate 5 (0.2 g, 0.78 mmol), and K₂CO₃ in DMF, 6-chloro nicotinonitrile (0.107 g, 0.8 mmol) was added. The reaction mixture heated at 80° C. for 7 hours. Reaction mixture was cooled to room temperature, diluted with water and extracted with ethyl acetate (2×100 mL). Combined organic layer was dried over Na₂SO₄ and concentrated to afford tert-butyl (1R,3S)-3-((5-cyanopyridin-2-ylamino)methyl)-1,2,2-trimethylcyclopentylcarbamate product. m/z (M+H): 359.1. A solution of saturated HCl in ethyl acetate (3 mL) was added to the stirred solution of tert-butyl (1R,3S)-3-((5-cyanopyridin-2-ylamino)methyl)-1, 2,2-trimethylcyclopentyl carbamate (0.15 g, 0.4 mmol) in ethyl acetate at room temperature. The reaction mixture was further stirred at room temperature for two hours. The solid separated was washed with ethyl acetate to afford 0.057 g of desired product. ¹H NMR (400 MHz, d₆-DMSO) δ ppm: 0.83 (s, 3H), 1.0 (s, 3H), 1.19 (m, 3H), 1.20-1.23 (m, 1H), 1.37-1.44 (m, 1H), 1.64-1.69 (m, 1H), 1.85-2.04 (m, 3H), 3.16-3.18 (m, 1H), 3.35-3.42 (m, 1H), 7.68 (bs, 1H), 7.84 (bs, 1H), 8.03 (m, 3H). 8.40 (s, 1H).

Step 2: 6-(((1S,3R)-3-(2-((2S,4S)-2-Cyano-4-fluoropyrrolidin-1-yl)-2-oxoethyl amino)-2,2,3-trimethylcyclopentyl)methylamino)nicotinonitrile

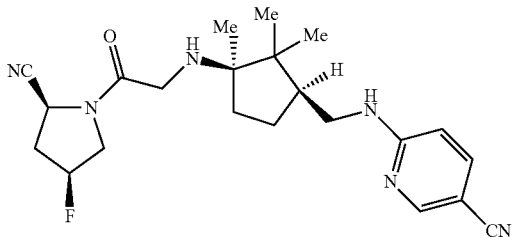 [SMILES: CC1(C)[C@@H](CNc2ccc(C#N)cn2)CC[C@@]1(C)NCC(=O)N1C[C@@H](F)C[C@H]1C#N]

To a stirred suspension of the step-1 intermediate (0.08 g, 0.257 mmol), K₂CO₃ (0.149 g, 1.08 mmol) and KI (0.042 g, 0.257 mmol) in 2 mL of DMSO, intermediate 20 (0.048 g, 0.257 mmol) was added. The reaction mixture was stirred for 24 hours under nitrogen atmosphere. After completion of the reaction, it was diluted with ethyl acetate and water. The layers were separated and the aqueous layer was washed twice with ethyl acetate. The combined organic layer was dried over anhydrous Na₂SO₄, concentrated and purified by column chromatography to give 0.02 g product as off white solid. ¹H NMR (400 MHz, CDCl₃) δ ppm: 0.85 (s, 6H), 1.0 (s, 3H), 1.5-1.7 (m, 4H), 1.85-1.87 (m, 1H), 2.12-2.17 (m, 1H), 2.3-2.5 (m, 1H), 2.7-2.78 (m, 1H), 3.14-3.18 (m, 1H), 3.49-3.45 (m, 2H), 3.66-3.67 (m, 1H), 3.91-3.96 (m, 1H), 4.9 (d, J=9.1 Hz, 0.2H), 4.99 (d, J=9.1 Hz, 0.8H), 5.37 (d, J=52.2 Hz, 0.2H), 5.52 (d, J=52.2 Hz, 0.8H), 6.41-6.43 (m, 1H), 7.47-7.49 (m, 1H), 8.31 (s, 1H). m/z (M+H): 413.2.

Example 25

6-(((1R,3S)-3-(2-((2S,4S)-2-Cyano-4-fluoropyrrolidin-1-yl)-2-oxo ethylamino)-2,2,3-trimethylcyclopentyl)methylamino)nicotinonitrile

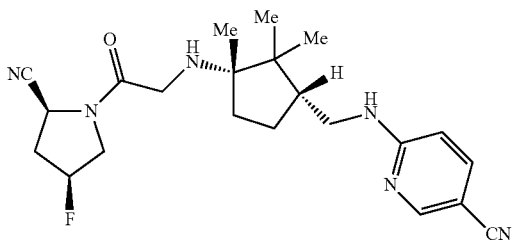 [SMILES: CC1(C)[C@H](CNc2ccc(C#N)cn2)CC[C@]1(C)NCC(=O)N1C[C@@H](F)C[C@H]1C#N]

Prepared similar to Example 24 using intermediate 12. 0.05 g, Off White solid. ¹H NMR (400 MHz, CDCl₃) δ ppm: 0.88 (s, 3H), 0.96 (s, 3H), 0.99 (s, 3H), 1.50-1.67 (m, 4H), 1.84-1.92 (m, 1H), 2.13 (m, 1H), 2.42-2.73 (m, 1H), 3.18-3.97 (m, 7H), 4.97 (d, J=9.2, 0.2H), 4.99 (d, J=9.2, 0.8H), 5.01 (m, 1H), 5.37 (d, J=52, 0.2H), 5.39 (d, J=52, 0.8), 6.4 (m, 1H), 7.46 (m, 1H), 8.2 (m, 1H). m/z (M+H): 413.2.

Example 26

2-(((1S,3R)-3-(2-((2S,4S)-2-Cyano-4-fluoropyrrolidin-1-yl)-2-oxo ethylamino)-2,2,3-trimethylcyclopentyl)methylamino)nicotinonitrile

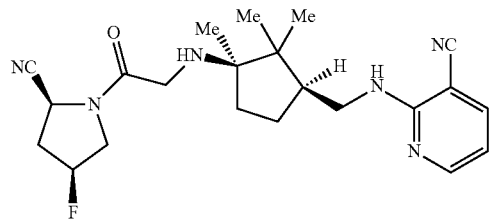 [SMILES: CC1(C)[C@@H](CNc2ncccc2C#N)CC[C@@]1(C)NCC(=O)N1C[C@@H](F)C[C@H]1C#N]

Step 1: 2-(((1S,3R)-3-Amino-2,2,3-trimethylcyclopentyl)methylamino)nicotino nitrilehydrochloride

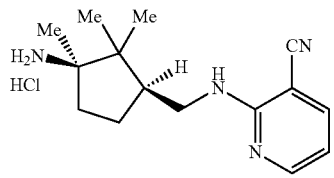 [SMILES: CC1(C)[C@@H](CNc2ncccc2C#N)CC[C@@]1(C)N ; Cl]

Prepared similar to procedure described in example 24 step 1 using intermediate 5 (0.2 g, 0.78 mmol), and K₂CO₃ (0.32 g, 2.34 mmol) in DMF, 2-chloropyridine-3-carbonitrile (0.107 g, 0.78 mmol) to afford 0.057 g of desired product. ¹H NMR (400 MHz, d₆-DMSO) δ ppm: 0.8 (s, 3H), 1.06 (s, 3H), 1.23 (s, 3H), 1.46 (m, 1H), 1.65 (m, 1H), 1.77 (m, 1H), 2.09 (m, 1H), 2.19 (m, 1H), 3.33 (m, 1H), 3.42-3.45 (m, 1H), 6.61-6.65 (m, 1H), 7.0 (s, 1H), 7.88-7.92 (m, 2H), 8.26-8.28 (s, 3H), m/z (M+H): 259.2.

Step 2: 2-(((1S,3R)-3-(2-((2S,4S)-2-Cyano-4-fluoropyrrolidin-1-yl)-2-oxoethylamino)-2,2,3-trimethylcyclopentyl)methylamino)nicotinonitrile

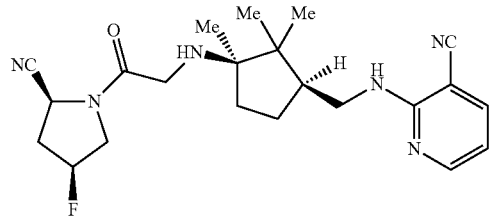 [SMILES: CC1(C)[C@@H](CNc2ncccc2C#N)CC[C@@]1(C)NCC(=O)N1C[C@@H](F)C[C@H]1C#N]

To a stirred suspension of the step 1 intermediate (0.08 g, 0.257 mmol), K₂CO₃ (0.149 g, 1.08 mmol) and KI (0.042 g, 0.257 mmol) in 2 mL of DMSO, intermediate 20 (0.048 g, 0.257 mmol) was added. The reaction mixture was stirred for 24 h under nitrogen atmosphere. After completion of reaction, it was diluted with ethyl acetate and water. The separated aqueous layer was washed twice with ethyl acetate. The combined organic layer was dried over anhydrous Na₂SO₄, concentrated and purified by chromatography to yield the product. 0.015 g, Off-white solid. M.p.: 96-99° C. ¹H NMR (400 MHz, CDCl₃) δ ppm: 0.9 (s, 6H), 1.04 (s, 3H), 1.65-1.76 (m, 4H), 1.86-1.9 (m, 1H), 2.18-2.25 (m, 1H), 2.3-2.5 (m, 1H), 2.64-2.72 (m, 1H), 3.33-3.53 (m, 3H), 3.64-3.72 (m, 2H), 3.77-4.0 (m, 1H), 4.93-4.95 (d, 1H), 5.27 (d, J=51.3, 0.8H), 5.39 (d, J=51.3, 0.2H), 6.45-6.53 (m, 1H), 7.49-7.6 (dd, 1H), 8.25 (d, 1H). m/z (M+H): 413.2.

Example 27

(2S,4S)-4-Fluoro-1-(2-((1R,3S)-1,2,2-trimethyl-3-((5-(trifluoro methyl)pyridin-2-ylamino)methyl)cyclopentylamino)acetyl)pyrrolidine-2-carbonitrile

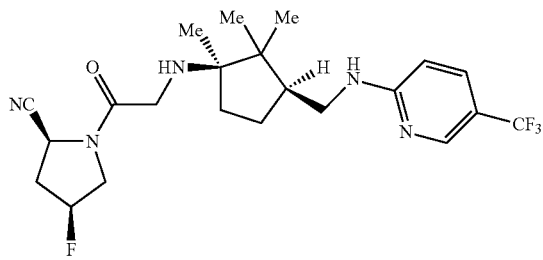 [SMILES: CC1(C)[C@@H](CNc2ccc(C(F)(F)F)cn2)CC[C@@]1(C)NCC(=O)N1C[C@@H](F)C[C@H]1C#N]

Prepared according to procedure described in example 24 using 2-chloro-4-(trifluoromethyl)pyridine in step 1. 0.01 g, Off-white solid. Melting point: 52-58° C. ¹H NMR (400 MHz, CDCl₃) δ ppm: 0.98 (s, 6H), 1.04 (s, 3H), 1.41-1.59 (m, 3H), 1.66-1.69 (m, 2H), 1.88 (m, 1H), 2.12-2.18 (m, 1H), 2.29-2.39 (m, 1H), 2.63-2.76 (m, 1H), 3.14-3.19 (m, 1H), 3.42-3.65 (m, 2H), 3.69-3.99 (m, 2H), 4.98 (d, J=9.2, 0.8H), 5.0 (d, J=9.2, 0.2H), 5.31 (d, J=52, 0.2H), 5.38 (d, J=52, 0.8H), 6.35-6.43 (m, 1H), 7.51-7.53 (d, 1H), 8.25-8.28 (d, 1H). m/z (M+H): 455.2.

Example 28

(2S,4S)-1-(2-((1R,3S)-3-[(1,1-Dioxidoisothiazolidin-2-yl)methyl]-1,2,2-trimethylcyclopentylamino)acetyl)-4-fluoropyrrolidine-2-carbonitrile

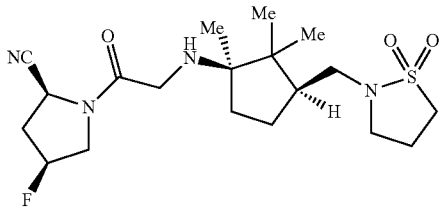 [SMILES: CC1(C)[C@@H](CN2CCCS2(=O)=O)CC[C@@]1(C)NCC(=O)N1C[C@@H](F)C[C@H]1C#N]

Step 1: (1R,3S)-3-[(1,1-Dioxidoisothiazolidin-2-yl)methyl]N-tert-butoxy carbonyl-1,2,2-trimethyl cyclopentanamine

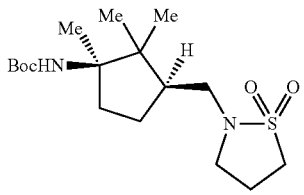 [SMILES: CC(C)(C)OC(=O)N[C@]1(C)CC[C@H](CN2CCCS2(=O)=O)C1(C)C]

To a stirred solution of intermediate 5 (0.2 g, 0.7 mmol) and triethylamine (0.12 mL, 0.85 mmol) in dichloromethane maintained at 0-5° C., chloropropane sulfonyl chloride (0.09 mL, 0.7 mmol) was added. After 6 h the reaction mixture was diluted with dichloromethane, washed with water, dried with Na₂SO₄ and concentrated. The crude material purified by silica column using ethyl acetate and hexane. The obtained product (0.24 g, 0.6 mmol) was dissolved in methanol. To this NaOMe (0.063 g, 1.3 mmol) was added and refluxed under N₂ atmosphere. After 24 hours, reaction mixture was concentrated, residue dissolved in ethyl acetate. Ethyl acetate layer washed with water, brine, dried over Na₂SO₄ and concentrated. Crude material purified by silica column using ethyl acetate and hexane. ¹H NMR (400 MHz, CDCl₃) δ ppm: 0.76 (s, 3H), 0.96 (s, 3H), 1.18 (s, 3H), 1.36 (s, 9H), 1.79-1.96 (m, 2H), 2.22-2.28 (m, 2H), 2.80 (t, 1H), 2.90 (m, 1H), 3.10 (m, 2H), 3.20 (m, 2H), 4.43 (s, 1H). m/z (M+H): 261.2.

Step 2: (1R,3S)-3-[(1,1-Dioxidoisothiazolidin-2-yl)methyl]-1,2,2-trimethylcyclo pentanamine hydrochloride

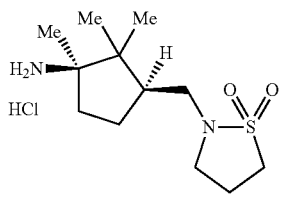 [SMILES: Cl ; CC1(C)[C@@H](CN2CCCS2(=O)=O)CC[C@@]1(C)N]

A solution of saturated HCl in ethyl acetate (3 mL) was added to a solution of the step-1 intermediate (0.36 g, 0.1 mmol) in ethyl acetate and the reaction mixture was stirred at room temperature for two hours. The solid that separated out was washed with ethyl acetate to afford 0.28 g of desired product. ¹H NMR (400 MHz, CDCl₃) δ ppm: 0.9 (s, 3H), 1.0 (s, 3H), 1.32 (s, 3H), 1.87-1.89 (m, 1H), 1.92-1.98 (m, 3H), 2.04 (m, 1H), 3.16 (m, 1H), 3.45 (m, 1H), 4.5 (s, 1H), 4.96 (bs, 1H), 6.36 (d, 1H), 7.55-7.58 (d, 1H), 8.35 (s, 1H). m/z (M+H): 261.2.

Step 3: (2S,4S)-1-(2-((1R,3S)-3-[(1,1-Dioxido-isothiazolidin-2-yl)methyl]-1,2,2-trimethylcyclopentylamino)acetyl)-4-fluoropyrrolidine-2-carbonitrile

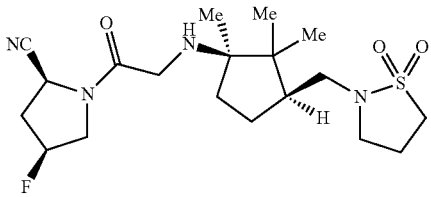 [SMILES: CC1(C)[C@@H](CN2CCCS2(=O)=O)CC[C@@]1(C)NCC(=O)N1C[C@@H](F)C[C@H]1C#N]

To a stirred suspension of the step-2 intermediate (0.120 g, 0.405 mmol), K$_2$CO$_3$ (0.167 g, 1.21 mmol) and KI (0.067 g, 0.405 mmol) in 2 mL of DMSO, intermediate 20 (0.076 g, 0.405 mmol) was added. The reaction mixture was stirred for 24 h under N$_2$ atmosphere. After completion of the reaction, it was diluted with ethyl acetate and water. The separated aqueous layer was washed twice with ethyl acetate. The combined organic layer was dried over anhydrous Na$_2$SO$_4$, concentrated and purified by chromatography to yield the product as 0.012 g, Off-White solid. M.P.: 126-128° C. $^1$H NMR (400 MHz, CDCl$_3$) δ ppm: 0.88 (s, 3H), 0.96 (s, 3H), 1.06 (s, 3H), 1.42-1.44 (m, 1H), 1.66-1.68 (m, 2H), 1.70-1.80 (m, 1H), 1.83-1.85 (m, 1H), 1.98-2.04 (m, 1H), 2.29-2.36 (m, 2H), 2.52-2.53 (m, 1H), 2.76-2.79 (m, 1H), 3.04-3.17 (m, 3H), 3.3-3.6 (m, 1.5H), 3.4-3.5. (m, 1.5H), 3.6-3.9 (m, 2H), -4.9 (d, J=9.2 Hz, 0.8H), 5.12 (d, J=9.2 Hz, 0.2H), 5.36 (d, J=52 Hz, 0.8H), 5.4 (d, J=52 Hz, 0.2H). m/z (M+H): 415.2.

Example 29

(2S,4S)-1-(2-((1S,3R)-3-[(1,1-Dioxidoisothiazolidin-2-yl)methyl]-1,2,2-trimethyleyclopentylamino)acetyl)-4-fluoropyrrolidine-2-carbonitrile

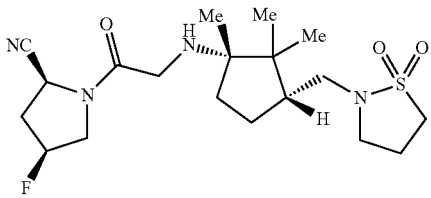 [SMILES: CC1(C)[C@H](CN2CCCS2(=O)=O)CC[C@]1(C)NCC(=O)N1C[C@@H](F)C[C@H]1C#N]

Prepared similar to example 28 using intermediate 12. 0.015 g, off-white solid. M.P: 171-174° C. $^1$H NMR (400 MHz, CDCl$_3$) δ ppm: 0.86 (s, 3H), 0.88 (s, 3H), 1.06 (s, 3H), 1.43-1.44 (m, 1H), 1.66-1.68 (m, 1H), 1.70-1.80 (m, 1H), 1.83-1.85 (m, 1H), 1.98-2.04 (m, 1H), 2.29-2.36 (m, 3H), 2.52-2.53 (m, 1H), 2.76-4.2 (m, 10H), 4.8 (d, J=9.2, 0.8H), 5.12 (d, J=9.2, 0.2H), 5.25 (d, J=51.2, 0.2H), 5.35 (d, J=51.2, 0.8H), m/z (M+H): 415.2.

Example 30

(2S,4S)-1-(2-((1S,3R)-3-[(1,1-Dioxido-1,2-thiazinan-2-yl)methyl]-1,2,2-trimethylcyclopentylamino)acetyl)-4-fluoropyrrolidine-2-carbonitrile

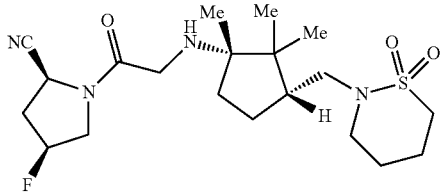 [SMILES: CC1(C)[C@H](CN2CCCCS2(=O)=O)CC[C@]1(C)NCC(=O)N1C[C@@H](F)C[C@H]1C#N]

Step 1: (1S,3R)-3-[(1,1-Dioxido-1,2-thiazinan-2-yl)methyl]-1,2,2-trimethylcyclo pentanamine

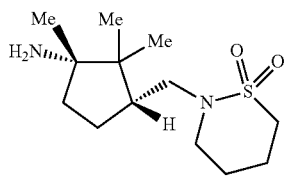 [SMILES: CC1(C)[C@H](CN2CCCCS2(=O)=O)CC[C@]1(C)N]

To a solution of intermediate 12 (0.375 g, 1.5 mmol) in acetonitrile, 1,4-butanesultone (0.2 g, 1.5 mmol) was added and stirred over night. To this phosphrous oxychloride (0.46 mL, 3 mmol) was added and stirred for another 6 hours. The reaction mixture was concentrated and to this was added 50 mL ethyl acetate. The ethyl acetate layer was washed with 20% NaOH, water, brine, dried with anhydrous Na$_2$SO$_4$ and concentrated. The crude material purified by alumina column chormatography using 2% methanol in dichloromethane. $^1$H NMR (400 MHz, DMSO) δ ppm: 0.86 (s, 3H), 0.95 (m, 3H), 1.1 (s, 3H), 1.3-1.66 (m, 6H), 1.83-1.9 (m, 1H), 1.94-2.01 (m, 1H), 2.18-2.2 (m, 1H), 2.94-3.15 (m, 4H), 3.18-3.2 (m, 2H). m/z (M+H): 275.1.

Step 2: (2S,4S)-1-(2-((1S,3R)-3-[(1,1-Dioxido-1,2-thiazinan-2-yl)methyl]-1,2,2-trimethyl cyclopentylamino)acetyl)-4-fluoropyrrolidine-2-carbonitrile

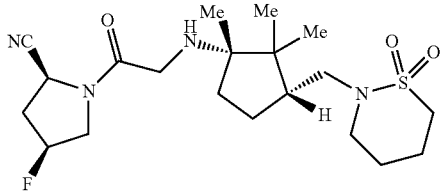 [SMILES: CC1(C)[C@H](CN2CCCCS2(=O)=O)CC[C@]1(C)NCC(=O)N1C[C@@H](F)C[C@H]1C#N]

To a stirred suspension of the step 1 intermediate (0.13 g, 0.5 mmol), K$_2$CO$_3$ (0.138 g, 1 mmol) and KI catalytic amount in 2 mL of DMSO, intermediate 4 (0.085 g, 0.45 mmol) was added. The reaction mixture was stirred for 8 h under N$_2$ atmosphere. After completion of reaction, it was diluted with ethyl acetate and water. The layers were separated and the aqueous layer was washed twice with ethyl acetate. The combined organic layer was dried over anhydrous Na$_2$SO$_4$, concentrated and purified by chromatography using 2% methanol in DCM to yield the product; white solid (0.02 g). M.P.: 186-190° C. $^1$H NMR (400 MHz, d$_6$-DMSO) δ ppm: 0.86 (s, 3H), 0.95 (m, 3H), 1.1 (s, 3H), 1.4-1.66 (m, 6H), 1.83-1.98 (m, 2H), 2.04-2.18 (m, 2H), 2.2-2.4 (m, 1H), 2.62-2.70 (m, 1H), 2.94-3.05 (m, 3H), 3.18-3.92 (m, 6H), 4.94 (d, J=9.0, 0.8H), 5.12 (d, J=9.0, 0.2H), 5.3 (d, J=52.1, 0.2H), 5.4 (d, J=52.1, 0.8H). m/z (M+H): 429.1.

Example 31

(2S,4S)-1-(2-((1R,3S)-3-((1H-Tetrazol-1-yl)methyl)-1,2,2-trimethylcyclopentylamino)acetyl)-4-fluoropyrrolidine-2-carbonitrile methanesulfonate

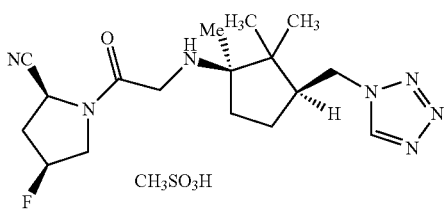

Step 1: tert-Butyl (1R,3S)-3-((1H-tetrazol-1-yl)methyl)-1,2,2-trimethyl cyclopentyl carbamate

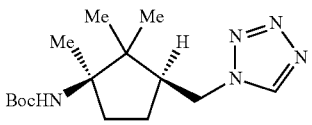 [SMILES: CC(C)(C)OC(=O)N[C@]1(C)CC[C@H](Cn2cnnn2)C1(C)C]

To a solution of intermediate 5 in acetic acid (1 mL), NaN$_3$ and triethylorthoformate (0.25 mL) was added and the reaction mixture refluxed for 6 h. The reaction was cooled to room temperature and ice-cold water (20 mL) was added, extracted with ethyl acetate. The ethyl acetate layer was washed with saturated NaHCO$_3$ solution, water, brine, dried with anhydrous Na$_2$SO$_4$ and concentrated. The crude product was purified by column using 50% ethyl acetate in hexane. $^1$H NMR (400 MHz, CDCl$_3$) δ ppm: 0.95 (s, 3H), 1.12 (s, 3H), 1.27 (s, 3H), 1.48 (s, 9H), 1.69 (m, 2H), 2.35 (m, 2H), 4.24 (m, 1H), 4.54 (m, 2H), 8.58 (s, 1H). m/z (M+H): 310.2.

Step 2: (1R,3S)-3-((1H-Tetrazol-1-yl)methyl)-1,2,2-trimethylcyclopentanamine hydrochloride

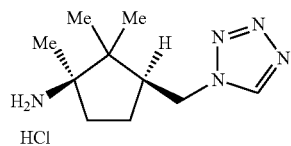 [SMILES: CC1(C)[C@@H](Cn2cnnn2)CC[C@@]1(C)N ; Cl]

A solution of saturated HCl in ethyl acetate (3.5 mL) was added to a solution of the step-1 intermediate (0.15 g, 0.48 mmol) in ethyl acetate and the reaction mixture was stirred at room temperature for two hours. The solid that separated out was washed with ethyl acetate to afford 60 mg of desired product. $^1$H NMR (400 MHz, d$_6$-DMSO) δ ppm: 0.81 (s, 3H), 0.99 (s, 3H), 1.25 (s, 3H), 1.55 (m, 2H), 1.66 (m, 1H), 2.0 (m, 1H), 2.36 (m, 1H), 4.4 (m, 1H), 4.57 (m, 1H), 8.15 (bs, 3H), 9.47 (s, 1H). m/z (M+H): 210.2.

Step 3: (2S,4S)-1-(2-((1R,3S)-3-((1H-Tetrazol-1-yl)methyl)-1,2,2-trimethyl cyclopentylamino)acetyl)-4-fluoropyrrolidine-2-carbonitrile methanesulfonate

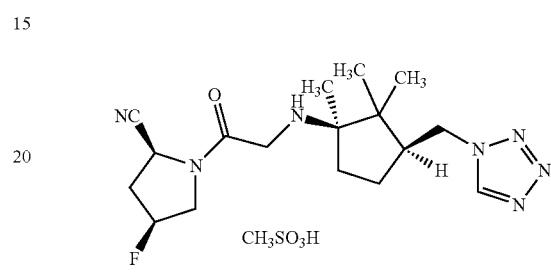

To a stirred suspension of the step-2 intermediate (0.09 g, 0.47 mmol), K$_2$CO$_3$ (0.25 g, 1.8 mmol) and KI (0.078 g, 0.47 mmol) in 2 mL of DMSO, intermediate 20 (0.088 g, 0.47 mmol) was added. The reaction mixture was stirred for 8 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by chromatography using 2% methanol in dichloromethane to yield the product. The product that obtained (0.04 g, 0.11 mmol) was dissolved in ethyl acetate, to this was added methanesulfonic acid (0.0105 g, 0.11 mmol) diluted in ethyl acetate and stirred for 2 h. The solid that separated out was decanted washed with ethyl acetate and dried. Yield: 0.041 g; Melting point: 210-214° C.; $^1$H NMR (400 MHz, D$_2$O) δ ppm: 1.1 (s, 3H), 1.17 (s, 3H), 1.38 (s, 3H), 1.76 (m, 2H), 1.89 (m, 1H), 2.12 (m, 1H), 2.57 (m, 2H), 2.7 (m, 1H), 2.8 (s, 3H), 3.8-3.9 (m, 1H), 4.01-4.15 (m, 2H), 4.48-4.54 (m, 1H), 4.70-4.75 (m, 1H), 4.81-4.87 (m, 1H), 5.08 (d, J=9.2 Hz, 0.8H), 5.12 (d, J=9.2 Hz, 0.2H), 5.53 (d, J=52.2 Hz, 0.2H), 5.6 (d, J=52.2 Hz, 0.8H), 9.2 (s, 1H). m/z (M+H): 364.2.

Example 32

(2S,4S)-1-(2-((1S,3R)-3-((1H-Tetrazol-1-yl)methyl)-1,2,2-trimethyl cyclopentylamino)acetyl)-4-fluoropyrrolidine-2-carbonitrile

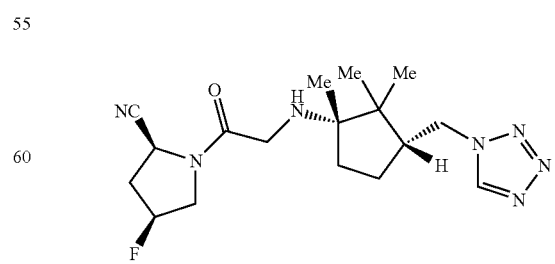

Prepared similar to example 31 using intermediate 12. 0.03 g Off-white solid. Melting point: 151-154° C. $^1$H NMR (400

MHz, CDCl₃) δ ppm: 0.95 (s, 6H), 1.2 (s, 3H), 1.39-1.42 (m, 1H), 1.59-1.74 (m, 4H), 2.33-2.4 (m, 2H), 2.66-2.74 (m, 1H), 3.28-3.32 (d, 1H), 3.43-3.47 (d, 1H), 3.69-3.93 (m, 2H), 4.49-4.53 (m, 2H), 4.94-4.96 (m, 1H), 5.32 (d, J=54 Hz, 0.2H), 5.4 (d, J=54 Hz, 0.8H), 8.62 (s, 1H). m/z (M+H): 364.2.

Example 33

(2S,4S)-4-Fluoro-1-(2-((1R,3S)-1,2,2-trimethyl-3-(morpholinomethyl)cyclopentylamino)acetyl)pyrrolidine-2-carbonitrile

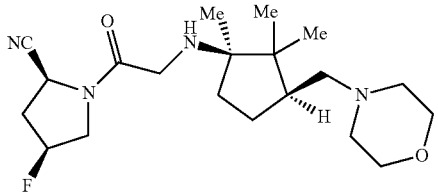 [SMILES: CC1(C)[C@@H](CN2CCOCC2)CC[C@@]1(C)NCC(=O)N1C[C@@H](F)C[C@H]1C#N]

Step 1: tert-Butyl(1R,3S)-1,2,2-trimethyl-3-(morpholinomethyl)cyclopentyl carbamate

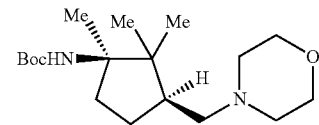 [SMILES: CC(C)(C)OC(=O)N[C@]1(C)CC[C@H](CN2CCOCC2)C1(C)C]

Intermediate-3 was heated in morpholine at 80° C. over night. The reaction mixture was poured into water, extracted with ethyl acetate, organic layer separated, washed with water, dried with anhydrous Na₂SO₄ and concentrated. The residue was purified by silica column chromatography using dichloromethane and methanol. ¹H NMR (400 MHz, CDCl₃) δ ppm: 0.79 (s, 3H), 1.01 (s, 3H), 1.35 (s, 3H), 1.43 (s, 9H), 1.65-1.68 (m, 1H), 1.83-1.88 (m, 2H), 1.91-1.95 (m, 2H), 2.18-2.22 (m, 1H), 2.35-2.38 (m, 1H), 2.42-2.49 (m, 4H), 3.68-3.71 (m, 4H), 4.51 (s, 1H), m/z (M+1): 327.3.

Step 2: (1R,3S)-1,2,2-Trimethyl-3-(morpholinomethyl)cyclopentanamine hydrochloride

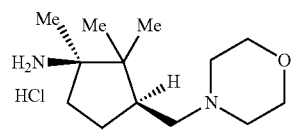 [SMILES: Cl ; CC1(C)[C@@H](CN2CCOCC2)CC[C@@]1(C)N]

To a solution of Step 1 intermediate in ethyl acetate, 3 mL of saturated thy HCl in ethyl acetate was added and stirred for 2 hours. The solid that separated out was decanted and washed with ethyl acetate and dried. ¹H NMR (400 MHz, D₂O) δ ppm: 0.90 (s, 3H), 1.06 (s, 3H), 1.35 (s, 3H), 1.72-1.74 (m, 1H), 1.93-1.95 (m, 1H), 2.08-2.13 (m, 2H), 2.25-2.27 (m, 1H), 3.16-3.25 (m, 4H), 3.51-3.61 (m, 2H), 3.82-3.87 (m, 2H), 4.09-4.12 (m, 2H), m/z (M+1): 227.3.

Step 3: (2S,4S)-4-Fluoro-1-(2-((1R,3S)-1,2,2-trimethyl-3-(morpholinomethyl)cyclo pentylamino)acetyl)pyrrolidine-2-carbonitrile

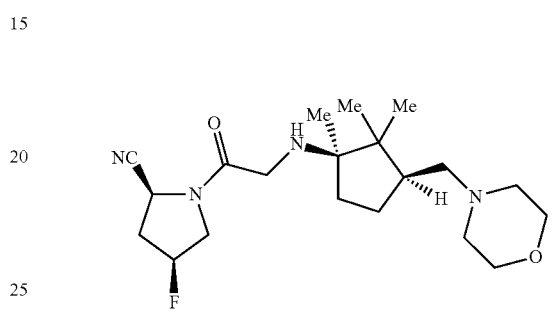

Coupling of the step-2 intermediate (0.097 g, 0.42 mmol), K₂CO₃ (0.138 g, 1.0 mmol) and KI (0.033 g, 0.2 mmol) in 1 mL of DMSO with intermediate 20 (0.079 g, 0.42 mmol) was carried out similar to step-3 of example-1 to afford off-white hygroscopic solid (0.032 g). ¹H NMR (400 MHz, CDCl₃) δ ppm: 0.86 (s, 3H), 0.96 (s, 3H), 1.06 (s, 3H), 1.33-1.38 (m, 2H), 1.81-1.86 (m, 1H), 2.0-2.03 (m, 1.5H), 2.22-2.28 (m, 1.5H), 2.37-2.43 (m, 5H), 2.64-2.72 (q, 1H), 3.35-3055 (m, 2H), 3.66-3.79 (m, 6H), 3.88-3.97 (m, 1H), 4.95 (d, J=9.2 Hz, 0.8H), 5.35 (d, J=9.2 Hz, 0.2H), 5.40 (d, J=52.2 Hz. 0.2H), 5.45 (d, J=52.2 Hz, 0.8H). m/z (M+H): 381.3.

Example 34

(2S,4S)-4-Fluoro-1-(2-((1S,3R)-1,2,2-trimethyl-3-(morpholino methyl)cyclopentylamino)acetyl)pyrrolidine-2-carbonitrile

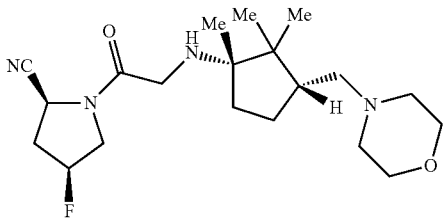 [SMILES: CC1(C)[C@H](CN2CCOCC2)CC[C@]1(C)NCC(=O)N1C[C@@H](F)C[C@H]1C#N]

Prepared similar to example 33 starting from intermediate 10 and mopholine in Step-1.

0.01 gm, Off-white hygroscopic solid. Melting point: 163-166° C. ¹H NMR (400 MHz, CDCl₃) δ ppm: 0.82 (s, 3H), 0.96 (s, 3H), 1.08 (s, 3H), 1.33-1.38 (m, 2H), 1.80-1.85 (m, 1H), 1.99-2.03 (m, 1H), 2.17-2.23 (m, 1H), 2.35-2.41 (m, 5H), 2.64-2.72 (q, 1H), 3.31-3.35 (d, 1H), 3.35-3.62 (m, 1H), 3.66-3.70 (m, 6H), 3.75-3.79 (m, 1H), 3.89-3.98 (m, 1H), 4.95 (d, J=9.2 Hz, 0.8H), 5.25 (d, J=9.2 Hz, 0.2H), 5.38 (d, J=51.1 Hz, 0.2H), 5.5 (d, J=51.1 Hz, 0.8H). m/z (M+H): 381.3.

Example 35

(2S,4S)-4-Fluoro-1-(2-((1S,3R)-1,2,2-trimethyl-3-(morpholino methyl)cyclopentylamino)acetyl)pyrrolidine-2-carbonitrile dimethanesulfonate

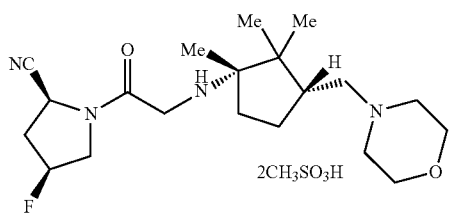 [SMILES: CC1(C)[C@H](CN2CCOCC2)CC[C@]1(C)NCC(=O)N1C[C@@H](F)C[C@H]1C#N]

Example 34 (70 mg, 0.184 mmol) was dissolved in ethyl acetate, to this was added (34 mg, 0.36 mmol) methanesulfonic acid diluted in ethyl acetate and stirred for 2 h. The solid that separated out was decanted washed with ethyl acetate and dried. 0.055 g, White solid. Melting point: 220-225° C. ¹H NMR (400 MHz, D₂O) δ ppm: 1.01 (s, 3H), 1.14 (s, 3H), 1.36 (s, 3H), 1.7-1.74 (m, 1H), 1.90-1.93 (m, 1H), 2.1-2.17 (m, 1H), 2.26-2.28 (m, 1H), 2.5-2.71 (m, 1H), 2.71-2.75 (m, 1H), 2.81 (s, 6H), 3.15-3.18 (m, 2H), 3.25-3.28 (m, 3H), 3.3-3.4 (m, 2H), 3.77-4.14 (m, 9H) 5.05 (d, J=9.2 Hz, 0.8H), 5.52 (d, J=9.2 Hz, 0.2H), 5.4 (d, J=52.0 Hz, 0.2H), 5.5 (d, J=52.0 Hz, 0.8H). m/z (M+H): 381.2.

Example 36

(2S,4S)-4-Fluoro-1-(2-((1R,3S)-1,2,2-trimethyl-3-(pyrrolidin-1-yl methyl)cyclopentylamino)acetyl) pyrrolidine-2-carbonitrile

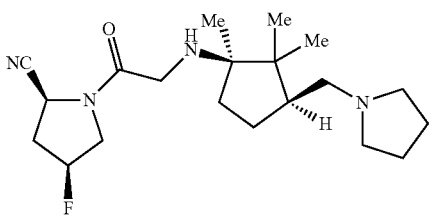 [SMILES: CC1(C)[C@@H](CN2CCCC2)CC[C@@]1(C)NCC(=O)N1C[C@@H](F)C[C@H]1C#N]

Prepared according to example 33 off-white solid (0.045 g). mp: 108-112° C.; IR (KBr): 2244 & 1670 cm⁻¹; 1H NMR (CDCl₃): 400 MHz δ 0.81 (s, 3H), 0.93 (s, 3H), 1.10 (s, 3H), 1.63-1.70 (m, 5H), 1.95 (m, 2H), 2.30-2.71 (m, 8H), 3.35-3.97 (m, 5H), 4.94 (dd, dd, J=4.4 & 13.6 Hz, 1H), 5.25 (d, J=9.2 Hz, 0.2H), 5.35 (d, J=9.2 Hz, 0.8H), 5.42 (d, J=48 Hz, 0.2H), 5.48 (d, J=48 Hz, 0.8H); m/z (M+1): 365.3.

Example 37

(2S,4S)-4-Fluoro-1-(2-((1S,3R)-1,2,2-trimethyl-3-(pyrrolidin-1-yl methyl)cyclopentylamino)acetyl) pyrrolidine-2-carbonitrile

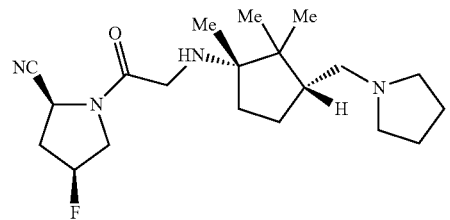 [SMILES: CC1(C)[C@H](CN2CCCC2)CC[C@]1(C)NCC(=O)N1C[C@@H](F)C[C@H]1C#N]

Prepared similar to example 33 starting from intermediate 10 and pyrrolidine. 0.036 g, White solid. Melting point: 123-126° C. ¹H NMR (400 MHz, D₂O) δ ppm: 0.79 (s, 3H), 0.95 (s, 3H), 1.08 (s, 3H), 1.40-1.44 (m, 1H), 1.60-1.63 (m, 2H), 1.76 (s, 4H), 1.95 (m, 2H), 2.2-2.33 (m, 2H), 2.48-2.5 (m, 5H), 2.64-2.68 (m, 1H), 3.3-3.34 (d, 1H), 3.49-3.53 (m, 1H), 3.61-3.79 (m, 1H), 3.88-3.97 (m, 1H), 4.94-4.96 (m, 1H), 5.22-5.48 (m, 1H). m/z (M+H): 365.2.

Example 38

(2S,4S)-4-fluoro-1-(2-((1R,3S)-3-(((R)-3-hydroxypyrrolidin-1-yl)methyl)-1,2,2-trimethylcyclopentylamino)acetyl)pyrrolidine-2-carbonitrile

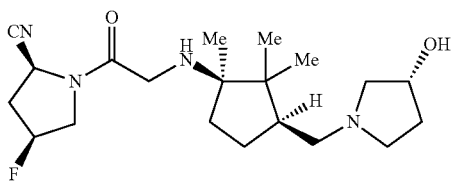 [SMILES: CC1(C)[C@@H](CN2CC[C@@H](O)C2)CC[C@@]1(C)NCC(=O)N1C[C@@H](F)C[C@H]1C#N]

Prepared similar to example 33 starting from intermediate 3 and 3-hydroxypyrrolidine. 0.01 g, Off white solid; Melting point: 130-135° C.; ¹H NMR (400 MHz, CDCl₃) δ ppm: 0.83 (s, 3H), 0.93 (s, 3H), 1.06 (s, 3H), 1.35-1.42 (m, 1H), 1.64-1.73 (m, 6H), 1.85-1.98 (m, 3H), 2.15-2.51 (m, 5H), 2.64-2.68 (m, 2H), 2.87-2.88 (m, 1H), 3.35-3.48 (m, 1H), 3.65-3.69 (m, 1H), 3.89-3.98 (m, 1H), 4.3 (bs, 1H), 4.94 (d, J=8 Hz, 0.8H), 5.35 (d, J=8.0 Hz, 0.2H), 5.4 (d, J=51.2 Hz, 0.2H), 5.45 (d, J=51.2 Hz, 0.8H). m/z (M+H): 381.2.

Example 39

(2S,4S)-4-Fluoro-1-(2-((1R,3S)-1,2,2-trimethyl-3-(piperidin-1-yl methyl)cyclopentylamino)acetyl)pyrrolidine-2-carbonitrile

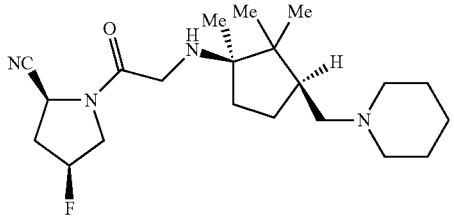 [SMILES: CC1(C)[C@@H](CN2CCCCC2)CC[C@@]1(C)NCC(=O)N1C[C@@H](F)C[C@H]1C#N]

Prepared similar to example 33 using intermediate 3 and piperidine. 0.04 gm, Creamy white solid. Melting point: 100-103° C. $^1$H NMR (400 MHz, CDCl$_3$) δ ppm: 0.81 (s, 3H), 0.9 (s, 3H), 1.06 (s, 3H), 1.39-1.41 (m, 2H), 1.55-1.57 (m, 4H), 1.62-1.65 (m, 4H), 1.85-1.87 (m, 1H), 1.99-2.01 (s, 1H), 2.14-2.16 (m, 1H), 2.33-2.36 (m, 4H), 2.64-2.72 (m, 1H), 3.35-3.53 (m, 2H), 3.66-3.75 (m, 1H), 3.88-3.98 (m, 1H), 4.94 (d, J=9.2 Hz, 1H), 5.28 (d, J=52.2 Hz, 0.2H), 5.4 (d, J=52.2 Hz, 0.8H). m/z (M+H): 379.3.

Example 40

(2S,4S)-4-Fluoro-1-(2-((1S,3R)-1,2,2-trimethyl-3-(piperidin-1-yl methyl)cyclopentylamino)acetyl)pyrrolidine-2-carbonitrile

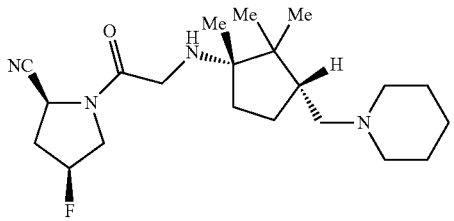 [SMILES: CC1(C)[C@H](CN2CCCCC2)CC[C@]1(C)NCC(=O)N1C[C@@H](F)C[C@H]1C#N]

Prepared similar to example 35 using intermediate 10 and piperidine 0.09 g, Pale green solid. Melting point: 135-137° C. $^1$H NMR (400 MHz, CDCl$_3$) δ ppm: 0.93 (s, 3H), 0.95 (s, 3H), 1.04 (s, 3H), 1.39-1.42 (m, 1H), 1.61-1.88 (m, 7H), 1.98-2.01 (m, 3H), 2.25-2.34 (s, 6H), 2.63-2.71 (m, 1H), 3.3-3.34 (d, 1H), 3.49-3.53 (m, 1H), 3.55-3.97 (m, 3H), 4.95 (d, J=9.2 Hz, 0.8H), 5.33 (d, J=9.2 Hz, 0.2H), 5.4 (d, J=52.2 Hz, 0.2H), 5.45 (d, J=52.2 Hz, 0.8H). m/z (M+H): 457.2.

Example 41

(2S,4S)-4-Fluoro-1-(2-((1R,3S)-3-((4-hydroxypiperidin-1-yl)methyl)1,2,2-trimethylcyclopentylamino)acetyl)pyrrolidine-2-carbonitrile Prepared similar to example 33 using intermediate 3 and 4-hydroxy piperidine

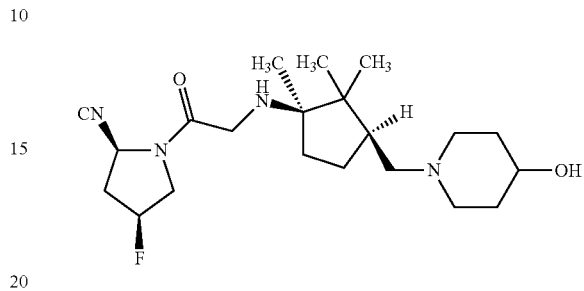

0.007 g Off white solid. $^1$H NMR (400 MHz, CDCl$_3$) δ ppm: 0.83 (s, 3H), 0.93 (s, 3H), 1.06 (s, 3H), 1.55-1.64 (m, 5H), 1.86-1.94 (m, 3H), 2.0-2.19 (m, 3H), 2.2-2.35 (m, 1H), 2.38-2.45 (m, 2H), 2.64-2.74 (m, 3H), 3.38-3.47 (m, 2H), 3.66-3.78 (m, 2H), 3.88-3.94 (m, 1H), 4.93-4.95 (d, J=9.4 Hz, 1H), 5.36 (d, J=51.0 Hz, 0.2H), 5.48 (d, J=51.0 Hz, 0.8H). m/z (M+H): 395.3.

Example 42

(2S,4S)-4-Fluoro-1-(2-((1R,3S)-1,2,2-trimethyl-3-((4-(methylsulfonyl)phenyl sulfonyl)methyl)cyclopentylamino)acetyl)pyrrolidine-2-carbonitrile

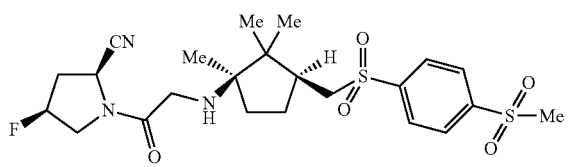 [SMILES: CC1(C)[C@@H](CS(=O)(=O)c2ccc(S(C)(=O)=O)cc2)CC[C@@]1(C)NCC(=O)N1C[C@@H](F)C[C@H]1C#N]

Step 1: tert-Butyl (1R,3S)-1,2,2-trimethyl-3-((4-(methylthio)phenylthio)methyl)cyclopentylcarbamate

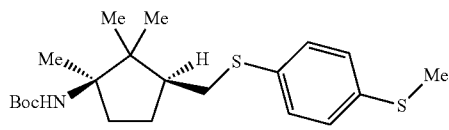 [SMILES: CSc1ccc(SC[C@H]2CC[C@@](C)(NC(=O)OC(C)(C)C)C2(C)C)cc1]

To a suspension of Intermediate-3 (0.40 g, 1.19 mmol) and cesium carbonate (0.972 g, 2.98 mmol) in DMF, 4-(methylsulfanyl)thiophenol (0.16 g, 2.98 mmol) was added and the reaction heated at 80° C. over night. The reaction mixture poured into water, extracted with ethyl acetate, washed with water, dried with Na$_2$SO$_4$ and concentrated. The residue was purified by column using ethyl acetate and hexane. 0.295 g, Off-white solid, $^1$H NMR (400 MHz, CDCl$_3$) δ ppm: 0.85 (s, 3H), 0.94 (s, 3H), 1.30 (s, 3H), 1.43 (s, 9H), 1.79-2.04 (m, 5H), 2.14 (s, 3H), 2.63-2.70 (m, 1H), 3.03-3.06 (m, 1H), 4.48 (s, 1H), 7.16-7.19 (m, 2H), 7.24-7.26 (m, 2H). m/z (M−100)+ H, 296.2.

Step 2: (1R,3S)N-tert-Butoxycarbonyl-1,2,2-trimethyl-3-({[4-(methylsulfonyl)phenyl]sulfonyl}methyl)cyclopentanamine

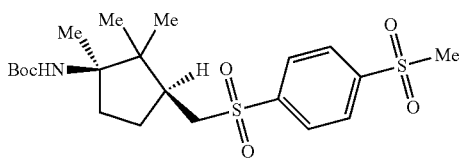 [SMILES: CC(C)(C)OC(=O)N[C@]1(C)CC[C@H](CS(=O)(=O)c2ccc(S(C)(=O)=O)cc2)C1(C)C]

To a dichloromethane solution of step 1 intermediate (0.274 g, 0.69 mmol), mCPBA (meta-chloroperbenzoic acid) (1.2 g, 4.17 mmol) was added and stirred at room temperature for 4 hours. Reaction mixture was diluted and extracted with dichloromethane, washed with NaHCO₃ solution and dried with anhydrous Na₂SO₄ and concentrated. The compound obtained was purified by silica column chromatography. 0.250 g, Off white solid, Melting point 200-203° C., ¹H NMR (400 MHz, CDCl₃) δ ppm: 0.78 (s, 3H), 0.95 (s, 3H), 1.35 (s, 3H), 1.45 (s, 9H), 1.46-1.49 (m, 1H), 1.85-2.08 (m, 3H), 2.25-2.35 (m, 1H), 2.95-3.14 (m, 2H), 3.14 (s, 3H), 4.45 (s, 1H), 8.13-8.18 (m, 4H), m/z (M−56)+H: 404.

Step-3: (1R,3S)-1,2,2-Trimethyl-3-((4-(methylsulfonyl)phenylsulfonyl)methyl)cyclopentanaminehydrochloride

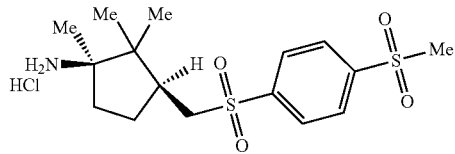 [SMILES: Cl ; CC1(C)[C@@H](CS(=O)(=O)c2ccc(S(C)(=O)=O)cc2)CC[C@@]1(C)N]

To a solution of Step 2 intermediate (0.200 g, 0.0043 mol) in ethyl acetate, 3 mL of saturated dry HCl in ethyl acetate was added and stirred for 2 hours. The separated solid out was decanted and washed with ethyl acetate and dried. ¹H NMR (400 MHz, DMSO-d₆) δ ppm: 0.74 (s, 3H), 0.86 (s, 3H), 1.15 (s, 3H), 1.50-1.55 (m, 1H), 1.67 (m, 1H), 1.81 (m, 2H), 2.08-2.10 (m, 1H), 2.47 (s, 3H), 3.42-3.52 (m, 2H), 7.8 (bs, 3H), 8.2 (m, 4H). m/z (M+H): 360.1.

Step 4: (2S,4S)-4-Fluoro-1-(2-((1R,3S)-1,2,2-trimethyl-3-((4-(methylsulfonyl)phenylsulfonyl)methyl)cyclopentylamino)acetyl)pyrrolidine-2-carbonitrile

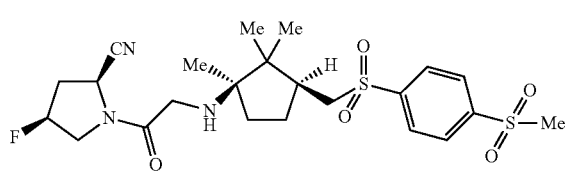 [SMILES: CC1(C)[C@@H](CS(=O)(=O)c2ccc(S(C)(=O)=O)cc2)CC[C@@]1(C)NCC(=O)N1C[C@@H](F)C[C@H]1C#N]

The Step 3 intermediate (0.080 g, 0.22 mmol) was added to a stirred suspension of intermediate 20 (0.018 g, 0.11 mmol), K₂CO₃, (0.038 g, 0.20 mmol), KI (0.013 g, 0.08 mmol) in 2 mL DMSO. The reaction mixture was stirred at room temperature for 8 hours. After completion of the reaction, the reaction mixture was diluted with water and extracted with ethyl acetate. The organic layer was dried over anhydrous Na₂SO₄ and concentrated under reduced pressure. The crude product obtained was purified by column chromatography using 0.5% methanol in dichloromethane. 0.01 g, White solid. Melting point: 220-224° C. ¹H NMR (400 MHz, CDCl₃) δ ppm: 0.79 (s, 3H), 0.88 (s, 3H), 1.04 (s, 3H), 1.46-1.53 (m, 1H), 1.60-1.70 (m, 2H), 2.0-2.05 (m, 2H), 2.29-2.39 (m, 2H), 2.65-2.73 (m, 1H), 3.11 (s, 3H), 3.13-3.15 (m, 2H), 3.32-3.49 (m, 2H), 3.3-3.75 (m, 1H), 3.87-3.96 (m, 1H), 4.92 (d, J=9.2 Hz, 0.8H), 5.1 (d, J=9.2 Hz, 0.2H), 5.4 ((d, J=54 Hz, 0.2H), 5.5 (d, J=54 Hz, 0.8H), 8.15-8.19 (s, 4H). m/z (M+H): 514.1.

Example 43

(2S,4R)-4-Fluoro-1-(2-((1R,3S)-1,2,2-trimethyl-3-((4-(methylsulfonyl)phenylsulfonyl)methyl)cyclopentylamino)acetyl)pyrrolidine-2-carbonitrile

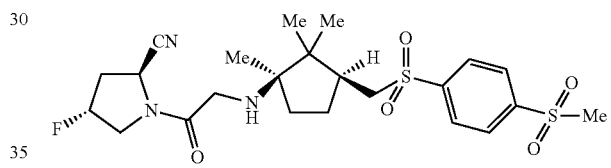

Step 3 intermediate of example 42 (0.097 g, 0.244 mmol), K₂CO₃ (0.14 g, 1.0 mmol) and KI (0.02 g, 0.12 mmol) in 1 mL of DMSO was coupled with intermediate 22 (0.046 g, 0.244 mmol), similar to step-4 of example 42 to afford 0.02 g of title compound as white solid. Melting point 163-166° C. ¹H NMR (400 MHz, CDCl₃) ppm: 0.79 (s, 6H), 0.88 (s, 3H), 1.08 (s, 3H), 1.45-1.51 (m, 1H), 1.98-2.03 (m, 1H), 2.32-2.37 (m, 1H), 2.61-2.63 (m, 1H), 2.76-2.78 (m, 1H), 3.11 (s, 3H), 3.13-3.18 (m, 2H), 3.26-3.87 (m, 4H), 4.75 (d, J=9.2 Hz, 0.8H), 5.1 (d, J=9.2 Hz, 0.2H), 5.3 (d, J=52 Hz, 0.2H), 5.4 (d, J=52 Hz, 0.8H), 8.15-8.18 (m, 4H). m/z (M+H): 514.2.

Example 44

(S)-1-(2-((1R,3S)-1,2,2-Trimethyl-3-((4-(methylsulfonyl)phenyl sulfonyl)methyl)cyclopentylamino)acetyl)pyrrolidine-2-carbonitrile

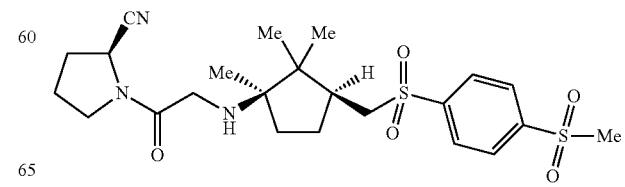

Step 3 intermediate of example 42 (0.097 g, 0.255 mmol), K₂CO₃ (0.138 g, 1 mmol) and KI (0.019 g, 0.12 mmol) in 1 mL of DMSO is coupled with intermediate 21 (0.042 g, 0.25 mmol) similar to step-4 of example 40 afforded 0.025 g of title compound as white solid. Melting point: 162-166° C. ¹H NMR (400 MHz, CDCl₃) δ ppm: 0.79 (s, 3H), 0.88 (s, 3H), 1.03 (s, 3H), 1.48-1.51 (m, 1H), 1.58-1.69 (m, 3H), 1.98-2.03 (m, 1H), 2.14-2.19 (m, 2H), 2.22-2.35 (m, 3H), 3.11 (s, 3H), 3.14-3.15 (m, 2H), 3.29-3.59 (m, 3H), 3.62-3.73 (m, 1H), 4.73-4.75 (m, 1H) 8.18 (s, 4H). m/z (M+H): 496.1.

Example 45

(2S,4S)-4-Fluoro-1-(2-((1S,3R)-1,2,2-trimethyl-3-((4-(methylsulfonyl)phenylsulfonyl)methyl)cyclo-pentylamino)acetyl)pyrrolidine-2-carbonitrile

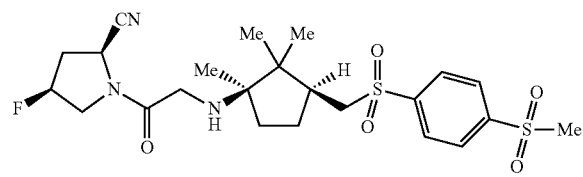 [SMILES: CC1(C)[C@@H](CS(=O)(=O)c2ccc(S(C)(=O)=O)cc2)CC[C@@]1(C)NCC(=O)N1C[C@@H](F)C[C@H]1C#N]

Prepared similar to example 42 replacing intermediate 3 with intermediate 10; 0.03 g, white solid. M.P.: 211-216° C. ¹H NMR (400 MHz, CDCl₃) δ ppm: 0.79 (s, 3H), 0.88 (s, 3H), 1.06 (s, 3H), 1.45-1.70 (m, 4H), 1.98-2.04 (m; 1H), 2.26-2.37 (m, 2H), 2.65-2.72 (m, 1H), 3.11 (s, 3H), 3.15-3.30 (m, 3H), 3.47-3.91 (m, 3H), 4.92 (d, J=9.3 Hz, 1H), 5.37 (d, J=53 Hz, 0.2H), 5.49 (d, J=53 Hz, 0.8H) 8.12 (s, 4H). m/z (M+H): 514.1. m/z (M+H): 514.1.

Example 46

(S)-1-(2-((1S,3R)-1,2,2-Trimethyl-3-((4-(methylsulfonyl)phenyl sulfonyl)methyl)cyclopentylamino) acetyl)pyrrolidine-2-carbonitrile

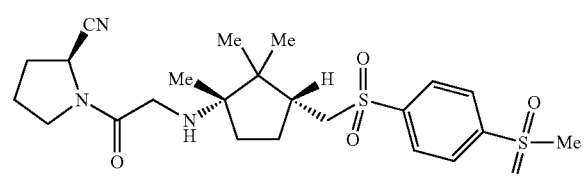

Prepared similar to example 44 replacing intermediate 3 with intermediate 10. 0.03 g, White solid. Melting point: 158-160° C. ¹H NMR (400 MHz, CDCl₃) δ ppm: 0.79 (s, 3H), 0.88 (s, 3H), 1.05 (s, 3H), 1.47-1.71 (m, 4H), 1.98-2.02 (m, 1H), 2.15-2.33 (m, 5H), 3.11 (s, 3H), 3.12-3.61 (m, 5H), 4.74-4.75 (m, 1H), 8.17 (s, 4H). m/z (M+H): 496.1.

Example 47

(2S,4R)-4-Fluoro-1-(2-((1S,3R)-1,2,2-trimethyl-3-((4-(methyl sulfonyl)phenylsulfonyl)methyl)cyclo-pentylamino)acetyl)pyrrolidine-2-carbonitrile

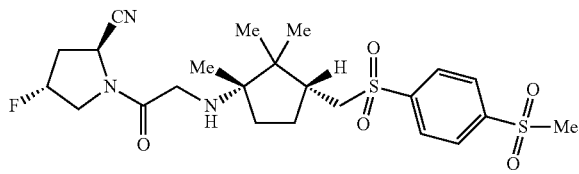 [SMILES: CC1(C)[C@H](CS(=O)(=O)c2ccc(S(C)(=O)=O)cc2)CC[C@]1(C)NCC(=O)N1C[C@H](F)C[C@H]1C#N]

Prepared similar to example 43 starting from intermediate 10. 0.02 g Off White solid, Melting point 172-175° C. ¹H NMR (400 MHz, CDCl₃) δ ppm: 0.79 (s, 3H), 0.88 (m, 3H), 1.04 (s, 3H), 1.45-1.75 (m, 4H), 1.98-2.03 (m, 1H), 2.32-2.7 (m, 1H), 2.4-2.53 (m, 1H), 2.72-2.79 (m, 1H), 3.11 (s, 3H), 3.13-3.18 (m, 2H), 3.38-3.39 (m, 2H), 3.65-3.95 (m, 2H), 4.75 (d, J=8.4 Hz, 0.8H), 4.82 (d, J=8.4 Hz, 0.2H), 5.25 (d, J=52 Hz, 0.2H), 5.4 (d, J=52 Hz, 0.8H), 8.13-8.18 (m, 4H). m/z (M+H): 514.1.

Example 48

(2S,4S)-4-Fluoro-1-(2-((1R,3S)-3-(3-(4-fluorophe-nyl)-1,2,4-oxadiazol-5-yl)-1,2,2-trimethyleyclopen-tylamino)acetyl)pyrrolidine-2-carbonitrile

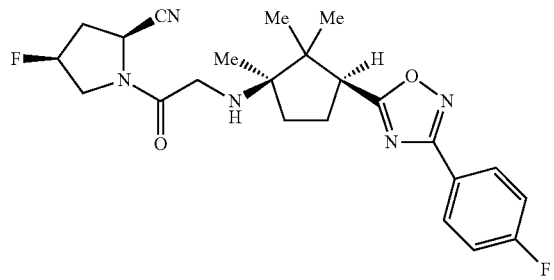 [SMILES: CC1(C)[C@@H](c2nc(-c3ccc(F)cc3)no2)CC[C@@]1(C)NCC(=O)N1C[C@@H](F)C[C@H]1C#N]

Step 1: tert-Butyl [(1R,3S)-1,2,2-trimethyl-3-(3-(4-Fluorophenyl)-1,2,4-oxadiazol-5-yl)cyclopentyl] carbamate

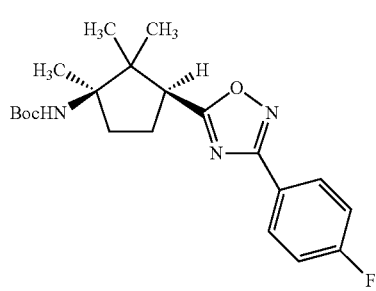 [SMILES: CC(C)(C)OC(=O)N[C@]1(C)CC[C@H](c2nc(-c3ccc(F)cc3)no2)C1(C)C]

A solution of intermediate 6 (0.5 g, 1.84 mmol), carbonyldiimidazole (0.59 g, 3.68 mmol) and 4-fluoro-N-hydroxybenzenecarboximidamide (0.284 g, 1.84 mmol) in dichloromethane was stirred at room temperature for 24 hours. The reaction mixture was concentrated; toluene was added and refluxed of another 24 hours. Toluene was removed under reduced pressure, crude mixture purified by column using ethyl acetate 5% in hexane. $^1$H NMR (400 MHz, CDCl$_3$) δ ppm: 0.81 (s, 3H), 1.21 (m, 3H), 1.44 (s, 9H), 1.57 (s, 3H), 2.08-2.2 (m, 4H), 3.3-3.37 (m, 1H), 7.13-7.26 (m, 2H), 8.09-8.12 (m, 2H. m/z (M+H-100): 290.1.

Step 2: (1R,3S)-3-(3-(4-Fluorophenyl)-1,2,4-oxadiazol-5-yl)-1,2,2-trimethylcyclo pentanamine hydrochloride

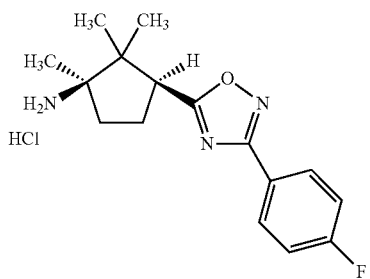 [SMILES: Cl ; CC1(C)[C@@H](c2nc(-c3ccc(F)cc3)no2)CC[C@@]1(C)N]

A saturated solution of dry HCl in ethyl acetate (2 mL) was added to ethyl acetate solution of step-1 intermediate and stirred for 2 h. Ethyl acetate was removed under reduced pressure; the residue was triturated with ether, separated solid was washed with ether and dried. $^1$H NMR (400 MHz, d$_6$-DMSO) δ ppm: 0.76 (s, 3H), 1.20 (m, 3H), 1 (s, 3H), 1.9 (m, 1H), 2.18 (m, 2H), 2.8 (m, 1H), 3.62 (m, 1H), 7.4-7.44 (m, 2H), 8.05-8.09 (m, 2H), 8.14 (bs, 3H). m/z (M+H): 290.1.

Step-3: (2S,4S)-4-Fluoro-1-(2-((1R,3S)-3-(3-(4-fluorophenyl)-1,2,4-oxadiazol-5-yl)-1,2,2-trimethylcyclopentylamino)acetyl)pyrrolidine-2-carbonitrile

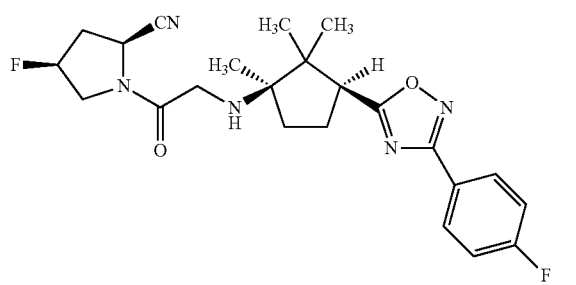 [SMILES: CC1(C)[C@@H](c2nc(-c3ccc(F)cc3)no2)CC[C@@]1(C)NCC(=O)N1C[C@@H](F)C[C@H]1C#N]

To a stirred suspension of the step-2 intermediate (0.1 g, 0.30 mmol), K$_2$CO$_3$ (0.17 g, 1.22 mmol) and KI (0.02 g, 0.12 mmol) in 1 ml of DMSO were added a DMSO solution of intermediate 20 (0.058 g, 0.30 mmol) and the reaction mixture was stirred for 12 hours under nitrogen atmosphere. After completion of the reaction, it was diluted with ethyl acetate and water. The layers were separated and the aqueous layer was washed twice with ethyl acetate. The combined organic layer was dried over anhydrous Na$_2$SO$_4$, concentrated and purified by chromatography to yield the product. 0.025 g, White solid. $^1$H NMR (400 MHz, CDCl$_3$) δ ppm: 0.82 (s, 3H), 1.18 (s, 3H), 1.19 (s, 3H), 1.22 (m, 1H), 1.59 (m, 1H), 1.88 (m, 1H), 1.97 (m, 1H), 2.61 (m, 1H), 2.69 (m, 1H), 2.89 (m, 1H), 3.41 (m, 1H), 3.45 (m, 1H), 3.69 (m, 1H), 3.98 (m, 1H), 4.95 (d, J=9.2, 0.8H), 5.34 (d, J=9.2, 0.2H), 5.35 (d, J=51, 0.2H), 5.5 (d, J=51, 0.8H), 7.14-7.19 (m, 2H), 8.09-8.12 (m, 2H). m/z (M+H): 442.1.

Example 49

(2S,4S)-4-Fluoro-1-(2-((1S,3R)-3-(3-(4-fluorophenyl)-1,2,4-oxadiazol-5-yl)-1,2,2-trimethylcyclopentylamino)acetyl)pyrrolidine-2-carbonitrile

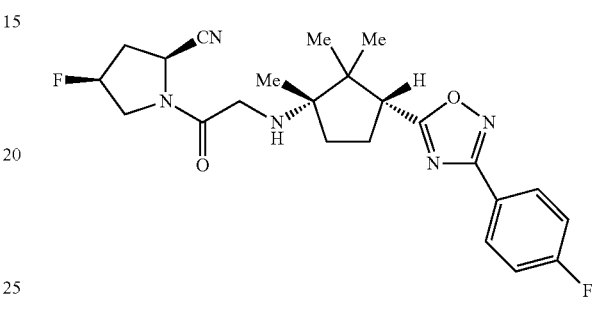

Prepared similar to example 48 using intermediate 13, carbonyldiimidazole and 4-fluoro-N'-hydroxybenzenecarboximidamide. 0.065 g, Off white solid. MP 160-163° C. $^1$H NMR (400 MHz, CDCl$_3$) δ ppm: 0.82 (s, 3H), 1.18 (s, 3H), 1.22 (s, 3H), 1.77-1.80 (m, 1H), 1.93-1.98 (m, 1H), 2.09-2.13 (m, 1H), 2.46-2.49 (m, 2H), 2.65-2.73 (m, 1H), 3.35-3.41 (m, 2H), 3.41-3.78 (m, 3H), 3.9-3.99 (m, 1H), 4.96 (d, J=9.2 Hz, 0.8H), 5.2 (d, J=9.2 Hz, 0.2H), 5.35 (d, J=51 Hz, 0.2H), 5.45 (d, J=51.1 Hz, 0.8H), 7.14-7.19 (m, 2H), 8.08-8.11 (m, 2H). m/z (M+H): 444.1.

Example 50

(2S,4S)-4-Fluoro-1-(2-((1R,3S)-1,2,2-trimethyl-3-(3-methyl-1,2,4-oxadiazol-5-yl)cyclopentylamino)acetyl)pyrrolidine-2-carbonitrile

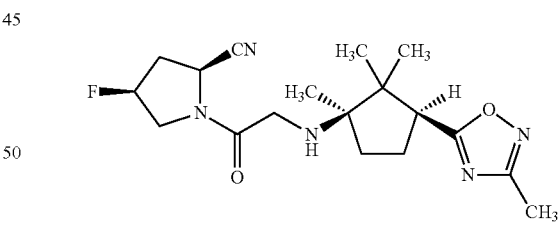

Step 1: tert-Butyl [(1R,3S)-1,2,2-trimethyl-3-(5-methyl-1,2,4-oxadiazol-3-yl)cyclopentyl]carbamate

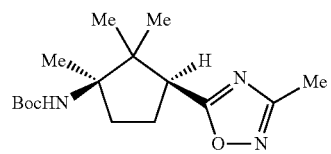 [SMILES: Cc1noc([C@H]2CC[C@@](C)(NC(=O)OC(C)(C)C)C2(C)C)n1]

A solution of intermediate 6, carbonyldiimidazole and N'-hydroxyacetimidamide in dichloromethane was stirred at room temperature for 24 hours. The reaction mixture was concentrated. Toluene was added and refluxed of another 24 h. Toluene was removed under reduced pressure and crude mixture was purified by column chromatography using ethyl acetate 5% in hexane. m/z (M+H): 310.2.

Step 2: (1R,3S)-1,2,2-Trimethyl-3-(3-methyl-1,2,4-oxadiazol-5-yl)cyclopentan aminehydrochloride

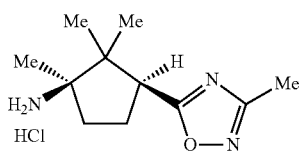 [SMILES: Cl ; Cc1noc([C@H]2CC[C@@](C)(N)C2(C)C)n1]

A saturated solution of dry HCl in ethyl acetate (2 mL) was added to ethyl acetate solution of step-1 intermediate and stirred for 2 hours. Ethyl acetate was removed under reduced pressure; the residue was triturated with ether and solid separated was washed with ether and dried. $^1$H NMR (400 MHz, CDCl$_3$) δ ppm: 0.85 (s, 3H), 1.19 (s, 3H), 1.45 (s, 3H), 2.07 (m, 1H), 2.22-2.37 (m, 3H), 2.4 (s, 3H), 3.58 (t, 1H).

Step: 3: (2S,4S)-4-Fluoro-1-(2-((1R,3S)-1,2,2-trimethyl-3-(3-methyl-1,2,4-oxadiazol-5-yl)cyclopentylamino)acetyl)pyrrolidine-2-carbonitrile

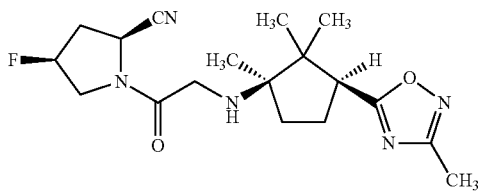 [SMILES: Cc1noc([C@H]2CC[C@@](C)(NCC(=O)N3C[C@@H](F)C[C@H]3C#N)C2(C)C)n1]

To a stirred suspension of the step-2 intermediate (0.1 g, 0.40 mmol), K$_2$CO$_3$ (0.225 g, 1.62 mmol) and KI (0.033 g, 0.2° mmol) in 1 mL of DMSO was added a DMSO solution of intermediate 20 (0.069 g, 0.36 mmol) and the reaction mixture was stirred for 12 h under nitrogen atmosphere. After completion of the reaction, it was diluted with ethyl acetate and water. The layers were separated and the aqueous layer was washed twice with ethyl acetate. The combined organic layer was dried over anhydrous Na$_2$SO$_4$, concentrated and purified by chromatography to yield the product as an off-white solid. 0.050 g, White solid. Melting point: 147-151° C. $^1$H NMR (400 MHz, CDCl$_3$) δ ppm: 0.85 (s, 3H), 1.11 (s, 3H), 1.2 (s, 3H), 1.86-1.88 (m, 1H), 1.90-1.93 (m, 1H), 2.05-2.07 (m, 1H), 2.29-2.37 (m, 1H), 2.39 (s, 3H), 2.61-2.75 (m, 1H), 3.27-3.32 (m, 1H), 3.39-3.50 (m, 2H), 3.67-3.75 (m, 2H), 3.90-3.99 (m, 1H), 4.94 (d, J=9.2, 0.8H), 5.31 (d, J=9.2, 0.2H), 5.35 (d, J=52, 0.2H) 5.45 (d, J=52, 0.8H). m/z (M+H): 364.2.

Example 51

(2S,4S)-4-Fluoro-1-(2-((1S,3R)-1,2,2-trimethyl-3-(3-methyl-1,2,4-oxadiazol-5-yl)cyclopentylamino)acetyl)pyrrolidine-2-carbonitrile Prepared similar to example 50 starting from intermediate 13 and N'-hydroxyacetimidamide

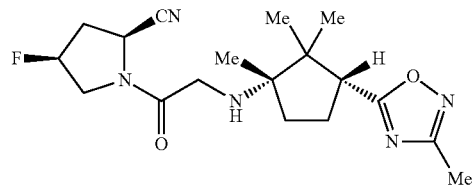 [SMILES: Cc1noc([C@@H]2CC[C@](C)(NCC(=O)N3C[C@@H](F)C[C@H]3C#N)C2(C)C)n1]

0.024 g, Off white solid. Melting point: 160-163° C. $^1$H NMR (400 MHz, CDCl$_3$) δ ppm: 0.77 (s, 3H), 1.13 (s, 3H), 1.17 (s, 3H), 1.7-1.73 (m, 1H), 1.86-1.89 (m, 2H), 2.04-2.05 (m, 1H), 2.2-2.3 (m, 1H), 2.39 (s, 3H), 2.65-2.8 (m, 1H), 3.28-3.39 (m, 2H), 3.51-3.55 (m, 1H), 3.61-3.68 (m, 1H), 3.89-3.95 (m, 1H), 4.95 (d, J=9.2 Hz, 0.8H), 5.20 (d, J=9.20 Hz, 0.2H), 5.35 (d, J=52 Hz, 0.2H), 5.45 (d, J=52 Hz, 0.8H); m/z (M+H): 364.2.

Example 52

(2S,4S)-4-Fluoro-1-(2-((1R,3S)-3-(3-isopropyl-1,2,4-oxadiazol-5-yl)-1,2,2-trimethylcyclopentylamino)acetyl)pyrrolidine-2-carbonitrile

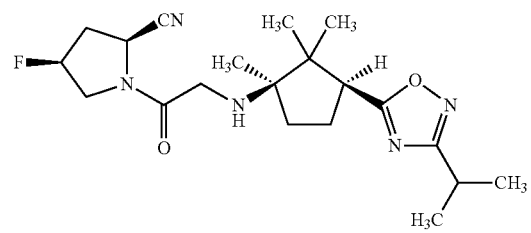 [SMILES: CC(C)c1noc([C@H]2CC[C@@](C)(NCC(=O)N3C[C@@H](F)C[C@H]3C#N)C2(C)C)n1]

Prepared similar to example 50 using intermediate 6 and 1V'-hydroxy-2-methyl propanimidamide in step 1. 0.015 g, Off-white hygroscopic solid. Melting point: 91-94° C. $^1$H NMR (400 MHz, CDCl$_3$) δ ppm: 0.75 (s, 3H), 1.09 (s, 3H), 1.16 (s, 3H), 1.32-1.35 (d, J=6.9, 6H), 1.79-1.83 (m, 1H), 1.92-1.93 (m, 1H), 2.05-2.07 (m, 1H), 2.35-2.39 (m, 2H), 2.65-2.73 (m, 1H), 3.06-3.09 (m, 1H), 3.29-3.80 (m, 4H), 3.95-4.0 (m, 1H), 4.95 (d, J=9.2 Hz, 0.8H), 5.20 (d, J=9.2 Hz, 0.2H), 5.35 (d, J=52 Hz, 0.2H), 5.45 (d, J=52 Hz, 0.8H); m/z (M+H): 392.2.

Example 53

(2S,4S)-1-(2-((1R,3R)-3-(Cyanomethyl)-1,2,2-trimethylcyclopentyl amino)acetyl)-4-fluoropyrrolidine-2-carbonitrile

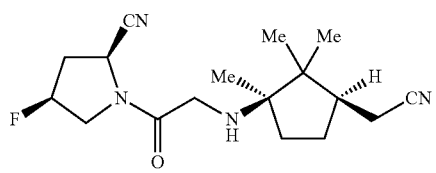 [SMILES: CC1(C)[C@@H](CC#N)CC[C@@]1(C)NCC(=O)N1C[C@@H](F)C[C@H]1C#N]

To a solution of intermediate 7 (0.2 g, 0.75 mmole) in Acetonitrile was added p-toluenesulphonic acid (0.28 g, 1.50 mmol) and the reaction mixture was stirred at room temperature for five hours. The volatiles were removed under reduced pressure and triturated with diethyl ether to afford the desired product. The product thus obtained was dissolved in 1 mL of DMSO and K$_2$CO$_3$ (0.202 g, 1.47 mmol), KI (0.081 g, 0.49 mmol) and intermediate-20 (0.142 g, 0.75 mmol) were added. The reaction mixture was stirred for 12 hours under nitrogen atmosphere. After completion of the reaction, it was diluted with ethyl acetate and water. The layers were separated and the aqueous layer was washed twice with ethyl acetate. The combined organic layer was dried over anhydrous Na$_2$SO$_4$, concentrated and purified by chromatography to yield the product as an off-white solid. 0.08 g, Off white solid. $^1$H NMR (400 MHz, CDCl$_3$) δ ppm: 0.89 (s, 3H), 0.95 (s, 3H), 1.2 (s, 3H), 1.59-1.61 (m, 1H), 2.01-2.05 (m, 2H), 2.11-2.15 (m, 2H), 2.25-2.42 (m, 3H), 2.62-2.73 (m, 1H), 3.34-3.50 (m, 2H), 3.65-3.76 (m, 1H), 3.88-3.97 (m, 1H), 4.94 (d, J=9.2 Hz, 0.8H), 5.08 (d, J=9.2 Hz, 0.2H), 5.35 (d, J=52 Hz, 0.2H), 5.45 (d, J=52 Hz, 0.8H); m/z (M+H): 321.2.

Example 54

(2S,4S)-4-Fluoro-1-(2-((1R,3R)-1,2,2-trimethyl-3-((5-methyl-1,2,4-oxadiazol-3-yl)methyl)cyclopentylamino)acetyl)pyrrolidine-2-carbonitrile

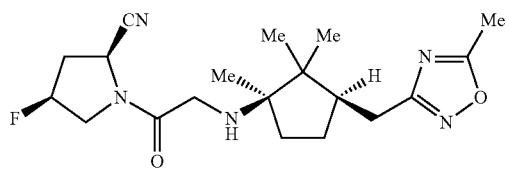 [SMILES: Cc1nc(C[C@H]2CC[C@@](C)(NCC(=O)N3C[C@@H](F)C[C@H]3C#N)C2(C)C)no1]

Step 1: tert-Butyl {(1R,3R)-3-[(2Z)-2-amino-2-(hydroxyimino)ethyl]-1,2,2-trimethyl cyclopentyl}carbamate

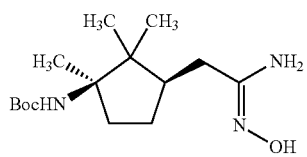 [SMILES: CC(C)(C)OC(=O)N[C@]1(C)CC[C@H](C/C(N)=N/O)C1(C)C]

To a solution intermediate 7 (0.80 g, 0.003 mol) in ethanol, 50% of hydroxylamine aqueous solution (6 mL) is added and heated to 80-85° C. for five hours. After completion of reaction, ethanol was removed and diluted with water and ethyl acetate. The layers are separated and the organic layer is dried over Na$_2$SO$_4$, and concentrated on a rotavapor. It gave 0.85 g, off-white solid, m/z (M+1): 300.2.

Step 2: tert-Butyl (1R,3R)-1,2,2-trimethyl-3-((5-methyl-1,2,4-oxadiazol-3-yl)methyl)cyclopentylcarbamate

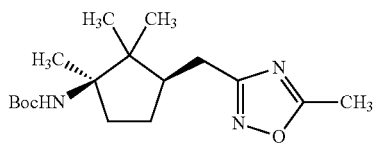 [SMILES: Cc1nc(C[C@H]2CC[C@@](C)(NC(=O)OC(C)(C)C)C2(C)C)no1]

To a solution of Step-1 intermediate (0.42 g, 0.0014 mol) in trimethylorthoacetate (5 mL), (1R)-(−)-camphorsulphonic acid (10 mg) is added and heated to 100-105° C. for five hours. After completion of reaction, trimethylorthoacetate was removed under reduced pressure and diluted with water and ethyl acetate. The layers were separated and the organic layer was dried over anhydrous Na$_2$SO$_4$, and concentrated on a rotavapor. The crude material was purified, by column chromatography. 0.270 g, Off-white sticky mass, $^1$H NMR (400 MHz, CDCl$_3$) δ ppm: 0.85 (s, 3H), 1.10 (s, 3H), 1.35 (s, 3H), 1.43 (s, 9H), 1.74-1.78 (m, 1H), 1.88-1.89 (m, 2H), 2.15-2.20 (m, 2H), 2.50-2.52 (m, 1H), 2.53 (s, 3H), 2.82-2.86 (m, 1H), 4.52 (s, 1H). m/z (M−100)+H: 224.2.

Step 3: (1R,3R)-1,2,2-Trimethyl-3-((5-methyl-1,2,4-oxadiazol-3-yl)methyl) cyelopentanaminehydrochloride

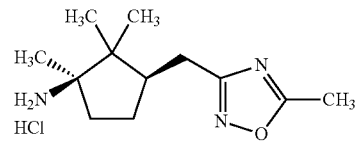

A solution of saturated HCl in ethyl acetate (2 mL) was added to a solution of intermediate step-1 (0.26 g, 0.0008 moles)) in ethyl acetate at 0° C. and the reaction mixture was stirred at room temperature for 2 h. The volatiles were removed under reduced pressure and triturated with diethyl ether to afford the desired product. 0.180 g, Off white sticky mass, $^1$H NMR (400 MHz, DMSO) δ ppm: 0.85 (s, 3H), 0.95 (s, 3H), 1.12 (s, 3H), 1.65-1.74 (m, 2H), 1.90-1.95 (m, 1H), 2.16-2.16 (m, 2H), 2.57-2.63 (m, 1H), 2.64 (s, 3H), 2.80-2.85 (m, 1H), 7.42 (BS, 3H). m/z (M+1): 224.2.

Step 4: (2S,4S)-4-Fluoro-1-(2-((1R,3R)-1,2,2-trimethyl-3-((5-methyl-1,2,4-oxadiazol-3-yl)methyl) cyclopentylamino)acetyl)pyrrolidine-2-carbonitrile

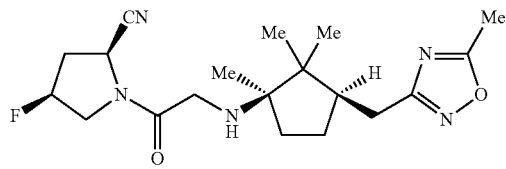 [SMILES: Cc1nc(C[C@H]2CC[C@@](C)(NCC(=O)N3C[C@@H](F)C[C@H]3C#N)C2(C)C)no1]

To a stirred suspension of the step 3 intermediate (0.07 g, 0.269 mmol), K$_2$CO$_3$ (0.148 g, 1.07 mmol) and KI (0.020 g, 0.12 mmol) in 1 mL of DMSO was added a DMSO solution of intermediate 20 (0.051 g, 0.269 mmol) and the reaction mixture was stirred for 12 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by chromatography to yield the product as 0.03 g, off-white solid. Melting point: 121-123° C. $^1$H NMR (400 MHz, CDCl$_3$) δ ppm: 0.98 (s, 6H), 1.04 (s, 3H), 1.3-1.42 (m, 1H), 1.84-1.9 (m, 3H), 2.17-2.4 (m, 2H), 2.58 (s, 3H), 2.62-2.88 (m, 2H), 3.41-4.02 (m, 4H), 4.96 (d, J=9.2, 0.8H), 5.25 (d, J=9.2, 0.2H), 5.37 (d, J=52, 0.2H), 5.45 (d, J=51, 0.8H); m/z (M+H): 378.2.

Example 55

(2S,4S)-4-Fluoro-1-(2-((1S,3S)-1,2,2-trimethyl-3-((5-methyl-1,2,4-oxadiazol-3-yl)methyl)cyclopentylamino)acetyl)pyrrolidine-2-carbonitrile

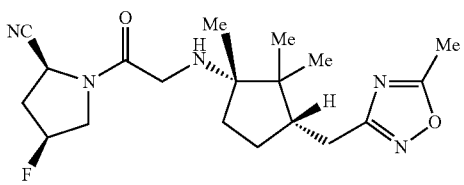 [SMILES: Cc1nc(C[C@@H]2CC[C@](C)(NCC(=O)N3C[C@@H](F)C[C@H]3C#N)C2(C)C)no1]

Prepared similar to example 54 using intermediate 14 as starting material. 0.024 g, White solid. Melting point: 131-133° C. $^1$H NMR (400 MHz, CDCl$_3$) δ ppm: 0.90 (s, 3H), 0.94 (s, 3H), 1.09 (s, 3H), 1.34-1.37 (m, 1H), 1.57-1.76 (m, 4H), 2.2-2.4 (m, 2H), 2.56 (s, 3H), 2.58-2.77 (m, 2H), 3.3-3.93 (m, 4H), 4.95 (d, J=9.2 Hz, 0.8H), 5.16 (d, J=9.2 Hz, 0.2H), 5.36 (d, J=52 Hz, 0.2H), 5.45 (d, J=51.6 Hz, 0.8H); m/z (M+H): 378.2.

Example 56

(2S,4S)-4-Fluoro-1-(2-((1S,3S)-1,2,2-trimethyl-3-((5-(trifluoromethyl)-1,2,4-oxadiazol-3-yl)methyl)cyclopentylamino)acetyl)pyrrolidine-2-carbonitrile

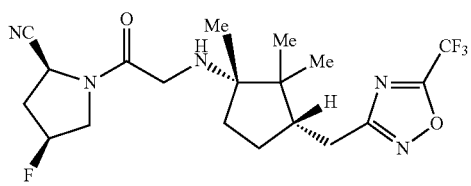 [SMILES: CC1(C)[C@H](Cc2noc(C(F)(F)F)n2)CC[C@]1(C)NCC(=O)N1C[C@@H](F)C[C@H]1C#N]

Step-1: tert-Butyl (1S,3S)-1,2,2-trimethyl-3-((5-(trifluoromethyl)-1,2,4-oxadiazol-3-yl)methyl)cyclopentylcarbamate

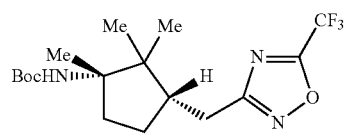 [SMILES: CC(C)(C)OC(=O)N[C@@]1(C)CC[C@@H](Cc2noc(C(F)(F)F)n2)C1(C)C]

To a solution of tert-butyl {(1S,3S)-3-[(2Z)-2-amino-2-(hydroxyimino)ethyl]-1,2,2-trimethylcyclopentyl}carbamate (prepared by reacting intermediate 14 and 50% hydroxylamine solution as described in example 54 step 1) in THF, trifluoroacetic anhydride was added and stirred at room temperature for 8 h. The reaction mixture was concentrated under reduced pressure, saturated NaHCO$_3$ solution was added and extracted with ethyl acetate (2×50 mL), and organic layers are combined, washed with water and brine, dried with anhydrous Na$_2$SO$_4$ and concentrated. Crude material purified by column chromatography. $^1$H NMR (400 MHz, CDCl$_3$) δ ppm: 0.79 (s, 3H), 0.94 (s, 3H), 1.39-1.40 (m, 1H), 1.43 (s, 3H), 1.5 (s, 9H), 1.75-1.83 (m, 1H), 1.95-2.0 (m, 2H), 2.22-2.27 (m, 1H), 2.64-2.70 (dd, 1H), 2.85-2.9 (dd, 1H), 4.52 (s, 1H).

Step-2: (1S,3S)-1,2,2-Trimethyl-3-{[5-(trifluoromethyl)-1,2,4-oxadiazol-3-yl]methyl}cyclopentanamine hydrochloride

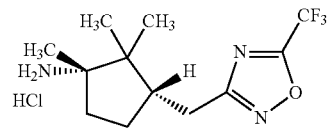 [SMILES: Cl ; CC1(C)[C@H](Cc2noc(C(F)(F)F)n2)CC[C@]1(C)N]

A solution of saturated HCl in ethyl acetate (2 mL) was added to a solution of intermediate step-1 (0.26 g, 0.83 mol) in ethyl acetate and the reaction mixture was stirred at room temperature for 2 h. The volatiles were removed under reduced pressure and triturated with hexane to afford the desired product. $^1$H NMR (400 MHz, d$_6$-DMSO) δ ppm: 0.89 (s, 3H), 0.98 (s, 3H), 1.21 (s, 3H), 1.33-1.49 (s, 1H), 1.65-1.83 (m, 2H), 1.9-1.96 (m, 1H), 1.21-2.22 (m, 1H), 2.68-2.74 (dd, 1H), 2.92-2.97 (dd, 1H), 8.0 (bs, 3H). m/z (M+H): 278.1.

Step 3: (2S,4S)-4-Fluoro-1-(2-((1S,3S)-1,2,2-trimethyl-3-((5-trifluoromethyl-1,2,4-oxadiazol-3-yl)methyl)cyclopentylamino)acetyl)pyrrolidine-2-carbonitrile

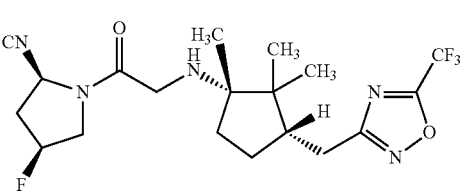

To a stirred suspension of the step-2 intermediate (0.095 g, 0.50 mmol), $K_2CO_3$ (0.138 g, 1.0 mmol) and KI (0.033 g, 0.2 mmol) in 1 mL of DMSO was added a DMSO solution of intermediate-20 (0.095 g, 0.5 mmol) and the reaction mixture was stirred for 12 hours under nitrogen atmosphere. After completion of the reaction, it was diluted with ethyl acetate and water. The layers were separated and the aqueous layer was washed twice with ethyl acetate. The combined organic layers was dried over anhydrous $Na_2SO_4$, concentrated and purified by chromatography to yield the product 0.02 g, White solid. Melting Point 130-131° C. $^1$H NMR (400 MHz, DMSO) δ ppm: 0.92 (s, 6H), 1.12 (m, 3H), 1.3-1.45 (m, 1H), 1.6 (m, 1H), 1.7-1.75 (m, 2H), 1.27-2.29 (m, 2H), 2.69-2.78 (m, 2H), 2.86-2.91 (d, 1H), 3.3-3.99 (m, 4H), 4.94 (d, J=9.2, 0.8H), 5.15 (d, J=9.2, 0.2H), 5.35 (d, J=51.2, 0.2H), 5.44 (d, J=51, 0.8H); m/z (M+H): 432.1.

Example 57

(2S,4S)-4-Fluoro-1-(2-((1S,3S)-1,2,2-trimethyl-3-((5-(trifluoromethyl)-1,2,4-oxadiazol-3-yl)methyl)cyclopentylamino)acetyl)pyrrolidine-2-carbonitrile methanesulfonate

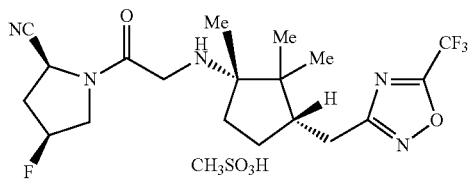

Example 56 (20 mg, 0.046 mmol) was dissolved in ethyl acetate, to this added (4.4 mg, 0.046 mmol) methanesulfonic acid diluted in ethyl acetate and stirred for 2 h. The solid separated out was decanted, washed with ethyl acetate and dried. 0.02 g, White solid. Melting Point 130-131° C. $^1$H NMR (400 MHz, $D_2O$) δ ppm: 1.11 (s, 6H), 1.39 (m, 3H), 1.52-1.61 (m, 1H), 1.83-1.9 (m, 2H), 2.06-2.11 (m, 1H), 2.38-2.4 (m, 1H), 2.49-2.5 (m, 1H), 2.61-2.63 (m, 1H), 2.75 (s, 3H), 2.79-2.81 (m, 1H), 2.82-2.85 (m, 1H), 3.76-3.95 (m, 2H), 4.02-4.24 (m, 1H), 4.74-4.79 (m, 1H), 5.10 (d, J=9.2 Hz, 0.8H), 5.28 (d, J=9.2 Hz, 0.2H), 5.50 (d, J=51.2 Hz, 0.2H), 5.55 (d, J=52 Hz, 0.8H); m/z (M+H): 432.1.

Example 58

(2S,4S)-1-(2-((1S,3S)-3-((5-tert-Butyl-1,2,4-oxadiazol-3-yl)methyl)-1,2,2-trimethylcyclopentylamino)acetyl)-4-fluoropyrrolidine-2-carbonitrile

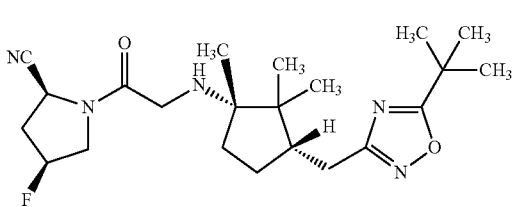 [SMILES: CC(C)(C)c1nc(C[C@@H]2CC[C@](C)(NCC(=O)N3C[C@@H](F)C[C@H]3C#N)C2(C)C)no1]

Step 1: tert-butyl(1S,3S)-3-((5-tert-butyl-1,2,4-oxadiazol-3-yl)methyl)-1,2,2-trimethylcyclopentylcarbamate

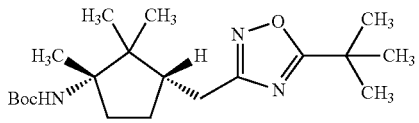 [SMILES: CC(C)(C)OC(=O)N[C@@]1(C)CC[C@@H](Cc2noc(C(C)(C)C)n2)C1(C)C]

To a solution of trimethylacetic acid (0.150 g, 0.0014 mol) in DCM, CDI (0.356 g, 0.0021 moles) was added and stirred for 2 h. tert-butyl {(1S,3S)-3-[(2-amino-2-(hydroxyimino)ethyl]-1,2,2-trimethylcyclopentyl}carbamate prepared in Step-1 example 56) (0.483 g, 0.00161 mol) was added and continued the stirring. After completion of reaction, it is diluted with water. The layer was separated and the organic layer was dried over anhydrous $Na_2SO_4$, and concentrated on a rotavapor. The crude material was dissolved in toluene (20 mL) and heated to 120-125° C. for ten hours. After completion of reaction, toluene was removed under reduced pressure and diluted with ethyl acetate and water. The layer was separated. The organic layer is dried over $Na_2SO_4$ and concentrated on a rotavapor. The crude material is purified by column. 0.321 g, Off white sticky mass, $^1$H NMR (400 MHz, $CDCl_3$) δ ppm: 0.85 (s, 3H), 1.10 (s, 3H), 1.35 (s, 3H), 1.40 (s, 9H), 1.43 (s, 9H), 1.74-1.78 (m, 1H), 1.88-1.89 (m, 2H), 2.15-2.20 (m, 2H), 2.50-2.52 (m, 1H), 2.82-2.86 (m, 1H), 4.52 (s, 1H). m/z (M−100)+H: 266.2.

Step 2: (1S,3S)-3-((5-tert-Butyl-1,2,4-oxadiazol-3-yl)methyl)-1,2,2-trim ethyl cyclopentanamine hydrochloride

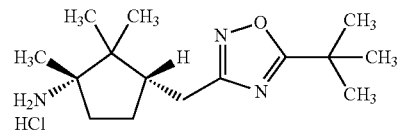 [SMILES: CC(C)(C)c1nc(C[C@@H]2CC[C@](C)(N)C2(C)C)no1 ; Cl]

A solution of saturated HCl in ethyl acetate (2 mL) was added to a solution of intermediate step-1 (0.315 g, 0.86 mmol) in ethyl acetate and the reaction mixture was stirred at room temperature for 2 h. The volatiles were removed under reduced pressure and triturated with hexane to afford the desired product. 0.250 g, White solid, $^1$H NMR (400 MHz, $d_6$ DMSO) ppm: 0.80 (s, 3H), 1.11 (s, 3H), 1.35 (s, 3H), 1.40 (s, 9H), 1.74-1.78 (m, 1H), 1.88-1.89 (m, 2H), 2.15-2.20 (m, 2H), 2.50-2.52 (m, 1H), 2.82-2.86 (m, 1H), 8.04 (bs, 3H). m/z (M+1): 266.2.

Step 3: (2S,4S)-1-(2-((1S,3S)-3-((5-tert-Butyl-1,2,4-oxadiazol-3-yl)methyl)-1,2,2-trimethylcyclopentylamino)acetyl)-4-fluoropyrrolidine-2-carbonitrile

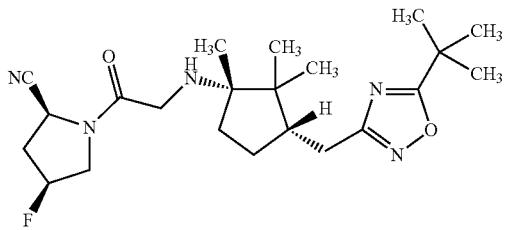 [SMILES: CC(C)(C)c1nc(C[C@@H]2CC[C@](C)(NCC(=O)N3C[C@@H](F)C[C@H]3C#N)C2(C)C)no1]

To a stirred suspension of the step-2 intermediate (0.3 g, 1.01 mmol), K₂CO₃ (0.540 g, 4.05 mmol) and KI (0.084 g, 0.5 mmol) in 1 mL of DMSO was added a DMSO solution of intermediate 20 (0.182 g, 0.96 mmol) and the reaction mixture was stirred for 12 h under nitrogen atmosphere. After completion of the reaction, it was diluted with ethyl acetate and water. The layers were separated and the aqueous layer was washed twice with ethyl acetate. The combined organic layers was dried over anhydrous Na₂SO₄, concentrated and purified by chromatography to yield the product 0.13 g Off White solid, melting point: 152-154° C. ¹H NMR (400 MHz, CDCl₃) ppm: 0.89 (s, 3H), 0.91 (s, 3H), 1.09 (s, 3H), 1.42 (s, 9H), 1.58-1.79 (m, 4H), 2.27-2.36 (m, 2H), 2.56-2.79 (m, 3H), 3.30-3.60 (m, 2H), 3.75-3.77 (m, 1H), 3.90-3.93 (m, 1H), 4.95 (d, J=9.2 Hz, 0.8H), 5.15 (d, J=9.20 Hz, 0.2H), 5.35 (d, J=51 Hz, 0.2H), 5.5 (d, J=51 Hz, 0.8H); m/z (M+1): 420.2.

Example 59

(2S,4S)-1-(2-((1S,3S)-3-((5-Cyclohexyl-1,2,4-oxadiazol-3-yl)methyl)-1,2,2-trimethylcyclopentylamino)acetyl)-4-fluoropyrrolidine-2-carbonitrile

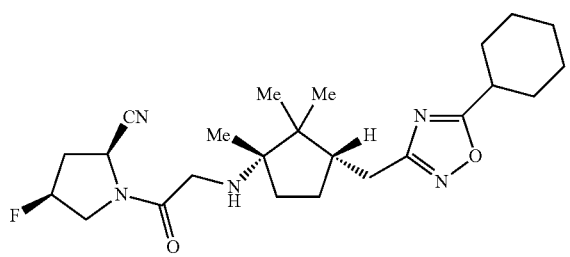 [SMILES: CC1(C)[C@H](Cc2noc(C3CCCCC3)n2)CC[C@]1(C)NCC(=O)N1C[C@@H](F)C[C@H]1C#N]

Step 1: (1S,3S)-3-((5-Cyclohexyl-1,2,4-oxadiazol-3-yl)methyl)-1,2,2-trimethyl cyclopentanamine

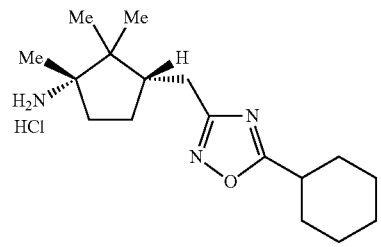 [SMILES: Cl ; CC1(C)[C@H](Cc2noc(C3CCCCC3)n2)CC[C@]1(C)N]

To a solution of tert-butyl {(1S,3S)-3-[(2Z)-2-amino-2-(hydroxyimino)ethyl]-1,2,2-trimethylcyclopentyl}carbamate (prepared in Step-1 example 56)(0.3 g, 1 mmol) in toluene, pyridine (0.079 g, 1 mmol) and cyclohexanecarbonylchloride was added and stirred for 3 hours. The reaction mixture was refluxed for another 12 h. The reaction mixture diluted with ethyl acetate, washed with 0.1N HCl. Ethyl acetate layer was separated, dried and concentrated, residue purified by silica column chromatography using 20% ethyl acetate in hexane. m/z (M+1)–100: 292.1. The product that obtained was dissolved in ethyl acetate. To this a solution of saturated HCl in ethyl acetate (2 mL) was added and reaction mixture was stirred at room temperature for two hours. The volatiles were removed under reduced pressure and triturated with hexane to afford the desired product. ¹H NMR (400 MHz, d₆-DMSO) δ ppm: 0.8 (s, 3H), 0.9 (s, 3H), 1.2 (s, 3H), 1.42-1.50 (m, 3H), 1.52-1.72 (m, 2H), 1.89-1.92 (m, 5H), 1.95-1.98 (m, 3H), 2.13-2.15 (m, 1H), 2.51-2.54 (m, 1H), 2.74 (m, 1H), 3.02 (m, 1H), 7.95 (bs, 3H).

Step 2: (2S,4S)-1-(2-((1S,3S)-3-((5-Cyclohexyl-1,2,4-oxadiazol-3-yl)methyl)-1,2,2-trimethylcyclopentylamino)acetyl)-4-fluoropyrrolidine-2-carbonitrile

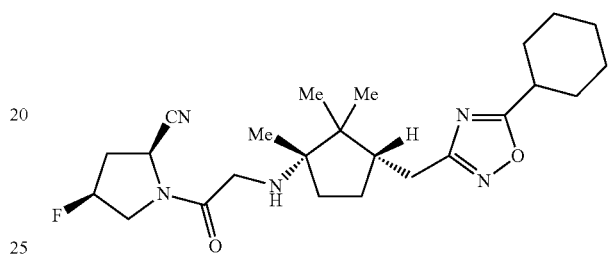

To a stirred suspension of the step-2 intermediate (0.15 g, 0.50 mmol), K₂CO₃ (0.138 g, 1 mmol) and KI catalytic amount in 1 mL of DMSO was added a DMSO solution of intermediate 20 (0.95 g, 0.5 mmol) and the reaction mixture was stirred for 12 h under nitrogen atmosphere. After completion of the reaction, it was diluted with ethyl acetate and water. The layers were separated and the aqueous layer was washed twice with ethyl acetate. The combined organic layers was dried over anhydrous Na₂SO₄, concentrated and purified by chromatography to yield the product. 0.050 g, Off white solid. Melting point: 152-153° C. ¹H NMR (400 MHz, CDCl₃) δ ppm: 0.9 (s, 6H), 1.2 (s, 3H), 1.3-1.45 (m, 2H), 1.40-1.85 (m, 11H), 2.04-2.07 (m, 2H), 2.26-2.29 (m, 2H), 2.56-2.68 (m, 1H), 2.74-2.78 (m, 2H), 2.90-2.92 (m, 1H), 3.30-3.34 (m, 1H), 3.48-3.53 (m, 1H), 3.60-3.8 (m, 1H), 3.85-3.95 (m, 1H), 4.95 (d, J=9.2, 0.8H), 5.25 (d, J=9.2, 0.2H), 5.35 (d, J=51, 0.2H), 5.5 (d, J=51, 0.8H)). m/z (M+H): 446.2.

Example 60

(2S,4S)-4-Fluoro-1-(2-((1S,3S)-3-((5-(hydroxymethyl)-1,2,4-oxadiazol-3-yl)methyl)-1,2,2-trimethylcyclopentylamino)acetyl)pyrrolidine-2-carbonitrile

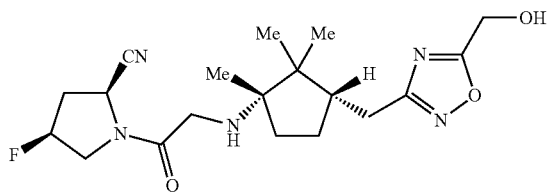 [SMILES: CC1(C)[C@H](Cc2noc(CO)n2)CC[C@]1(C)NCC(=O)N1C[C@@H](F)C[C@H]1C#N]

Step 1: Ethyl 3-(((1S,3S)-3-(tert-butoxycarbonylamino)-2,2,3-trimethylcyclopentyl)methyl)-1,2,4-oxadiazole-5-carboxylate

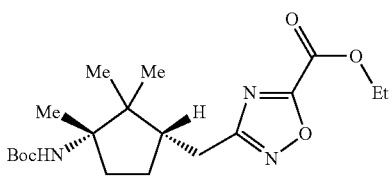 [SMILES: CCOC(=O)c1nc(C[C@@H]2CC[C@](C)(NC(=O)OC(C)(C)C)C2(C)C)no1]

To a solution of tert-butyl {(1S,3S)-3-[(2Z)-2-amino-2-(hydroxyimino)ethyl]-1,2,2-trimethylcyclopentyl}carbamate (prepared in Step-1 example 56) (0.40 g, 1.3 mmoles) in toluene (10 mL), pyridine (0.317 mL, 4.0 moles) and ethyloxalyl chloride (0.233 g, 2.0 mmoles) were added at 0-5° C., and stirred for two hours. After two hours reaction mixture was heated to 120-125° C. for 12 hours in an oil bath. After completion of reaction, toluene was removed under reduced pressure and diluted with water and ethyl acetate. The organic layer was dried over Na$_2$SO$_4$ and concentrated on a rotavapor. It gave brown colour sticky mass, which is purified by column chromatography. 0.25 g, Off white sticky mass, $^1$H NMR (400 MHz, CDCl$_3$) δ ppm: 0.85 (s, 3H), 0.97 (s, 3H), 1.32 (s, 3H), 1.43 (s, 9H), 1.46 (s, 3H), 1.72-1.78 (m, 1H), 1.88-1.89 (m, 2H), 1.97-2.00 (m, 2H), 2.40-2.42 (m, 1H), 2.64-2.68 (m, 1H), 2.84-2.88 (m, 1H). 4.50 (s, 1H), 4.52-4.56 (m, 2H), m/z (M−56)+H: 326.1.

Step 2: tert-Butyl (1S,3S)-3-((5-(hydroxymethyl)-1,2,4-oxadiazol-3-yl)methyl)-1,2,2-trimethylcyclopentylcarbamate

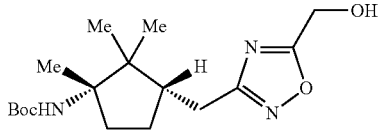

To a solution of step-1 intermediate (0.26 g, 0.6 mmol) in THF (10 mL), NaBH$_4$ (0.051 g, 1.36 mmole) is added and stirred for two hours at 0-5° C. After completion of reaction, THF was removed under reduced pressure and diluted with water and ethyl acetate. The layer was separated and the organic layer dried over Na$_2$SO$_4$, and concentrated on a rotavapor. The crude material was purified by column chromatography. 0.090 g, Off white sticky mass, m/z (M+1)-100: 240.2.

Step 3: (3-(((1S,3S)-3-Amino-2,2,3-trimethylcyclopentyl)methyl)-1,2,4-oxadiazol-5-yl)methanol hydrochloride

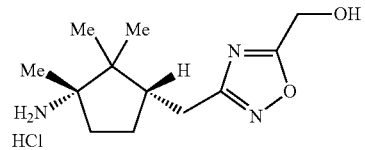 [SMILES: CC1(C)[C@H](Cc2noc(CO)n2)CC[C@]1(C)N ; Cl]

A solution of saturated HCl in ethyl acetate (2 mL) was added to a solution of intermediate step-1 (0.085 g, 0.2 mmoles) in ethyl acetate and the reaction mixture was stirred at room temperature for 2 h. The volatiles were removed under reduced pressure and triturated with hexane to afford the desired product 0.055 g, White solid, $^1$H NMR (400 MHz, d$_6$ DMSO) δ ppm: 0.85 (s, 3H), 0.95 (s, 3H), 1.27 (s, 3H), 1.45-1.47 (m, 1H), 1.69-1.75 (m, 2H), 1.95-2.00 (m, 1H), 2.12-2.15 (m, 1H), 2.53-2.57 (dd, 1H), 2.75-2.78 (dd, 1H), 4.68 (s, 2H), 5.97 (bs, 1H). 8.03 (bs, 3H), m/z (M+1): 240.1.

Step 4: (2S,4S)-4-Fluoro-1-(2-((1S,3S)-3-((5-(hydroxymethyl)-1,2,4-oxadiazol-3-yl)methyl)-1,2,2-trimethyleyclopentylamino)acetyl)pyrrolidine-2-carbonitrile

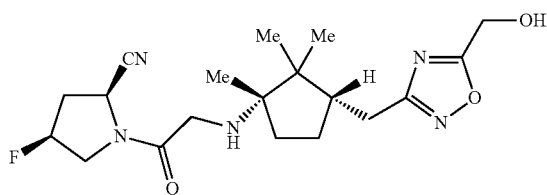 [SMILES: CC1(C)[C@H](Cc2noc(CO)n2)CC[C@]1(C)NCC(=O)N1C[C@@H](F)C[C@H]1C#N]

To a stirred suspension of the step-3 intermediate (0.15 g, 0.54 mmol), K$_2$CO$_3$ (0.138 g, 1 mmol) and KI catalytic amount in 1 mL of DMSO were added a DMSO solution of intermediate 20 (0.95 g, 0.5 mmol) and the reaction mixture was stirred for 12 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by chromatography to yield the product. 0.016 g, Off white solid. Melting point-147-149° C. $^1$H NMR (400 MHz, CDCl$_3$) δ ppm: 0.94 (s, 3H), 0.97 (s, 3H), 1.10 (s, 3H), 1.40-1.42 (m, 1H), 1.55-1.80 (m, 3H), 2.20-2.40 (m, 2H), 2.55-2.70 (m, 2H), 2.81-2.87 (m, 1H), 3.30-3.34 (m, 2H), 3.40 (s, 2H), 3.50-3.55 (m, 1H), 3.61-3.69 (m, 1H), 3.90-3.99 (m, 1H), 4.95 (d, J=9.16 Hz, 0.8H), 5.15 (d, J=9.16 Hz, 0.2H), 5.37 (d, J=50.8 Hz, 0.2H), 5.44 (d, J=50.8 Hz, 0.8H), m/z (M+H): 394.2.

Example 61

(2S,4S)-4-Fluoro-1-(2-((1S,3S)-3-((5-isopropyl-1,2,4-oxadiazol-3-yl)methyl)-1,2,2-trimethylcyclopentylamino)acetyl)pyrrolidine-2-carbonitrile methanesulfonate

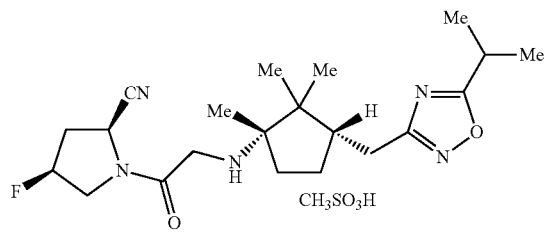

Step 1: tert-Butyl (1S,3S)-3-((5-isopropyl-1,2,4-oxadiazol-3-yl)methyl)-1,2,2-trimethylcyclopentylcarbamate

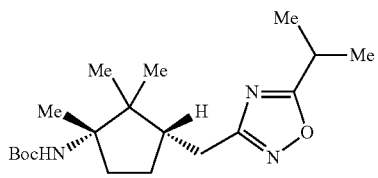 [SMILES: CC(C)c1nc(C[C@@H]2CC[C@](C)(NC(=O)OC(C)(C)C)C2(C)C)no1]

To a solution of tert-butyl {(1S,3S)-3-[(2Z)-2-amino-2-(hydroxyimino)ethyl]-1,2,2-trimethylcyclopentyl}carbamate (prepared in Step-1 example 56) (0.300 g, 1.0 mmoles) in isobutyronitrile (7 mL), $ZnCl_2$ (0.0410 g, 3.0 mmol), PTSA (0.057 g, 3.0 mmol) were added under $N_2$ atmosphere. It was heated to 90-95° C. for six hours. After completion of reaction, isopropyl cyanide was removed under reduced pressure and diluted with water and ethyl acetate. The layers are separated and the organic layer was dried over $Na_2SO_4$, and concentrated on a rotavapor. The crude material is purified by column. 0.120 g, Off white sticky mass, $^1$H NMR (400 MHz, $CDCl_3$) δ ppm: 0.81 (s, 3H), 0.97 (s, 3H), 1.21 (s, 3H), 1.34 (d, 6H), 1.43 (s, 9H), 1.70-1.73 (m, 1H), 1.95-2.00 (m, 2H), 2.22-2.25 (m, 2H), 2.55-2.59 (m, 1H), 2.79-2.83 (m, 1H), 3.17-3.19 (m, 1H), 4.51 (s, 1H). m/z (M−100)+H, 252.2.

Step 2: (1S,3S)-3-((5-Isopropyl-1,2,4-oxadiazol-3-yl)methyl)-1,2,2-trimethylcyclo pentanamine hydrochloride

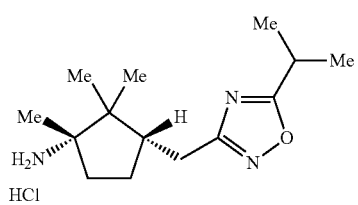 [SMILES: CC(C)c1nc(C[C@@H]2CC[C@](C)(N)C2(C)C)no1 ; Cl]

A solution of saturated HCl in ethyl acetate (2 mL) was added to a solution of intermediate step-2 (0.11 g, 0.3 mmole) in ethyl acetate and the reaction mixture was stirred at room temperature for 2 h. The volatiles were removed under reduced pressure and triturated with hexane to afford the desired product. 0.070 g, Off-white sticky mass, $^1$H NMR (400 MHz, $CDCl_3$) δ ppm: 0.87 (s, 3H), 0.98 (s, 3H), 1.22 (s, 3H), 1.34 (d, 6H), 1.69-1.73 (m, 1H), 1.95-2.00 (m, 2H), 2.10-2.15 (m, 2H), 2.55-2.59 (m, 1H), 2.80-2.82 (m, 1H), 3.22-3.24 (m, 1H), 8.04 (bs, 3H). m/z (M+1): 252.2.

Step 3: (2S,4S)-4-Fluoro-1-(2-((1S,3S)-3-((5-isopropyl-1,2,4-oxadiazol-3-yl)methyl)-1,2,2-trimethylcyclopentylamino)acetyl)pyrrolidine-2-carbonitrile methanesulfonate

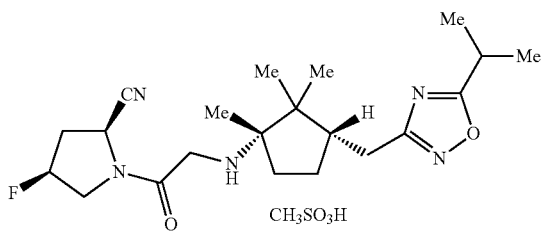

To a stirred suspension of the step-2 intermediate (0.15 g, 0.52 mmol), $K_2CO_3$ (0.138 g, 1 mmol) and KI catalytic amount in 1 mL of DMSO was added a DMSO solution of intermediate 20 (0.98 g, 0.5 mmol) and the reaction mixture was stirred for 12 hours under nitrogen atmosphere. After completion of the reaction, it was diluted with ethyl acetate and water. The layers were separated and the aqueous layer was washed twice with ethyl acetate. The combined organic layers was dried over anhydrous $Na_2SO_4$, concentrated and purified by chromatography to yield (2S,4S)-4-fluoro-1-(2-((1S,3S)-3-((5-isopropyl-1,2,4-oxadiazol-3-yl)methyl)-1,2,2-trimethylcyclopentylamino)acetyl)pyrrolidine-2-carbonitrile. (2S,4S)-4-fluoro-1-(2-((1S,3S)-3-((5-isopropyl-1,2,4-oxadiazol-3-yl)methyl)-1,2,2-trimethylcyclopentylamino)acetyl)pyrrolidine-2-carbonitrile (0.032 g, 0.08 mmole) was dissolved in ethyl acetate and solution of methanesulphonic acid (7.9 mg, 0.08 mmole) in 1 mL ethyl acetate was added and stirred for one hour. Then ethyl acetate was concentrated and washed with diethyl ether to obtain the title compound. 0.03 g, Off white hygroscopic solid. $^1$H NMR (400 MHz, $D_2O$) δ ppm: 1.02 (s, 3H), 1.09 (s, 3H), 1.35 (s, 3H), 1.37 (d, 6H), 1.49-1.57 (m, 1H), 1.84-1.89 (m, 2H), 2.04-2.08 (m, 1H), 2.35-2.38 (m, 1H), 2.40-2.75 (m, 3H), 2.80 (s, 3H), 2.9-2.94 (m, 1H), 3.26-3.29 (m, 1H), 3.77-3.80 (m, 1H), 3.90-3.95 (m, 1H), 4.01-4.15 (m, 1H), 4.20-4.35 (m, 1H), 5.10, d, J=9.36 Hz, 0.8H), 5.25 (d, J=9.36 Hz, 0.2H), 5.55 (d, J=51 Hz, 0.2H), 5.56 (d, J=51 Hz, 0.8H). m/z (M+H): 406.2.

Example 62

(2S,4S)-4-Fluoro-1-(2-((1S,3S)-3-((5-(4-fluorophenyl)-1,2,4-oxadiazol-3-yl)methyl)-1,2,2-trimethylcyclopentylamino)acetyl)pyrrolidine-2-carbonitrile

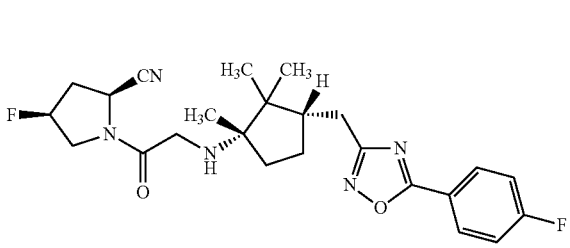 [SMILES: CC1(C)[C@H](Cc2noc(-c3ccc(F)cc3)n2)CC[C@]1(C)NCC(=O)N1C[C@@H](F)C[C@H]1C#N]

Step 1: (1S,3S)-3-((5-(4-Fluorophenyl)-1,2,4-oxadiazol-3-yl)methyl)-1,2,2-trimethylcyclopentanamine hydrochloride Prepared similar to example 58 using intermediate tert-butyl {(1S,3S)-3-[(2Z)-2-amino-2-(hydroxyimino)ethyl]-1,2,2-trimethylcyclopentyl}carbamate (prepared in Step-1 example 56, carbonyldiimidazole and 4-fluorobenzoic acid.

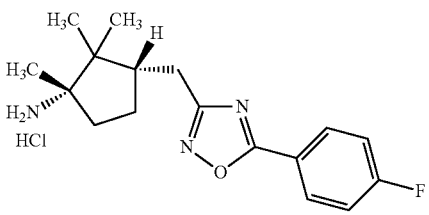 [SMILES: Cl ; CC1(C)[C@H](Cc2noc(-c3ccc(F)cc3)n2)CC[C@]1(C)N]

$^1$H NMR (400 MHz, $d_6$-DMSO) δ ppm: 0.9 (s, 3H), 1.0 (s, 3H), 1.21 (s, 3H), 1.43-1.48 (m, 1H), 1.65-1.69 (m, 1H), 1.71-1.8 (m, 1H), 1.91-1.96 (m, 1H), 2.20-2.23 (m, 1H), 2.59-2.63 (m, 1H), 2.66-2.88 (m, 1H), 7.45-7.5 (m, 2H), 8.0 (bs, 3H), 8.14-8.18 (m, 2H). m/z (M+H): 303.2.

Step 2: (2S,4S)-4-Fluoro-1-(2-((1S,3S)-3-((5-(4-fluorophenyl)-1,2,4-oxadiazol-3-yl)methyl)-1,2,2-trimethylcyclopentylamino)acetyl)pyrrolidine-2-carbonitrile

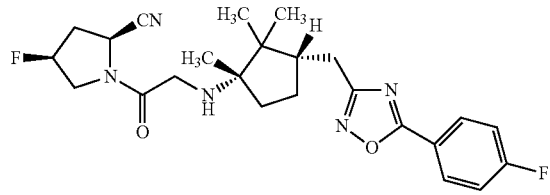 [SMILES: CC1(C)[C@H](Cc2noc(-c3ccc(F)cc3)n2)CC[C@]1(C)NCC(=O)N1C[C@@H](F)C[C@H]1C#N]

To a stirred suspension of the step-2 intermediate (0.2 g, 0.58 mmol), $K_2CO_3$ (0.138 g, 1 mmol) and KI catalytic amount in 1 mL of DMSO were added a DMSO solution of intermediate 20 (0.112 g, 0.58 mmol) and the reaction mixture was stirred for 12 hours under nitrogen atmosphere. After completion of the reaction, it was diluted with ethyl acetate and water. The layers were separated and the aqueous layer was washed twice with ethyl acetate. The combined organic layers was dried over anhydrous $Na_2SO_4$, concentrated and purified by chromatography to yield the product. 0.12 g, Off white solid. Melting Point 158-16 0° C. $^1$H NMR (400 MHz, DMSO) δ ppm: 0.96 (s, 6H), 1.11 (m, 3H), 1.41-1.71 (m, 6H), 2.32-2.37 (m, 2H), 2.61-2.88 (m, 3H), 3.32-3.54 (m, 2H), 4.95 (d, J=9.2 Hz, 0.8H), 5.25 (d, J=9.2 Hz, 0.2H), 5.35 (d, J=51 Hz, 0.2H), 5.45 (d, J=51 Hz, 0.8H), 7.19-7.23 (m, 2H), 8.13-8.15 (m, 2H); m/z (M+H): 458.1.1.

Example 63

(2S,4S)-4-Fluoro-1-(2-((1S,3S)-1,2,2-trimethyl-3-((5-(pyridin-4-yl)-1,2,4-oxadiazol-3-yl)methyl)cyclopentylamino)acetyl)pyrrolidine-2-carbonitrile Prepared similar to example 62 tert-butyl {(1S,3S)-3-[(2Z)-2-amino-2-(hydroxyimino)ethyl]-1,2,2-trimethylcyclopentyl}carbamate (prepared in Step-1 example 56, carbonyldiimidazole and pyridine-4-carboxylic acid.

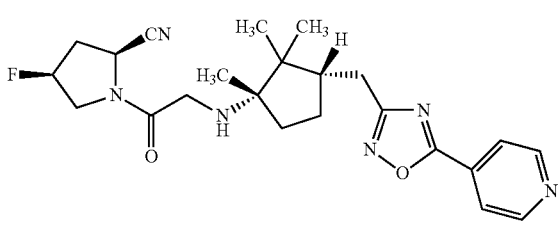 [SMILES: CC1(C)[C@H](Cc2noc(-c3ccncc3)n2)CC[C@]1(C)NCC(=O)N1C[C@@H](F)C[C@H]1C#N]

0.025 g, Off-White solid. Melting Point 180-184° C. $^1$H NMR (400 MHz, DMSO) δ ppm: 0.96 (s, 6H), 1.11 (m, 3H), 1.41-1.71 (m, 6H), 2.32-2.37 (m, 2H), 2.65-2.75 (m, 2H), 2.86-2.90 (m, 1H), 3.32-3.54 (m, 2H), 4.94-4.97 (d, 0.8H), 5.12-5.15 (d, 0.2H) 5.28-5.4 (m, 1H), 7.96-7.97 (m, 2H), 8.84-8.85 (m, 2H). m/z (M+H): 441.2.

Example 64

(2S,4S)-4-Fluoro-1-(2-((1R,3S)-3-(3-(4-fluorophenyl)-1,2,4-oxadiazol-5-yl)-2,2,3-trimethylcyclopentylamino)acetyl)pyrrolidine-2-carbonitrile

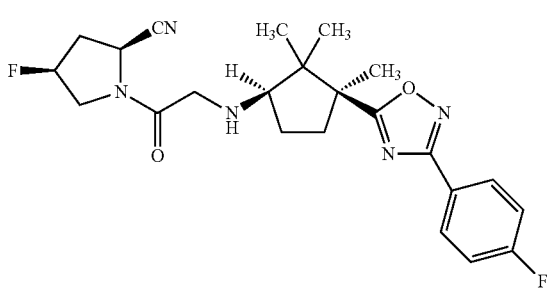 [SMILES: CC1(C)[C@H](NCC(=O)N2C[C@@H](F)C[C@H]2C#N)CC[C@]1(C)c1nc(-c2ccc(F)cc2)no1]

Step 1: (1R,3S)-Methyl 3-(3-(4-fluorophenyl)-1,2,4-oxadiazol-5-34)-2,2,3-trimethyl cyclopentanecarboxylate

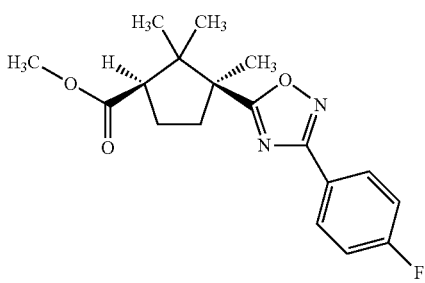 [SMILES: COC(=O)[C@@H]1CC[C@](C)(c2nc(-c3ccc(F)cc3)no2)C1(C)C]

To a solution of (1S,3R)-3-(methoxycarbonyl)-1,2,2-trimethylcyclopentanecarboxylic acid (1 g, 9.35 mmol) in dichloromethane, carbonyldiimidazole (1.51 g, 9.34 mmol), 4-fluoroN'-hydroxybenzene carboximidamide (0.791 g, 5.14 mmol) were added and stirred for 12 h. After the completion of the reaction an aqueous $NH_4Cl$ and dichloromethane was added. The organic layer separated, dried and concentrated. The residue obtained was dissolved in toluene and refluxed for 24 hours. The volatiles were removed under high vacuum, crude compound purified by column. Yield: 0.8 g; $^1$H NMR (400 MHz, $CDCl_3$) δ ppm: 0.64 (s, 3H), 1.28 (s, 3H), 1.36 (s, 3H), 1.58-1.60 (m, 1H), 1.95-2.09 (m, 1H), 2.35-2.49 (m, 1H), 2.85-3.00 (m, 2H), 3.75 (s, 3H), 7.14-7.26 (m, 2H), 8.07-8.11 (m, 2H). m/z (M+H): 333.1.

Step 2: (1R,3S)-3-(3-(4-Fluorophenyl)-1,2,4-oxadiazol-5-yl)-2,2,3-trimethylcyclo pentanecarboxylic acid

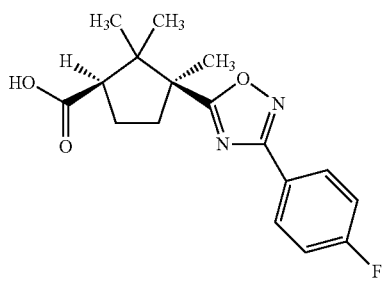 [SMILES: CC1(C)[C@H](C(=O)O)CC[C@]1(C)c1nc(-c2ccc(F)cc2)no1]

To a solution of step-1 intermediate (0.8 g, 2.4 mmole) in THF, lithium hydroxide (0.11 g, 4.8 mmole) dissolved in water was added and stirred for 48 h. The reaction was concentrated under reduced pressure, diluted with water and washed with diethyl ether. Aqueous layer was acidified with con HCl and extracted with ethyl acetate, dried and concentrated. Yield: 0.5 g; $^1$H NMR (400 MHz, CDCl$_3$) δ ppm: 0.72 (s, 3H), 1.41 (s, 3H), 1.44 (s, 3H), 1.88 (m. 1H), 2.04 (m, 1H), 2.37 (m, 1H), 2.92 (m, 2H), 7.14-7.26 (m, 2H), 8.07-8.11 (m, 2H). m/z (M–H): 317.1.

Step 3: (1R,3S)-3-(3-(4-Fluorophenyl)-1,2,4-oxadiazol-5-yl)-2,2,3-trimethylcyclo pentanecarboxamide

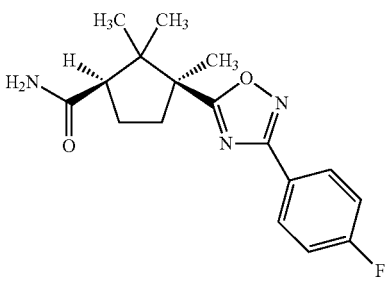 [SMILES: CC1(C)[C@H](C(N)=O)CC[C@]1(C)c1nc(-c2ccc(F)cc2)no1]

To a solution of intermediate 2 (0.5 g, 1.6 mmol) in dichloromethane maintained at −10° C., one drop of DMF followed by oxalyl chloride (0.16 mL, 1.73 mmol) was added and stirred for 2 h. The volatiles were removed by passing N$_2$ gas. The residue was dissolved in diethyl ether, aqueous ammonia (10 ml) was added and stirred for 0.5 h. The organic layer was separated, aqueous layer washed with dichloromethane (2×50 mL). Organic layer were combined, dried and concentrated. $^1$H NMR (400 MHz, CDCl$_3$) δ ppm: 0.71 (s, 3H), 1.39 (s, 3H), 1.45 (s, 3H), 1.84-1.90 (m. 1H), 1.96-1.99 (m, 1H), 2.35-2.38 (m, 1H), 2.81-2.93 (m, 1H), 2.96-2.99 (m, 1H), 5.39 (s, 1H), 5.56 (s, 1H), 7.14-7.18 (m, 2H), 8.08-8.11 (m, 2H). m/z (M+H): 318.2.

Step 4: (1R,3S)-3-(3-(4-Fluorophenyl)-1,2,4-oxadiazol-5-yl)-2,2,3-trimethylcyclo pentanamine hydrochloride

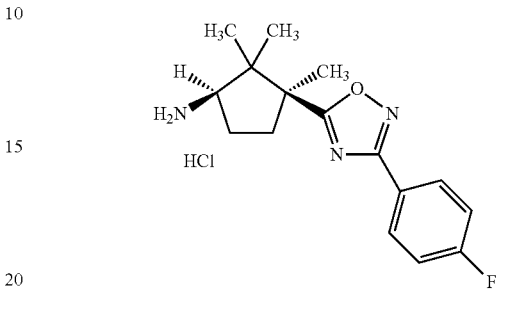

Step 3 intermediate (0.4 g, 1.26 mmol) was dissolved in a 3 mL solvent mixture of ethyl acetate, acetonitrile and water in the ratio 1:1:0.5 respectively. To this PIFA (0.76 g, 1.76 mmol) was added and stirred, maintaining the temperature at 45° C. for 5 h. The reaction was further stirred at room temperature for 8 h. Excess PIFA was decomposed by heating at 70° C. for 10 minutes. Reaction mixture was concentrated under reduced pressure, acidified with dilute HCl, washed with diethyl ether. Aqueous layer was separated, basified with NaHCO$_3$ solution and extracted with dichloromethane, washed with water, brine, dried and concentrated. The residue was dissolved in ethyl acetate and HCl in ethyl acetate was added and stirred. The separated solid was filtered and washed with ethyl acetate. $^1$H NMR (400 MHz, D$_2$O) δ ppm: 0.65 (s, 3H), 1.23 (s, 3H), 1.40 (s, 3H), 1.77-1.90 (m, 2H), 2.21-2.26 (m, 1H), 2.77-2.80 (m, 1H), 3.54-3.58 (m, 1H), 7.39-7.44 (m, 2H), 8.04-8.08 (m, 2H). m/z (M+H): 290.2.

Step 5: (2S,4S)-4-Fluoro-1-(2-((1R,3S)-3-(3-(4-fluorophenyl)-1,2,4-oxadiazol-5-yl)-2,2,3-trimethylcyclopentylamino)acetyl)pyrrolidine-2-carbonitrile

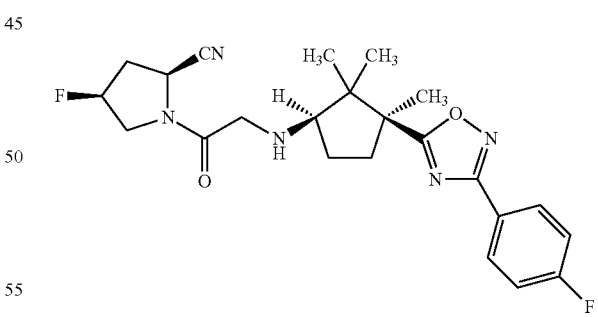

To a stirred suspension of the step-4 intermediate (0.07 g, 0.21 mmol), K$_2$CO$_3$ (0.116 g, 0.84 mmol) and KI catalytic amount in 1 mL of DMSO were added a DMSO solution of intermediate 20 (0.0.37 g, 0.19 mmol) and the reaction mixture was stirred for 12 hours under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by chromatography to yield the product. 0.04 g, White solid. ¹H NMR (400 MHz, CDCl₃) δ ppm: 0.68 (s, 3H), 1.23 (s, 3H), 1.41 (s, 3H), 1.59-1.62 (m. 2H), 1.65-1.83 (m, 1H), 2.23-2.29 (m, 2H), 2.61-2.73 (m, 1H), 2.9-2.93 (m, 1H), 3.02-3.06 (m, 1H), 3.41-3.78 (m, 3H), 3.92-4.01 (m, 1H), 4.95 (d, J=9.2, 0.8H), 5.12 (d, J=9.2, 0.2H), 5.20 (d, J=52, 0.2H), 5.35 (d, J=52, 0.8H) 7.14-7.26 (m, 2H), 8.08-8.11 (m, 2H). m/z (M+H): 444.2.

Example 65

(2S,4S)-4-Fluoro-1-(2-((1S,3R)-3-(3-(4-fluorophenyl)-1,2,4-oxadiazol-5-yl)-2,2,3-trimethylcyclopentylamino)acetyl)pyrrolidine-2-carbonitrile Prepared similar to example 64 starting form (1R,3S)-3-(methoxycarbonyl)-1,2,2-trimethylcyclopentanecarboxylic acid. 0.035 g, White solid: M.P: 127-131° C.

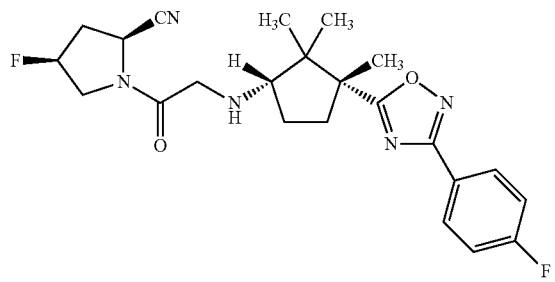 [SMILES: CC1(C)[C@@H](NCC(=O)N2C[C@@H](F)C[C@H]2C#N)CC[C@@]1(C)c1nc(-c2ccc(F)cc2)no1]

m/z (M+H): 444.2. ¹H NMR (400 MHz, CDCl₃) δ ppm: 0.66 (s, 3H), 1.21 (s, 3H), 1.42 (s, 3H), 1.42-1.62 (m, 2H) 1.75-1.82 (m, 1H), 2.18-2.40 (m, 2H), 2.66-3.08 (m, 3H), 3.60-3.97 (m, 4H), 4.95-4.97 (d, J=9.2 Hz, 0.8H), 5.1 (d, J=9.2 Hz, 0.2H), 5.25 (d, J=51 Hz, 0.2H), 5.44 (d, J=51 Hz, 0.8H), 7.14-7.18 (m, 2H), 8.07-8.11 (m, 2H).

Example 66

(S)-1-(2-((1S,3R)-3-(3-(4-Fluorophenyl)-1,2,4-oxadiazol-5-yl)-2,2,3-trimethylcyclopentylamino)acetyl)pyrrolidine-2-carbonitrile methanesulfonate Prepared similar to example 64 starting using intermediate 21 in step 5.

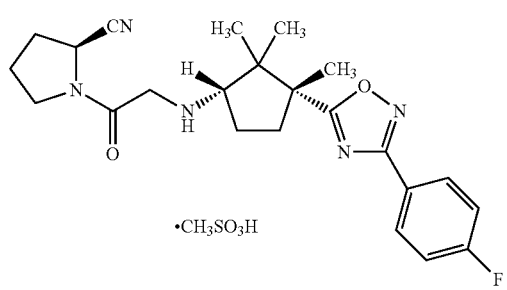

0.04 g, White solid. Melting point: 206-211° C. ¹H NMR (400 MHz, CDCl₃) δ ppm: 0.9 (s, 3H), 1.4 (s, 3H), 1.49 (s, 3H), 2.03-2.04 (m, 2H), 2.19-2.23 (m, 2H), 2.34-2.36 (m, 2H), 2.5-2:51 (m, 1H), 2.81 (s, 3H), 2.88-2.89 (m, 1H), 3.52- 3.54 (m, 1H), 3.62-3.65 (m, 1H), 3.78-3.82 (m, 1H), 4.1-4.2 (m, 2H), 4.82-4.84 (m, 1H), 7.3-7.34 (m, 2H), 8.0-8.06 (m, 2H). m/z (M+H): 426.1.2.

Example 67

(2S,4S)-4-Fluoro-1-(2-((1S,3R)-3-(3-isopropyl-1,2,4-oxadiazol-5-yl)-2,2,3-trimethylcyclopentylamino)acetyl)pyrrolidine-2-carbonitrile

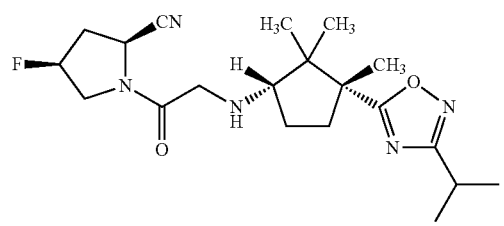 [SMILES: CC(C)c1noc([C@]2(C)CC[C@H](NCC(=O)N3C[C@@H](F)C[C@H]3C#N)C2(C)C)n1]

Prepared according to procedure described in example 64 starting form (1R,3S)-3-(methoxycarbonyl)-1,2,2-trimethylcyclopentanecarboxylic acid and N'-hydroxy-2-methylpropanimidamide. 0.045 g, White solid. Melting point: 82-85° C. ¹H NMR (400 MHz, CDCl₃) δ ppm: 0.60 (s, 3H), 1.18 (s, 3H), 1.32 (s, 3H), 1.36 (d, 6H), 1.50-1.8 (m, 3H), 2.15-2.39 (m, 2H), 2.61-2.86 (m, 2H), 2.99-3.09 (m, 2H), 3.44-3.78 (m, 2H), 3.87-4.05 (m, 2H), 4.95 (d, J=9.2, 0.8H), 5.20 (d, J=9.2, 0.2H), 5.35 (d, J=52, 0.2H), 5.45 (d, J=52, 0.8H); m/z (M+H): 392.2.

Example 68

(2S,4S)-4-Fluoro-1-(2-((1S,3R)-2,2,3-trimethyl-3-(3-(pyridin-3-yl)-1,2,4-oxadiazol-5-yl)cyclopentylamino)acetyl)pyrrolidine-2-carbonitrile Prepared similar to example 64 starting form (1R,3S)-3-(methoxycarbonyl)-1,2,2-trimethylcyclopentanecarboxylic acid N'-hydroxypyridine-3-carboximidamide.

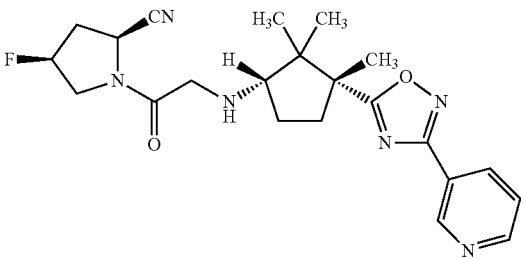 [SMILES: CC1(C)[C@@H](NCC(=O)N2C[C@@H](F)C[C@H]2C#N)CC[C@@]1(C)c1nc(-c2cccnc2)no1]

0.017 g, Off White solid. Melting point: 126-130° C. ¹H NMR (400 MHz, CDCl₃) ppm: 0.68 (s, 3H), 1.25 (s, 3H), 1.44 (s, 3H), 1.59-1.61 (m, 1H), 1.80-1.82 (m, 1H), 2.10-2.30 (m, 2H), 2.65-2.75 (m, 1H), 2.92-2.94 (m, 2H), 3.04-3.08 (m, 1H), 3.61-3.79 (m, 2H), 3.88-3.97 (m, 2H), 4.95 (d, J=9.2 Hz, 0.8H), 5.11 (d, J=9.2 Hz, 0.2H), 5.35 (d, J=52 Hz, 0.2H), 5.45 (d, J=52 Hz, 0.8H), 7.43 (t, J=5.48 Hz, 1H), 8.37 (d, J=8.16 Hz, 1H), 8.74 (d, J=4.64 Hz, 1H), 9.32 (s, 1H). m/z (M+H): 427.2.

Example 69

(2S,4S)-4-Fluoro-1-(2-((1R,3S)-2,2,3-trimethyl-3-(3-(pyridin-3-yl)-1,2,4-oxadiazol-5-yl)cyclopentylamino)acetyl)pyrrolidine-2-carbonitrile Prepared similar to example 64 using (1S,3R)-3-(methoxycarbonyl)-1,2,2-trimethylcyclopentanecarboxylic acid N'-hydroxypyridine-3-carboximidamide

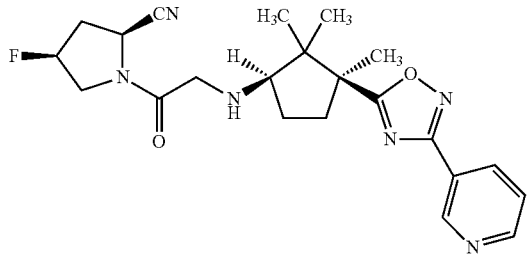 [SMILES: CC1(C)[C@H](NCC(=O)N2C[C@@H](F)C[C@H]2C#N)CC[C@]1(C)c1nc(-c2cccnc2)no1]

0.031 g, Off white solid. Melting point: 70-75° C. $^1$H NMR (400 MHz, CDCl$_3$) δ ppm: 0.63 (s, 3H), 1.2 (s, 3H), 1.4 (s, 3H), 1.59-1.63 (m, 1H), 1.77-1.84 (m, 1H), 2.24-2.3 (m, 2H), 2.66-2.74 (s, 1H), 2.9-2.95 (m, 1H), 3.02-3.06 (m, 1H), 3.41-3.78 (m, 3H), 3.93-4.02 (m, 1H), 4.96 (d, J=9.1 Hz, 0.8H), 5.25 (d, J=9.1 Hz, 0.2H), 5.35 (d, J=52 Hz, 0.2H), 5.45 (d, J=52 Hz, 0.8H), 7.42 (t, J=4.92 Hz, 1H), 8.37 (d, J=7.96 Hz, 1H), 8.73 (d, J=4.64 Hz, 1H), 9.31 (s, 1H); m/z (M+H): 427.2.

Example 70

(2S,4S)-4-Fluoro-1-(2-((1S,3R)-2,2,3-trimethyl-3-(3-(pyridin-4-yl)-1,2,4-oxadiazol-5-yl)cyclopentylamino)acetyl)pyrrolidine-2-carbonitrile Prepared similar to example 64 using ((1R,3S)-3-(methoxycarbonyl)-1,2,2-trimethyl cyclopentanecarboxylic acid and N'-hydroxypyridine-4-carboximidamide

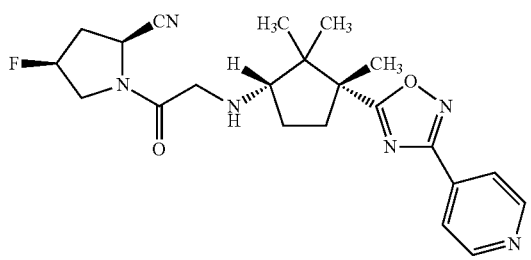 [SMILES: CC1(C)[C@@H](NCC(=O)N2C[C@@H](F)C[C@H]2C#N)CC[C@@]1(C)c1nc(-c2ccncc2)no1]

0.03 g. Off white solid. Melting point: 149-153° C. m/z (M+H): 427.2 $^1$H NMR (400 MHz, CDCl$_3$) δ ppm: 0.63 (s, 3H), 1.2 (s, 3H), 1.4 (s, 3H), 1.51-1.56 (m, 1H), 1.7-1.77 (m, 1H), 2.12-2.22 (m, 2H), 2.59-2.66 (s, 1H), 2.83-2.87 (m, 1H), 2.96-3.01 (m, 1H), 3.37-3.41 (m, 1H), 3.53-3.9 (m, 3H), 4.88 (d, J=9.1 Hz, 0.8H), 4.98 (d, J=9.1 Hz, 0.2H), 5.30 (d, J=52 Hz, 0.2H), 5.45 (d, J=51 Hz, 0.8H), 7.88 (d, J=5.88 Hz, 2H), 8.68 (d, J=4.72 Hz, 2H). m/z (M+H): 427.2.

Example 71

(2S,4S)-4-Fluoro-1-(2-((1R,3S)-2,2,3-trimethyl-3-(3-(pyridin-4-yl)-1,2,4-oxadiazol-5-yl)cyclopentylamino)acetyl)pyrrolidine-2-carbonitrile Prepared similar to example 63 using ((1S,3R)-3-(methoxycarbonyl)-1,2,2-trimethyl cyclopentanecarboxylic acid and N'-hydroxypyridine-4-carboximidamide.

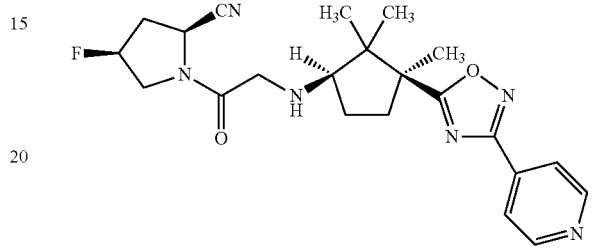

0.020 g, Off white solid. Melting point: 167-171° C. $^1$H NMR (400 MHz, CDCl$_3$) δ ppm: 0.68 (s, 3H), 1.23 (s, 3H), 1.43 (s, 3H), 1.60-1.62 (m, 1H), 1.78-1.85 (m, 1H), 2.24-2.31 (m, 2H), 2.66-2.74 (m, 1H), 2.90-2.93 (m, 1H), 3.04-3.08 (m, 1H), 3.43-3.54 (m, 2H), 3.64-3.79 (m, 1H), 3.93-4.02 (m, 1H), 4.96 (d, J=9.1 Hz, 0.8H), 5.15 (d, J=9.1 Hz, 0.2H), 5.32 (d, J=52 Hz, 0.2H), 5.45 (d, J=51 Hz, 0.8H), 7.97 (d, J=9.42 Hz, 2H), 8.77 (d, J=4.88 Hz, 2H); m/z (M+H): 427.2.

Example 72

(2S,4S)-4-Fluoro-1-(2-((1S,3R)-2,2,3-trimethyl-3-(3-(pyrazin-2-yl)-1,2,4-oxadiazol-5-yl)cyclopentylamino)acetyl)pyrrolidine-2-carbonitrile Prepared similar to example 64 ((1R,3S)-3-(methoxycarbonyl)-1,2,2-trimethyl cyclopentanecarboxylic acid and using N'-hydroxypyrazine-2-carboximidamide.

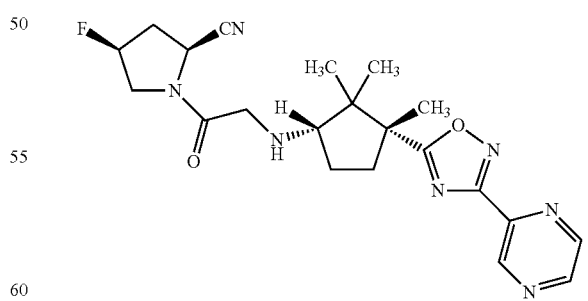

0.04 g, White solid. Melting point: 65-70° C. $^1$H NMR (400 MHz, CDCl$_3$) δ ppm: 0.7 (s, 3H), 1.2 (s, 3H), 1.46 (s, 3H), 1.5-1.6 (m, 2H), 1.8-1.87 (m, 1H), 2.2-2.39 (m, 2H), 2.66-2.77 (m, 1H), 2.98-3.09 (m, 2H), 3.44-3.88 (m, 2H), 3.91-3.97 (m, 1H), 4.95 (d, J=9.1 Hz, 0.8H), 5.10 (d, J=9.1 Hz, 0.2H), 5.29 (d, J=52 Hz, 0.2H), 5.45 (d, J=52.8 Hz, 0.8H), 8.72 (d, J=2.32 Hz, 1H), 8.77 (d, J=1.68 Hz, 1H), 9.3 (s, 1H). m/z (M+H): 428.2.

Example 73

(2S,4S)-4-Fluoro-1-(2-((1R,3S)-2,2,3-trimethyl-3-(3-methyl-1,2,4-oxadiazol-5-yl)cyclopentylamino)acetyl)pyrrolidine-2-carbonitrile

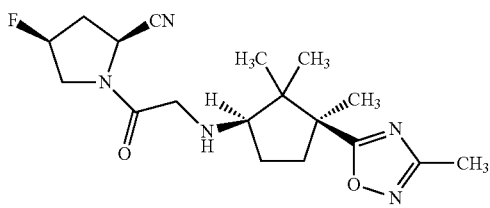 [SMILES: Cc1noc([C@@]2(C)CC[C@@H](NCC(=O)N3C[C@@H](F)C[C@H]3C#N)C2(C)C)n1]

Prepared similar to example 64 using ((1S,3R)-3-(methoxycarbonyl)-1,2,2-trimethylcyclopentanecarboxylic acid N'-hydroxyethanimidamide. 0.04 g, Off white solid. M.P: 144-147° C. $^1$H NMR (400 MHz, CDCl$_3$) δ ppm: 0.77 (s, 3H), 1.13 (s, 3H), 1.17 (s, 3H), 1.58-1.61 (m. 1H), 1.71-1.76 (m, 1H), 2.2-2.25 (m, 2H), 2.38 (s, 3H), 2.65-2.73 (m, 1H), 2.8-2.82 (m, 1H), 2.97-3.02 (m, 1H), 3.38-3.42 (m, 1H), 3.48-3.52 (m, 1H), 3.62-3.74 (m, 1H), 3.91-4.0 (m, 1H), 4.94 (d, J=9.2 Hz, 0.8H), 5.18 (d, J=9.2 Hz, 0.2H), 5.35 (d, J=52 Hz, 0.2H), 5.45 (d, J=52 Hz, 0.8H). m/z (M+H): 364.2.

Example 74

(2S,4S)-4-Fluoro-1-(2-((1S,3R)-2,2,3-trimethyl-3-(3-methyl-1,2,4-oxadiazol-5-yl)cyclopentylamino)acetyl)pyrrolidine-2-carbonitrile

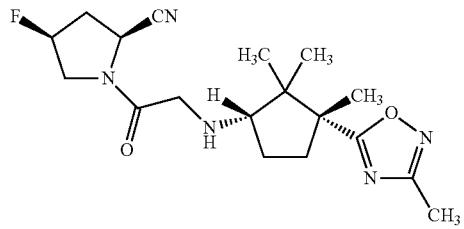 [SMILES: Cc1noc([C@]2(C)CC[C@H](NCC(=O)N3C[C@@H](F)C[C@H]3C#N)C2(C)C)n1]

Prepared similar to example 64 using ((1R,3S)-3-(methoxycarbonyl)-1,2,2-trimethyl cyclopentanecarboxylic acid N'-hydroxyethanimidamide. 0.06 g, Off white solid. Melting point: 137-141° C. $^1$H NMR (400 MHz, CDCl$_3$) δ ppm: 0.63 (s, 3H), 1.1 (s, 3H), 1.19 (s, 3H), 1.55-1.58 (m. 1H), 1.69-1.77 (m, 2H), 2.14-2.29 (m, 1H), 2.38 (s, 3H), 2.65-2.85 (m, 2H), 2.97-3.02 (m, 1H), 3.42-4.05 (m, 4H), 4.95 (d, J=9.2 Hz, 0.8H), 5.25 (d, J=9.2 Hz, 0.2H), 5.36 (d, J=52 Hz, 0.2H), 5.45 (d, J=52 Hz, 0.8H). m/z (M+H): 364.2.

Example 75

(S)-1-(2-((1R,5R)-3,5,8,8-Tetramethyl-2,4-dioxo-3-azabicyclo[3.2.1]octan-1-ylamino)acetyl)pyrrolidine-2-carbonitrile

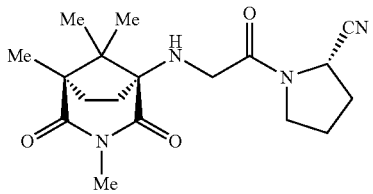 [SMILES: CN1C(=O)[C@]2(C)CC[C@](NCC(=O)N3CCC[C@H]3C#N)(C1=O)C2(C)C]

To a stirred suspension of the intermediate 15 (0.13 g, 0.61 mmol), K$_2$CO$_3$ (0.17 g, 1.2 mmol) and KI catalytic amount in 2 mL of DMSO, intermediate 21 (0.106 g, 0.61 mmol) was added. The reaction mixture was stirred for 8 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by silica column using 2% methanol in dichloromethane to yield the product as 0.025 g, white solid. Melting point 141-144° C. $^1$H NMR (400 MHz, CDCl$_3$) δ ppm: 0.8 (s, 3H), 1.1 (s, 3H), 1.2 (s, 3H), 1.80-1.88 (m, 2H), 1.91-1.98 (m, 3H), 2.09-2.21 (m, 3H), 2.29-2.31 (m, 2H), 3.08 (s, 3H), 3.5 (m, 1H), 3.54 (m, 1H), 3.88-3.92 (dd, 1H), 4.81 (s, 1H). m/z (M+H): 347.1.

Example 76

(2S,4S)-4-Fluoro-1-(2-((1R,5R)-3,5,8,8-tetramethyl-3-azabicyclo[3.2.1]octan-1-ylamino)acetyl)pyrrolidine-2-carbonitrile

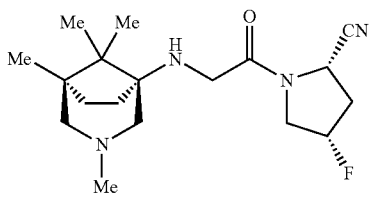 [SMILES: CN1C[C@]2(C)CC[C@](NCC(=O)N3C[C@@H](F)C[C@H]3C#N)(C1)C2(C)C]

To a stirred suspension of the intermediate 16 (0.12 g, 0.66 mmol), K$_2$CO$_3$ (0.27 g, 1.8 mmol) and KI catalytic amount in 2 mL of DMSO, intermediate 20 (0.125 g, 0.66 mmol) were added. The reaction mixture was stirred for 8 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by silica column chromatography using 2% methanol in dichloromethane to yield the product as 0.055 g, Off white solid. Melting point 122-126° C., $^1$H NMR (400 MHz, CDCl$_3$) δ ppm: 0.82-0.85 (2s; 6H), 0.92 (s, 3H), 1.57-1.68 (m, 3H), 1.87-1.89 (m, 2H), 1.91-1.98 (m, 1H), 2.16-2.29 (m, 1H), 2.3 (s, 3H), 2.38 (s, 2H), 2.52-2.55 (m, 1H), 2.64-2.71 (m, 1H), 3.37-3.96 (m, 3H), 4.92 (d, J=9.2, 0.8H), 5.22 (d, J=9.2, 0.2H), 5.35 (d, J=51, 0.2H), 5.45 (d, J=51, 0.8H); m/z (M+H): 337.

Example 77

(2S,4R)-4-Fluoro-1-(2-((1R,5R)-3,5,8,8-tetramethyl-3-azabicyclo[3.2.1]octan-1-ylamino)acetyl)pyrrolidine-2-carbonitrile Prepared similar to example 75 by coupling intermediate 16 and intermediate 22.

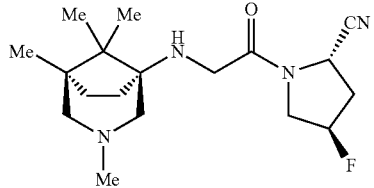 [SMILES: CN1C[C@]2(C)CC[C@](NCC(=O)N3C[C@H](F)C[C@H]3C#N)(C1)C2(C)C]

0.015 g, White solid. Melting point 74-79° C. $^1$H NMR (400 MHz, CDCl$_3$) δ ppm: 0.8 (s, 3H), 0.9 (s, 3H), 1.0 (s, 3H), 1.59-1.66 (m, 2H), 1.85 (m, 1H), 2.16-2.19 (d, 1H), 2.29 (s, 3H), 2.31-2.34 (m, 3H), 2.5 (m, 1H), 2.56-2.58 (m, 1H), 2.75-2.77 (m, 1H), 3.31-3.91 (m, 4H), 4.75 (t, J=8.2 Hz, 0.8H), 5.08 (t, J=8.2 Hz, 0.2H), 5.25 (d, J=51.2 Hz, 0.2H), 5.35 (d, J=51.2 Hz, 0.8H). m/z (M+H): 337.1.

Example 78

(S)-1-(2-((1R,5R)-3,5,8,8-Tetramethyl-3-azabicyclo[3.2.1]octan-1-yl amino)acetyl)pyrrolidine-2-carbonitrile

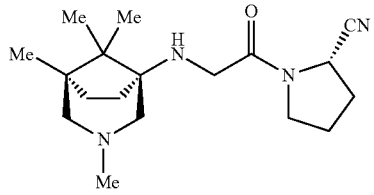 [SMILES: CN1C[C@]2(C)CC[C@](NCC(=O)N3CCC[C@H]3C#N)(C1)C2(C)C]

Prepared similar to example 75, by coupling intermediate 16 and intermediate 21. 0.03 g, White solid. $^1$H NMR (400 MHz, CDCl$_3$) δ ppm: 0.82 (s, 3H), 0.86 (s, 3H), 0.9 (s, 3H), 1.25 (s, 1H), 1.59-1.67 (m, 3H), 1.86 (m, 1H), 2.16-2.19 (m, 3H), 2.23 (s, 3H), 2.29-2.35 (m, 4H), 2.53-2.56 (dd, 1H), 3.35-3.43 (m, 2H), 3.59 (bs, 1H), 4.74-4.76-4.96 (m, 1H); m/z (M+H): 319.3.

Example 79

(S)-1-(2-((1R,5R)-5,8,8-Trimethyl-2-oxo-3-oxabicyclo[3.2.1]octan-1-ylamino)acetyl)pyrrolidine-2-carbonitrile

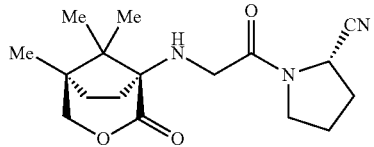 [SMILES: CC1(C)[C@@]2(C)CC[C@]1(NCC(=O)N1CCC[C@H]1C#N)C(=O)OC2]

To a stirred suspension of the intermediate 17 (0.05 g, 0.27 mmol), K$_2$CO$_3$ (0.11 g, 0.79 mmol) and KI (0.049 g, 0.3 mmol) in 2 mL of DMSO, intermediate-21 (0.046 g, 0.27 mmol) was added. The reaction mixture was stirred for 8 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by silica column chromatography using methanol in dichloromethane to yield the product. 0.009 g, White solid. Melting point 174-177° C. $^1$H NMR (400 MHz, CDCl$_3$) δ ppm: 0.99 (s, 3H), 1.04 (s, 6H), 1.78-2.34 (m, 8H), 3.39-3.60 (m, 4H), 3.88 (m, 2H), 4.06 (d, J=1.0.6 Hz, 1H), 4.80 (m, 1H); m/z (M+H): 319.3.

Example 80

(S)-1-(2-((1R,5R)-5,8,8-Trimethyl-3-oxabicyclo[3.2.1]octan-1-yl amino)acetyl)pyrrolidine-2-carbonitrile

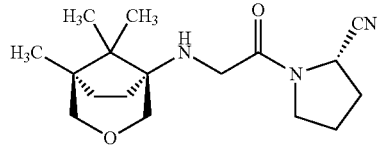 [SMILES: CC1(C)[C@@]2(C)CC[C@]1(NCC(=O)N1CCC[C@H]1C#N)COC2]

To a stirred suspension of the intermediate 18 (0.1 g, 0.59 mmol), K$_2$CO$_3$ (0.16 g, 1.1 mmol) and KI (0.049 g, 0.29 mmol) in 2 mL of DMSO, intermediate 21 (0.081 g, 0.47 mmol) was added. The reaction mixture was stirred for 8 h under nitrogen atmosphere. After completion of the reaction, it was diluted with ethyl acetate and water. The layers were separated and the aqueous layer was washed twice with ethyl acetate. The combined organic layers was dried over anhydrous Na$_2$SO$_4$, concentrated and purified by silica column chromatography using methanol in dichloromethane to yield the product. 0.01 g, Yellow sticky solid. $^1$H NMR (400 MHz, CDCl$_3$) δ ppm: 0.75 (s, 3H), 0.94 (s, 3H), 1.01 (s, 3H), 1.57-1.68 (m, 4H), 1.88-1.93 (m, 1H), 2.18-2.21 (m, 2H), 2.23-2.31 (m, 2H), 3.04-3.07 (d, J=10.8 Hz, 1H), 3.34-3.38 (m, 3H), 3.53-3.56 (m, 1H), 3.69-3.72 (d, J=10.52 Hz, 2H), 4.74-4.75 (d, J=6:0 Hz, 0.8H), 5.8-5.82 (d, J=6.0 Hz, 0.2H); m/z (M+H): 306.2.

Example 81

(2S,4S)-4-Fluoro-1-(2-((1R,5R)-5,8,8-trimethyl-3-oxabicyclo[3.2.1]octan-1-ylamino)acetyl)pyrrolidine-2-carbonitrile

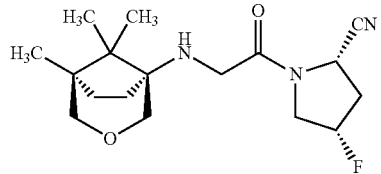 [SMILES: CC1(C)[C@@]2(C)CC[C@]1(NCC(=O)N1C[C@@H](F)C[C@H]1C#N)COC2]

To a stirred suspension of intermediate 1.8 (0.0.55 g, 0.325 mmol), K$_2$CO$_3$ (0.134 g, 0.97 mmol) and KI (0.053 g, 0.33 mmol) in 2 mL of DMSO, intermediate 20 (0.61 g, 0.325 mmol) was added. The reaction mixture was stirred for 8 h under nitrogen atmosphere. After completion of the reaction, it was diluted with ethyl acetate and water. The layers were separated and the aqueous layer was washed twice with ethyl acetate. The combined organic layer was dried over anhydrous Na₂SO₄, concentrated and purified by silica column chromatography using methanol in dichloromethane to yield the product. 0.007 g, White solid. ¹H NMR (400 MHz, CDCl₃) δ ppm: 0.75 (s, 3H), 0.86 (s, 3H), 0.94 (s, 3H), 1.6-1.73 (m, 4H), 1.89-1.95 (m, 1H), 2.25-2.45 (m, 1H), 2.64-2.72 (m, 1H), 3.05-3.08 (d, J=10.8 Hz, 1H), 3.28-3.39 (m, 2H), 3.49-3.58 (m. 1H), 3.69-3.71 (d, J=9.6 Hz, 2H), 3.83-3.92 (m, 1H), 4.93 (d, J=9.2 Hz, 0.8H), 5.12 (d, J=9.2 Hz, 0.2H), 5.35 (d, J=51 Hz, 0.2H), 5.45 (d, J=51 Hz, 0.8H). m/z (M+H): 324.2.

Example 82

(2S,4S)-4-Fluoro-1-(2-((1S,5S)-5,8,8-trim ethyl-3-oxabicyclo[3.2.1]octan-1-ylamino)acetyl)pyrrolidine-2-carbonitrile Prepared similar to example-80 by coupling intermediate 19 and intermediate 20

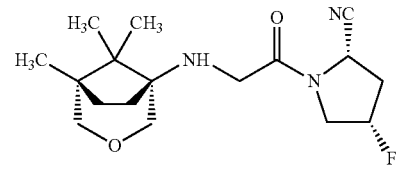 [SMILES: CC1(C)[C@]2(C)CC[C@@]1(NCC(=O)N1C[C@@H](F)C[C@H]1C#N)COC2]

0.005 g White solid. ¹H NMR (400 MHz, CDCl₃) δ ppm: 0.75 (s, 3H), 0.86 (s, 3H), 0.94 (s, 3H), 1.6-1.73 (m, 4H), 1.89-1.95 (m, 1H), 2.25-2.45 (m, 1H), 2.64-2.72 (m, 1H), 3.05-3.08 (d, J=10.7 Hz, 1H), 3.28-3.39 (m, 2H), 3.49-3.58 (m. 1H), 3.70-3.71 (d, J=9.9 Hz, 2H), 3.83-3.92 (m, 1H), 4.96 (d, J=9.2 Hz, 0.8H), 5.00 (d, J=9.2 Hz, 0.2H), 5.35 (d, J=52 Hz, 0.2H), 5.45 (d, J=52 Hz, 0.8H); m/z (M+H): 324.2.

Example 83

(2S,4S)-1-(2-((1S,3R)-3-(3-(1H-1,2,4-Triazol-1-yl)propyl)-2,2,3-trimethylcyclopentylamino)acetyl)-4-fluoropyrrolidine-2-carbonitrile

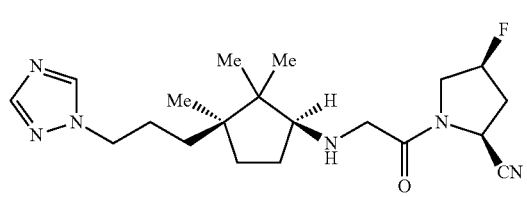 [SMILES: CC1(C)[C@@H](NCC(=O)N2C[C@@H](F)C[C@H]2C#N)CC[C@@]1(C)CCCn1cncn1]

Step 1: (1S,3R)-Methyl 3-(hydroxymethyl)-2,2,3-trimethylcyclopentane carboxylate

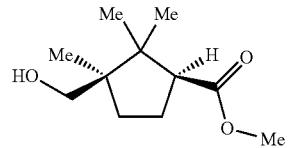 [SMILES: COC(=O)[C@H]1CC[C@@](C)(CO)C1(C)C]

To a solution of step 1 intermediate of Intermediate I (0.59 g, 2.7 mmol) in THF maintained under N₂ atmosphere, borane-dimethylsulfide complex (0.28 mL, 6 mmol) was added drop wise and stirred at room temperature. After completion of the reaction, the reaction was quenched by oxone and water. Reaction mixture was extracted with ethyl acetate, dried over Na₂SO₄ and concentrated under reduced pressure. The crude product was purified by column chromatography to give 0.55 g of the desired product. ¹H NMR (400 MHz, CDCl₃): δ 0.89 (s, 3H), 1.01 (s, 3H), 1.19 (s, 3H), 1.36-1.41 (m, 1H), 1.72-1.88 (m, 2H), 2.09-2.19 (m, 1H), 2.79-2.84 (t, J=9.2 oxone, 1H), 3.52-3.60 (q, J=10.8 oxone, 2H), 3.68 (s, 3H); m/z (M+H): 201.2.

Step 2: Methyl (1S,3R)-3-formyl-2,2,3-trimethylcyclopentane carboxylate

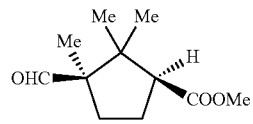

To solution of step I intermediate (1.1 g, 1.016 mmol) in 30 mL of dichloromethane, pyridinium chlorochromate (2.96 g, 13.75 mmol), MgSO₄ (1.72 g, 14.3 mmol) and 1.5 g of celite was added. The reaction mixture was stirred for 1.5 hours. After completion, reaction mixture was concentrated and the crude material was immediately purified by silica column chromatography (100% DCM.) to afford the desired product (0.8 g) as colorless liquid. ¹H NMR (CDCl₃) δ ppm: 0.89 (s, 3H) 1.18 (s, 3H), 1.29 (s, 3H), 1.52-1.61 (m, 1H), 1.89-1.98 (m, 1H), 1.99-2.32 (m, 1H), 2.39-2.52 (m, 1H), 2.80-2.85 (m, 1H), 3.68-3.69 (s, 3H), 9.67 (s, 1H). m/z (M+H): 199.

Step 3: Methyl(1S,3S)-3-[(3-tert-butoxy-3-oxoprop-1-en-1-yl]-2,2,3-trimethyl cyclopentanecarboxylate

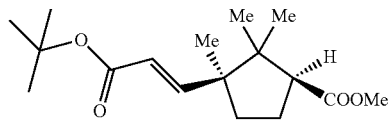 [SMILES: COC(=O)[C@H]1CC[C@@](C)(/C=C/C(=O)OC(C)(C)C)C1(C)C]

To a suspension of sodium hydride (0.242 g, 10.08 mmol) in dry tetrahydrofuran (10 mL), t-butyldiethylphosphonoacetate (1.23 g; 5.24 mmol) was added at 0° C. under N₂ atmosphere and stirred for 40 min. To this step 2 intermediate (0.3 g; 4.3 mmol) was added and stirred for 1.5 h. After completion, reaction mixture was acidified with KHSO₄ solution and extracted with ethyl acetate. The extracted organic layer was dried over Na₂SO₄, concentrated under reduced pressure and dried under high vacuum. The compound was purified by silica column chromatography to afford desired product (0.95 g) as colorless liquid. ¹H NMR (CDCl₃) δ ppm: 0.72 (s, 3H), 1.02 (s, 3H), 1.07 (s, 3H), 1.46 (s, 9H), 1.52-1.54 (m, 1H) 1.58-1.93 (m, 1H), 1.94-2.04 (m, 1H), 2.09-2.29 (m, 1H), 2.83-2.87 (m, 1H), 3.66 (s, 3H), 5.68 (d, J=4, 1H), 6.93 (d, J=8, 1H).

Step 4: tert-butyl 3-(1S,3S)-3-acetoxy-1,2,2-trimethylcyclopentyl)propanoate

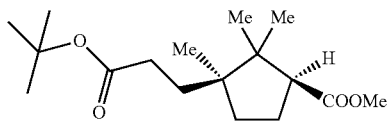 [SMILES: COC(=O)[C@H]1CC[C@@](C)(CCC(=O)OC(C)(C)C)C1(C)C]

To a solution of step 3 intermediate (0.95 g; 3.2 mmol) in methanol (30 mL), ammonium formate (1.21 g; 19.26 mmol) and of dry 10% Pd/C (0.225 g) was added and stirred at 60-65° C. for 20 min. After completion, the reaction mixture was filtered through celite bed and the filtrate obtained was concentrated on rotavapor, dried under high vacuum to afford the desired compound (0.865 g) as colorless sticky mass. ¹H NMR (CDCl₃) δ ppm: 0.71 (s, 3H), 0.82 (s, 3H), 1.01 (s, 3H), 1.41 (s, 9H), 1.45-1.80 (m, 5H), 2.09-2.15 (m, 2H), 2.22-2.29 (m, 1H), 2.80-2.85 (m, 1H), 3.68 (s, 3H).

Step 5: 3-[(1S,3S)-3-(methoxycarbonyl)-1,2,2-trimethylcyclopentyl]propanoic acid

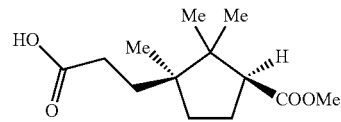

To a stirred solution of step 4 intermediate (0.86 g, 2.88 mmol) in dichloromethane (15 mL) at room temperature, trifluoroacetic acid (6.14 mL) was added. After 1.5 hours, the reaction mixture was concentrated and dried under reduced pressure. The compound was purified by silica column chromatography to afford the desired product (0.664 g) as colorless sticky mass. ¹H NMR (CDCl₃) δ ppm: 0.71 (s, 3H), 0.83 (s, 3H), 1.02 (s, 3H), 1.22-1.28 (m, 1H), 1.41-1.48 (m, 1H), 1.52-1.76 (m, 3H), 1.79-1.88 (m, 1H), 2.15-2.23 (m, 1H), 2.25-2.41 (m, 1H), 2.39-2.52 (m, 1H), 2.81-2.86 (m, 1H), 3.68 (s, 3H). m/z (M–H): 241.

Step 6: Methyl (1S,3S)-3-(3-hydroxypropyl)-2,2,3-trimethylcyclopentane carboxylate

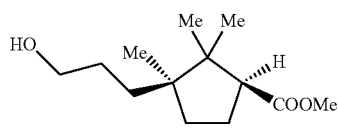 [SMILES: COC(=O)[C@H]1CC[C@@](C)(CCCO)C1(C)C]

To a solution of step 5 intermediate (0.645 g, 2.66 mmol) in dry THF (10 mL) under N₂ atmosphere, borane dimethylsulphide (0.328 mL, 3.46 mmol) was added slowly for 30 min through a septum and stirred for overnight. The reaction mixture was quenched with water, oxone then stirred for 30 mins. Then the reaction mixture was extracted with ethyl acetate, dried over sodium sulphate and concentrated under reduced pressure to afford the desired product (0.565 g) as colorless liquid. m/z (M+18): 246.

Step-7: Synthesis of methyl (1S,3S)-2,2,3-trimethyl-3-{3-[(methylsulfonyl)oxy]propyl}cyclopentane carboxylate

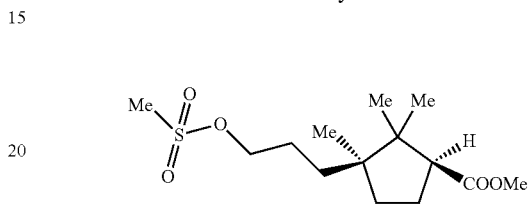

To a solution of step 6 intermediate (0.565 g, 2.47 mmol) and triethylamine (1.036 mL, 7.43 mmol) in dichloromethane (15 mL), methanesulfonyl chloride (0.886 mL, 4.95 mmol) was added at 0° C. After 1 hour, the reaction mixture was extracted with dichloromethane. The organic layer was dried over Na₂SO₄, concentrated under reduced pressure. The residue was purified by silica column chromatography to afford the desired product (0.695 g) as colorless sticky mass. ¹H NMR (CDCl₃) δ ppm: 0.73 (s, 3H), 0.88 (s, 3H), 1.02 (s, 3H), 1.28-1.43 (m, 2H), 1.44-1.48 (m, 1H), 1.62-1.69 (m, 2H), 1.73-1.86 (m, 2H), 2.17-2.22 (m, 1H), 2.81-2.86 (m, 1H), 2.94 (s, 3H), 3.68 (s, 3H), 4.22-4.23 (t, 2H).

Step 8: Methyl (1S,3S)-2,2,3-trimethyl-3-[3-(1H-1,2,4-triazol-1-yl)propyl]cyclopentane carboxylate

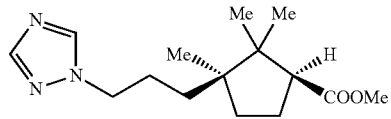 [SMILES: COC(=O)[C@H]1CC[C@@](C)(CCCn2cncn2)C1(C)C]

To suspension of 1,2,4-triazole (0.108 g, 1.56 mmol) and K₂CO₃ (0.325 g, 2.3 mmol) in DMF (1 mL), between 60-65° C., step 7 intermediate (0.48 g, 1.56 mmol) dissolved in DMF (0.5 mL) was added. The reaction mixture was stirred at 80° C. for 2.5 h. Then the reaction mixture was diluted with water and extracted with ethyl acetate. The extracted organic layer was dried over Na₂SO₄, concentrated under reduced pressure and dried under high vacuum to afford the desired product; (0.34 g) pale brown sticky mass. ¹H NMR (CDCl₃) δ ppm: 0.71 (s, 3H), 0.85 (s, 3H), 1.03 (s, 3H), 1.27-1.32 (m, 2H), 1.39-1.51 (m, 1H), 1.52-1.66 (m, 2H), 1.82-1.88 (m, 2H), 2.79-2.84 (m, 1H), 2.84-2.88 (m, 1H), 3.67 (s, 3H), 4.12-4.17 (t, 2H), 7.94 (s, 1H), 8.05 (s, 1H). m/z (M+1) 279.

Step 9: (1S,3S)-2,2,3-trimethyl-3-[3-(1H-1,2,4-triazol-1-1)propyl]cyclopentane carboxylic acid

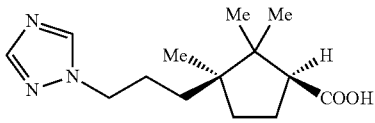 [SMILES: CC1(C)[C@@H](C(=O)O)CC[C@@]1(C)CCCn1cncn1]

To solution of step 8 intermediate (0.51 g, 1.82 mmol) tetrahydrofuran (9 mL) and MeOH (5 mL), LiOH (0.52 g, 21.93 mmol) in 3 mL of water was added and stirred. The reaction mixture was heated at 70-75° C. for 7-8 hours. The reaction mixture was concentrated under reduced pressure. The residue was dissolved in water and extracted with ethyl acetate. The aqueous layer was acidified with KHSO$_4$ solution (pH 1) and extracted with ethyl acetate. The extracted organic layer was dried over Na$_2$SO$_4$, concentrated under reduced pressure to afford the desired product (0.3 g) as white solid. $^1$H NMR (CDCl$_3$) δ ppm: 0.67 (s, 3H), 0.79 (s, 3H), 0.92 (s, 3H), 1.03-1.17 (m, 2H), 1.26-1.39 (m, 1H), 1.40-1.48 (m, 1H), 1.56-1.64 (m, 2H), 1.71-1.83 (m, 1H), 1.84-1.89 (m, 1H), 2.63-2.67 (m, 1H), 4.07 (t, J=8, 2H), 7.87 (s, 1H), 8.43 (s, 1H), 11.90 (bs, 1H). m/z (M+H) 266.

Step-10: Synthesis of (1S,3S)-2,2,3-trimethyl-3-[3-(1H-1,2,4-triazol-1-yl)propyl]cyclopentanecarboxamide

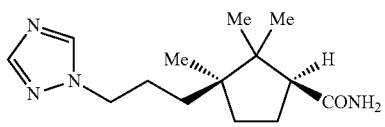 [SMILES: CC1(C)[C@@H](C(N)=O)CC[C@@]1(C)CCCn1cncn1]

To solution of step 9 intermediate (0.3 g, 1.13 mmol) and triethylamine (0.173 g, 1.24 mmol) in THF (7 mL), ethyl chloroformate (0.118 mL, 1.24 mmol) was added at 0° C. The reaction mixture was stirred for 30 minutes at 0° C. To this reaction mixture 23% aq. ammonia (9 mL) was added dropwise and stirred overnight. The reaction mixture was extracted with ethyl acetate, dried over Na$_2$SO$_4$, and concentrated under reduced pressure to afford the desired product (0.23 g) as off-white solid. $^1$H NMR (CDCl$_3$) δ ppm: 0.63 (s, 3H), 0.80 (s, 3H), 0.90 (s, 3H), 1.12-1.18 (m, 3H), 1.27-1.38 (m, 1H), 1.42-1.53 (m, 2H), 1.58-1.75 (m, 1H), 1.77-1.85 (m, 1H), 1.87-1.97 (m, 1H), 4.14 (t, J=8 Hz, 2H), 6.73 (bs, 1H), 6.97 (bs, 1H), 7.95 (s, 1H), 8.50 (s, 1H). m/z (M+H) 265.

Step 11: (1S,3R)-2,2,3-trimethyl-3-[3-(1H-1,2,4-triazol-1-yl)propyl]cyclopentanamine

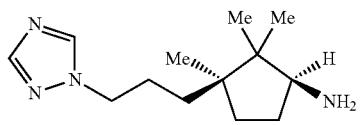 [SMILES: CC1(C)[C@@H](N)CC[C@@]1(C)CCCn1cncn1]

Step 10 intermediate (0.24 g, 1.016 mmol) was dissolved in a solvent mixture of acetonitrile (3 mL), ethyl acetate (3 mL), water (1.5 mL). To this PIFA (0.547 g, 1.272 mmol) was added and at stirred at 10° C. for 40 minutes. After that the temperature was maintained at 50° C. for 7 h. The reaction stirred for another 8 h at room temperature. The reaction mixture was heated upto 70° C. for 10 mins and concentrated under reduced pressure, acidified with KHSO$_4$ solution (pH 1) and extracted with dichloromethane. The aqueous layer was basified with NaOH solution and extracted with dichloromethane. The organic layer was concentrated and dried under high vacuum. The compound was purified by alumina column chromatography to afford desired product (0.1 g) as pale brown sticky mass. m/z (M+1): 237.

Step 12: (2S,4S)-1-(2-((1S,3R)-3-(3-(1H-1,2,4-triazol-1-yl)propyl)-2,2,3-trimethyl cyclopentylamino)acetyl)-4-fluoropyrrolidine-2-carbonitrile

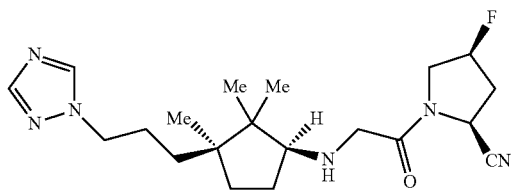 [SMILES: CC1(C)[C@@H](NCC(=O)N2C[C@@H](F)C[C@H]2C#N)CC[C@@]1(C)CCCn1cncn1]

To a suspension of step 11 intermediate (0.095 g, 0.40 mmol), K$_2$CO$_3$ (0.167 g, 1.207 mmol) and KI (3 mg) in DMSO (1 mL) were stirred at room temperature. To this intermediate 20 (0.06 g, 0.32 mmol) was added and stirred for 3.5 h. The reaction mixture was diluted with water and extracted with ethyl acetate. The organic layer was dried over Na$_2$SO$_4$, concentrated under reduced pressure and dried under vacuum. The compound was purified by silica column chromatography to afford the desired product (0.023 g) as pale brown solid. M.P 152-154° C. $^1$H NMR (CDCl$_3$) δ ppm: 0.77 (s, 3H), 0.88 (s, 3H), 0.88 (s, 3H), 1.19-1.31 (m, 3H), 1.39-1.47 (m, 1H), 1.50-1.71 (m, 1H), 1.72-1.89 (m, 1H), 1.90-2.16 (m, 2H), 2.30-2.43 (m, 1H), 2.68-2.89 (m, 1H), 2.91-2.97 (m, 1H), 3.37-3.55 (m, 1H), 3.62-3.77 (m, 2H), 3.89-4.02 (m, 1H), 4.14 (t, J=8 Hz, 2H), 4.95 (d, J=11.2 Hz. 0.8H), 5.11 (d, J=11.2 Hz, 0.2H), 5.35 (d, J=51.2 Hz, 0.2H), 5.48 (d, J=51.2 Hz, 0.8H), 7.94 (s, 1H), 8.05 (s, 1H). m/z (M+1) 391.2.

Demonstration of In Vitro Efficacy of Test Compounds
Protocol for DPP IV Assay:
DPP IV Measurement In Vitro:

DPP IV activity was determined by the cleavage rate of 7-amino 4-methylcoumarin (AMC) from the substrate H-Gly-Pro-AMC. In brief, the assay was conducted by adding 3 ng of human recombinant Dipeptidyl peptidase IV enzyme (hrDPP IV, available commercially from R&D systems) in 70 µL of the assay buffer (25 mM HEPES, 140 mM NaCl and 1% BSA, pH 7.8) to a 96 well black flat bottom microtitre plate. Test compounds were added as 10 µL additions to all wells except blank and total activity wells. After incubation of test substance with enzyme for 60 minutes at room temperature, 10 µL of 100 µM substrate H-Gly-Pro-AMC was added. After mixing, the plate was left for 20 minutes at room temperature. Then the reaction was terminated by addition of 10 µL of 25% glacial acetic acid. Fluorescence was measured using Spectra Max Gemini XS (Molecular Devices, USA) at an excitation filter of 360 nm and emission filter of 460 nm.

Test for IC$_{50}$ Studies:

Test compounds dissolved in DMSO were diluted with assay buffer at different concentrations and tested in duplicates. Percentage inhibition was calculated with respect to total activity. IC$_{50}$ value was calculated using Prism Software.

Protocol for DPP 8 Assay:

DPP 8 Measurement In Vitro:

DPP 8 activity was determined by the cleavage rate of 7-amino 4-fluoromethylcoumarin (AFC) from the substrate H-Ala-Pro-AFC. In brief, the assay was conducted by adding 30 ng of human recombinant Dipeptidyl peptidase 8 enzyme (hrDPP 8, available commercially from R&D systems) in 70 µL of the assay buffer (50 mM TRIS and 5 mM EDTA, pH 7.7) to a 96 well black flat bottom microtitre plate. Test compound was added as 10 µL additions to all wells except blank and total activity wells. After incubation of test substance with enzyme for 30 minutes at room temperature, 10 µL of 100 µM substrate H-Ala-Pro-AFC was added. After mixing, the plate was left for 30 minutes at room temperature. Then the reaction was terminated by addition of 10 µL of 25% Glacial Acetic Acid. Fluorescence was measured using Spectra Max Gemini XS (Molecular Devices, USA) at an excitation filter of 400 nm and emission filter of 505 nm.

Test for IC$_{50}$ Studies:

Test compound dissolved in DMSO were diluted with assay buffer at different concentrations and tested in duplicates. Percentage inhibition was calculated with respect to total activity. IC$_{50}$ value was calculated using Prism Software.

Protocol for DPP 9 Assay:

DPP 9 Measurement In Vitro:

DPP 9 activity was determined by the cleavage rate of 7-amino 4-methylcoumarin (AMC) from the substrate H-Gly-Pro-AMC. In brief, the assay was conducted by adding 10 ng of human recombinant Dipeptidyl peptidase 9 enzyme (hrDPP 9, available commercially from R&D systems) in 70 µL of the assay buffer (50 mM TRIS and 5 mM EDTA, pH 7.7) to a 96 well black flat bottom microtitre plate. Test compound was added as 10 µL additions to all wells except blank and total activity wells. After incubation of test substance with enzyme for 30 minutes at room temperature, 10 µL of 100 µM substrate H-Gly-Pro-AMC was added. After mixing, the plate was left for 30 minutes at room temperature. Then the reaction was terminated by addition of 10 µL of 25% Glacial Acetic Acid. Fluorescence was measured using Spectra Max Gemini XS (Molecular Devices, USA) at an excitation filter of 360 nm and emission filter of 460 nm.

Test for IC$_{50}$ Studies:

Test compound dissolved in DMSO were diluted with assay buffer at different concentrations and tested in duplicates. Percentage inhibition was calculated with respect to total activity. IC$_{50}$ value was calculated by using Prism Software.

DPP IV inhibition data (expressed either as IC$_{50}$ in nanomolar or percentage at 300 nM compound concentration) is presented in table 1.

TABLE 1

DPP-IV inhibition using human recombinant DPP-IV enzyme and selectivity towards DPP 8 & 9

| Example No | Inhibition at 300 nM | IC$_{50}$ (nM) | Selectivity (Fold) DPP 8 | DPP 9 |
|---|---|---|---|---|
| 1 | — | 222.25 ± 56.85 | — | — |
| 2* | 10.50 | — | — | — |
| 3 | — | 11.02 ± 0.16 | >27000 | >5000 |
| 5* | 4.10 | — | — | — |
| 6 | — | 123.10 | — | — |
| 7 | — | 99.84 | — | — |
| 8 | — | 1170.00 ± 0.14 | — | — |
| 9 | — | 780.60 ± 91.63 | — | — |
| 10 | — | 214.80 | — | — |
| 11 | — | 232.30 | — | — |
| 12 | — | 37.17 ± 3.67 | — | — |
| 13 | — | 27.83 | — | — |
| 14 | 73.19 | — | — | — |
| 15 | 60.49 | — | — | — |
| 16 | — | 32.5 | — | — |
| 17 | 46.65 | — | — | — |
| 18 | 84.86 | — | — | — |
| 19 | — | 304.80 ± 2.10 | — | — |
| 20 | — | 104.70 | — | — |
| 21* | — | 329.80 | — | — |
| 22 | 72.71 | — | — | — |
| 23 | 86.21 | — | — | — |
| 24 | — | 133.60 | — | — |
| 25 | — | 29.43 | — | — |
| 26 | 63.18 | — | — | — |
| 27 | 47.36 | — | — | — |
| 28 | — | 183.20 | — | — |
| 29 | — | 7.61 | >13000 | >1100 |
| 30 | — | 7.29 | — | >1250 |
| 31 | — | 264.20 | — | — |
| 32 | — | 6.01 | >9500 | >1900 |
| 33 | — | 250.30 | — | — |
| 34 | — | 8.94 | >10000 | >1500 |
| 36 | 31.90 | — | — | — |
| 37 | — | 22.38 | — | — |
| 38 | 42.57 | — | — | — |
| 39 | 45.94 | — | — | — |
| 40 | 84.68 | — | — | — |
| 41 | 26.08 | — | — | — |
| 42 | — | 91.31 | — | — |
| 44 | — | 582.30 | — | — |
| 45 | — | 58.99 | >300 (µM) | >300 (µM) |
| 46 | 40.90 | — | — | — |
| 47* | 13.53 | — | — | — |
| 48* | 4.46 | — | — | — |
| 49* | — | 421.90 | — | — |
| 50 | 14.99 | — | — | — |
| 51 | — | 91.41 | — | — |
| 52* | 29.20 | — | — | — |
| 53 | 56.45 | — | — | — |
| 54 | 64.86 | — | — | — |
| 55 | — | 4.39 | — | >9000 |
| 56 | 95.70 | 19.62 | — | — |
| 58 | 91.43 | — | — | — |
| 59 | 67.69 | — | — | — |
| 60 | 94.74 | 6.59 | >19000 | >7000 |
| 61 | 96.24 | 13.78 | — | >7271 |
| 62 | 79.78 | — | — | — |
| 63 | 92.57 | 19.18 | — | >1850 |
| 64 | — | 76.09 | >450 | >250 |
| 65* | — | 237.80 | — | — |
| 66* | 23.19 | — | — | — |
| 67 | 79.24 | — | — | — |
| 68 | — | 40.19 | >250 | >15 |
| 69 | — | 18.62 | >1800 | >150 |
| 70 | — | 26.67 | >550 | >25 |
| 71 | — | 22.82 | — | — |
| 72 | — | 32.32 | >1250 | >35 |
| 73 | — | 41.04 | >2300 | >150 |
| 74 | — | 54.72 | >900 | >25 |
| 76 | 4.25 | — | — | — |
| 77* | 13.38 | — | — | — |
| 78 | 23.29 | — | — | — |
| 80 | 2.28 | — | — | — |

TABLE 1-continued

DPP-IV inhibition using human recombinant DPP-IV enzyme and selectivity towards DPP 8 & 9

| Example No | Inhibition at 300 nM | IC$_{50}$ (nM) | Selectivity (Fold) DPP 8 | DPP 9 |
|---|---|---|---|---|
| 81 | 21.31 | — | — | — |
| 82 | 22.35 | — | — | — |
| 83 | 93.86 | 4.03 | — | — |

*Compounds screened by using human plasma

As Shown in table 1 compounds of formula (I) exerted potent DPP IV inhibition with good selectivity over DPP 8 and DPP 9 enzymes.

Demonstration of In Vivo Efficacy of Test Compounds
Protocol For Oral Glucose Tolerance Test:

Effect of compound on glucose tolerance was examined in 7 week old C57BL/6 mice. Animals were kept for 18 h fasting and were challenged with glucose (2 g/kg) 30 min after compound (10 mg/kg) administration. Blood samples for glucose measurement were obtained by tail bleed pre dose and at serial time points after the glucose load (30, 60 and 120 minutes). Blood glucose estimation was done by using ContourTS active strips on glucometer (Bayer). To find the time response on glucose excursion, animals were challenged with glucose at different time point after compound administration (0.5, 2, 4, 6, 8, 12 or 24 hours) at blood glucose was measured at pre (0 minute) and post (30, 60 and 120 minutes) glucose load.

Results of blood glucose were expressed as area under curve (AUC) was calculated using Prism software.

TABLE 2

Antihyperglycemic activity of selected compounds in mice, as determined by oral glucose tolerance test.

| Example No. | Time (hr) | | | | | |
|---|---|---|---|---|---|---|
| | 0.50 | 4.00 | 6.00 | 8.00 | 12.00 | 24.00 |
| 3 | 53.89 | — | — | — | — | — |
| 34 | 54.32 | — | NA | — | — | — |
| 32 | 17.80 | — | — | — | — | — |
| 29 | 42.52 | — | 20.21 | — | — | — |
| 55 | 48.30 | 45.69 | 28.28 | 18.63 | — | — |
| 30 | — | — | 30.90 | — | — | — |
| 56 | — | — | 7.07 | — | — | — |
| 60 | 47.70 | — | 51.55 | — | 29.62 | NA |

NA—No activity

As summarized in table 2, examples of present invention showed upto 29.62% reduction in AUC (Area under curve) at 12 h post administration of compound.

We claim:

1. A compound of formula (I),

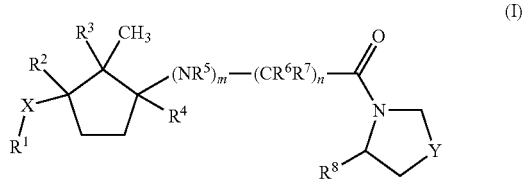

(I)

or a tautomeric form, stereoisomer, intermediate, or a pharmaceutically acceptable salt thereof, wherein:

Y represents —O—, —S(O)$_p$—, —CH$_2$—, —CHOH—, —CHF— or —CF$_2$—;

m is an integer selected from 1 or 2, and n and p are integers independently selected from 0, 1 or 2;

X represents a bond, a C$_1$-C$_5$ alkylene, or —C(=O)—;

R$^1$ represents hydrogen, an optionally substituted group selected from alkyl, cycloalkyl, cycloalkylalkyl, cycloalkenyl, aryl, arylalkyl, arylalkenyl, arylalkynyl, heteroaryl, heterocyclyl, heterocycloalkyl, heterocyclylalkyl, heteroarylalkyl, heteroarylalkenyl, heteroarylalkynyl, —N$_3$, —S(O)$_p$R$^{10}$, —NR$^{10}$S(O)$_p$R$^{11}$, —CN, —COOR$^{10}$, —CONR$^{10}$R$^{11}$, —OR$^{10}$, —NR$^{10}$R$^{11}$ or —NR$^{10}$COR$^{11}$, or a group selected from:

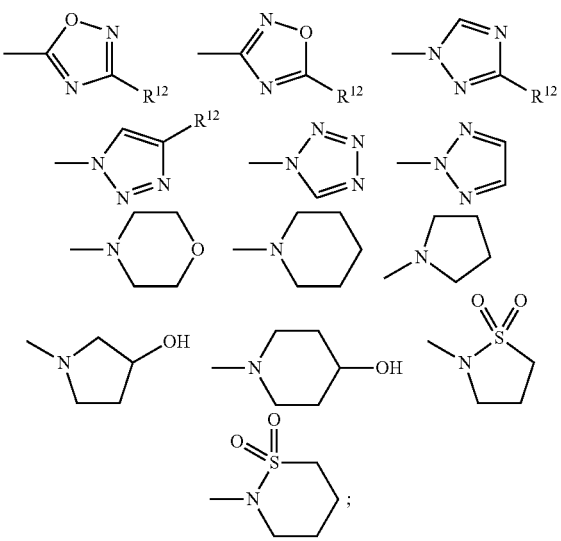

R$^{12}$ represents hydrogen or a substituted or unsubstituted group selected from alkyl, alkoxy, acyl, hydroxylalkyl, haloalkyl, alkenyl, alkynyl, cycloalkyl, cycloalkylalkyl, cycloalkenyl, aryl, arylalkyl, heteroaryl, heterocyclic ring, heterocycloalkyl, heterocyclylalkyl, heteroarylalkyl, carboxylic acid, and carboxylic acid derivatives selected from esters, amides, acid halides, hydroxamic acid, and hydroxamates;

R$^2$ and R$^4$ independently represent hydrogen or an alkyl group, wherein:
when one of R$^2$ and R$^4$ is hydrogen, the other is alkyl; and
when one of R$^2$ and R$^4$ is alkyl, the other is hydrogen; or
R$^2$ and R$^4$ together form an optionally substituted 4 to 10 membered ring having 0 to 4 hetero atoms selected from N, O and S;

R$^3$ represents an alkyl group;

R$^5$ represents hydrogen or an optionally substituted alkyl group;

R$^6$ represents hydrogen or an optionally substituted group selected from alkyl, alkoxyalkyl, hydroxyalkyl, amino, R$^9$NHalkyl, and R$^9$NHC(NH)NHalkyl;

R$^7$ and R$^9$ independently represent hydrogen, an alkyl group, or a hydroxylyroup;

R$^8$ is hydrogen, —CN, —COOH, or a group selected from —SO$_3$H, —B(OH)$_2$, —PO$_3$R$^{10}$R$^{11}$, —SO$_2$NR$^{10}$R$^{11}$, tetrazole, —COOR$^{10}$, —CONR$^{10}$R$^{11}$, —NR$^{10}$COR$^{11}$, and —COOCOR$^{10}$;

R$^{10}$ and R$^{11}$ independently represent hydrogen, nitro, hydroxy, cyano, formyl, acetyl, halogen, or an optionally substituted group selected from amino, alkyl, alkoxy, alkenyl, alkynyl, cycloalkyl cycloalkylalkyl, cycloalkenyl, aryl, arylalkyl, heteroaryl, heterocyclyl, heterocycloalkyl, heterocyclylalkyl, heteroarylalkyl, carboxylic acid, and carboxylic acid derivatives selected from esters, amides, acid halides, hydroxamic acid and hydroxamates;

when any of $R^1$, $R^2$, $R^4$, $R^5$, $R^6$, $R^7$, $R^8$, $R^9$, $R^{10}$, $R^{11}$, and $R^{12}$ are substituted or when the term "substituted" is used, the substituents are one or more and are selected from halogens, hydroxy, nitro, cyano, azido, nitroso, oxo (=O), thioxo (=S), thioalkyl, amino, hydrazino, formyl, alkyl, haloalkyl, alkoxy, haloalkoxy, arylalkoxy, cycloalkyl, cycloalkyloxy, aryl, heterocycloalkyl, heteroaryl, alkylamino, tolyl, —$COOR^a$, —$C(O)R^a$, —$C(S)R^a$, —$C(O)NR^aR^b$, —$C(S)NR^aR^b$, —$NR^aC(O)NR^bR^c$, —$NR^aC(S)NR^bR^c$, —$N(R^a)SOR^b$, —$N(R^a)SO_2R^b$, —$NR^aC(O)OR^b$, —$NR^aR^b$, —$NR^aC(O)R^b$, —$NR^aC(S)R^b$, —$SONR^aR^b$, —$SO_2NR^aR^b$, —$OR^a$, —$OR^aC(O)OR^b$, —$OC(O)NR^aR^b$, —$OC(O)R^a$, —$R^aNR^bR^c$, —$R^aOR^b$, —$SR^a$, —$SOR^a$, and —$SO_2R^a$; the substituents are further optionally substituted by one or more substituents as defined above; and $R^a$, $R^b$, and $R^c$ independently represent hydrogen or a substituted or unsubstituted group selected from alkyl, alkylene, aryl, arylalkyl, heteroaryl, heteroarylalkyl, heterocycloalkyl, cycloalkyl, and cylcoalkenyl; or $R^a$ and $R^b$ together form a ring structures having 4 to 8 atoms.

2. The compound according to claim 1, wherein:

when an alkoxy group is present, the alkoxy group is selected from methoxy, ethoxy, n-propoxy, isopropoxy, n-butoxy, isobutoxy, and t-butoxy;

when an aryloxy group is present, the aryloxy group is selected from phenoxy and naphthyloxy;

when a halogen is present, the halogen is fluorine, chlorine, bromine, or iodine;

when an alkyl group is present, the alkyl group is methyl, ethyl, n-propyl, isopropyl, butyl, isobutyl, t-butyl, pentyl, hexyl, heptyl, or octyl;

when an alkenyl group is present, the alkenyl group is ethenyl, 1-propenyl, 2-propenyl, iso-propenyl, 2-methyl-1-propenyl, 1-butenyl, or 2-butenyl;

when an alkynyl group is present, the alkynyl group is ethynyl, propynyl, or butynyl;

when a cycloalkyl group is present, the cycloalkyl group is cyclopropyl, cyclobutyl, cyclopentyl, cyclohexyl, cyclooctyl, cycloheptyl, perhydronaphthyl, adamantyl, a bridged cyclic group, or a spirobicyclic group;

when a cycloalkenyl group is present, the cycloalkenyl group is selected from cyclopentenyl and cyclohexenyl;

when a heterocycloalkyl or heteroaryl group is present, the heterocycloalkyl or heteroaryl group is a heterocyclyl group selected from azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, 2-oxoazepinyl, azepinyl, pyrrolyl, piperonyl, pyrazinyl, pyrimidinyl, pyridazinyl, pyrazolyl, oxazolyl, oxazolinyl, triazolyl, indanyl, isoxazolyl, isoxazolidinyl, thiazolyl, thiazolinyl, thiazolidinyl, thienyl, isothiazolyl, quinuclidinyl, isothiazolidinyl, indolyl, isoindolyl, indolinyl, isoindolinyl, octahydroindolyl, octahydroisoindolyl, decahydroisoquinolyl, benzimidazolyl, thiadiazolyl, benzo pyranyl, benzothiazolyl, benzothiadiazolyl, benzoxadiazolyl, benzotriazolyl, benzothienyl, benzoxazolyl, oxadiazolyl, benzindazolyl, indazolyl, phenylpiperidinyl, furyl, tetrahydrofuryl, tetrahydropyranyl, piperazinyl, homopiperazinyl, piperidyl, piperidopiperidyl, morpholinyl, thiomorpholinyl, piperidonyl, 2-oxopiperazinyl, 2-oxopiperidinyl, pyrrolidinyl, 2-oxopyrrolidinyl, oxazolidinyl, chromanyl, isochromanyl, oxabicyclo[3.2.1]octane, 3-oxabicyclo[3.2.1]octanone, 3-azabicyclo[3.2.1]octane-2,4-dione, and 3-azabicyclo[3.2.1]octane;

when an aryl group is present, the aryl group is phenyl, naphthyl, anthracenyl, indanyl, or biphenyl;

when an alkylene group is present, the alkylene group is methylene, ethylene, propylene, or butylene;

when a hydroxyalkyl group is present, the hydroxyalkyl group is hydroxymethyl or hydroxyethyl;

when a haloalkyl group is present, the haloalkyl group is trifluoromethyl, tribromomethyl, or trichloromethyl;

when a haloalkoxy group is present, the haloalkoxy group is selected from chloromethoxy, chloroethoxy, trifluoromethoxy, trifluoroethoxy, and trichloromethoxy;

when a heterocyclylalkyl group is present, the heterocyclylalkyl group is selected from oxadiazolylmethyl, triazolylmethyl, tetrazolylmethyl, morpholinylmethyl, pyrrolidinylmethyl, piperidinylmethyl, 1,2-thiazinane-1,1-dioxide-ylmethyl, and isothiazolidine1,1-dioxide-ylmethyl;

when a heteroarylalkenyl group is present, the heteroarylalkenyl group is selected from pyridinylethenyl, thienylethenyl, and triazolylethenyl; and when a heteroarylalkynyl group is present, the heteroarylalkynyl group is selected from pyridinylethynyl and thienylethynyl.

3. A compound of formula (I), as claimed in claim 1, which is selected from:

1. (2S,4S)-1-(2-((1R,3S)-3-((1H-1,2,4-Triazol-1-yl)methyl)-1,2,2-trimethylcyclopentyl amino)acetyl)-4-fluoropyrrolidine-2-carbonitrile;
2. (2S,4R)-1-(2-((1R,3S)-3-((1H-1,2,4-Triazol-1-yl)methyl)-1,2,2-trimethyl cyclopentylamino)acetyl)-4-fluoropyrrolidine-2-carbonitrile methanesulfonate;
3. (2S,4S)-1-(2-((1S,3R)-3-((1H-1,2,4-Triazol-1-yl)methyl)-1,2,2-trimethylcyclopentyl amino)acetyl)-4-fluoropyrrolidine-2-carbonitrile;
4. (2S,4S)-1-(2-((1S,3R)-3-((1H-1,2,4-Triazol-1-yl)methyl)-1,2,2-trimethyl cyclopentylamino)acetyl)-4-fluoropyrrolidine-2-carbonitrile methanesulfonate;
5. (2S,4R)-1-(2-((1S,3R)-3-((1H-1,2,4-Triazol-1-yl)methyl)-1,2,2-trimethyl cyclopentylamino)acetyl)-4-fluoropyrrolidine-2-carbonitrile methanesulfonate;
6. (S)-1-(2-((1S,3R)-3-((1H-1,2,4-Triazol-1-yl)methyl)-1,2,2-trimethylcyclopentylamino)acetyl)pyrrolidine-2-carbonitrile;
7. (S)-1-(2-((1S,3R)-3-((1H-1,2,4-Triazol-1-yl)methyl)-1,2,2-trimethylcyclopentylamino)acetyl)pyrrolidine-2-carbonitrile methanesulfonate;
8. (S)-1-(2-((1R,3S)-3-((1H-1,2,4-Triazol-1-yl)methyl)-1,2,2-trimethylcyclopentyl amino)acetyl)pyrrolidine-2-carbonitrile;
9. (S)-1-(2-((1R,3S)-3-((1H-1,2,4-Triazol-1-yl)methyl)-1,2,2-trimethylcyclopentyl amino)acetyl)pyrrolidine-2-carbonitrile methanesulfonate;
10. (2S,4S)-1-(2-((1R,3S)-3-((2H-1,2,3-Triazol-2-yl)methyl)-1,2,2-trimethylcyclopentyl amino)acetyl)-4-fluoropyrrolidine-2-carbonitrile;

11. (2S,4S)-1-(2-((1R,3S)-3-((1H-1,2,3-Triazol-1-yl)methyl)-1,2,2-trimethylcyclopentyl amino)acetyl)-4-fluoropyrrolidine-2-carbonitrile;
12. (2S,4S)-1-(2-((1S,3R)-3-((2H-1,2,3-Triazol-2-yl)methyl)-1,2,2-trimethylcyclopentyl amino)acetyl)-4-fluoropyrrolidine-2-carbonitrile;
13. (2S,4S)-1-(2-((1S,3R)-3-((1H-1,2,3-Triazol-1-yl)methyl)-1,2,2-trimethyl cyclopentylamino)acetyl)-4-fluoropyrrolidine-2-carbonitrile methanesulfonate;
14. (2S,4S)-4-Fluoro-1-(2-((1R,3S)-1,2,2-trimethyl-3-(piperidine-1-carbonyl)cyclopentylamino)acetyl)pyrrolidine-2-carbonitrile;
15. (2S,4S)-4-Fluoro-1-(2-((1R,3S)-3-((4-(hydroxymethyl)-1H-1,2,3-triazol-1-yl)methyl)-1,2,2-trimethylcyclopentylamino)acetyl)pyrrolidine-2-carbonitrile;
16. (2S,4S)-4-Fluoro-1-(2-((1S,3R)-3-((4-(hydroxymethyl)-1H-1,2,3-triazol-1-yl)methyl)-1,2,2-trimethylcyclopentylamino)acetyl)pyrrolidine-2-carbonitrile;
17. N-(((1S,3R)-3-(2-((2S,4S)-2-Cyano-4-fluoropyrrolidin-1-yl)-2-oxoethylamino)-2,2,3-trimethylcyclopentyl)methyl)methanesulfonamide;
18. N-(((1R,3S)-3-(2-((2S,4S)-2-Cyano-4-fluoropyrrolidin-1-yl)-2-oxoethylamino)-2,2,3-trimethylcyclopentyl)methyl)methanesulfonamide;
19. N-(((1S,3R)-3-(2-((2S,4S)-2-Cyano-4-fluoropyrrolidin-1-yl)-2-oxoethylamino)-2,2,3-trimethylcyclopentyl)methyl)-4-fluorobenzenesulfonamide;
20. N-(((1R,3S)-3-(2-((2S,4S)-2-Cyano-4-fluoropyrrolidin-1-yl)-2-oxoethylamino)-2,2,3-trimethylcyclopentyl)methyl)-4-fluorobenzenesulfonamide;
21. N-(((1S,3R)-3-(2-((2S,4S)-2-Cyano-4-fluoropyrrolidin-1-yl)-2-oxoethylamino)-2,2,3-trimethylcyclopentyl)methyl)-2-fluorobenzamide;
22. N-(((1S,3R)-3-(2-((2S,4S)-2-Cyano-4-fluoropyrrolidin-1-yl)-2-oxoethylamino)-2,2,3-trimethylcyclopentyl)methyl)-4,4-difluorocyclohexane carboxamide;
23. N-(((1R,3S)-3-(2-((2S,4S)-2-Cyano-4-fluoropyrrolidin-1-yl)-2-oxoethylamino)-2,2,3-trimethylcyclopentyl)methyl)-4,4-difluorocyclohexanecarboxamide;
24. 6-(((1S,3R)-3-(2-((2S,4S)-2-Cyano-4-fluoropyrrolidin-1-yl)-2-oxoethylamino)-2,2,3-trimethylcyclopentyl)methylamino)nicotinonitrile;
25. 6-(((1R,3S)-3-(2-((2S,4S)-2-Cyano-4-fluoropyrrolidin-1-yl)-2-oxoethylamino)-2,2,3-trimethylcyclopentyl)methylamino)nicotinonitrile;
26. 2-(((1S,3R)-3-(2-((2S,4S)-2-Cyano-4-fluoropyrrolidin-1-yl)-2-oxoethylamino)-2,2,3-trimethylcyclopentyl)methylamino)nicotinonitrile;
27. (2S,4S)-4-Fluoro-1-(2-((1R,3S)-1,2,2-trimethyl-3-((5-(trifluoromethyl)pyridin-2-ylamino)methyl)cyclopentylamino)acetyl)pyrrolidine-2-carbonitrile;
28. (2S,4S)-1-(2-((1R,3S)-3-[(1,1-Dioxidoisothiazolidin-2-yl)methyl]-1,2,2-trimethylcyclopentylamino)acetyl)-4-fluoropyrrolidine-2-carbonitrile;
29. (2S,4S)-1-(2-((1S,3R)-3-[(1,1-Dioxidoisothiazolidin-2-yl)methyl]-1,2,2-trimethylcyclopentylamino)acetyl)-4-fluoropyrrolidine-2-carbonitrile;
30. (2S,4S)-1-(2-((1S,3R)-3-[(1,1-Dioxido-1,2-thiazinan-2-yl)methyl]-1,2,2-trimethylcyclopentylamino)acetyl)-4-fluoropyrrolidine-2-carbonitrile;
31. (2S,4S)-1-(2-((1R,3S)-3-((1H-Tetrazol-1-yl)methyl)-1,2,2-trimethyl cyclopentylamino)acetyl)-4-fluoropyrrolidine-2-carbonitrile methanesulfonate;
32. (2S,4S)-1-(2-((1S,3R)-3-((1H-Tetrazol-1-yl)methyl)-1,2,2-trimethylcyclopentylamino)acetyl)-4-fluoropyrrolidine-2-carbonitrile;
33. (2S,4S)-4-Fluoro-1-(2-((1R,3S)-1,2,2-trimethyl-3-(morpholinomethyl)cyclopentyl amino)acetyl)pyrrolidine-2-carbonitrile;
34. (2S,4S)-4-Fluoro-1-(2-((1S,3R)-1,2,2-trimethyl-3-(morpholinomethyl)cyclopentylamino)acetyl)pyrrolidine-2-carbonitrile;
35. (2S,4S)-4-Fluoro-1-(2-((1S,3R)-1,2,2-trimethyl-3-(morpholinomethyl)cyclo pentylamino)acetyl)pyrrolidine-2-carbonitrile dimethanesulfonate;
36. (2S,4S)-4-Fluoro-1-(2-((1R,3S)-1,2,2-trimethyl-3-(pyrrolidin-1-ylmethyl)cyclo pentylamino)acetyl)pyrrolidine-2-carbonitrile;
37. (2S,4S)-4-Fluoro-1-(2-((1S,3R)-1,2,2-trimethyl-3-(pyrrolidin-1-ylmethyl)cyclopentylamino)acetyl)pyrrolidine-2-carbonitrile;
38. (2S,4S)-4-Fluoro-1-(2-((1R,3S)-3-(((R)-3-hydroxypyrrolidin-1-yl)methyl)-1,2,2-trimethylcyclopentylamino)acetyl)pyrrolidine-2-carbonitrile;
39. (2S,4S)-4-Fluoro-1-(2-((1R,3S)-1,2,2-trimethyl-3-(piperidin-1-ylmethyl)cyclopentylamino)acetyl)pyrrolidine-2-carbonitrile;
40. (2S,4S)-4-Fluoro-1-(2-((1S,3R)-1,2,2-trimethyl-3-(piperidin-1-ylmethyl)cyclopentylamino)acetyl)pyrrolidine-2-carbonitrile;
41. (2S,4S)-4-Fluoro-1-(2-((1R,3S)-3-((4-hydroxypiperidin-1-yl)methyl)-1,2,2-trimethylcyclopentylamino)acetyl)pyrrolidine-2-carbonitrile;
42. (2S,4S)-4-Fluoro-1-(2-((1R,3S)-1,2,2-trimethyl-3-((4-(methylsulfonyl)phenylsulfonyl)methyl)cyclopentylamino)acetyl)pyrrolidine-2-carbonitrile;
43. (2S,4R)-4-Fluoro-1-(2-((1R,3S)-1,2,2-trimethyl-3-((4-(methylsulfonyl)phenylsulfonyl)methyl)cyclopentylamino)acetyl)pyrrolidine-2-carbonitrile;
44. (S)-1-(2-((1R,3S)-1,2,2-Trimethyl-3-((4-(methylsulfonyl)phenylsulfonyl)methyl)cyclopentylamino)acetyl)pyrrolidine-2-carbonitrile;
45. (2S,4S)-4-Fluoro-1-(2-((1S,3R)-1,2,2-trimethyl-3-((4-(methylsulfonyl)phenylsulfonyl)methyl)cyclopentylamino)acetyl)pyrrolidine-2-carbonitrile;
46. (S)-1-(2-((1S,3R)-1,2,2-Trimethyl-3-((4-(methylsulfonyl)phenylsulfonyl)methyl)cyclopentylamino)acetyl)pyrrolidine-2-carbonitrile;
47. (2S,4R)-4-Fluoro-1-(2-((1S,3R)-1,2,2-trimethyl-3-(4-(methylsulfonyl)phenylsulfonyl)methyl)cyclopentylamino)acetyl)pyrrolidine-2-carbonitrile;
48. (2S,4S)-4-Fluoro-1-(2-((1R,3S)-3-(3-(4-fluorophenyl)-1,2,4-oxadiazol-5-yl)-1,2,2-trimethylcyclopentylamino)acetyl)pyrrolidine-2-carbonitrile;
49. (2S,4S)-4-Fluoro-1-(2-((1S,3R)-3-(3-(4-fluorophenyl)-1,2,4-oxadiazol-5-yl)-1,2,2-trimethylcyclopentylamino)acetyl)pyrrolidine-2-carbonitrile;
50. (2S,4S)-4-Fluoro-1-(2-((1R,3S)-1,2,2-trimethyl-3-(3-methyl-1,2,4-oxadiazol-5-yl)cyclopentylamino)acetyl)pyrrolidine-2-carbonitrile;
51. (2S,4S)-4-Fluoro-1-(2-((1S,3R)-1,2,2-trimethyl-3-(3-methyl-1,2,4-oxadiazol-5-yl)cyclopentylamino)acetyl)pyrrolidine-2-carbonitrile;
52. (2S,4S)-4-Fluoro-1-(2-((1R,3S)-3-(3-isopropyl-1,2,4-oxadiazol-5-yl)-1,2,2-trimethylcyclopentylamino)acetyl)pyrrolidine-2-carbonitrile;
53. (2S,4S)-1-(2-((1R,3R)-3-(Cyanomethyl)-1,2,2-trimethylcyclopentylamino)acetyl)-4-fluoropyrrolidine-2-carbonitrile;
54. (2S,4S)-4-Fluoro-1-(2-((1R,3R)-1,2,2-trimethyl-3-((5-methyl-1,2,4-oxadiazol-3-yl)methyl)cyclopentylamino)acetyl)pyrrolidine-2-carbonitrile;

55. (2S,4S)-4-Fluoro-1-(2-((1S,3S)-1,2,2-trimethyl-3-((5-methyl-1,2,4-oxadiazol-3-yl)methyl)cyclopentylamino)acetyl)pyrrolidine-2-carbonitrile;

56. (2S,4S)-4-Fluoro-1-(2-((1S,3S)-1,2,2-trimethyl-3-((5-(trifluoromethyl)-1,2,4-oxadiazol-3-yl)methyl)cyclopentylamino)acetyl)pyrrolidine-2-carbonitrile;

57. (2S,4S)-4-Fluoro-1-(2-((1S,3S)-1,2,2-trimethyl-3-((5-(trifluoromethyl)-1,2,4-oxadiazol-3-yl)methyl)cyclopentylamino)acetyl)pyrrolidine-2-carbonitrile methanesulfonate;

58. (2S,4S)-1-(2-((1S,3S)-3-((5-tert-Butyl-1,2,4-oxadiazol-3-yl)methyl)-1,2,2-trimethylcyclopentylamino)acetyl)-4-fluoropyrrolidine-2-carbonitrile;

59. (2S,4S)-1-(2-((1S,3S)-3-((5-Cyclohexyl-1,2,4-oxadiazol-3-yl)methyl)-1,2,2-trimethylcyclopentylamino)acetyl)-4-fluoropyrrolidine-2-carbonitrile;

60. (2S,4S)-4-Fluoro-1-(2-((1S,3S)-3-((5-(hydroxymethyl)-1,2,4-oxadiazol-3-yl)methyl)-1,2,2-trimethylcyclopentylamino)acetyl)pyrrolidine-2-carbonitrile;

61. (2S,4S)-4-Fluoro-1-(2-((1S,3S)-3-((5-isopropyl-1,2,4-oxadiazol-3-yl)methyl)-1,2,2-trimethylcyclopentylamino)acetyl)pyrrolidine-2-carbonitrilemethane sulfonate;

62. (2S,4S)-4-Fluoro-1-(2-((1S,3S)-3-((5-(4-fluorophenyl)-1,2,4-oxadiazol-3-yl)methyl)-1,2,2-trimethylcyclopentylamino)acetyl)pyrrolidine-2-carbonitrile;

63. (2S,4S)-4-Fluoro-1-(2-((1S,3S)-1,2,2-trimethyl-3-((5-(pyridin-4-yl)-1,2,4-oxadiazol-3-yl)methyl)cyclopentylamino)acetyl)pyrrolidine-2-carbonitrile;

64. (2S,4S)-4-Fluoro-1-(2-((1R,3S)-3-(3-(4-fluorophenyl)-1,2,4-oxadiazol-5-yl)-2,2,3-trimethylcyclopentylamino)acetyl)pyrrolidine-2-carbonitrile 65. (2S,4S)-4-Fluoro-1-(2-((1S,3R)-3-(3-(4-fluorophenyl)-1,2,4-oxadiazol-5-yl)-2,2,3-trimethylcyclopentylamino)acetyl)pyrrolidine-2-carbonitrile;

66. (S)-1-(2-((1S,3R)-3-(3-(4-Fluorophenyl)-1,2,4-oxadiazol-5-yl)-2,2,3-trimethylcyclopentylamino)acetyl)pyrrolidine-2-carbonitrile methanesulfonate;

67. (2S,4S)-4-Fluoro-1-(2-((1S,3R)-3-(3-isopropyl-1,2,4-oxadiazol-5-yl)-2,2,3-trimethylcyclopentylamino)acetyl)pyrrolidine-2-carbonitrile;

68. (2S,4S)-4-Fluoro-1-(2-((1S,3R)-2,2,3-trimethyl-3-(3-(pyridin-3-yl)-1,2,4-oxadiazol-5-yl)cyclopentylamino)acetyl)pyrrolidine-2-carbonitrile;

69. (2S,4S)-4-Fluoro-1-(2-((1R,3S)-2,2,3-trimethyl-3-(3-(pyridin-3-yl)-1,2,4-oxadiazol-5-yl)cyclopentylamino)acetyl)pyrrolidine-2-carbonitrile;

70. (2S,4S)-4-Fluoro-1-(2-((1S,3R)-2,2,3-trimethyl-3-(3-(pyridin-4-yl)-1,2,4-oxadiazol-5-yl)cyclopentylamino)acetyl)pyrrolidine-2-carbonitrile;

71. (2S,4S)-4-Fluoro-1-(2-((1R,3S)-2,2,3-trimethyl-3-(3-(pyridin-4-yl)-1,2,4-oxadiazol-5-yl)cyclopentylamino)acetyl)pyrrolidine-2-carbonitrile;

72. (2S,4S)-4-Fluoro-1-(2-((1S,3R)-2,2,3-trimethyl-3-(3-(pyrazin-2-yl)-1,2,4-oxadiazol-5-yl)cyclopentylamino)acetyl)pyrrolidine-2-carbonitrile;

73. (2S,4S)-4-Fluoro-1-(2-((1R,3S)-2,2,3-trimethyl-3-(3-methyl-1,2,4-oxadiazol-5-yl)cyclopentylamino)acetyl)pyrrolidine-2-carbonitrile;

74. (2S,4S)-4-Fluoro-1-(2-((1S,3R)-2,2,3-trimethyl-3-(3-methyl-1,2,4-oxadiazol-5-yl)cyclopentylamino)acetyl)pyrrolidine-2-carbonitrile;

75. (S)-1-(2-((1R,5R)-3,5,8,8-Tetramethyl-2,4-dioxo-3-azabicyclo[3.2.1]octan-1-ylamino)acetyl)pyrrolidine-2-carbonitrile;

76. (2S,4S)-4-Fluoro-1-(2-((1R,5R)-3,5,8,8-tetramethyl-3-azabicyclo[3.2.1]octan-1-ylamino)acetyl)pyrrolidine-2-carbonitrile;

77. (2S,4R)-4-Fluoro-1-(2-((1R,5R)-3,5,8,8-tetramethyl-3-azabicyclo[3.2.1]octan-1-ylamino)acetyl)pyrrolidine-2-carbonitrile;

78. (S)-1-(2-((1R,5R)-3,5,8,8-Tetramethyl-3-azabicyclo[3.2.1]octan-1-ylamino)acetyl)pyrrolidine-2-carbonitrile;

79. (S)-1-(2-((1R,5R)-5,8,8-Trimethyl-2-oxo-3-oxabicyclo[3.2.1]octan-1-ylamino)acetyl)pyrrolidine-2-carbonitrile;

80. (S)-1-(2-((1R,5R)-5,8,8-Trimethyl-3-oxabicyclo[3.2.1]octan-1-ylamino)acetyl)pyrrolidine-2-carbonitrile;

81. (2S,4S)-4-Fluoro-1-(2-((1R,5R)-5,8,8-trimethyl-3-oxabicyclo[3.2.1]octan-1-ylamino)acetyl)pyrrolidine-2-carbonitrile;

82. (2S,4S)-4-Fluoro-1-(2-((1S,5S)-5,8,8-trimethyl-3-oxabicyclo[3.2.1]octan-1-ylamino)acetyl)pyrrolidine-2-carbonitrile; and 83. (2S,4S)-1-(2-((1S,3R)-3-(3-(1H-1,2,4-Triazol-1-yl)propyl)-2,2,3-trimethylcyclopentyl amino)acetyl)-4-fluoropyrrolidine-2-carbonitrile.

4. A process for preparing a compound of formula (I) according to claim 1, comprising:
coupling a compound of formula (II), which is in its free, salt, or protected form, with a compound of formula (III):

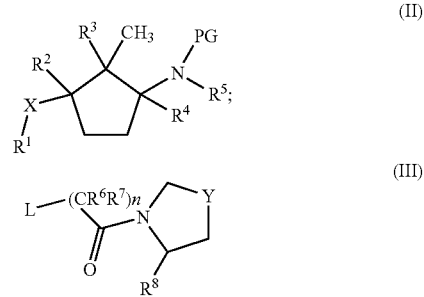

wherein:
L represents a leaving group selected from the group consisting of chloro, bromo, iodo, tosylates, mesylates, and triflates;
PG represents hydrogen or a protecting group selected from the group consisting of acetyl, trifluoroacetyl, arylsulphonyl, nosyl, tosyl, -Boc, and —CBz; and
n, $R^1$, $R^2$, $R^3$, $R^4$, $R^5$, $R^6$, $R^7$, $R^8$, Y, and X are defined as in claim 1.

5. A pharmaceutical composition comprising a compound of formula (I) as claimed in claim 1, or a pharmaceutically acceptable salt thereof as an active ingredient along with a pharmaceutically acceptable carrier, diluent, excipient or solvate.

6. A method of treatment of diabetes comprising administering a compound of formula (I) or its pharmaceutically acceptable salts as claimed in claim 1 to a patient in need thereof.

7. A method of treatment of Type II diabetes; impaired glucose tolerance; insulin resistance; or hypercholesterolemia, comprising administering a compound of formula (I) or its pharmaceutically acceptable salt as claimed in claim 1 to a patient in need thereof.

8. A pharmaceutical composition comprising a compound of formula (I) as claimed in claim 3, or a pharmaceutically acceptable salt thereof as an active ingredient along with a pharmaceutically acceptable carrier, diluent, excipient or solvate.

9. A pharmaceutical composition as claimed in claim 8, in the form of a tablet, capsule, powder, syrup, solution, aerosol or suspension.

10. A method of treatment of diabetes comprising administering a compound of formula (I) or its pharmaceutically acceptable salts as claimed in claim 3 to a patient in need thereof.

11. A method of treatment of Type II diabetes; impaired glucose tolerance; insulin resistance; or hypercholesterolemia, comprising administering a compound of formula (I) or its pharmaceutically acceptable salt as claimed in claim 3 to a patient in need thereof.

\* \* \* \* \*